(12) United States Patent
Jaehne et al.

(10) Patent No.: US 7,759,366 B2
(45) Date of Patent: Jul. 20, 2010

(54) ARYLAMINOARYL-ALKYL-SUBSTITUTED IMIDAZOLIDINE-2,4-DIONES, PROCESS FOR PREPARING THEM, MEDICAMENTS COMPRISING THESE COMPOUNDS, AND THEIR USE

(75) Inventors: Gerhard Jaehne, Frankfurt am Main (DE); Siegfried Stengelin, Frankfurt am Main (DE); Matthias Gossel, Frankfurt am Main (DE); Thomas Klabunde, Frankfurt am Main (DE); Irvin Winkler, Frankfurt am Main (DE)

(73) Assignee: Sanofi-Aventis, Paris (FR)

( * ) Notice: Subject to any disclaimer, the term of this patent is extended or adjusted under 35 U.S.C. 154(b) by 0 days.

(21) Appl. No.: 12/365,940

(22) Filed: Feb. 5, 2009

(65) Prior Publication Data

US 2009/0215728 A1 Aug. 27, 2009

Related U.S. Application Data

(63) Continuation of application No. PCT/EP2007/006594, filed on Jul. 25, 2007.

(30) Foreign Application Priority Data

Aug. 8, 2006 (DE) .................. 10 2006 036 930
Aug. 30, 2006 (DE) .................. 10 2006 040 592

(51) Int. Cl.
*A61K 31/4439* (2006.01)
*A61K 31/4166* (2006.01)
*C07D 401/04* (2006.01)
*C07D 233/72* (2006.01)
*C07D 233/74* (2006.01)
*C07D 209/54* (2006.01)

(52) U.S. Cl. .................. 514/341; 514/389; 548/321.1; 548/301.4; 546/274.1

(58) Field of Classification Search .................. 514/341, 514/389; 546/274.1; 548/321.1, 301.4
See application file for complete search history.

(56) References Cited

U.S. PATENT DOCUMENTS 5,411,981 A 5/1995 Gaillard-Kelly et al.

FOREIGN PATENT DOCUMENTS

| WO | WO01/09090 | 2/2001 |
|---|---|---|
| WO | WO2004/070050 | 8/2004 |
| WO | WO 2005/049580 | 6/2005 |
| WO | WO2007/083017 | 7/2007 |

OTHER PUBLICATIONS

Carai et al. CNS Drug Reviews 2006, 12(2), 91-99.*
Pagotto et al. www.thelancet.com, Apr. 16, 2005, vol. 365, pp. 1363-1364.*
Campbell et al., Chapter 15 in Cannabinoids and the Brain, Kofalvi (ed.), 2008, pp. 317-329.*
King, F. D., et. al., Bioisosteres, Conformational Restriction, and Pro-Drugs—Case History: An Example of a Conformational Restriction Approach, Medicinal Chemistry: Principles and Practice, (1994), pp. 206-225.

* cited by examiner

*Primary Examiner*—Rebecca L Anderson
*Assistant Examiner*—Jason M Nolan
(74) *Attorney, Agent, or Firm*—Balaram Gupta

(57) ABSTRACT

This invention relates to arylaminoaryl-alkyl-substituted imidazolidone-2,4-diones of formula (I) and also to their physiologically tolerated salts:

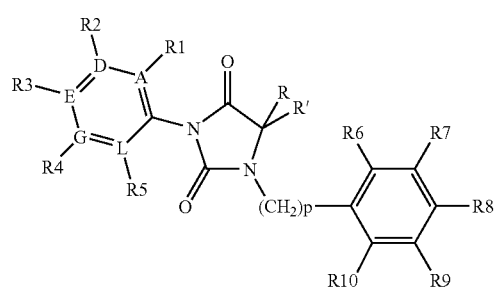

Wherein R, R', R1 to R10, A, D, E, G, L and p are as defined herein. The invention also relates to processes for preparing them, pharmaceutical compositions comprising them and their therapeutic use. The compounds are suitable, for example, as anti-obesity drugs and for treating cardiometabolic syndrome.

19 Claims, No Drawings

ARYLAMINOARYL-ALKYL-SUBSTITUTED IMIDAZOLIDINE-2,4-DIONES, PROCESS FOR PREPARING THEM, MEDICAMENTS COMPRISING THESE COMPOUNDS, AND THEIR USE

CROSS REFERENCE TO RELATED APPLICATIONS

This application is a continuation of International application No. PCT/EP2007/006,594, filed Jul. 25, 2007, which is incorporated herein by reference in its entirety; which claims the benefit of priority of German Patent Application No. 10 2006 036 930.0, filed Aug. 8, 2006 and German Patent Application No. 10 2006 040 592.7, filed Aug. 30, 2006.

BACKGROUND OF THE INVENTION

1. Field of the Invention

The invention relates to imidazolidine-2,4-diones which are substituted by an arylaminoarylalkyl radical and to the physiologically compatible salts thereof.

2. Description of the Art

Structurally similar imidazoline-2,4-diones have already been described (see U.S. Pat. No. 5,411,981).

It was an object of the invention to provide compounds which display a therapeutically utilizable action. In particular, it was an object of the invention to find novel compounds which are suitable for the treatment of metabolic syndrome, of type II diabetes and of obesity.

SUMMARY OF THE INVENTION

The invention therefore relates to compounds of the formula I

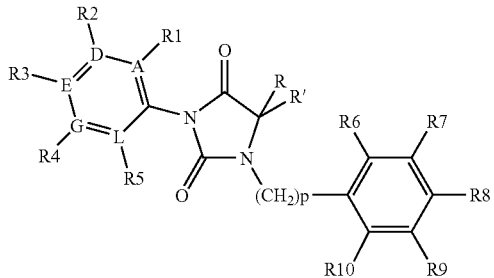

in which

R, R' are each independently H, $(C_1-C_6)$-alkyl, where $(C_1-C_6)$-alkyl may be substituted by halogen, O—R14, $S(O)_m$—R12 or NR13R15;

or R and R' together form a ring having from three to eight carbon atoms, where one carbon atom may be replaced by O, $S(O)_m$, NR13 or NR15;

m is 0, 1, 2;
n is 0, 1, 2, 3, 4;
p is 1, 2, 3, 4, 5;
q is 1, 2, 3, 4;
r is 2, 3, 4, 5, 6;
v is 0, 1, 2, 3, 4;

A, D, E, G, L are each independently C or N, where there is no corresponding R1, R2, R3, R4, R5 substituent when they are defined as N;

R1, R2, R3, R4, R5 are each independently H, F, Cl, Br, I, CN, $N_3$, NC, $NO_2$, $CF_3$, $(C_1-C_8)$-alkyl, $(C_3-C_8)$-cycloalkyl, $(CH_2)_n$—[$(C_3-C_8)$-cycloalkenyl], $(CH_2)_q$—[$(C_3-C_8)$-cycloalkyl], $(CH_2)_n$—[$(C_7-C_{12})$-bicycloalkyl], $(CH_2)_n$—[$(C_7-C_{12})$-bicycloalkenyl], $(CH_2)_n$—[$(C_7-C_{12})$-tricycloalkyl], adamantan-1-yl, adamantan-2-yl, $(CH_2)_n$-aryl, $(CH_2)_n$-heteroaryl, $OCF_3$, O—R11, NR13R15, NH—CN, $S(O)_m$—R12, $SO_2$—$NH_2$, $SO_2$—N=CH—$N(CH_3)_2$, $SO_2$—NH—CO—R12, $SO_2$—NH—CO—NHR12, $SO_2$—NH—CO—R16, $SO_2$—NH—[$(C_1-C_8)$-alkyl], $SO_2$—NH—[$(C_3-C_8)$-cycloalkyl], $SO_2$—NH—$(CH_2)_r$—OH, $SO_2$—NH—$(CH_2)_n$-aryl, $SO_2$—NH—$(CH_2)_n$-heteroaryl, $SO_2$—N[$(C_1-C_8)$-alkyl]$_2$, $SO_2$—R16, $SF_5$, CO—O[$(C_1-C_8)$-alkyl], CO—O[$(C_3-C_8)$-cycloalkyl], CO—O—$(CH_2)_r$—$NH_2$, CO—O—$(CH_2)_n$-aryl, CO—O—$(CH_2)_n$-heteroaryl, CO—$NH_2$, CO—NH—CN, CO—NH—[$(C_1-C_8)$-alkyl], CO—NH—$(CH_2)_r$—OH, CO—N[$(C_1-C_8)$-alkyl]$_2$, CO—NH—[$(C_3-C_8)$-cycloalkyl], CO—N[$(C_3-C_8)$-cycloalkyl]$_2$, C(=NH)—O—[$(C_1-C_6)$-alkyl)], C(=NH)—$NH_2$, C(=NH)—NHOH, C(=NH)—[NHO—$(C_1-C_6)$-alkyl], C(=NH)—NR12R13, C(=NH)—R16, C(=NR13)—NR12R13, CO—NH—$SO_2$—R16, CO—NH—$SO_2$—NHR12, CO—R16, COOH, CO—$(C_1-C_8)$-alkyl, CO—$(C_3-C_8)$-cycloalkyl, CO—$(CH_2)_n$—[$(C_7-C_{12})$-bicycloalkyl], CO—$(CH_2)_n$—[$(C_7-C_{12})$-tricycloalkyl], CO-aryl, CO-heteroaryl, CH(OH)-aryl, CH(OH)-heteroaryl, CH[O—$(C_1-C_6)$-alkyl]-aryl, CH[O—$(C_1-C_6)$-alkyl]-heteroaryl, CHF-aryl, CHF-heteroaryl, $CF_2$-aryl, $CF_2$-heteroaryl, CHO, $CH_2$—OH, $CH_2$—CN, $CH_2$—O—R12, $CH_2$—O—$(CH_2)_n$—CO—O[$(C_1-C_8)$-alkyl], $CH_2$—O—$(CH_2)_n$—CO—$NH_2$, $CH_2$—O—$(CH_2)_q$—COOH, where the alkyl, cycloalkyl, cycloalkenyl, bicycloalkyl, bicycloalkenyl and tricycloalkyl radicals may be substituted by fluorine atoms and where the aryl or heteroaryl radicals may be substituted by halogen, CN, $(C_1-C_6)$-alkyl, $(C_3-C_6)$-cycloalkyl, O—$(C_1-C_6)$-alkyl, $S(O)_m$—$(C_1-C_6)$-alkyl, $SO_2$—$NH_2$, COOH, $CONH_2$, CO—O$(C_1-C_6)$-alkyl, CO—$(C_1-C_6)$-alkyl and where the alkyl radicals may be substituted by fluorine atoms;

R6, R7, R8, R9, R10 are each independently R11, NR17-bicyclic heterocycle, NR17-aryl, NR17-heteroaryl, where the aryl or heteroaryl radical may be fused to a 5- or 6-membered aromatic or nonaromatic carbon ring in which one or more CH or $CH_2$ groups may be replaced by oxygen atoms and where the 5- or 6-membered aromatic or nonaromatic carbon ring may be substituted by F, =O or —$(C_1-C_6)$-alkyl and where the bicyclic heterocycle may contain from 9 to 12 ring members and up to five CH or $CH_2$ groups may each independently be replaced by N, NR20, O, $S(O)_m$ or C=O and where the aryl or heteroaryl radical or bicyclic heterocycle may be unsubstituted or mono- or polysubstituted by R11, F, Cl, Br, I, CN, $N_3$, NC, $NO_2$, $CF_3$, $(CH_2)_n$—O—R11, $(CH_2)_n$—O—$(CH_2)_r$—OH, $(CH_2)_n$—O—CH$(CH_2OH)_2$, $(CH_2)_n$—O—$(CH_2)_n$—CO—O—$(CH_2)_r$—$NH_2$, $(CH_2)_n$—O—$(CH_2)_n$—CO—NH—$(CH_2)_r$—OH, $(CH_2)_n$—O-sugar, $(CH_2)_n$—O-sugar acid, $(CH_2)_n$—O-glucoside, $(CH_2)_n$—O-galactoside, $(CH_2)_n$—O-glucuronide, O—R13, $OCF_3$, $(CH_2)_n$—O—$(CH_2)_r$—$NH_2$, $(CH_2)_n$—NH—R11, $(CH_2)_n$—N[$(CH_2)_q$—CO—O($C_1-C_6$)-alkyl]$_2$, $(CH_2)_n$—N[$(CH_2)_q$—COOH]$_2$, $(CH_2)_n$—N[$(CH_2)_q$—$CONH_2$]$_2$, $(CH_2)_n$—NH—R13, $(CH_2)_n$—N(R13)$_2$, $(CH_2)_n$—NH—CN, $(CH_2)_n$—NH—$SO_2$—R16, $(CH_2)_n$—NH—$(CH_2)_n$—$SO_2$—R12, $(CH_2)_n$—NR12—CO—R16, $(CH_2)_n$—NR12—CO—NR12R13, $(CH_2)_n$—NR12—CO—N(R12)$_2$, $(CH_2)_n$—NR12—

CO—NHR11, $(CH_2)_n$—NH—C(=NH)—$NH_2$, $(CH_2)_n$—NH—C(=NH)—R16, $(CH_2)_n$—NH—C(=NH)—NHR12, $(CH_2)_n$—NR12-C(=NR13)—NHR12, $(CH_2)_n$—NR12-C(=NR12)-NR12R13, $(CH_2)_n$—NH—$(CH_2)_n$—CO—O—$(CH_2)_r$—$NH_2$, $(CH_2)_n$—NH—$(CH_2)_n$—CO—NH—[$(C_1$-$C_8)$-alkyl], $(CH_2)_n$—NH—$(CH_2)_n$—CO—NH—$(CH_2)_r$—OH, $(CH_2)_n$—NH—$(CH_2)_n$—CO—N[(C1-C8)-alkyl]$_2$, $(CH_2)_n$—NH—$(CH_2)_n$—CO—NH—[$(C_3$-$C_8)$-cycloalkyl], $(CH_2)_n$—NH—$(CH_2)_n$—CO—N[$(C_3$-$C_8)$-cycloalkyl]$_2$, $(CH_2)_n$—NH—$C(CH_3)_2$—CO—O$(C_1$-$C_8)$-alkyl, $(CH_2)_n$—NH—$C(CH_3)_2$—CO—O$(C_3$-$C_8)$-cycloalkyl, $(CH_2)_n$—NH—$C(CH_3)_2$—CO—O—$(CH_2)_r$—$NH_2$, $(CH_2)_n$—NH—$C(CH_3)_2$—CO—O—$(CH_2)_n$-aryl, $(CH_2)_n$—NH—$C(CH_3)_2$—CO—O—$(CH_2)_n$-heteroaryl, $(CH_2)_n$—NH—$C(CH_3)_2$—CO—$NH_2$, $(CH_2)_n$—NH—$C(CH_3)_2$—CO—NH—[$(C_1$-$C_8)$-alkyl], $(CH_2)_n$—NH—$C(CH_3)_2$—CO—NH—$(CH_2)_r$—OH, $(CH_2)_n$—NH—$C(CH_3)_2$—CO—N[$(C_1$-$C_8)$-alkyl]$_2$, $(CH_2)_n$—NH—$(CH_3)_2$—CO—NH—[$(C_3$-$C_8)$-cycloalkyl], $(CH_2)_n$—NH—$C(CH_3)_2$—CO—N[$(C_3$-$C_8)$-cycloalkyl]$_2$, $(CH_2)_n$—NH—$C(CH_3)_2$—COOH, $S(O)_m$—R12, $SO_2$—R16, $SO_2$—N=CH—N$(CH_3)_2$,

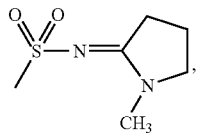

$SO_2$—NH—CO—R12, $SO_2$—NHR12, $SO_2$—NH—$(CH_2)_r$—OH, $SO_2$—N[$(C_1$-$C_8)$-alkyl]$_2$, $SO_2$—NH—$(CH_2)_r$—$NH_2$, $SF_5$, COOH, CO—$NH_2$, $(CH_2)_q$—CN, $(CH_2)_n$—CO—NH—CN, $(CH_2)_n$—CO—NH-piperidin-1-yl, $(CH_2)_n$—CO—NH—$SO_2$—NHR12, $(CH_2)_n$—CO—NH—$SO_2$—R18, $(CH_2)_n$—CHO, $(CH_2)_n$—C(=NH)—$NH_2$, $(CH_2)_n$—C(=NH)—NHOH, $(CH_2)_n$—C(=NH)—[NH—O—$(C_1$-$C_6)$-alkyl], $(CH_2)_n$—C(=NH)(R16), $(CH_2)_n$—C(=NR13)NHR12, $(CH_2)_n$—C(=NR12)NR12R13, $(CH_2)_n$—C(=NH)O[$(C_1$-$C_6)$-alkyl], where the alkyl and cycloalkyl radicals may be substituted by fluorine atoms and where the aryl or heteroaryl radicals may be substituted by halogen, CN, $(C_1$-$C_6)$-alkyl, $(C_3$-$C_6)$-cycloalkyl, O—$(C_1$-$C_6)$-alkyl, $S(O)_m$—$(C_1$-$C_6)$-alkyl, $SO_2$—$NH_2$, COOH, CONH$_2$, CO—O$(C_1$-$C_6)$-alkyl, CO—$(C_1$-$C_6)$-alkyl and where the alkyl radicals may be substituted by fluorine atoms;

F, Cl, Br, I, CN, $N_3$, NC, $NO_2$, $CF_3$, $(CH_2)_n$—O—R11, $(CH_2)_n$—O—$(CH_2)_r$—OH, $(CH_2)_n$—O—CH$(CH_2OH)_2$, $(CH_2)_n$—O—$(CH_2)_n$—CO—O—$(CH_2)_r$—$NH_2$, $(CH_2)_n$—O—$(CH_2)_n$—CO—NH—$(CH_2)_r$—OH, $(CH_2)_n$—O-sugar, $(CH_2)_n$—O-sugar acid, $(CH_2)_n$—O-glucoside, $(CH_2)_n$—O-galactoside, $(CH_2)_n$—O-glucuronide, O—R13, OCF$_3$, $(CH_2)_n$—NH—R11, $(CH_2)_n$—NH—R13, $(CH_2)_n$—NH—CN, $(CH_2)_n$—NH—$SO_2$—R16, $(CH_2)_n$—NH—$(CH_2)_n$—$SO_2$—R12, $(CH_2)_n$—NR12—CO—R16, $(CH_2)_n$—NR12-CO—NR12R13, $(CH_2)_n$—NR12—CO—N(R12)$_2$, $(CH_2)_n$—NR12—CO—NHR11, $(CH_2)_n$—NH—C(=NH)—$NH_2$, $(CH_2)_n$—NH—C(=NH)—R16, $(CH_2)_n$—NH—C(=NH)—NHR12, $(CH_2)_n$—NR12-C(=NR13)-NHR12, $(CH_2)_n$—NR12-C(=NR12)-NR12R13, $(CH_2)_n$—NH—$(CH_2)_n$—CO—O—$(CH_2)_r$—$NH_2$, $(CH_2)_n$—NH—$(CH_2)_n$—CO—NH—[$(C_1$-$C_3)$-alkyl], $(CH_2)_n$—NH—$(CH_2)_n$—CO—NH—$(CH_2)_r$—OH, $(CH_2)_n$—NH—$(CH_2)_n$—CO—N[$(C_1$-$C_8)$-alkyl]$_2$, $(CH_2)_n$—NH—$(CH_2)_n$—CO—NH—[$(C_3$-$C_8)$-cycloalkyl], $(CH_2)_n$—NH—$(CH_2)_n$—CO—N[$(C_3$-$C_8)$-cycloalkyl]$_2$, $(CH_2)_n$—NH—$C(CH_3)_2$—CO—O$(C_1$-$C_8)$-alkyl, $(CH_2)_n$—NH—$C(CH_3)_2$—CO—O$(C_3$-$C_8)$-cycloalkyl, $(CH_2)_n$—NH—$C(CH_3)_2$—CO—O—$(CH_2)_r$—$NH_2$, $(CH_2)_n$—NH—$C(CH_3)_2$—CO—O—$(CH_2)_n$-aryl, $(CH_2)_n$—NH—$C(CH_3)_2$—CO—O—$(CH_2)_n$-heteroaryl, $(CH_2)_n$—NH—$C(CH_3)_2$—CO—$NH_2$, $(CH_2)_n$—NH—$C(CH_3)_2$—CO—NH—[$(C_1$-$C_8)$-alkyl], $(CH_2)_n$—NH—$C(CH_3)_2$—CO—NH—$(CH_2)_r$—OH, $(CH_2)_n$—NH—$C(CH_3)_2$—CO—N[$(C_1$-$C_8)$-alkyl]$_2$, $(CH_2)_n$—NH—$(CH_3)_2$—CO—NH—[$(C_3$-$C_8)$-cycloalkyl], $(CH_2)_n$—NH—$C(CH_3)_2$—CO—N[$(C_3$-$C_8)$-cycloalkyl]$_2$, $(CH_2)_n$—NH—$C(CH_3)_2$—COOH, $S(O)_m$—R12, $SO_2$—R16, $SO_2$—N=CH—N$(CH_3)_2$,

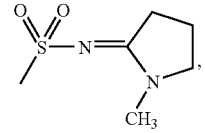

$SO_2$—NH—CO—R12, $SO_2$—NHR12, $SO_2$—NH—$(CH_2)_r$—OH, $SO_2$—N[$(C_1$-$C_8)$-alkyl]$_2$, $SO_2$—NH—$(CH_2)_r$—$NH_2$, $SF_5$, COOH, CONH$_2$, $(CH_2)_q$—CN, $(CH_2)_n$—CO—NH—CN, $(CH_2)_n$—CO—NH-piperidin-1-yl, $(CH_2)_n$—CO—NH—$SO_2$—NHR12, $(CH_2)_n$—CO—NH—$SO_2$—R18, $(CH_2)_n$—CHO, $(CH_2)_n$—C(=NH)$NH_2$, $(CH_2)_n$—C(=NH)NHOH, $(CH_2)_n$—C(=NH)(R16), $(CH_2)_n$—C(=NR13)NHR12, $(CH_2)_n$—C(=NR12)NR12R13, $(CH_2)_n$—C(=NH)O[$(C_1$-$C_6)$-alkyl], where the alkyl and cycloalkyl radicals may be substituted by fluorine atoms and where the aryl or heteroaryl radicals may be substituted by halogen, CN, $(C_1$-$C_6)$-alkyl, $(C_3$-$C_6)$-cycloalkyl, O—$(C_1$-$C_6)$-alkyl, $S(O)_m$—$(C_1$-$C_6)$-alkyl, $SO_2$—$NH_2$, COOH, CONH$_2$, CO—[O$(C_1$-$C_6)$-alkyl], CO—$(C_1$-$C_6)$-alkyl and where the alkyl radicals may be substituted by fluorine atoms;

where at least one of the R6, R7, R8, R9 and R10 radicals is always defined as NR17-aryl or NR17-bicyclic heterocycle or NR17-heteroaryl;

where one of the four radical pairs of R6 and R7, or R7 and R8, or R8 and R9, or R9 and R10 may in each case together form the —$CH_2$—$CH_2$—$CH_2$— or —$CH_2$—$CH_2$—$CH_2$—$CH_2$— groups in which up to two —$CH_2$— groups may be replaced by —O— and where the —$CH_2$—$CH_2$—$CH_2$— or —$CH_2$—$CH_2$—$CH_2$—$CH_2$— groups may be substituted by F, $(C_1$-$C_8)$-alkyl or =O;

R11 is H, $(C_1$-$C_8)$-alkyl, $(C_2$-$C_{10})$-alkenyl, $(C_2$-$C_{10})$-alkynyl, $(C_3$-$C_8)$-cycloalkyl, $(CH_2)_q$—[$(C_3$-$C_8)$-cycloalkyl], $(CH_2)_n$—[$(C_7$-$C_{12})$-bicycloalkyl], $(CH_2)_n$—[$(C_3$-$C_{10})$-cycloalkenyl], $(CH_2)_n$—[$(C_3$-$C_{10})$-bicycloalkenyl], $(CH_2)_n$—[$(C_7$-$C_{12})$-tricycloalkyl], $(CH_2)_n$-aryl, $(CH_2)_n$—CO—[O—$(C_1$-$C_8)$-alkyl], $(CH_2)_n$—CO—[O—$(C_3$-$C_8)$-cycloalkyl], $(CH_2)_n$CO—[$(C_1$-$C_8)$-alkyl], $(CH_2)_n$—CO—[$(C_3$-$C_8)$-cycloalkyl], $(CH_2)_n$—CO-aryl, $(CH_2)_n$—CO-heteroaryl, $(CH_2)_n$—CO—[O—$(CH_2)_v$-aryl], $(CH_2)_n$—CO—[O—$(CH_2)_v$-heteroaryl], $(CH_2)_q$—CO—$NH_2$, $(CH_2)_q$—COOH, $(CH_2)_q$—CO—NH—CN, $(CH_2)_n$—P(O)(OH)[O—$(C_1$-$C_6)$-alkyl], $(CH_2)_n$—P(O)[O—$(C_1$-$C_6)$- alkyl]$_2$, (CH$_2$)$_n$—P(O)(OH)(O—CH$_2$-aryl), (CH$_2$)$_n$—P(O)(O—CH$_2$-aryl)$_2$, (CH$_2$)$_n$—P(O)(OH)$_2$, (CH$_2$)$_n$—SO$_3$H, (CH$_2$)$_n$—SO$_2$—NH$_2$, (CH$_2$)$_n$—CO—NH—[(C$_1$-C$_8$)-alkyl], (CH$_2$)$_n$—CO—N[(C$_1$-C$_8$)-alkyl]$_2$, (CH$_2$)$_n$—CO—NH—[(C$_3$-C$_8$)-cycloalkyl], (CH$_2$)$_n$—CO—N[(C$_3$-C$_8$)-cycloalkyl]$_2$, (C$_2$-C$_{10}$)-alkenyl-CO—O [(C$_1$-C$_6$)-alkyl], (C$_2$-C$_{10}$)-alkenyl-CONH$_2$, (C$_2$-C$_{10}$)-alkenyl-COOH, (C$_2$-C$_{10}$)-alkynyl-CO—O[(C$_1$-C$_6$)-alkyl], (C$_2$-C$_{10}$)-alkynyl-CONH$_2$, (C$_2$-C$_{10}$)-alkynyl-COOH, (CH$_2$)$_n$—CR21[(CO—O(C$_1$-C$_6$)-alkyl)]$_2$, (CH$_2$)$_n$—CR21(CONH$_2$)$_2$, (CH$_2$)$_n$—CR21(COOH)$_2$, (CH$_2$)$_n$—CR21R22CO—O[(C$_1$-C$_6$)-alkyl], (CH$_2$)$_n$—CR21R22CONH$_2$, (CH$_2$)$_n$—CR21R22COOH, (CH$_2$)$_n$—CO—R16, (CH$_2$)$_n$—C(CH$_3$)$_2$—CO—O [(C$_1$-C$_8$)-alkyl], (CH$_2$)$_n$—C(CH$_3$)$_2$—CO—O [(C$_3$-C$_8$)-cycloalkyl], (CH$_2$)$_n$—C(CH$_3$)$_2$—CO—O—(CH$_2$)$_r$—NH$_2$, (CH$_2$)$_n$—C(CH$_3$)$_2$—CO—O—(CH$_2$)$_n$-aryl, (CH$_2$)$_n$—C(CH$_3$)$_2$—CO—O—(CH$_2$)$_n$-heteroaryl, (CH$_2$)$_n$—C(CH$_3$)$_2$—CO—NH$_2$, (CH$_2$)$_n$—C(CH$_3$)$_2$—CO—NH—[(C$_1$-C$_8$)-alkyl], (CH$_2$)$_n$—C(CH$_3$)$_2$—CO—NH—(CH$_2$)$_r$—OH, (CH$_2$)$_n$—C(CH3)$_2$—CO—N[(C$_1$-C$_8$)-alkyl]$_2$, (CH$_2$)$_n$—C(CH$_3$)$_2$—CO—NH—[(C$_3$-C$_8$)-cycloalkyl], (CH$_2$)$_n$—C(CH$_3$)$_2$—CO—N[(C$_3$-C$_8$)-cycloalkyl]$_2$, (CH$_2$)$_n$—C(CH$_3$)$_2$—COOH, (CH$_2$)$_n$—CO—NH—C(CH$_3$)$_2$—CO—O[(C$_1$-C$_8$)-alkyl], (CH$_2$)$_n$—CO—NH—C(CH$_3$)$_2$—CONH$_2$, (CH$_2$)$_n$—CO—NH—C(CH$_3$)$_2$—COOH, where the alkyl, alkenyl, alkynyl and cycloalkyl, bicycloalkyl, cycloalkenyl and bicycloalkenyl radicals may be substituted by fluorine atoms and where the aryl or heteroaryl radical may be substituted by halogen, CN, (C$_1$-C$_6$)-alkyl, (C$_3$-C$_6$)-cycloalkyl, O—(C$_1$-C$_6$)-alkyl, S(O)$_m$—(C$_1$-C$_6$)-alkyl, SO$_2$—NH$_2$, COOH, CONH$_2$, CO—O(C$_1$-C$_6$)-alkyl, CO—(C$_1$-C$_6$)-alkyl and where the alkyl radicals may be substituted by fluorine atoms;

R12 is H, (C$_1$-C$_8$)-alkyl, (C$_3$-C$_8$)-cycloalkyl, (CH$_2$)$_q$—[(C$_3$-C$_8$)-cycloalkyl], (CH$_2$)$_n$—[(C$_7$-C$_{12}$)-bicycloalkyl], (CH$_2$)$_n$—[(C$_7$-C$_{12}$)-tricycloalkyl], (CH$_2$)$_n$-aryl, (CH$_2$)$_n$-heteroaryl, where the alkyl or cycloalkyl radicals may be substituted by fluorine atoms, and where the aryl or heteroaryl radical may be substituted by halogen, CN, (C$_1$-C$_6$)-alkyl, O—(C$_1$-C$_6$)-alkyl, SO$_2$—NH$_2$, COOH, CONH$_2$, CO—O(C$_1$-C$_6$)-alkyl, CO—(C$_1$-C$_6$)-alkyl and where the alkyl radicals may be substituted by fluorine atoms;

R13 is H, SO$_2$—[(C$_1$-C$_8$)-alkyl], SO$_2$—[(C$_3$-C$_8$)-cycloalkyl], SO$_2$—(CH$_2$)$_n$-aryl, SO$_2$—(CH$_2$)$_n$-heteroaryl, SO$_2$—(CH$_2$)$_n$—NH—R12, SO$_2$—(CH$_2$)$_n$—N(R12)$_2$, where the alkyl and cycloalkyl radicals may be substituted by fluorine atoms and where the aryl or heteroaryl radical may be substituted by halogen, CN, CF$_3$, (C$_1$-C$_6$)-alkyl, (C$_3$-C$_6$)-cycloalkyl, O—[(C$_1$-C$_6$)-alkyl], S(O)$_m$—[(C$_1$-C$_6$)-alkyl], SO$_2$—NH$_2$, COOH, CONH$_2$, CO—[O(C$_1$-C$_6$)-alkyl], CO—(C$_1$-C$_6$)-alkyl and where the alkyl radicals may be substituted by fluorine atoms;

R14 is H, (C$_1$-C$_8$)-alkyl, (C$_3$-C$_8$)-cycloalkyl, (CH$_2$)$_q$—[(C$_3$-C$_8$)-cycloalkyl], (CH$_2$)$_n$-aryl, (CH$_2$)$_n$-heteroaryl, (CH$_2$)$_n$—CO—[O—(C$_1$-C$_8$)-alkyl], (CH$_2$)$_n$—CO—[O—(C$_3$-C$_8$)-cycloalkyl], (CH$_2$)$_n$—CO—[O—(CH$_2$)$_n$-aryl], (CH$_2$)$_n$—CO—[O—(CH$_2$)$_n$-heteroaryl], (CH$_2$)$_n$—CO—[(C$_1$-C$_8$)-alkyl], (CH$_2$)$_n$—CO—[(C$_3$-C$_8$)-cycloalkyl], (CH$_2$)$_n$—CO-aryl, (CH$_2$)$_n$—CO-heteroaryl, (CH$_2$)$_q$—CO—NH$_2$, (CH$_2$)$_q$—COOH, (CH$_2$)$_n$—SO$_2$—NH$_2$, (CH$_2$)$_n$—CO—NH—[(C$_1$-C$_3$)-alkyl], (CH$_2$)$_n$—CO—N[(C$_1$-C$_8$)-alkyl]$_2$, (CH$_2$)$_n$—CO—NH—[(C$_3$-C$_8$)-cycloalkyl], (CH$_2$)$_n$—CO—N[(C$_3$-C$_8$)-cycloalkyl]$_2$, (CH$_2$)$_n$—C(CH$_3$)$_2$—CO—O[(C$_1$-C$_8$)-alkyl], (CH$_2$)$_n$—C(CH$_3$)$_2$—CO—O[(C$_3$-C$_8$)-cycloalkyl, (CH$_2$)$_n$—C(CH$_3$)$_2$—CO—O—(CH$_2$)$_r$—NH$_2$, (CH$_2$)$_n$—C(CH$_3$)$_2$—CO—NH$_2$, (CH$_2$)$_n$—C(CH$_3$)$_2$—CO—NH—(CH$_2$)$_r$—OH, (CH$_2$)$_n$—C(CH$_3$)$_2$—COOH, where the alkyl and cycloalkyl radicals may be substituted by fluorine atoms and where the aryl or heteroaryl radical may be substituted by halogen, CN, (C$_1$-C$_6$)-alkyl, (C$_3$-C$_6$)-cycloalkyl, O—(C$_1$-C$_6$)-alkyl, S(O)$_m$—(C$_1$-C$_6$)-alkyl, SO$_2$—NH$_2$, COOH, CONH$_2$, CO—O(C$_1$-C$_6$)-alkyl, CO—(C$_1$-C$_6$)-alkyl and where the alkyl radicals may be substituted by fluorine atoms;

R15 is H, (C$_1$-C$_8$)-alkyl, (C$_3$-C$_8$)-cycloalkyl, (CH$_2$)$_n$-aryl, (CH$_2$)$_n$-heteroaryl, (CH$_2$)$_n$—CO—[O—(C$_1$-C$_8$)-alkyl], (CH$_2$)$_n$—CO—[O—(C3-C8)-cycloalkyl], (CH$_2$)$_n$—CO—[O—(CH$_2$)$_n$-aryl], (CH$_2$)$_n$—CO—[O—(CH$_2$)$_n$-heteroaryl], CO—[(C$_1$-C$_8$)-alkyl], CO—[(C3-C8)-cycloalkyl], CO-aryl, CO-heteroaryl, (CH$_2$)$_n$—CO—NH$_2$, (CH$_2$)$_q$—COOH, (CH$_2$)$_n$—SO$_2$—NH$_2$, (CH$_2$)$_n$—CO—NH—[(C$_1$-C$_8$)-alkyl], (CH$_2$)$_n$—CO—N[(C$_1$-C$_8$)-alkyl]$_2$, (CH$_2$)$_n$—CO—NH—[(C$_3$-C$_8$)-cycloalkyl], (CH$_2$)$_n$—C(CH$_3$)$_2$—CO—NH$_2$, (CH$_2$)$_n$—C(CH$_3$)$_2$—COOH, where the alkyl and cycloalkyl radicals may be substituted by fluorine atoms and where the aryl or heteroaryl radical may be substituted by halogen, CN, (C$_1$-C$_6$)-alkyl, O—(C$_1$-C$_6$)-alkyl, SO$_2$—NH$_2$, COOH, CONH$_2$, CO—O(C$_1$-C$_6$)-alkyl, CO—(C$_1$-C$_6$)-alkyl and where the alkyl radicals may be substituted by fluorine atoms;

R16 is aziridine-1-yl, azetidin-1-yl, 3-hydroxyazetidin-1-yl, piperidin-1-yl, 3-hydroxypiperidin-1-yl, 4-hydroxypiperidin-1-yl, 3-oxopiperidin-1-yl, 4-oxopiperidin-1-yl, pyrrolidin-1-yl, 3-pyrrolidinol-1-yl, 2-cyanopyrrolidin-1-yl, morpholin-N-yl, piperazin-1-yl, 4-[(C$_1$-C$_6$)-alkyl]piperazin-1-yl, piperazin-2-on-1-yl, piperazin-2-on-4-yl, piperazine-2,3-dion-1-yl, piperazine-2,6-dion-1-yl, piperazine-2,6-dion-4-yl, thiomorpholin-4-yl, thiomorpholine-1,1-dioxide-4-yl, NH—(CH$_2$)$_r$—OH, NH—CH(CH$_2$OH)$_2$, NH—C(CH$_2$OH)$_3$, N[(C$_1$-C$_6$)-alkyl-OH]$_2$, N[(C$_1$-C$_6$)-alkyl][(C$_1$-C$_6$)-alkyl-OH], D-glucamine-N-yl, N-methyl-D-glucamine-N-yl, NH—[(C$_1$-C$_8$)-alkyl]-CO—O(C$_1$-C$_6$)-alkyl, NH—[(C$_1$-C$_8$)-alkyl]-COOH, NH—[(C$_1$-C$_8$)-alkyl]-CONH$_2$, N[(C$_1$-C$_6$)-alkyl][(C$_1$-C$_8$)-alkyl]-CO—O(C$_1$-C$_6$)-alkyl, N[(C$_1$-C$_6$)-alkyl][(C$_1$-C$_8$)-alkyl]-COOH, N[(C$_1$-C$_6$)-alkyl][(C$_1$-C$_8$)-alkyl]-CONH$_2$, NH—[C(H)(aryl)]-CO—O(C$_1$-C$_6$)-alkyl, NH—[C(H)(aryl)]-COOH, NH—[C(H)(aryl)]-CONH$_2$, N[(C$_1$-C$_6$)-alkyl][C(H)(aryl)]—CO—O(C$_1$-C$_6$)-alkyl, N[(C$_1$-C$_6$)-alkyl][C(H)(aryl)]-COOH, N[(C$_1$-C$_6$)-alkyl][C(H)(aryl)]-CONH$_2$, NH—[C(H)(heteroaryl)]-CO—O(C$_1$-C$_6$)-alkyl, NH—[C(H)(heteroaryl)]-COOH, NH—[C(H)(heteroaryl)]-CONH$_2$, N[(C$_1$-C$_6$)-alkyl][C(H)(heteroaryl)]-CO—O(C$_1$-C$_6$)-alkyl, N[(C$_1$-C$_6$)-alkyl][C(H)(heteroaryl)]-COOH, N[(C$_1$-C$_6$)-alkyl][C(H)(heteroaryl)]-CONH$_2$, N[(C$_1$-C$_6$)-alkyl][(C$_3$-C$_8$)-cycloalkyl]-CO—O(C$_1$-C$_6$)-alkyl, N[(C$_1$-C$_6$)-alkyl][(C$_3$-C$_8$)-cycloalkyl]-COOH, N[(C$_1$-C$_6$)-alkyl][(C$_3$-C$_8$)-cycloalkyl]—CONH$_2$, NH—[(C$_3$-C$_8$)-cycloalkyl]-CO—O(C$_1$-C$_6$)-alkyl, NH—[(C$_3$-C$_8$)-cycloalkyl]—COOH, NH—[(C$_3$-C$_8$)-cycloalkyl]-CONH$_2$, NH—(CH$_2$)$_r$—SO$_2$—(C$_1$-C$_6$)-alkyl, NH—[(C$_1$-C$_6$)-alkyl]-SO$_3$H, NH—[(C$_1$-C$_6$)-alkyl]-SO$_2$—NH$_2$, N[(C$_1$-C$_6$)-alkyl]{[(C$_1$-C$_6$)-alkyl]-SO$_3$H}, where the alcohol (OH) or ketone (C=O) functions may be replaced by F or CF$_2$;

R17 is R18, R13, (CH$_2$)$_n$—CO—[O—(C$_1$-C$_8$)-alkyl], (CH$_2$)$_n$—CO—[O—(C$_3$-C$_8$)-cycloalkyl], (CH$_2$)$_n$—CO—[(C$_1$-C$_8$)-alkyl], (CH$_2$)$_n$—CO—[(C$_3$-C$_8$)-cycloalkyl], (CH$_2$)$_n$—CO-aryl, (CH$_2$)$_n$—CO-heteroaryl, (CH$_2$)$_n$—CO—[O—(CH$_2$)$_n$-aryl], (CH$_2$)$_n$—CO—NH$_2$, $(CH_2)_q$—COOH, where the alkyl and cycloalkyl radicals may be substituted by fluorine atoms and where the aryl or heteroaryl radical may be substituted by halogen, CN, $(C_1-C_6)$-alkyl, $(C_3-C_6)$-cycloalkyl, O—$(C_1-C_6)$-alkyl, $S(O)_m$—$(C_1-C_6)$-alkyl, $SO_2$—$NH_2$, COOH, $CONH_2$, CO—[O$(C_1-C_6)$-alkyl], CO—$(C_1-C_6)$-alkyl and where the alkyl radicals may be substituted by fluorine atoms;

R18 is $(C_1-C_8)$-alkyl, $(C_3-C_8)$-cycloalkyl, $(CH_2)_q$—[$(C_3-C_8)$-cycloalkyl], $(CH_2)_n$-aryl, $(CH_2)_n$-heteroaryl, where the alkyl and cycloalkyl radicals may be substituted by fluorine atoms and where the aryl or heteroaryl radical may be substituted by halogen, CN, $(C_1-C_6)$-alkyl, O—$(C_1-C_6)$-alkyl, $SO_2$—$NH_2$, COOH, $CONH_2$, CO—[O$(C_1-C_6)$-alkyl], CO—$(C_1-C_6)$-alkyl and where the alkyl radicals may be substituted by fluorine atoms;

R20 is H, $(C_1-C_6)$-alkyl, $(C_3-C_8)$-cycloalkyl, aryl, [$(C_1-C_6)$-alkyl]-aryl;

R21 is H, F, $CF_3$, $(C_1-C_6)$-alkyl, $(C_3-C_8)$-cycloalkyl, OH, O—$(C_1-C_6)$-alkyl, O—$(C_3-C_8)$-cycloalkyl, O—$(CH_2)_n$-aryl, O—(CO)—$(C_1-C_6)$-alkyl, O—(CO)—$(C_3-C_8)$-cycloalkyl, O—(CO)—O—$(C_1-C_6)$-alkyl, O—(CO)—O—$(C_3-C_8)$-cycloalkyl, NH—[$(C_1-C_6)$-alkyl]-aryl, $NH_2$, NH—$(C_1-C_6)$-alkyl, NH—(CO)—$(C_1-C_6)$-alkyl;

R22 is H, $CF_3$, $(C_1-C_6)$-alkyl, aryl, [$(C_1-C_6)$-alkyl]-aryl;

and physiologically compatible salts thereof.

Preference is given to compounds of the formula I in which one or more radicals are each defined as follows:

R, R' are each $(C_1-C_6)$-alkyl, where $(C_1-C_6)$-alkyl may be substituted by halogen; or R and R' together form a ring having from three to eight carbon atoms;

m is 0, 1, 2;

n is 0, 1, 2, 3, 4;

p is 1, 2, 3;

q is 1, 2, 3;

r is 2, 3, 4;

v is 0, 1, 2, 3;

A, D, E, G, L are each independently C or N, where there is no corresponding R1, R2, R3, R4, R5 substituent when they are defined as N;

R1, R2, R3, R4, R5 are each independently H, F, Cl, Br, CN, $NO_2$, $CF_3$, $(C_1-C_8)$-alkyl, $(C_3-C_8)$-cycloalkyl, $(CH_2)_q$—[$(C_3-C_8)$-cycloalkyl], $(CH_2)_n$—[$(C_7-C_{12})$-bicycloalkyl], $(CH_2)_n$—[$(C_7-C_{12})$-tricycloalkyl], adamantan-1-yl, adamantan-2-yl, $(CH_2)_n$-aryl, $(CH_2)_n$-heteroaryl, $OCF_3$, O—R11, NR13R15, $S(O)_m$—R12, $SO_2$—$NH_2$, $SO_2$—NH—[$(C_1-C_8)$-alkyl], $SO_2$—NH—[$(C_3-C_8)$-cycloalkyl], $SO_2$—NH—$(CH_2)_r$-aryl, $SO_2$—N[$(C_1-C_8)$-alkyl]$_2$, $SO_2$—R16, $SF_5$, CO—O[$(C_1-C_8)$-alkyl], CO—O—$(CH_2)_r$—$NH_2$, CO—$NH_2$, CO—NH—[$(C_1-C_8)$-alkyl], CO—N[$(C_1-C_8)$-alkyl]$_2$, C(=NH)—$NH_2$, C(=NH)—NHOH, C(=NH)—[NH—O—$(C_1-C_6)$-alkyl], C(=NH)—NR12R13, C(=NH)—R16, C(=NR13)—NR12R13, CO—NH—$SO_2$—R16, CO—NH—$SO_2$—NHR12, CO—R16, COOH, CO—$(C_1-C_8)$-alkyl, CO—$(C_3-C_8)$-cycloalkyl, CO-aryl, CO-heteroaryl, CH(OH)-aryl, CH(OH)-heteroaryl, CH[O—$(C_1-C_6)$-alkyl]-aryl, CH[O—$(C_1-C_6)$-alkyl]-heteroaryl, CHF-aryl, CHF-heteroaryl, $CF_2$-aryl, $CH_2$—O—R12, where the alkyl, cycloalkyl, bicycloalkyl and tricycloalkyl radicals may be substituted by fluorine atoms and where the aryl or heteroaryl radicals may be substituted by halogen, CN, $(C_1-C_6)$-alkyl, $(C_3-C_6)$-cycloalkyl, O—$(C_1-C_6)$-alkyl, $S(O)_m$—$(C_1-C_6)$-alkyl, $SO_2$—$NH_2$, COOH, $CONH_2$, CO—O$(C_1-C_6)$-alkyl, CO—$(C_1-C_6)$-alkyl and where the alkyl radicals may be substituted by fluorine atoms;

R6, R7, R8, R9, R10 are each independently R11, NR17-bicyclic heterocycle, NR17-aryl, NR17-heteroaryl, where the aryl or heteroaryl radical may be fused to a 5- or 6-membered aromatic or nonaromatic carbon ring in which one or more CH or $CH_2$ groups may be replaced by oxygen atoms and where the 5- or 6-membered aromatic or nonaromatic carbon ring may be substituted by F, =O or —$(C_1-C_6)$-alkyl and where the bicyclic heterocycle contains from 9 to 10 ring members and up to five CH or $CH_2$ groups may each independently be replaced by N, NR20, O, $S(O)_m$ or C=O and where the aryl or heteroaryl radical or bicyclic heterocycle may be unsubstituted or mono- or polysubstituted by R11, F, Cl, Br, CN, $NO_2$, $CF_3$, $(CH_2)_n$—O—R11, $(CH_2)_n$—O—$(CH_2)_r$—OH, $(CH_2)_n$—O—CH$(CH_2OH)_2$, $(CH_2)_n$—O—$(CH_2)_n$—CO—O—$(CH_2)_r$—$NH_2$, $(CH_2)_n$—O-sugar, $(CH_2)_n$—O-sugar acid, $(CH_2)_n$—O-glucoside, $(CH_2)_n$—O-galactoside, $(CH_2)_n$—O-glucuronide, O—R13, $OCF_3$, $(CH_2)_n$—O—$(CH_2)_r$—$NH_2$, $(CH_2)_n$—NH—R11, $(CH_2)_n$—N[$(CH_2)_q$—CO—O$(C_1-C_6)$-alkyl]$_2$, $(CH_2)_n$—N[$(CH_2)_q$—COOH]$_2$, $(CH_2)_n$—N[$(CH_2)_q$—$CONH_2$]$_2$, $(CH_2)_n$—NH—R13, $(CH_2)_n$—N(R13)$_2$, $(CH_2)_n$—NH—CN, $(CH_2)_n$—NH—$SO_2$—R16, $(CH_2)_n$—NH—$(CH_2)_n$—$SO_2$—R12, $(CH_2)_n$—NR12—CO—R16, $(CH_2)_n$—NR12—CO—NR12R13, $(CH_2)_n$—NR12—CO—N(R12)$_2$, $(CH_2)_n$—NR12—CO—NHR11, $(CH_2)_n$—NH—C(=NH)—$NH_2$, $(CH_2)_n$—NH—C(=NH)—R16, $(CH_2)_n$—NH—C(=NH)—NHR12, $(CH_2)_n$—NR12—C(=NR13)—NHR12, $(CH_2)_n$—NR12—C(=NR12)—NR12R13, $(CH_2)_n$—NH—$(CH_2)_n$—CO—O—$(CH_2)_r$—$NH_2$, $(CH_2)_n$—NH—$(CH_2)_n$—CO—NH—[$(C_1-C_8)$-alkyl], $(CH_2)_n$—NH—$(CH_2)_n$—CO—NH—$(CH_2)_r$—OH, $(CH_2)_n$—NH—$(CH_2)_n$—CO—N[$(C_1-C_8)$-alkyl]$_2$, $(CH_2)_n$—NH—$(CH_2)_n$—CO—NH—[$(C_3-C_8)$-cycloalkyl], $(CH_2)_n$—NH—C$(CH_3)_2$—CO—O$(C_1-C_8)$-alkyl, $(CH_2)_n$—NH—C$(CH_3)_2$—CO—O—$(CH_2)_r$—$NH_2$, $(CH_2)_n$—NH—C$(CH_3)_2$—CO—$NH_2$, $(CH_2)_n$—NH—C$(CH_3)_2$—CO—NH—$(CH_2)_r$—OH, $(CH_2)_n$—NH—C$(CH_3)_2$—COOH, $S(O)_m$—R12, $SO_2$—R16, $SO_2$—N=CH—N$(CH_3)_2$, $SO_2$—NH—CO—R12, $SO_2$—NHR12, $SO_2$—NH—$(CH_2)_r$—OH, $SO_2$—N[$(C_1-C_8)$-alkyl]$_2$, $SO_2$—NH—$(CH_2)_r$—$NH_2$, $SF_5$, POOH, CO—$NH_2$, $(CH_2)_q$—CN, $(CH_2)_n$—CO—NH-piperidin-1-yl, $(CH_2)_n$—CO—NH—$SO_2$—NHR12, $(CH_2)_n$—CO—NH—$SO_2$—R18, $(CH_2)_n$—C(=NH)$NH_2$, $(CH_2)_n$—C(=NH)—NHOH, C(=NH)—[NH—O—$(C_1-C_6)$-alkyl], $(CH_2)_n$—C(=NH)(R16), $(CH_2)_n$—C(=NR13)NHR12, $(CH_2)_n$—C(=NR12)NR12R13, $(CH_2)_n$—C(=NH)O[$(C_1-C_6)$-alkyl], where the alkyl and cycloalkyl radicals may be substituted by fluorine atoms and where the aryl or heteroaryl radicals may be substituted by halogen, CN, $(C_1-C_6)$-alkyl, $(C_3-C_6)$-cycloalkyl, O—$(C_1-C_6)$-alkyl, $S(O)_m$—$(C_1-C_6)$-alkyl, $SO_2$—$NH_2$, COOH, $CONH_2$, CO—O$(C_1-C_6)$-alkyl, CO—$(C_1-C_6)$-alkyl and where the alkyl radicals may be substituted by fluorine atoms;

F, Cl, Br, CN, $CF_3$, $(CH_2)_n$—O—R11, $(CH_2)_n$—O—$(CH_2)_r$—OH, $(CH_2)_n$—O-sugar, $(CH_2)_n$—O-sugar acid, $(CH_2)_n$—O-glucoside, $(CH_2)_n$—O-galactoside, $(CH_2)_n$—O-glucuronide, O—R13, $OCF_3$, $(CH_2)_n$—NH—R11, $(CH_2)_n$—NH—R13, $(CH_2)_n$—NH—CN, $(CH_2)_n$—NH—$SO_2$—R16, $(CH_2)_n$—NH—$(CH_2)_n$—$SO_2$—R12, $(CH_2)_n$—NR12—CO—NR12R13, $(CH_2)_n$—NR12—CO—N(R12)$_2$, $(CH_2)_n$—NR12—CO—NHR11, $(CH_2)_n$—NH—C(=NH)—$NH_2$, $(CH_2)_n$—NH—C(=NH)—R16, $(CH_2)_n$—NH—C(=NH)—NHR12, $(CH_2)_n$—NR12—C(=NR13)—NHR12, $(CH_2)_n$—NR12—C(=NR12)—NR12R13, $(CH_2)_n$—NH—$(CH_2)_n$—CO—NH—[$(C_1$-$C_8)$-alkyl], $(CH_2)_n$—NH—$(CH_2)_n$—CO—N[$(C_1$-$C_8)$-alkyl]$_2$, $(CH_2)_n$—NH—C(CH$_3$)$_2$—CO—O($C_1$-$C_8$)-alkyl, $(CH_2)_n$—NH—C(CH$_3$)$_2$—CO—O($C_3$-$C_8$)-cycloalkyl, $(CH_2)_n$—NH—C(CH$_3$)$_2$—CO—NH$_2$, $(CH_2)_n$—NH—C(CH$_3$)$_2$—CO—NH—$(CH_2)_r$—OH, $(CH_2)_n$—NH—C(CH$_3$)$_2$—CO—N[$(C_1$-$C_8)$-alkyl]$_2$, $(CH_2)_n$—NH—C(CH$_3$)$_2$—COOH, S(O)$_m$—R12, SO$_2$—R16, SO$_2$—NH—CO—R12, SO$_2$—NHR12, SO$_2$—NH—$(CH_2)_r$—OH, SO$_2$—N[$(C_1$-$C_8)$-alkyl]$_2$, SF$_5$, $(CH_2)_n$—COOH, $(CH_2)_n$—CONH$_2$, $(CH_2)_q$—CN, $(CH_2)_n$—CO—NH—CN, $(CH_2)_n$—CO—NH—SO$_2$—NHR12, $(CH_2)_n$—CO—NH—SO$_2$—R18, $(CH_2)_n$—C(=NH)NH$_2$, $(CH_2)_n$—C(=NH)NHOH, $(CH_2)_n$—C(=NH)(R16), $(CH_2)_n$—C(=NR13)NHR12, $(CH_2)_n$—C(=NR12)NR12R13, $(CH_2)_n$—C(=NH)O[$(C_1$-$C_6)$-alkyl], where the alkyl and cycloalkyl radicals may be substituted by fluorine atoms and where the aryl or heteroaryl radicals may be substituted by halogen, CN, $(C_1$-$C_6)$-alkyl, $(C_3$-$C_6)$-cycloalkyl, O—$(C_1$-$C_6)$-alkyl, S(O)$_m$—$(C_1$-$C_6)$-alkyl, SO$_2$—NH$_2$, COOH, CONH$_2$, CO—[O($C_1$-$C_6)$-alkyl], and where the alkyl radicals may be substituted by fluorine atoms;

where at least one of the R6, R7, R8, R9 and R10 radicals is always defined as NR17-aryl or NR17-bicyclic heterocycle or NR17-heteroaryl;

where one of the four radical pairs of R6 and R7, or R7 and R8, or R8 and R9, or R9 and R10 may in each case together form the —CH$_2$—CH$_2$—CH$_2$— or —CH$_2$—CH$_2$—CH$_2$—CH$_2$— groups in which up to two —CH$_2$— groups may be replaced by —O— and where the —CH$_2$—CH$_2$—CH$_2$— or —CH$_2$—CH$_2$—CH$_2$—CH$_2$— groups may be substituted by F, methyl or =O;

R11 is H, $(C_1$-$C_6)$-alkyl, $(C_2$-$C_6)$-alkenyl, $(C_2$-$C_6)$-alkynyl, $(C_3$-$C_7)$-cycloalkyl, $(CH_2)_q$—[$(C_3$-$C_6)$-cycloalkyl], $(CH_2)_n$-[$(C_7$-$C_{10})$-bicycloalkyl], $(CH_2)_n$-[$(C_3$-$C_6)$-cycloalkenyl], $(CH_2)_n$-[$(C_7$-$C_{10})$-bicycloalkenyl], $(CH_2)_n$-[$(C_7$-$C_{12})$-tricycloalkyl], $(CH_2)_n$-aryl, $(CH_2)_n$—CO—[O—$(C_1$-$C_6)$-alkyl], $(CH_2)_n$—CO—[O—$(C_3$-$C_6)$-cycloalkyl], $(CH_2)_n$—CO—[$(C_1$-$C_6)$-alkyl], $(CH_2)_n$—CO—[$(C_3$-$C_6)$-cycloalkyl], $(CH_2)_n$—CO-aryl, $(CH_2)_n$—CO-heteroaryl, $(CH_2)_n$—CO—[O—$(CH_2)_v$-aryl], $(CH_2)_n$—CO—[O—$(CH_2)_v$-heteroaryl], $(CH_2)_q$—CO—NH$_2$, $(CH_2)_q$—COOH, $(CH_2)_n$—P(O)(OH)[O—$(C_1$-$C_3)$-alkyl], $(CH_2)_n$—P(O)[O—$(C_1$-$C_3)$-alkyl]$_2$, $(CH_2)_n$—P(O)(OH)(O—CH$_2$-aryl), $(CH_2)_n$—P(O)(O—CH$_2$-aryl)$_2$, $(CH_2)_n$—P(O)(OH)$_2$, $(CH_2)_n$—SO$_3$H, $(CH_2)_n$—SO$_2$—NH$_2$, $(CH_2)_n$—CO—NH—[$(C_1$-$C_6)$-alkyl], $(CH_2)_n$—CO—N[$(C_1$-$C_6)$-alkyl]$_2$, $(CH_2)_n$—CO—NH—[$(C_3$-$C_6)$-cycloalkyl], $(CH_2)_n$—CO—N[$(C_3$-$C_6)$-cycloalkyl]$_2$, $(C_2$-$C_6)$-alkenyl-CO—O[$(C_1$-$C_6)$-alkyl], $(C_2$-$C_6)$-alkenyl-CONH$_2$, $(C_2$-$C_6)$-alkenyl-COOH, $(C_2$-$C_6)$-alkynyl-CO—O[$(C_1$-$C_6)$-alkyl], $(C_2$-$C_6)$-alkynyl-CONH$_2$, $(C_2$-$C_6)$-alkynyl-COOH, $(CH_2)_n$—CR21[(CO—O($C_1$-$C_4)$-alkyl)]$_2$, $(CH_2)_n$—CR21(CONH$_2$)$_2$, $(CH_2)_n$—CR21(COOH)$_2$, $(CH_2)_n$—CR21R22CO—O [$(C_1$-$C_4)$-alkyl], $(CH_2)_n$—CR21R22CONH$_2$, $(CH_2)_n$—CR21R22COOH, $(CH_2)_n$—CO—R16, $(CH_2)_n$—C(CH$_3$)$_2$—CO—O[$(C_1$-$C_6)$-alkyl], $(CH_2)_n$—C(CH$_3$)$_2$—CO—O[$(C_3$-$C_6)$-cycloalkyl], $(CH_2)_n$—C(CH$_3$)$_2$—CO—O—$(CH_2)_n$-aryl, $(CH_2)_n$—C(CH$_3$)$_2$—CO—O—$(CH_2)_n$-heteroaryl, $(CH_2)_n$—C(CH$_3$)$_2$—CO—NH$_2$, $(CH_2)_n$—C(CH$_3$)$_2$—CO—NH—[$(C_1$-$C_6)$-alkyl], $(CH_2)_n$—C(CH$_3$)$_2$—CO—NH—$(CH_2)_r$—OH, $(CH_2)_n$—C(CH$_3$)$_2$—CO—N[$(C_1$-$C_6)$-alkyl]$_2$, $(CH_2)_n$—C(CH$_3$)$_2$—CO—NH—[$(C_3$-$C_6)$-cycloalkyl], $(CH_2)_n$—C(CH$_3$)$_2$—CO—N[$(C_3$-$C_6)$-cycloalkyl]$_2$, $(CH_2)_n$—C(CH$_3$)$_2$—COOH, $(CH_2)_n$—CO—NH—C(CH$_3$)$_2$—CO—O[$(C_1$-$C_6)$-alkyl], $(CH_2)_n$—CO—NH—C(CH$_3$)$_2$—CONH$_2$, $(CH_2)_n$—CO—NH—C(CH$_3$)$_2$—COOH, where the alkyl, alkenyl, alkynyl and cycloalkyl, bicycloalkyl, tricycloalkyl, cycloalkenyl and bicycloalkenyl radicals may be substituted by fluorine atoms and where the aryl or heteroaryl radical may be substituted by halogen, CN, $(C_1$-$C_6)$-alkyl, $(C_3$-$C_6)$-cycloalkyl, O—$(C_1$-$C_6)$-alkyl, S(O)$_m$—$(C_1$-$C_6)$-alkyl, SO$_2$—NH$_2$, COOH, CONH$_2$, CO—O($C_1$-$C_6)$-alkyl, CO—$(C_1$-$C_6)$-alkyl, and where the alkyl radicals may be substituted by fluorine atoms;

R12 is H, $(C_1$-$C_6)$-alkyl, $(C_3$-$C_6)$-cycloalkyl, $(CH_2)_q$—[$(C_3$-$C_6)$-cycloalkyl], $(CH_2)_n$-[$(C_7$-$C_{10})$-bicycloalkyl], $(CH_2)_n$-[$(C_7$-$C_{10})$-tricycloalkyl], $(CH_2)_n$-aryl, $(CH_2)_n$-heteroaryl, where the alkyl, cycloalkyl, bicycloalkyl or tricycloalkyl radicals may be substituted by fluorine atoms, and where the aryl or heteroaryl radical may be substituted by halogen, CN, $(C_1$-$C_3)$-alkyl, O—$(C_1$-$C_3)$-alkyl, SO$_2$—NH$_2$, COOH, CONH$_2$, CO—O($C_1$-$C_3)$-alkyl, CO—$(C_1$-$C_3)$-alkyl and where the alkyl radicals may be substituted by fluorine atoms;

R13 is H, SO$_2$—[$(C_1$-$C_6)$-alkyl], SO$_2$—[$(C_3$-$C_6)$-cycloalkyl], SO$_2$—$(CH_2)_n$-aryl, SO$_2$—$(CH_2)_n$-heteroaryl, SO$_2$—$(CH_2)_n$—NH—R12, SO$_2$—$(CH_2)_n$—N(R12)$_2$, where the alkyl and cycloalkyl radicals may be substituted by fluorine atoms and where the aryl or heteroaryl radical may be substituted by halogen, CN, $(C_1$-$C_3)$-alkyl, $(C_3$-$C_6)$-cycloalkyl, O—[$(C_1$-$C_3)$-alkyl], S(O)$_m$—[$(C_1$-$C_3)$-alkyl], SO$_2$—NH$_2$, COOH, CONH$_2$, CO—[O($C_1$-$C_3)$-alkyl], CO—$(C_1$-$C_3)$-alkyl, and where the alkyl radicals may be substituted by fluorine atoms;

R16 is aziridine-1-yl, azetidin-1-yl, piperidin-1-yl, 3-hydroxypiperidin-1-yl, 4-hydroxypiperidin-1-yl, 3-oxopiperidin-1-yl, 4-oxopiperidin-1-yl, pyrrolidin-1-yl, 3-pyrrolidinol-1-yl, 2-cyanopyrrolidin-1-yl, morpholin-N-yl, piperazin-1-yl, 4-[$(C_1$-$C_3)$-alkyl]piperazin-1-yl, piperazin-2-on-1-yl, piperazin-2-on-4-yl, piperazine-2,6-dion-1-yl, piperazine-2,6-dion-4-yl, thiomorpholine-1,1-dioxide-4-yl, NH—$(CH_2)_r$—OH, NH—CH(CH$_2$OH)$_2$, NH—C(CH$_2$OH)$_3$, N[$(C_1$-$C_6)$-alkyl-OH]$_2$, D-glucamine-N-yl, N-methyl-D-glucamine-N-yl, NH—[$(C_1$-$C_6)$-alkyl]-CO—O($C_1$-$C_3)$-alkyl, NH—[$(C_1$-$C_3)$-alkyl]-COOH, NH—[$(C_1$-$C_3)$-alkyl]-CONH$_2$, N[$(C_1$-$C_3)$-alkyl][$(C_1$-$C_3)$-alkyl]-CO—O($C_1$-$C_3)$-alkyl, N[$(C_1$-$C_3)$-alkyl][$(C_1$-$C_3)$-alkyl]—COOH, N[$(C_1$-$C_3)$-alkyl][$(C_1$-$C_3)$-alkyl]-CONH$_2$, NH—[C(H)(aryl)]-CO—O($C_1$-$C_3)$-alkyl, NH—[C(H)(aryl)]-COOH, NH—[C(H)(aryl)]-CONH$_2$, N[$(C_1$-$C_3)$-alkyl][C(H)(aryl)]-CO—O($C_1$-$C_3)$-alkyl, N[$(C_1$-$C_3)$-alkyl][C(H)(aryl)]—COOH, N[$(C_1$-$C_3)$-alkyl][C(H)(aryl)]-CONH$_2$, NH—[C(H)(heteroaryl)]-CO—O($C_1$-$C_3)$-alkyl, NH—[C(H)(heteroaryl)]-COOH, NH—[C(H)(heteroaryl)]—CONH$_2$, N[$(C_1$-$C_3)$-alkyl][C(H)(heteroaryl)]-CO—O($C_1$-$C_3)$-alkyl, N[$(C_1$-$C_3)$-alkyl][C(H)(heteroaryl)]-COOH, N[$(C_1$-$C_3)$-alkyl][C(H)(heteroaryl)]-CONH$_2$, N[$(C_1$-$C_3)$-alkyl][$(C_3$-$C_6)$-cycloalkyl]-CO—O($C_1$-$C_3)$-alkyl, N[$(C_1$-$C_3)$-alkyl][$(C_3$-$C_6)$-cycloalkyl]-COOH, N[$(C_1$-$C_3)$-alkyl][$(C_3$-$C_6)$-cycloalkyl]—CONH$_2$, NH—[$(C_3$-$C_6)$-cycloalkyl]-CO—O($C_1$-$C_3)$-alkyl, NH—[$(C_3$-$C_6)$-cycloalkyl]—COOH, NH—[$(C_3$-$C_6)$-cycloalkyl]-CONH$_2$, NH—$(CH_2)_r$—SO2-$(C_1$-$C_4)$-alkyl, NH—[$(C_1$-$C_4)$-alkyl]-SO$_3$H, NH—[$(C_1$-$C_4)$-alkyl]-SO$_2$—NH$_2$, N[$(C_1$-$C_4)$-alkyl]{[$(C_1$-$C_4)$-alkyl]-SO$_3$H}, where the alcohol (OH) or ketone (C=O) functions may be replaced by F or $CF_2$;

R17 is R18, R13, $(CH_2)_n$—CO—[O—$(C_1$-$C_3)$-alkyl], $(CH_2)_n$—CO—[O—$(C_3$-$C_6)$-cycloalkyl], $(CH_2)_n$—CO—[$(C_1$-$C_3)$-alkyl], $(CH_2)_n$—CO—[$(C_3$-$C_6)$-cycloalkyl], $(CH_2)_n$—CO-aryl, $(CH_2)_n$—CO-heteroaryl, $(CH_2)_n$—CO—[O—$(CH_2)_n$-aryl], $(CH_2)_n$—CO—$NH_2$, $(CH_2)_q$—COOH, where the alkyl and cycloalkyl radicals may be substituted by fluorine atoms and where the aryl or heteroaryl radical may be substituted by halogen, CN, $(C_1$-$C_3)$-alkyl, $(C_3$-$C_6)$-cycloalkyl, O—$(C_1$-$C_3)$-alkyl, $S(O)_m$—$(C_1$-$C_3)$-alkyl, $SO_2$—$NH_2$, COOH, $CONH_2$, CO—[O$(C_1$-$C_3)$-alkyl], CO—$(C_1$-$C_3)$-alkyl, and where the alkyl radicals may be substituted by fluorine atoms;

R18 is $(C_1$-$C_4)$-alkyl, $(C_3$-$C_6)$-cycloalkyl, $(CH_2)_q$—[$(C_3$-$C_6)$-cycloalkyl], $(CH_2)_n$-aryl, $(CH_2)_n$-heteroaryl, where the alkyl and cycloalkyl radicals may be substituted by fluorine atoms and where the aryl or heteroaryl radical may be substituted by halogen, CN, $(C_1$-$C_3)$-alkyl, O—$(C_1$-$C_3)$-alkyl, $SO_2$—$NH_2$, COOH, $CONH_2$, CO—[O$(C_1$-$C_3)$-alkyl], CO—$(C_1$-$C_6)$-alkyl, and where the alkyl radicals may be substituted by fluorine atoms;

R20 is H, $(C_1$-$C_3)$-alkyl, $(C_3$-$C_6)$-cycloalkyl, aryl, [$(C_1$-$C_6)$-alkyl]-aryl;

R21 is H, F, $CF_3$, $(C_1$-$C_3)$-alkyl, $(C_3$-$C_6)$-cycloalkyl, OH, O—$(C_1$-$C_3)$-alkyl, O—$(C_3$-$C_6)$-cycloalkyl, O—$(CH_2)_n$-aryl, O—(CO)—$(C_1$-$C_3)$-alkyl, O—(CO)—$(C_3$-$C_6)$-cycloalkyl, O—(CO)—O—$(C_1$-$C_3)$-alkyl, O—(CO)—O—$(C_3$-$C_6)$-cycloalkyl, $NH_2$, NH—[$(C_1$-$C_3)$-alkyl]-aryl, NH—$(C_1$-$C_3)$-alkyl, NH—(CO)—$(C_1$-$C_3)$-alkyl;

R22 is H, $CF_3$, $(C_1$-$C_3)$-alkyl, aryl, [$(C_1$-$C_6)$-alkyl]-aryl;

and the physiologically compatible salts thereof.

DETAILED DESCRIPTION OF THE INVENTION

Particular preference is given to compounds of the formula I in which one or more radicals are each defined as follows:

R, R' are each independently $(C_1$-$C_3)$-alkyl where $(C_1$-$C_3)$-alkyl may be substituted by halogen or R and R' together form a ring having three to six carbon atoms;

m is 0, 1, 2;

n is 0, 1, 2, 3;

p is 1, 2, 3;

q is 1, 2;

r is 2, 3, 4;

v is 0, 1, 2;

A, D, E, G, L are each independently C or N, where there is no corresponding R1, R2, R3, R4, R5 substituents when they are defined as N;

R1, R2, R3, R4, R5 are each independently H, F, Cl, Br, CN, $CF_3$, $(C_1$-$C_4)$-alkyl, $(C_3$-$C_6)$-cycloalkyl, $(CH_2)_q$—[$(C_3$-$C_6)$-cycloalkyl], $(CH_2)_n$-[$(C_7$-$C_{10})$-bicycloalkyl], $(CH_2)_n$—[$(C_7$-$C_{10})$-tricycloalkyl], adamantan-1-yl, adamantan-2-yl, $(CH_2)_n$-aryl, $(CH_2)_n$-heteroaryl, $OCF_3$, O—$(C_1$-$C_6)$-alkyl, O—$(C_3$-$C_7)$-cycloalkyl, O—$(CH_2)_n$-aryl, O—$(CH_2)_n$-heteroaryl, NH—$(C_1$-$C_4)$-alkyl, N[$(C_1$-$C_4)$-alkyl]$_2$, NH-aryl, NH-heteroaryl, NH—$SO_2$—$(C_1$-$C_4)$-alkyl, NH—$SO_2$-aryl, $S(O)_m$—$(C_1$-$C_4)$-alkyl, $S(O)_m$—$(C_3$-$C_6)$-cycloalkyl, $S(O)_m$-aryl, $SO_2$—$NH_2$, $SO_2$—NH—[$(C_1$-$C_4)$-alkyl], $SO_2$—NH—[$(C_3$-$C_6)$-cycloalkyl], $SO_2$—NH—$(CH_2)_n$-aryl, $SO_2$—N[$(C_1$-$C_4)$-alkyl]$_2$, $SF_5$, CO—O[$(C_1$-$C_4)$-alkyl], CO—$NH_2$, CO—NH—[$(C_1$-$C_4)$-alkyl], CO—N[$(C_1$-$C_4)$-alkyl]$_2$, C(=NH)—$NH_2$, C(=N—OH)$NH_2$, COOH, CO—$(C_1$-$C_6)$-alkyl, CO—$(C_3$-$C_6)$-cycloalkyl, CO-aryl, CO-heteroaryl, CH(OH)-aryl, CH(OH)-heteroaryl, CH[O—$(C_1$-$C_4)$-alkyl]-aryl, CH[O—$(C_1$-$C_4)$-alkyl]-heteroaryl, CHF-aryl, CHF-heteroaryl, $CF_2$-aryl, where the alkyl, cycloalkyl, bicycloalkyl and tricycloalkyl radicals may be substituted by fluorine atoms and where the aryl or heteroaryl radicals may be substituted by halogen, CN, $(C_1$-$C_4)$-alkyl, $(C_3$-$C_6)$-cycloalkyl, O—$(C_1$-$C_4)$-alkyl, $S(O)_m$—$(C_1$-$C_3)$-alkyl, $SO_2$—$NH_2$, COOH, $CONH_2$, CO—O$(C_1$-$C_3)$-alkyl, CO—$(C_1$-$C_3)$-alkyl, and where the alkyl radicals may be substituted by fluorine atoms;

R6, R7, R8, R9, R10 are each independently NR17-bicyclic heterocycle, NR17-aryl, NR17-heteroaryl, where the aryl or heteroaryl radical may be fused to a 5- or 6-membered aromatic or nonaromatic carbon ring in which one or more CH or $CH_2$ groups may be replaced by oxygen atoms and where the 5- or 6-membered aromatic or nonaromatic carbon ring may be substituted by F, =O or —$(C_1$-$C_6)$-alkyl and where the bicyclic heterocycle contains from 9 to 10 ring members and up to five CH or $CH_2$ groups may each independently be replaced by N, NR20, O, $S(O)_m$ or C=O and where the aryl or heteroaryl radical or bicyclic heterocycle may be unsubstituted or mono- or polysubstituted by R11, F, Cl, Br, CN, $NO_2$, $CF_3$, $(CH_2)_n$—O—R11, $(CH_2)_n$—O—$(CH_2)_r$—OH, $(CH_2)_n$—O—CH($CH_2$OH)$_2$, $(CH_2)_n$—O—$(CH_2)_n$—CO—O—$(CH_2)_r$—$NH_2$, $(CH_2)_n$—O-sugar acid, $(CH_2)_n$—O-glucoside, $(CH_2)_n$—O-galactoside, $(CH_2)_n$—O-glucuronide, $OCF_3$, O—R13, $(CH_2)_n$—O—$(CH_2)_r$—$NH_2$, $(CH_2)_n$—NH—R11, $(CH_2)_n$—N[$(CH_2)_q$—CO—O$(C_1$-$C_4)$-alkyl]$_2$, $(CH_2)_n$—N[$(CH_2)_q$—COOH]$_2$, $(CH_2)_n$—N[$(CH_2)_q$—$CONH_2$]$_2$, $(CH_2)_n$—NH—R13, $(CH_2)_n$—N(R13)$_2$, $(CH_2)_n$—NH—$SO_2$—R16, $(CH_2)_n$—NH—$(CH_2)_n$—$SO_2$—R12, $(CH_2)_n$—NR12—CO—R16, $(CH_2)_n$—NR12—CO—NR12R13, $(CH_2)_n$—NR12—CO—N(R12)$_2$, $(CH_2)_n$—NR12—CO—NHR11, $(CH_2)_n$—NH—C(=NH)—$NH_2$, $(CH_2)_n$—NH—C(=NH)—R16, $(CH_2)_n$—NH—C(=NH)—NHR12, $(CH_2)_n$—NR12—C(=NR13)—NHR12, $(CH_2)_n$—NR12—C(=NR12)—NR12R13, $(CH_2)_n$—NH—$(CH_2)_n$—CO—O—$(CH_2)_r$—$NH_2$, $(CH_2)_n$—NH—$(CH_2)_n$—CO—NH—[$(C_1$-$C_8)$-alkyl], $(CH_2)_n$—NH—$(CH_2)_n$—CO—NH—$(CH_2)_r$—OH, $(CH_2)_n$—NH—$(CH_2)_n$—CO—N[(C1-C8)-alkyl]$_2$, $(CH_2)_n$—NH—$(CH_2)_n$—CO—NH—[$(C_3$-$C_8)$-cycloalkyl], $(CH_2)_n$—NH—C($CH_3)_2$—CO—O$(C_1$-$C_8)$-alkyl, $(CH_2)_n$—NH—C($CH_3)_2$—CO—O—$(CH_2)_r$—$NH_2$, $(CH_2)_n$—NH—C($CH_3)_2$—CO—$NH_2$, $(CH_2)_n$—NH—C($CH_3)_2$—CO—NH—$(CH_2)_r$—OH, $(CH_2)_n$—NH—C($CH_3)_2$—COOH, $S(O)_m$—R12, $SO_2$—R16, $SO_2$—N=CH—N($CH_3)_2$, $SO_2$—NH—CO—R12, $SO_2$—NHR12, $SO_2$—NH—$(CH_2)_r$—OH, $SO_2$—N[$(C_1$-$C_8)$-alkyl]$_2$, $SO_2$—NH—$(CH_2)_r$—$NH_2$, $SF_5$, COOH, CO—$NH_2$, $(CH_2)_q$—CN, $(CH_2)_n$—CO—NH-piperidin-1-yl, $(CH_2)_n$—CO—NH—$SO_2$—NHR12, $(CH_2)_n$—CO—NH—$SO_2$—R18, $(CH_2)_n$—C(=NH)$NH_2$, $(CH_2)_n$—C(=NH)—NHOH, C(=NH)—[NH—O—$(C_1$-$C_6)$-alkyl], $(CH_2)_n$—C(=NH)(R16), $(CH_2)_n$—C(=NR13)NHR12, $(CH_2)_n$—C(=NR12)NR12R13, $(CH_2)_n$—C(=NH)O[$(C_1$-$C_6)$-alkyl], where the alkyl and cycloalkyl radicals may be substituted by fluorine atoms and where the aryl or heteroaryl radicals may be substituted by halogen, CN, $(C_1$-$C_6)$-alkyl, $(C_3$-$C_6)$-cycloalkyl, O—$(C_1$-$C_6)$-alkyl, $S(O)_m$—$(C_1$-$C_6)$-alkyl, $SO_2$—$NH_2$, COOH, $CONH_2$, CO—O$(C_1$-$C_6)$-alkyl, CO—$(C_1$-$C_6)$-alkyl, and where the alkyl radicals may be substituted by fluorine atoms;

H, F, Cl, Br, CN, $CF_3$, $(C_1-C_6)$-alkyl, $(C_2-C_6)$-alkenyl, $(C_2-C_6)$-alkynyl, $(C_3-C_7)$-cycloalkyl, $(CH_2)_n$—OH, $(CH_2)_n$—O—$(C_1-C_4)$-alkyl, $(CH_2)_n$—O—$(C_3-C_6)$-cycloalkyl, $(CH_2)_n$—O-aryl, $(CH_2)_n$—O-glucoside, $(CH_2)_n$—O-glucuronide, $OCF_3$, O—R13, $(CH_2)_n$—NH-aryl, $(CH_2)_n$—NH—$SO_2$—$(C_1-C_4)$-alkyl, $(CH_2)_n$—NH—$SO_2$-aryl, $(CH_2)_n$—NH—CO—$NH_2$, $(CH_2)_n$—NH—CO—NH—$(C_1-C_4)$-alkyl, $(CH_2)_n$—NH—CO—NH—$(C_3-C_6)$-cycloalkyl, $(CH_2)_n$—NH—C(=NH)—$NH_2$, $S(O)_m$—$(C_1-C_4)$-alkyl, $S(O)_m$-aryl, $SO_2$—$NH_2$, $SO_2$—NH—$(C_1-C_4)$-alkyl, $SO_2$—N[$C_1-C_4$]-alkyl]$_2$, $SF_5$, $(CH_2)_n$—CO—[O—$(C_1-C_4)$-alkyl], COOH, $(CH_2)_q$—COOH, $CONH_2$, $(CH_2)_q$—$CONH_2$, $(CH_2)_n$—C(=NH)$NH_2$, $(CH_2)_n$—C(=NH)NHOH, where the alkyl and cycloalkyl radicals may be substituted by fluorine atoms and where the aryl or heteroaryl radicals may be substituted by halogen, CN, $(C_1-C_3)$-alkyl, $(C_3-C_6)$-cycloalkyl, O—$(C_1-C_4)$-alkyl, $S(O)_m$—$(C_1-C_3)$-alkyl, $SO_2$—$NH_2$, COOH, $CONH_2$, CO—[O($C_1-C_3$)-alkyl] and where the alkyl radicals may be substituted by fluorine atoms;

where one of the R6, R7, R8, R9 and R10 radicals is always defined as NR17-aryl or NR17-bicyclic heterocycle or NR17-heteroaryl;

R11 is H, $(C_1-C_4)$-alkyl, $(C_2-C_3)$-alkenyl, $(C_2-C_4)$-alkynyl, $(C_3-C_5)$-cycloalkyl, $(CH_2)_q$—[$(C_3-C_4)$-cycloalkyl], $(CH_2)_n$—[$(C_7-C_{10})$-bicycloalkyl], $(CH_2)_n$—[$(C_3-C_6)$-cycloalkenyl], $(CH_2)_n$—[$(C_7-C_8)$-bicycloalkenyl], $(CH_2)_n$—[$(C_7-C_8)$-tricycloalkyl], $(CH_2)_n$-aryl, $(CH_2)_n$—CO—[O—$(C_1-C_4)$-alkyl], $(CH_2)_n$—CO—[O—$(C_3-C_5)$-cycloalkyl], $(CH_2)_n$—CO—[$(C_1-C_3)$-alkyl], $(CH_2)_n$—CO—[$(C_3-C_5)$-cycloalkyl], $(CH_2)_n$—CO-aryl, $(CH_2)_n$—CO-heteroaryl, $(CH_2)_n$—CO—[O—$(CH_2)_v$-aryl], $(CH_2)_n$—CO—[O—$(CH_2)_v$-heteroaryl], $(CH_2)_q$—CO—$NH_2$, $(CH_2)_q$—COOH, $(CH_2)_n$—P(O)(OH)[O—$(C_1-C_3)$-alkyl], $(CH_2)_n$—P(O)[O—$(C_1-C_3)$-alkyl]$_2$, $(CH_2)_n$—P(O)(OH)(O—$CH_2$-aryl), $(CH_2)_n$—P(O)(O—$CH_2$-aryl)$_2$, $(CH_2)_n$—P(O)(OH)$_2$, $(CH_2)_n$—$SO_3H$, $(CH_2)_n$—$SO_2$—$NH_2$, $(CH_2)_n$—CO—NH—[$(C_1-C_6)$-alkyl], $(CH_2)_n$—CO—N[$(C_1-C_4)$-alkyl]$_2$, $(CH_2)_n$—CO—NH—[$(C_3-C_5)$-cycloalkyl], $(CH_2)_n$—CO—N[$(C_3-C_4)$-cycloalkyl]$_2$, $(C_2-C_4)$-alkenyl-CO—O[$(C_1-C_4)$-alkyl], $(C_2-C_4)$-alkenyl-$CONH_2$, $(C_2-C_4)$-alkenyl-COOH, $(C_2-C_4)$-alkynyl-CO—O[$(C_1-C_6)$-alkyl], $(C_2-C_4)$-alkynyl-$CONH_2$, $(C_2-C_4)$-alkynyl-COOH, $(CH_2)_n$—CR21[(CO—O($C_1-C_4$)-alkyl)]$_2$, $(CH_2)_n$—CR21($CONH_2$)$_2$, $(CH_2)_n$—CR21(COOH)$_2$, $(CH_2)_n$—CR21R22CO—O[$(C_1-C_4)$-alkyl], $(CH_2)_n$—CR21R22$CONH_2$, $(CH_2)_n$—CR21R22COOH, $(CH_2)_n$—CO—R16, $(CH_2)_n$—C($CH_3$)$_2$—CO—O[$(C_1-C_3)$-alkyl], $(CH_2)_n$—C($CH_3$)$_2$—CO—O[$(C_3-C_5)$-cycloalkyl], $(CH_2)_n$—C($CH_3$)$_2$—CO—$NH_2$, $(CH_2)_n$—C($CH_3$)$_2$—CO—NH—[$(C_1-C_3)$-alkyl], $(CH_2)_n$—C($CH_3$)$_2$—CO—NH—$(CH_2)_r$—OH, $(CH_2)_n$—C($CH_3$)$_2$—CO—NH—[$(C_3-C_5)$-cycloalkyl], $(CH_2)_n$—CO—NH—C($CH_3$)$_2$—CO—O[$(C_1-C_4)$-alkyl], $(CH_2)_n$—C($CH_3$)$_2$—COOH, $(CH_2)_n$—CO—NH—C($CH_3$)$_2$—$CONH_2$, $(CH_2)_n$—CO—NH—C($CH_3$)$_2$—COOH, where the alkyl, alkenyl, alkynyl and cycloalkyl, bicycloalkyl, cycloalkenyl, bicycloalkenyl and tricycloalkyl radicals may be substituted by fluorine atoms and where the aryl or heteroaryl radical may be substituted by halogen, CN, $(C_1-C_4)$-alkyl, $(C_3-C_6)$-cycloalkyl, O—$(C_1-C_4)$-alkyl, $S(O)_m$—$(C_1-C_4)$-alkyl, $SO_2$—$NH_2$, COOH, $CONH_2$, CO—O($C_1-C_4$)-alkyl, CO—$(C_1-C_3)$-alkyl, and where the alkyl radicals may be substituted by fluorine atoms;

R12 is H, $(C_1-C_3)$-alkyl, $(C_3-C_5)$-cycloalkyl, $(CH_2)_q$—[$(C_3-C_5)$-cycloalkyl], $(CH_2)_n$-[$(C_7-C_8)$-bicycloalkyl], $(CH_2)_n$-[$(C_7-C_8)$-tricycloalkyl], $(CH_2)_n$-aryl, $(CH_2)_n$-heteroaryl, where the alkyl, cycloalkyl, bicycloalkyl or tricycloalkyl radicals may be substituted by fluorine atoms, and where the aryl or heteroaryl radical may be substituted by halogen, CN, $(C_1-C_3)$-alkyl, O—$(C_1-C_3)$-alkyl, $SO_2$—$NH_2$, COOH, $CONH_2$, CO—O($C_1-C_3$)-alkyl, CO—$(C_1-C_3)$-alkyl and where the alkyl radicals may be substituted by fluorine atoms;

R13 is H, $SO_2$—[$(C_1-C_3)$-alkyl], $SO_2$—[$(C_3-C_5)$-cycloalkyl], $SO_2$—$(CH_2)_n$-aryl, $SO_2$—$(CH_2)_n$-heteroaryl, $SO_2$—$(CH_2)_n$—NH—R12, $SO_2$—$(CH_2)_n$—N(R12)$_2$, where the alkyl and cycloalkyl radicals may be substituted by fluorine atoms and where the aryl or heteroaryl radical may be substituted by halogen, CN, $(C_1-C_3)$-alkyl, $(C_3-C_6)$-cycloalkyl, O—[$(C_1-C_3)$-alkyl], $S(O)_m$—[$(C_1-C_3)$-alkyl], $SO_2$—$NH_2$, COOH, $CONH_2$, CO—[O($C_1-C_3$)-alkyl], CO—$(C_1-C_3)$-alkyl, and where the alkyl radicals may be substituted by fluorine atoms;

R16 is aziridine-1-yl, azetidin-1-yl, piperidin-1-yl, 4-hydroxypiperidin-1-yl, 3-oxopiperidin-1-yl, 4-oxopiperidin-1-yl, pyrrolidin-1-yl, 3-pyrrolidinol-1-yl, 2-cyanopyrrolidin-1-yl, morpholin-N-yl, piperazin-1-yl, 4-[$(C_1-C_3)$-alkyl]piperazin-1-yl, piperazin-2-on-1-yl, piperazin-2-on-4-yl, thiomorpholine-1,1-dioxide-4-yl, NH—$(CH_2)_r$—OH, NH—CH($CH_2OH$)$_2$, NH—C($CH_2OH$)$_3$, N[$(C_1-C_3)$-alkyl-OH]$_2$, D-glucamine-N-yl, N-methyl-D-glucamine-N-yl, NH—[$(C_1-C_3)$-alkyl]-CO—O($C_1-C_3$)-alkyl, NH—[$(C_1-C_3)$-alkyl]-COOH, NH—[$(C_1-C_3)$-alkyl]-$CONH_2$, NH—[C(H)(aryl)]-CO—O($C_1-C_3$)-alkyl, NH—[C(H)(aryl)]-COOH, NH—[C(H)(aryl)]-$CONH_2$, NH—[C(H)(heteroaryl)]-CO—O($C_1-C_3$)-alkyl, NH—[C(H)(heteroaryl)]-COOH, NH—[C(H)(heteroaryl)]-$CONH_2$, NH—[$(C_3-C_6)$-cycloalkyl]-CO—O($C_1-C_3$)-alkyl, NH—[$(C_3-C_6)$-cycloalkyl]-COOH, NH—[$(C_3-C_6)$-cycloalkyl]-$CONH_2$, NH—$(CH_2)_r$—SO2-$(C_1-C_3)$-alkyl, NH—[$(C_1-C_4)$-alkyl]-$SO_3H$, NH—[$(C_1-C_4)$-alkyl]-$SO_2$—$NH_2$, N[$(C_1-C_3)$-alkyl]{[$(C_1-C_4)$-alkyl]-$SO_3H$}, where the alcohol (OH) or ketone (C=O) functions may be replaced by F or $CF_2$;

R17 is R18, H, $SO_2$—$CH_3$, $SO_2$-aryl, $(CH_2)_n$—CO—[O—$(C_1-C_3)$-alkyl], $(CH_2)_n$—CO—[$(C_1-C_3)$-alkyl], $(CH_2)_n$—CO-aryl, $(CH_2)_n$—CO—$NH_2$, $(CH_2)_q$—COOH, where the alkyl radicals may be substituted by fluorine atoms and where the aryl or heteroaryl radical may be substituted by halogen, CN, $(C_1-C_3)$-alkyl, O—$(C_1-C_3)$-alkyl, $S(O)_m$—$(C_1-C_3)$-alkyl, $SO_2$—$NH_2$, COOH, $CONH_2$, CO—[O($C_1-C_3$)-alkyl], CO—$(C_1-C_3)$-alkyl, and where the alkyl radicals may be substituted by fluorine atoms;

R18 is $(C_1-C_4)$-alkyl, $(C_3-C_4)$-cycloalkyl, $(CH_2)_n$-aryl, $(CH_2)_n$-heteroaryl, where the alkyl and cycloalkyl radicals may be substituted by fluorine atoms and where the aryl or heteroaryl radical may be substituted by halogen, CN, $(C_1-C_3)$-alkyl, O—$(C_1-C_3)$-alkyl, $SO_2$—$NH_2$, COOH, $CONH_2$, CO—[O($C_1-C_3$)-alkyl], CO—$(C_1-C_3)$-alkyl, and where the alkyl radicals may be substituted by fluorine atoms;

R20 is H, $(C_1-C_3)$-alkyl, $(C_3-C_6)$-cycloalkyl, aryl, [$(C_1-C_3)$-alkyl]-aryl;

R21 is H, F, $CF_3$, $(C_1-C_3)$-alkyl, $(C_3-C_4)$-cycloalkyl, OH, O—$(C_1-C_3)$-alkyl, O—$(C_3-C_4)$-cycloalkyl, O—$(CH_2)_n$-aryl, O—(CO)—$(C_1-C_3)$-alkyl, O—(CO)—$(C_3-C_4)$-cycloalkyl, O—(CO)—O—$(C_1-C_3)$-alkyl, O—(CO)—O—$(C_3-C_4)$-cycloalkyl, $NH_2$, NH—[$(C_1-C_2)$-alkyl]-aryl, NH—$(C_1-C_3)$-alkyl, NH—(CO)—$(C_1-C_3)$-alkyl;

R22 is H, $CF_3$, $(C_1-C_3)$-alkyl, aryl, [$(C_1-C_3)$-alkyl]-aryl;

and the physiologically compatible salts thereof.

Very particular preference is given to compounds of the formula I in which one or more radicals are each defined as follows:

R, R' are each independently $(C_1-C_3)$-alkyl; or R and R' together form a ring having from three to six carbon atoms;
m is 0, 1, 2;
n is 0, 1, 2;
p is 1, 2;
q is 1, 2;
r is 2, 3;
v is 0, 1;
A, D, E, G, L are each independently C or N, where there is no corresponding R1, R2, R3, R4, R5 substituent when they are defined as N;
R1, R2, R3, R4, R5 are each independently H, F, Cl, Br, CN, $CF_3$, $(C_1-C_4)$-alkyl, $(C_3-C_6)$-cycloalkyl, $(CH_2)_q$—$[(C_3-C_6)$-cycloalkyl], adamantan-1-yl, adamantan-2-yl, $(CH_2)_n$-aryl, $(CH_2)_n$-heteroaryl, $OCF_3$, O—$(C_1-C_4)$-alkyl, O—$(C_3-C_6)$-cycloalkyl, O—$(CH_2)_n$-aryl, O—$(CH_2)_n$-heteroaryl, NH—$(C_1-C_4)$-alkyl, N$[(C_1-C_4)$-alkyl$]_2$, NH-aryl, NH-heteroaryl, NH—$SO_2$—$(C_1-C_4)$-alkyl, NH—$SO_2$-aryl, $S(O)_m$—$(C_1-C_3)$-alkyl, $S(O)_m$—$(C_3-C_6)$-cycloalkyl, $S(O)_m$-aryl, $SO_2$—$NH_2$, $SO_2$—NH—$[(C_1-C_4)$-alkyl], $SO_2$—NH—$[(C_3-C_6)$-cycloalkyl], $SO_2$—NH—$(CH_2)_n$-aryl, $SO_2$—N$[(C_1-C_4)$-alkyl$]_2$, $SF_5$, CO—O$[(C_{1-4})$-alkyl], CO—$NH_2$, CO—NH—$[(C_1-C_3)$-alkyl], CO—N$[(C_1-C_3)$-alkyl$]_2$, COOH, CO—$(C_1-C_3)$-alkyl, CO—$(C_3-C_6)$-cycloalkyl, CO-aryl, CO-heteroaryl, CH(OH)-aryl, CH(OH)-heteroaryl, CH[O—$(C_1-C_4)$-alkyl]-aryl, CH[O—$(C_1-C_4)$-alkyl]-heteroaryl, CHF-aryl, CHF-heteroaryl, $CF_2$-aryl, where the alkyl or cycloalkyl radicals may be substituted by fluorine atoms and where the aryl or heteroaryl radicals may be substituted by halogen, CN, $(C_1-C_3)$-alkyl, O—$(C_1-C_4)$-alkyl, $S(O)_m$—$(C_1-C_3)$-alkyl, $SO_2$—$NH_2$, COOH, $CONH_2$, CO—$O(C_1-C_3)$-alkyl, CO—$(C_1-C_3)$-alkyl, and where the alkyl radicals may be substituted by fluorine atoms;
R6, R7, R8, R9, R10 are each independently NR17-bicyclic heterocycle, NR17-aryl, NR17-heteroaryl, where the aryl or heteroaryl radical may be fused to a 5- or 6-membered aromatic or nonaromatic carbon ring in which one or more CH or $CH_2$ groups may be replaced by oxygen atoms and where the 5- or 6-membered aromatic or nonaromatic carbon ring may be substituted by F, =O or —$(C_1-C_3)$-alkyl and where the bicyclic heterocycle contains from 9 to 10 ring members and up to five CH or $CH_2$ groups may each independently be replaced by N, NR20, O, $S(O)_m$ or C=O and where the aryl or heteroaryl radical or bicyclic heterocycle may be unsubstituted or mono- or polysubstituted by R11, F, Cl, Br, CN, $NO_2$, $CF_3$, $(CH_2)_n$—O—R11, $(CH_2)_n$—O—$(CH_2)_r$—OH, $(CH_2)_n$—O—$CH(CH_2OH)_2$, $(CH_2)_n$—O—$(CH_2)_n$—CO—O—$(CH_2)_r$—$NH_2$, $(CH_2)_n$—O-glucoside, $(CH_2)_n$—O-galactoside, $(CH_2)_n$—O-glucuronide, $OCF_3$, O—R13, $(CH_2)_n$—O—$(CH_2)_r$—$NH_2$, $(CH_2)_n$—NH—R11, $(CH_2)_n$—N$[(CH_2)_q$—CO—$O(C_1-C_4)$-alkyl$]_2$, $(CH_2)_n$—N$[(CH_2)_q$—COOH$]_2$, $(CH_2)_n$—N$[(CH_2)_q$—$CONH_2]_2$, $(CH_2)_n$—NH—R13, $(CH_2)_n$—N$(R13)_2$, $(CH_2)_n$—NH—$SO_2$—R16, $(CH_2)_n$—NH—$(CH_2)_n$—$SO_2$—R2, $(CH_2)_n$—NR12—CO—R16, $(CH_2)_n$—NR12—CO—NR12R13, $(CH_2)_n$—NR12—CO—N$(R12)_2$, $(CH_2)_n$—NR12—CO—NHR11, $(CH_2)_n$—NH—C(=NH)—R16, $(CH_2)_n$—NR12—C(=NR13)—NHR12, $(CH_2)_n$—NR12—C(=NR12)—NR12R13, $(CH_2)_n$—NH—$(CH_2)_n$—CO—O—$(CH_2)_r$—$NH_2$, $(CH_2)_n$—NH—$(CH_2)_n$—CO—NH—$[(C_1-C_3)$-alkyl], $(CH_2)_n$—NH—$(CH_2)_n$—CO—NH—$(CH_2)_r$—OH, $(CH_2)_n$—NH—$(CH_2)_n$—CO—N$[(C_1-C_3)$-alkyl$]_2$, $(CH_2)_n$—NH—$(CH_2)_n$—CO—NH—$[(C_3-C_5)$-cycloalkyl], $(CH_2)_n$—NH—$C(CH_3)_2$—CO—O—$(C_1-C_4)$-alkyl, $(CH_2)_n$—NH—$C(CH_3)_2$—CO—O—$(CH_2)_r$—$NH_2$, $(CH_2)_n$—NH—$C(CH_3)_2$—CO—$NH_2$, $(CH_2)_n$—NH—$C(CH_3)_2$—CO—NH—$(CH_2)_r$—OH, $(CH_2)_n$—NH—$C(CH_3)_2$—COOH, $S(O)_m$—R12, $SO_2$—R16, $SO_2$—N=CH—$N(CH_3)_2$, $SO_2$—NH—CO—R12, $SO_2$—NHR12, $SO_2$—NH—$(CH_2)_r$—OH, $SO_2$—N$[(C_1-C_3)$-alkyl$]_2$, $SO_2$—NH—$(CH_2)_r$—$NH_2$, $SF_5$, COOH, CO—$NH_2$, $(CH_2)_q$—CN, $(CH_2)_n$—CO—NH-piperidin-1-yl, $(CH_2)_n$—CO—NH—$SO_2$—NHR12, $(CH_2)_n$—CO—NH—$SO_2$—R18, $(CH_2)_n$—C(=NH)—NHOH, C(=NH)—[NH—O—$(C_1-C_3)$-alkyl], $(CH_2)_n$—C(=NH)(R16), $(CH_2)_n$—C(=NR12)NR12R13, $(CH_2)_n$—C(=NH)O$[(C_1-C_3)$-alkyl], where the alkyl and cycloalkyl radicals may be substituted by fluorine atoms and where the aryl or heteroaryl radicals may be substituted by halogen, CN, $(C_1-C_3)$-alkyl, $(C_3-C_6)$-cycloalkyl, O—$(C_1-C_3)$-alkyl, $S(O)_m$—$(C_1-C_3)$-alkyl, $SO_2$—$NH_2$, COOH, $CONH_2$, CO—$O(C_1-C_3)$-alkyl, CO—$(C_1-C_3)$-alkyl, and where the alkyl radicals may be substituted by fluorine atoms;

H, F, Cl, Br, CN, $CF_3$, $(C_1-C_6)$-alkyl, $(C_3-C_7)$-cycloalkyl, $(CH_2)_n$—OH, $(CH_2)_n$—O—$(C_1-C_4)$-alkyl, $(CH_2)_n$—O—$(C_3-C_6)$-cycloalkyl, $(CH_2)_n$—O-aryl, $(CH_2)_n$—O-glucoside, $(CH_2)_n$—O-glucuronide, $OCF_3$, O—R13, $(CH_2)_n$—NH-aryl, $(CH_2)_n$—NH—$SO_2$—$(C_1-C_4)$-alkyl, $(CH_2)_n$—NH—$SO_2$-aryl, $(CH_2)_n$—NH—CO—$NH_2$, $(CH_2)_n$—NH—CO—NH—$(C_1-C_3)$-alkyl, $(CH_2)_n$—NH—CO—NH—$(C_3-C_6)$-cycloalkyl, $(CH_2)_n$—NH—C(=NH)—$NH_2$, $S(O)_m$—$(C_1-C_4)$-alkyl, $S(O)_m$-aryl, $SO_2$—$NH_2$, $SO_2$—NH—$(C_1-C_3)$-alkyl, $SO_2$—N$[C_1-C_3]$-alkyl$]_2$, $SF_5$, $(CH_2)_n$—CO—[O—$(C_1-C_4)$-alkyl], $(CH_2)_n$—COOH, $(CH_2)_n$—$CONH_2$, $(CH_2)_n$—C(=NH)$NH_2$, where the alkyl and cycloalkyl radicals may be substituted by fluorine atoms and where the aryl or heteroaryl radicals may be substituted by halogen, CN, $(C_1-C_3)$-alkyl, $(C_3-C_6)$-cycloalkyl, O—$(C_1-C_4)$-alkyl, $S(O)_m$—$(C_1-C_3)$-alkyl, $SO_2$—$NH_2$, COOH, $CONH_2$, CO—[$O(C_1-C_3)$-alkyl], and where the alkyl radicals may be substituted by fluorine atoms;

where at least one of the R6, R7, R8, R9 and R10 radicals is always defined as NR17-aryl or NR17-bicyclic heterocycle or NR17-heteroaryl;

R11 is H, $(C_1-C_4)$-alkyl, $(C_3-C_5)$-cycloalkyl, $(CH_2)_q$—$[(C_3-C_4)$-cycloalkyl], $(CH_2)_n$-$[(C_7-C_8)$-bicycloalkyl], $(CH_2)_n$—$[(C_7-C_8)$-tricycloalkyl], $(CH_2)_n$-aryl, $(CH_2)_n$—CO—[O—$(C_1-C_4)$-alkyl], $(CH_2)_n$—CO—[O—$(C_3-C_5)$-cycloalkyl], $(CH_2)_n$—CO—$[(C_1-C_3)$-alkyl], $(CH_2)_n$—CO—$[(C_3-C_5)$-cycloalkyl], $(CH_2)_n$—CO-aryl, $(CH_2)_n$—CO-heteroaryl, $(CH_2)_n$—CO—[O—$(CH_2)_v$-aryl], $(CH_2)_n$—CO—[O—$(CH_2)_v$-heteroaryl], $(CH_2)_q$—CO—$NH_2$, $(CH_2)_q$—COOH, $(CH_2)_n$—P(O)(OH)[O—$(C_1-C_3)$-alkyl], $(CH_2)_n$—P(O)[O—$(C_1-C_3)$-alkyl$]_2$, $(CH_2)_n$—P(O)(OH)(O—$CH_2$-aryl), $(CH_2)_n$—P(O)(O—$CH_2$-aryl$)_2$, $(CH_2)_n$—P(O)(OH$)_2$, $(CH_2)_n$—$SO_3H$, $(CH_2)_n$—$SO_2$—$NH_2$, $(CH_2)_n$—CO—NH—$[(C_1-C_3)$-alkyl], $(CH_2)_n$—CO—N$[(C_1-C_3)$-alkyl$]_2$, $(CH_2)_n$—CO—NH—$[(C_3-C_5)$-cycloalkyl], $(C_2-C_3)$-alkenyl-CO—O$[(C_1-C_4)$-alkyl], $(C_2-C_3)$-alkenyl-$CONH_2$, $(C_2-C_3)$-alkenyl-COOH, $(C_2-C_4)$-alkynyl-CO—O$[(C_1-C_4)$-alkyl], $(C_2-C_4)$-alkynyl-$CONH_2$, $(C_2-C_4)$-alkynyl-COOH, $(CH_2)_n$—CR21-[CO—O$(C_1-C_4)$-alkyl)$]_2$, $(CH_2)_n$—CR21$(CONH_2)_2$, $(CH_2)_n$—CR21(COOH$)_2$, $(CH_2)_n$—CR21R22CO—O$[(C_1-C_4)$-alkyl], $(CH_2)_n$—CR21R22$CONH_2$, $(CH_2)_n$—CR21R22COOH, $(CH_2)_n$—CO—R16, $(CH_2)_n$—

C(CH$_3$)$_2$—CO—O[(C$_1$-C$_3$)]-alkyl, (CH$_2$)$_n$—C(CH$_3$)$_2$—CO—O[(C$_3$-C$_5$)]-cycloalkyl, (CH$_2$)$_n$—C(CH$_3$)$_2$—CO—NH$_2$, (CH$_2$)$_n$—C(CH$_3$)$_2$—CO—NH—[(C$_1$-C$_3$)-alkyl], (CH$_2$)$_n$—C(CH$_3$)$_2$—CO—NH—(CH$_2$)$_r$—OH, (CH$_2$)$_n$—C(CH$_3$)$_2$—CO—NH—[(C$_3$-C$_5$)-cycloalkyl], (CH$_2$)$_n$—C(CH$_3$)$_2$—COOH, (CH$_2$)$_n$—CO—NH—C(CH$_3$)$_2$—CONH$_2$, (CH$_2$)$_n$—CO—NH—C(CH$_3$)$_2$—CO—O[(C$_1$-C$_4$)-alkyl], (CH$_2$)$_n$—CO—NH—C(CH$_3$)$_2$—COOH, where the alkyl, cycloalkyl, bicycloalkyl and tricycloalkyl radicals may be substituted by fluorine atoms and where the aryl or heteroaryl radical may be substituted by halogen, CN, (C$_1$-C$_4$)-alkyl, (C$_3$-C$_6$)-cycloalkyl, O—(C$_1$-C$_4$)-alkyl, S(O)$_m$—(C$_1$-C$_4$)-alkyl, SO$_2$—NH$_2$, COOH, CONH$_2$, CO—O(C$_1$-C$_4$)-alkyl, CO—(C$_1$-C$_3$)-alkyl, and where the alkyl radicals may be substituted by fluorine atoms;

R12 is H, (C$_1$-C$_3$)-alkyl, (C$_3$-C$_5$)-cycloalkyl, (CH$_2$)$_n$-aryl, (CH$_2$)$_n$-heteroaryl, where the alkyl or cycloalkyl radicals may be substituted by fluorine atoms, and where the aryl or heteroaryl radical may be substituted by halogen, CN, (C$_1$-C$_3$)-alkyl, O—(C$_1$-C$_3$)-alkyl, SO$_2$—NH$_2$, COOH, CONH$_2$, CO—O(C$_1$-C$_3$)-alkyl, CO—(C$_1$-C$_3$)-alkyl, and where the alkyl radicals may be substituted by fluorine atoms;

R13 is H, SO$_2$—[(C$_1$-C$_3$)-alkyl], SO$_2$—[(C$_3$-C$_5$)-cycloalkyl], SO$_2$—(CH$_2$)$_n$-aryl, SO$_2$—(CH$_2$)$_n$-heteroaryl, SO$_2$—(CH$_2$)$_n$—NH—R12, SO$_2$—(CH$_2$)$_n$—N(R12)$_2$, where the alkyl and cycloalkyl radicals may be substituted by fluorine atoms and where the aryl or heteroaryl radical may be substituted by halogen, CN, (C$_1$-C$_3$)-alkyl, (C$_3$-C$_6$)-cycloalkyl, O—[(C$_1$-C$_3$)-alkyl], S(O)$_m$—[(C$_1$-C$_3$)-alkyl], SO$_2$—NH$_2$, COOH, CONH$_2$, CO—[O(C$_1$-C$_3$)-alkyl], CO—(C$_1$-C$_3$)-alkyl and where the alkyl radicals may be substituted by fluorine atoms;

R16 is aziridine-1-yl, azetidin-1-yl, piperidin-1-yl, 4-hydroxypiperidin-1-yl, 3-oxopiperidin-1-yl, 4-oxopiperidin-1-yl, pyrrolidin-1-yl, 3-pyrrolidinol-1-yl, 2-cyanopyrrolidin-1-yl, morpholin-N-yl, piperazin-1-yl, 4-[(C$_1$-C$_3$)-alkyl]piperazin-1-yl, piperazin-2-on-1-yl, piperazin-2-on-4-yl, thiomorpholine-1,1-dioxide-4-yl, NH—(CH$_2$)$_r$—OH, NH—CH(CH$_2$OH)$_2$, NH—C(CH$_2$OH)$_3$, N[(C$_1$-C$_3$)-alkyl-OH]$_2$, D-glucamine-N-yl, N-methyl-D-glucamine-N-yl, NH—[(C$_1$-C$_3$)-alkyl]-CO—O(C$_1$-C$_3$)-alkyl, NH—[(C$_1$-C$_3$)-alkyl]-COOH, NH—[(C$_1$-C$_3$)-alkyl]-CONH$_2$, NH—[C(H)(aryl)]-CO—O(C$_1$-C$_3$)-alkyl, NH—[C(H)(aryl)]-COOH, NH—[C(H)(aryl)]-CONH$_2$, NH—[C(H)(heteroaryl)]-CO—O(C$_1$-C$_3$)-alkyl, NH—[C(H)(heteroaryl)]-COOH, NH—[C(H)(heteroaryl)]-CONH$_2$, NH—[(C$_3$-C$_6$)-cycloalkyl]-CO—O(C$_1$-C$_3$)-alkyl, NH—[(C$_3$-C$_6$)-cycloalkyl]-COOH, NH—[(C$_3$-C$_6$)-cycloalkyl]-CONH$_2$, NH—(CH$_2$)$_r$—SO2—(C$_1$-C$_3$)-alkyl, NH—[(C$_1$-C$_4$)-alkyl]-SO$_3$H, NH—[(C$_1$-C$_4$)-alkyl]-SO$_2$—NH$_2$, N[(C$_1$-C$_3$)-alkyl]{[(C$_1$-C$_4$)-alkyl]-SO$_3$H}, where the alcohol (OH) or ketone (C=O) functionalities may be replaced by F or CF$_2$;

R17 is H, R18, SO$_2$—CH$_3$, SO$_2$-aryl, (CH$_2$)$_n$—CO—[O—(C$_1$-C$_3$)-alkyl], (CH$_2$)$_n$—CO—[(C$_1$-C$_3$)-alkyl], (CH$_2$)$_n$—CO-aryl, (CH$_2$)$_n$—CO—NH$_2$, (CH$_2$)$_q$—COOH, where the alkyl and cycloalkyl radicals may be substituted by fluorine atoms and where the aryl or heteroaryl radical may be substituted by halogen, CN, (C$_1$-C$_3$)-alkyl, O—(C$_1$-C$_3$)-alkyl, S(O)$_m$—(C$_1$-C$_3$)-alkyl, SO$_2$—NH$_2$, COOH, CONH$_2$, CO—[O(C$_1$-C$_3$)-alkyl], CO—(C$_1$-C$_3$)-alkyl, and where the alkyl radicals may be substituted by fluorine atoms;

R18 is (C$_1$-C$_4$)-alkyl, (C$_3$-C$_4$)-cycloalkyl, (CH$_2$)$_n$-aryl, (CH$_2$)$_n$-heteroaryl, where the alkyl and cycloalkyl radicals may be substituted by fluorine atoms and where the aryl or heteroaryl radical may be substituted by halogen, CN, (C$_1$-C$_3$)-alkyl, O—(C$_1$-C$_3$)-alkyl, SO$_2$—NH$_2$, COOH, CONH$_2$, CO—[O(C$_1$-C$_3$)-alkyl], CO—(C$_1$-C$_3$)-alkyl, and where the alkyl radicals may be substituted by fluorine atoms;

R20 is H, (C$_1$-C$_3$)-alkyl, (C$_3$-C$_5$)-cycloalkyl, aryl, [(C$_1$-C$_2$)-alkyl]-aryl;

R21 is H, F, CF$_3$, (C$_1$-C$_3$)-alkyl, (C$_3$-C$_4$)-cycloalkyl, OH, O—(C$_1$-C$_3$)-alkyl, O—(C$_3$-C$_4$)-cycloalkyl, O—(CH$_2$)$_n$-aryl, O—(CO)—(C$_1$-C$_3$)-alkyl, O—(CO)—O—(C$_1$-C$_3$)-alkyl, NH$_2$, NH—[(C$_1$-C$_2$)-alkyl]-aryl, NH—(C$_1$-C$_3$)-alkyl, NH—(CO)—(C$_1$-C$_3$)-alkyl;

R22 is H, CF$_3$, (C$_1$-C$_3$)-alkyl, aryl, [(C$_1$-C$_2$)-alkyl]-aryl;

and the physiologically compatible salts thereof.

Very particular preference is further given to compounds of the formula I in which one or more radicals are each defined as follows:

R, R' are each methyl;

or R and R' together form a cyclohexyl ring;

n is 0, 1, 2;

p is 1;

A, D, E, G, L are each independently C or N, where there is no corresponding R1, R2, R3, R4, R5 substituent when they are defined as N;

R1, R2, R5 are each independently H, F, Cl, Br, I, CN, CF$_3$, (C$_1$-C$_4$)-alkyl, O—(C$_1$-C$_4$)-alkyl, phenyl, —O-phenyl, SF$_5$, where the alkyl radicals may be substituted by fluorine atoms and where the phenyl radicals may be substituted by F, Cl, Br, I;

R3 is F, CN;

R4 is CF$_3$, (C$_1$-C$_4$)-alkyl, O—(C$_1$-C$_4$)-alkyl;

R6, R7, R8, R9, R10 are each independently H, F, Cl, Br, I, (C$_1$-C$_4$)-alkyl, O—(C$_1$-C$_4$)-alkyl, where the alkyl radicals may be substituted by fluorine atoms, NR17-aryl, where the aryl radical may be substituted by F, Cl, Br, I, (CH$_2$)$_n$—CO—NH$_2$, NH$_2$, —SO$_2$—NH$_2$, COOH, (CH$_2$)$_n$—P(O)(OH)[O—(C$_1$-C$_4$)-alkyl], (CH$_2$)$_n$—P(O)(OH)$_2$;

where one of the R6, R7, R8, R9 and R10 radicals is always defined as NR17-aryl;

R17 is H, (C$_1$-C$_4$)-alkyl;

and the physiologically compatible salts thereof.

Very particular preference is further given to compounds of the formula I in which R3 is F or CN and R4 is CF$_3$.

Very particular preference is further given to compounds of the formula I in which R3 is CN and R4 is CF$_3$.

Very particular preference is further given to compounds of the formula I in which A, D, E, G and L are each C.

Very particular preference is further given to compounds of the formula I in which p is 1.

When radicals or substituents (for example R12) can occur more than once in the compounds of the formula I, they may all each independently be defined as specified and be the same or different.

The invention further provides both stereoisomer mixtures of the formula I and the pure stereoisomers of the formula I, and also diastereoisomer mixtures of the formula I and the pure diastereoisomers. The mixtures are separated, for example, by a chromatographic route.

The invention relates to compounds of the formula I in the form of their tautomers, racemates, racemic mixtures, stereoisomer mixtures, pure stereoisomers, diastereoisomer mixtures, pure diastereoisomers. The mixtures are separated, for example, by a chromatographic route.

The alkyl radicals in the substituents R1 to R22 and R and R' may be either straight-chain or branched.

Owing to their high water solubility, pharmaceutically acceptable salts are particularly suitable for medical applications compared to the starting or base compounds. These salts must have a pharmaceutically acceptable anion or cation. Suitable pharmaceutically acceptable acid addition salts of the inventive compounds are salts of inorganic acids, such as hydrochloric acid, hydrobromic acid, phosphoric acid, metaphosphoric acid, nitric acid and sulfuric acid, and also organic acids, for example acetic acid, benzenesulfonic acid, benzoic acid, citric acid, ethanesulfonic acid, fumaric acid, gluconic acid, glycolic acid, isethionic acid, lactic acid, lactobionic acid, maleic acid, malic acid, methanesulfonic acid, succinic acid, p-toluenesulfonic acid and tartaric acid. Suitable pharmaceutically acceptable basic salts are ammonium salts, alkali metal salts (such as sodium and potassium salts), alkaline earth metal salts (such as magnesium and calcium salts), trometamol (2-amino-2-hydroxymethyl-1,3-propanediol), diethanolamine, lysine or ethylenediamine.

Salts with a pharmaceutically unacceptable anion, for example trifluoroacetate, are also included within the scope of the invention as useful intermediates for the preparation or purification of pharmaceutically acceptable salts and/or for use in non-therapeutic applications, for example in vitro applications.

The inventive compounds may also be present in different polymorphic forms, for example as amorphous and crystalline polymorphic forms. All polymorphic forms of the inventive compounds are included within the scope of the invention and are a further aspect of the invention.

Hereinafter, all references to "compound(s) of the formula I" relate to compound(s) of the formula I as described above, and to their salts and solvates as described herein.

An alkyl radical is understood to mean a straight-chain or branched hydrocarbon chain having from one to eight carbons, for example methyl, ethyl, isopropyl, tert-butyl, hexyl, heptyl, octyl. The alkyl radicals may be mono- or polysubstituted as described above.

A cycloalkyl radical is understood to mean a ring system which comprises one or more rings, is present in saturated or partially unsaturated form (with one or two double bonds) and is formed exclusively from carbon atoms, for example cyclopropyl, cyclopentyl, cyclopentenyl, cyclohexyl or adamantyl.

The cycloalkyl radicals may be mono- or polysubstituted by suitable groups as described above.

An aryl radical is understood to mean a phenyl, naphthyl, biphenyl, tetrahydronaphthyl, alpha- or beta-tetralonyl, indanyl or indan-1-onyl radical.

The aryl radicals may be mono- or polysubstituted by suitable groups as described above.

A heteroaryl radical is understood to mean aromatic rings and ring systems which, apart from carbon, also contain heteroatoms, for example nitrogen, oxygen or sulfur. This definition also includes ring systems in which the heteroaryl radical is fused to benzene rings. This likewise includes systems in which one or more CH group(s) has/have been replaced by C=O or C=S, preferably C=O.

Suitable heteroaryl radicals are, for example, furyl, imidazolyl, benzimidazolyl, indolyl, indolinyl, pyrimidinyl, pyridyl, pyrazinyl, pyrrolyl, thiazolyl, oxazolyl, thienyl, 1,2,3-triazolyl, 1,2,4-triazolyl, tetrazolyl, isoxazolyl, pyridazinyl, 1,3,5-triazinyl, 1,2,4-triazinyl; the 2H-pyridazin-3-one, dihydropyridazine-3,6-dione, imidazolidin-2-one, 1,3-dihydroimidazol-2-one, imidazolidin-2,5-dione, quinoline, isoquinoline, quinoxaline, quinazoline system.

The linkage to the heteroaryl radicals may be at any of the possible atoms; for example, pyridyl may be 2-, 3- or 4-pyridyl; thienyl may be 2- or 3-thienyl; furyl may be 2- or 3-furyl.

Also included are the corresponding N-oxides of these compounds, i.e., for example, 1-oxy-2-, -3- or -4-pyridyl.

The heteroaryl radicals may be mono- or polysubstituted by suitable groups as described above.

A bicyclic heterocycle is understood to mean aromatic and nonaromatic bicyclic ring systems having from 9 to 12 ring members. It is possible for up to five CH or $CH_2$ groups of the bicycle to be replaced independently by N, NR20, O, $S(O)_m$ or C=O, Suitable bicyclic heterocycles are, for example, benzimidazole, benzotriazole, indazole, indole, 2,3-dihydroindole, 1,3-dihydrobenzimidazole-2-one, 3-indazolinone, oxindole, isatin, indolin-3-one, 1-oxo-2-isoindoline, 2H-benzo[1,2,4]thiadiazine 1,1-dioxide, 1,3-dihydrobenzo[1,2,5]thiadiazole 2,2-dioxide, benzo[1,3,2]dithiazole 1,1,3,3-tetraoxide, saccharin, benzothiazole, benzoxazole.

The linkage to the bicyclic heterocycles may be at any of the possible atoms; for example, benzimidazolyl may be 2-, 4- or 5-benzimidazolyl; indolyl may be 2- or else 3-, 4-, 5-, 6- or 7-indolyl.

Also included are the corresponding N-oxides of these compounds.

The bicyclic heterocycles may be mono- or polysubstituted by suitable groups as described above.

Sugar is understood to mean polyhydroxy compounds, for example the D-aldoses erythrose, threose (tetroses); ribose, arabinose, xylose, lyxose (pentoses); allose, altrose, glucose, mannose, gulose, idose, galactose or talose (aldohexoses), in each case in their α- or β-form, and, where possible, in the furanose or pyranose form; see Peter M. Collins, Robert J. Ferrier: Monosaccharides, John Wiley & Sons Ltd, Chichester, England; 1995, pages 16-18 [ISBN 0 471 95342 3].

The term sugar is also understood to include D-ketoses (uloses), for example erythrulose, ribulose, xylulose, psicose, fructose, sorbose or tagatose, in each case in their α- or β-form, and, where possible, in the furanose or pyranose form; see Peter M. Collins, Robert J. Ferrier: Monosaccharides, John Wiley & Sons Ltd, Chichester, England; 1995, pages 19-21 [ISBN 0 471 95342 3].

Moreover, the term sugar is also understood to include acyclic polyhydroxy compounds, for example ethane-1,2-diol, glycerol, 1,2,3,4-tetrahydroxybutane (e.g. treitol), 1,2,3,4,5-pentahydroxypentane (e.g. arabitol), 1,2,3,4,5,6-hexahydroxyhexane (e.g. sorbitol) or D-glucamine.

The designation $(CH_2)_n$—O-sugar means that the ether can be formed with any hydroxyl function present in the sugar residue; when the linkage is via the anomeric hydroxyl function of the sugar, a glycosidic bond is present.

The designation $(CH_2)_n$—O-glucoside means that the linkage is via the anomeric hydroxyl group of the glucose.

The designation $(CH_2)_n$—O-galactoside means that the linkage is via the anomeric hydroxyl group of the galactose.

Sugar acid means aldonic acids; a representative example is D-gluconic acid; these acids may be present in free form or ring-closed to form lactones (see Peter M. Collins, Robert J. Ferrier: Monosaccharides, John Wiley & Sons Ltd, Chichester, England; 1995, pages 126-129 [ISBN 0 471 95342 3]).

The term "sugar acids" also refers to polyhydroxydicarboxylic acids which are derived from sugars; these acids may, under some circumstances, also be present in ring-closed form as lactones. Examples of such aldaric acids are D-glucaric acid, galactaric acid (mucic acid) or tartaric acid (see Peter M. Collins, Robert J. Ferrier: Monosaccharides, John Wiley & Sons Ltd, Chichester, England; 1995, pages 138-139 [ISBN 0 471 95342 3]).

The term "sugar acids" also includes those monosaccharide derivatives which contain an aldehyde function and a carboxylic acid function at the ends of the polyhydroxy-substituted chain (uronic acids). Representative examples include D-glucuronic acid, D-galacturonic acid and D-mannuronic acid. The uronic acids may also be present in ring-opened or ring-closed form (as the lactone) (see Peter M. Collins, Robert J. Ferrier: Monosaccharides, John Wiley & Sons Ltd, Chichester, England; 1995, pages 313-314 [ISBN 0 471 95342 3]).

The term "sugar acid" also includes L-ascorbic acid (vitamin C).

The designation $(CH_2)_n$—O-sugar acid means that the linkage to the sugar acid may be via a hydroxyl function as an ether, or in glycosidic form via the anomeric hydroxyl function or via the hydroxyl function of the carboxylic acid as an ester.

The designation $(CH_2)_n$—O-glucuronide means that the linkage to the D-glucuronic acid is in glycosidic form via the anomeric hydroxyl function of D-glucuronic acid.

The designation $(CH_2)_n$—O-sugar acid is also understood to mean those pyran derivatives which contain a double bond. These include, for example, hydroxylated 5,6-dihydro-4H-pyran-2-carboxylic acid or esters thereof. One example is methyl 4,5,6-trihydroxy-5,6-dihydro-4H-pyran-2-carboxylate.

The hydroxyl functions of the sugars and sugar acids may each independently be present in free form, in benzylated, acylated, particularly benzoylated or acetylated, or alkylated, particularly methylated, form; it is also possible for two hydroxyl groups to be reacted with acetone to give acetonide.

The invention also encompasses solvates or hydrates of the compounds of the formula I.

The compounds of the formula I are cannabinoid 1 receptor (CB1R) modulators and are, as such, suitable in humans and in animals for the treatment or for the prevention of diseases which are based on disruption of the endocannabinoid system.

For example, and without restriction, the compounds of the formula I are useful as psychotropic medicaments, especially for the treatment of psychiatric disorders including states of anxiety, depressions, disorders of the mind, insomnia, deliria, obsessive-compulsive neuroses, general psychoses, schizophrenia, attention deficit hyperactivity disorder (ADHD) in hyperkinetic children, and for the treatment of disorders in connection with the use of psychotropic substances, especially in the case of abuse of a substance and/or dependence on such a substance, including alcohol dependence and nicotine dependence, but also dependence on cocaine, methamphetamine and heroin (see, for example, Behavioral Pharmacology 2005, 16:275-296). Reviews of CBR1-mediated means of therapeutic intervention can be found, for example, in Ken Mackie: Annu. Rev. Pharmacol. Toxicol. 46, 101-122 (2006), S. C. Black: Curr. Opin. Investig. Drugs 5, 389-394 (2004), V. Di Marzio et al.: Nat. Rev. Drug Discov. 3, 771-784 (2004), B. Le Foll et al.: J. Pharmacol. Exp. Ther. 312, 875-883 (2005) or L. Walter et al.: Br. J. Pharmacol. 141, 775-785 (2004).

The inventive compounds of the formula I may be used as medicaments for the treatment of migraine, stress, disorders of psychosomatic origin, panic attacks, epilepsy, disrupted movement, especially dyskinesias or Parkinson's disease, trembling and dystonia. The inventive compounds of the formula I can also be used as medicaments for the treatment of disorders of memory, mental defects, especially for the treatment of age-related dementia, of Alzheimer's disease and for the treatment of reduced alertness or wakefulness. In addition, it is also possible to use the compounds of the formula I as neuroprotectors, for the treatment of ischemia, cranial injuries and the treatment of neurodegenerative disorders, including chorea, Huntington's chorea, Tourette's syndrome.

The inventive compounds of the formula I can also be used as medicaments in the treatment of pain; this includes neuropathic pain, acute peripheral pain, chronic pain of inflammatory origin.

The inventive compounds of the formula I may also serve as medicaments for the treatment of eating disorders (for example binge eating disorders, anorexia and bulimia), for the treatment of addiction to confectionery, carbohydrates, drugs, alcohol or other addictive substances.

The inventive compounds of the formula I are particularly suitable for the treatment of obesity or of bulimia, and for the treatment of type II diabetes and also for the treatment of dyslipidemias and of metabolic syndrome. The inventive compounds of the formula I are therefore useful for the treatment of obesity and of the risks associated with obesity, especially the cardiovascular risks.

Moreover, the inventive compounds may be used as medicaments for the treatment of gastrointestinal disorders, for the treatment of diarrhea, of gastric and intestinal ulcers, of vomiting, of bladder trouble and disorders of urination, of disorders of endocrine origin, of cardiovascular problems, of low blood pressure, of hemorrhagic shock, of septic shock, chronic liver cirrhosis, liver steatosis, of nonalcoholic steatohepatitis, of asthma, of Raynaud's syndrome, of glaucoma, of fertility problems, termination of pregnancy, early birth, inflammatory symptoms, disorders of the immune system, especially autoimmune and neuroinflammatory disorders, for example rheumatic inflammation of joints, reactive arthritis, of disorders which lead to demyelinization, of multiple sclerosis, of infection disorders and viral disorders, for example encephalitis, ischemic stroke, and as medicaments for chemotherapy of cancer, for the treatment of Guillain-Barré syndrome and for the treatment of osteoporosis.

The inventive compounds of the formula I may also find use as medicaments for the treatment of polycystic ovary syndrome (PCOS).

According to the present invention, the compounds of the formula I are particularly useful for the treatment of psychotic complaints, especially of schizophrenia, reduced alertness and hyperactivity (ADHD) in hyperkinetic children, for the treatment of eating disorders and of obesity, for the treatment of type II diabetes, for the treatment of deficits of memory and cognitive deficits, for the treatment of alcohol addiction, of nicotine addiction, i.e. for alcohol and tobacco withdrawal.

The inventive compounds of the formula I are very particularly useful for the treatment and prevention of eating disorders, appetite disorders, metabolic disorders, gastrointestinal disorders, inflammation symptoms, disorders of the immune system, psychotic disorders, alcohol addiction and nicotine addiction.

According to one of its aspects, the invention relates to the use of a compound of the formula I, the pharmaceutically acceptable salts thereof and the solvates or hydrates thereof for the treatment of the above-specified disorders and diseases.

The compound(s) of the formula I may also be administered in combination with further active ingredients.

The amount of a compound of the formula I which is required in order to achieve the desired biological effect is dependent upon a series of factors, for example the specific compound selected, the intended use, the mode of administration and the clinical condition of the patient. The daily dose is generally in the range from 0.3 mg to 100 mg (typically from 3 mg to 50 mg) per day per kilogram of bodyweight, for example 3-10 mg/kg/day. An intravenous dose may, for example, be in the range from 0.3 mg to 1.0 mg/kg and may suitably be administered as an infusion of from 10 ng to 100 ng per kilogram per minute. Suitable infusion solutions for these purposes may, for example, contain from 0.1 ng to 10 mg, typically from 1 ng to 10 mg, per milliliter. Single doses may contain, for example, from 1 mg to 10 g of the active ingredient. Ampoules for injections may therefore contain, for example, from 1 mg to 100 mg, and single dose formulations which can be administered orally, for example tablets or capsules, may contain, for example, from 1.0 to 1000 mg, typically from 10 to 600 mg. The compounds of the formula I may be used for therapy of the abovementioned conditions as the compounds themselves, although they are preferably in the form of a pharmaceutical composition with an acceptable carrier. The carrier of course has to be acceptable, in the sense that it is compatible with the other constituents of the composition and is not damaging to the health of the patient. The carrier may be a solid or a liquid or both and is preferably formulated with the compound as a single dose, for example as a tablet, which may contain from 0.05 to 95% by weight of the active ingredient. Further pharmaceutically active substances may likewise be present, including further compounds of the formula I. The inventive pharmaceutical compositions may be produced by one of the known pharmaceutical methods which consist essentially in mixing the constituents with pharmacologically acceptable carriers and/or excipients.

Inventive pharmaceutical compositions are those which are suitable for oral, rectal, topical, peroral (for example sublingual) and parenteral (for example subcutaneous, intramuscular, intradermal or intravenous) administration, although the most suitable mode of administration depends in each individual case on the nature and severity of the condition to be treated and on the type of the compound of the formula I used in each case. Coated formulations and coated slow-release formulations are also encompassed by the scope of the invention. Preference is given to acid- and gastric fluid-resistant formulations. Suitable gastric fluid-resistant coatings include cellulose acetate phthalate, polyvinyl acetate phthalate, hydroxypropylmethylcellulose phthalate and anionic polymers of methacrylic acid and methyl methacrylate.

Suitable pharmaceutical preparations for oral administration may be in the form of separate units, for example capsules, cachets, lozenges or tablets, each of which contains a certain amount of the compound of the formula I; as powder or granules; as solution or suspension in an aqueous or nonaqueous liquid; or as an oil-in-water or water-in-oil emulsion. These compositions may, as already mentioned, be prepared by any suitable pharmaceutical method which includes a step in which the active ingredient and the carrier (which may consist of one or more additional constituents) are brought into contact. In general, the compositions are prepared by uniform and homogeneous mixing of the active ingredient with a liquid carrier and/or finely divided solid carrier, after which the product is shaped if necessary. For example, a tablet can thus be produced by compressing or shaping a powder or granules of the compound, optionally with one or more additional constituents. Compressed tablets can be prepared by tableting the compound in free-flowing form, for example a powder or granules, optionally mixed with a binder, lubricant, inert diluent and/or one (or more) surfactants/dispersants in a suitable machine. Shaped tablets can be prepared by shaping the pulverulent compound moistened with an inert liquid diluent in a suitable machine.

Pharmaceutical compositions which are suitable for peroral (sublingual) administration include lozenges which contain a compound of the formula I with a flavoring, customarily sucrose, and gum arabic or tragacanth, and pastilles which include the compound in an inert base, such as gelatin and glycerol or sucrose and gum arabic.

Suitable pharmaceutical compositions for parenteral administration include preferably sterile aqueous preparations of a compound of the formula I which are preferably isotonic with the blood of the intended recipient. These preparations are preferably administered intravenously, although the administration may also be subcutaneous, intramuscular or intradermal as an injection. These preparations can preferably be produced by mixing the compound with water and making the solution obtained sterile and isotonic with the blood. Injectable compositions according to the invention generally contain from 0.1 to 5% by weight of the active compound.

Suitable pharmaceutical compositions for rectal administration are preferably in the form of single dose suppositories. These can be prepared by mixing a compound of the formula I with one or more conventional solid carriers, for example cocoa butter, and shaping the resulting mixture.

Suitable pharmaceutical compositions for topical application on the skin are preferably in the form of an ointment, cream, lotion, paste, spray, aerosol or oil. Useful carriers include petroleum jelly, lanolin, polyethylene glycols, alcohols and combinations of two or more of these substances. The active ingredient is generally present in a concentration of from 0.1 to 15% by weight of the composition, preferably from 0.5 to 2%.

Transdermal administration is also possible. Suitable pharmaceutical compositions for transdermal applications may be in the form of single plasters which are suitable for long-term close contact with the epidermis of the patient. Such plasters suitably contain the active ingredient in an optionally buffered aqueous solution, dissolved and/or dispersed in an adhesive or dispersed in a polymer. A suitable active ingredient concentration is from approx. 1% to 35%, preferably from approx. 3% to 15%. A particular means of releasing the active ingredient may be by electrotransport or iontophoresis, as described, for example, in Pharmaceutical Research, 2(6): 318 (1986).

Suitable further active ingredients for the combination products are:

All antidiabetics which are mentioned in the Rota Liste 2005, Chapter 12; all slimming agents/appetite suppressants which are mentioned in the Rota Liste 2005, Chapter 1; all lipid-lowering agents which are mentioned in the Rota Liste 2005, Chapter 58. They can be combined with the inventive compound of the formula I especially for synergistic improvement of action. The active ingredient combination can be administered either by separate addition of the active ingredients to the patient or in the form of combination preparations in which a plurality of active ingredients are present in a pharmaceutical formulation. Most of the active ingredients mentioned below are disclosed in USP Dictionary of USAN and International Drug Names, US Pharmacopeia, Rockville 2001.

Antidiabetics include insulin and insulin derivatives, for example LANTUS® (insulin glargine) (see www.lantus.com) or HMR1964 or LEVEMIR® (insulin detemir) or those as described in WO 2005005477 (Novo Nordisk), fast-acting insulins (see U.S. Pat. No. 6,221,633), inhalable insulins, for example EXUBERA®, or oral insulins, for example IN-105 (Nobex) or ORAL-LYN™ (Generex Biotechnology), GLP-1 derivatives and GLP-1 agonists, for example exenatide, liraglutide or those which have been disclosed in WO 98/08871, WO2005027978, WO2006037811, WO2006037810 by Novo Nordisk A/S, in WO 01/04156 by Zealand or in WO 00/34331 by Beaufour-Ipsen, pramlintide acetate (SYMLIN® Amylin Pharmaceuticals), BIM-51077, PC-DAC:Exendin-4 (an exendin-4 analog which is bonded covalently to recombinant human albumin), agonists as described, for example, in D. Chen et al., Proc. Natl. Acad. Sci. USA 104 (2007) 943, those as described in WO 2006124529, and orally active hypoglycemic ingredients.

Antidiabetics also include agonists of the glucose-dependent insulinotropic polypeptide (GIP) receptor, as described, for example, in WO 2006121860.

The orally active hypoglycemic ingredients preferably include sulfonylureas,
biguanidines,
meglitinides,
oxadiazolidinediones,
thiazolidinediones,
glucosidase inhibitors,
inhibitors of glycogen phosphorylase,
glucagon antagonists,
glucokinase activators,
inhibitors of fructose-1,6-bisphosphatase,
modulators of glucose transporter 4 (GLUT4),
inhibitors of glutamine: fructose-6-phosphate amidotransferase (GFAT),
GLP-1 agonists,
potassium channel openers, for example pinacidil, cromakalim, diazoxide, or those as described in R. D. Carr et al., Diabetes 52, 2003, 2513.2518, in J. B. Hansen et al, Current Medicinal Chemistry 11, 2004, 1595-1615, in T. M. Tagmose et al., J. Med. Chem. 47, 2004, 3202-3211 or in M. J. Coghlan et al., J. Med. Chem. 44, 2001, 1627-1653, or those which have been disclosed in WO 97/26265 and WO 99/03861 by Novo Nordisk A/S,
inhibitors of dipeptylpeptidase-IV (DPP-IV),
insulin sensitizers,
inhibitors of liver enzymes which are involved in the stimulation of gluconeogenesis and/or glycogenolysis,
modulators of glucose uptake, of glucose transport and of glucose reabsorption,
inhibitors of 11β-HSD1,
inhibitors of protein-tyrosine phosphatase 1B (PTP1B),
modulators of the sodium-dependent glucose transporter 1 or 2 (SGLT1, SGLT2),
lipid metabolism-modifying compounds, such as active antihyperlipidemic ingredients and active antilipidemic ingredients,
compounds which reduce nutrient intake,
compounds which increase thermogenesis,
PPAR and RXR modulators and
active ingredients which act on the ATP-dependent potassium channel of the beta cells.

In one embodiment of the invention, the compounds of the formula I are administered in combination with an HMG-CoA reductase inhibitor such as simvastatin, fluvastatin, pravastatin, lovastatin, atorvastatin, cerivastatin, rosuvastatin, L-659699.

In one embodiment of the invention, the compound of the formula I is administered in combination with a cholesterol absorption inhibitor, for example ezetimibe, tiqueside, pamaqueside, FM-VP4 (sitostanol/campesterol ascorbyl phosphate; Forbes Medi-Tech, WO2005042692, WO2005005453), MD-0727 (Microbia Inc., WO2005021497, WO2005021495), or with compounds as described in WO2002066464, WO2005000353 (Kotobuki Pharmaceutical Co. Ltd.) or WO2005044256 or WO2005062824 (Merck & Co.) or WO2005061451 and WO2005061452 (AstraZeneca AB) and WO2006017257 (Phenomix) or WO2005033100 (Lipideon Biotechnology AG) or as described in WO2004097655, WO2004000805, WO2004000804, WO2004000803, WO2002050068, WO2002050060, WO2005047248, WO2006086562, WO2006102674, WO2006116499, WO2006121861, WO2006122186, WO2006122216, WO2006127893, WO2006137794, WO2006137796, WO2006137782, WO2006137793, WO2006137797, WO2006137795, WO2006137792, WO2006138163.

In one embodiment of the invention, the compound of the formula I is administered in combination with VYTORIN™, a fixed combination of ezetimibe with simvastatin.

In one embodiment of the invention, the compound of the formula I is administered in combination with a fixed combination of ezetimibe with atorvastatin.

In one embodiment of the invention, the compound of the formula I is administered in combination with a fixed combination of ezetimibe with fenofibrate.

In a further embodiment of the invention, the compound of the formula I is administered in combination with a fixed combination of fenofibrate with rosuvastatin.

In a further embodiment of the invention, the compound of the formula I is administered in combination with SYNORDIA®, a fixed combination of fenofibrate with metformin.

In one embodiment of the invention, the compound of the formula I is administered in combination with ISIS-301012, an antisense oligonucleotide which is capable of regulating the apolipoprotein B gene.

In one embodiment of the invention, the compound of the formula I is administered in combination with a PPAR delta agonist, for example rosiglitazone, pioglitazone, JTT-501, GI 262570, R-483, CS-011 (rivoglitazone).

In one embodiment of the invention, the compound of the formula I is administered in combination with COMPETACT™, a fixed combination of pioglitazone hydrochloride with metformin hydrochloride.

In one embodiment of the invention, the compound of the formula I is administered in combination with TANDEMACT™, a fixed combination of pioglitazone with glimepiride.

In a further embodiment of the invention, the compound of the formula I is administered in combination with a fixed combination of pioglitazone hydrochloride with an angiotensin II agonist, for example TAK-536.

In one embodiment of the invention, the compound of the formula I is administered in combination with a PPAR alpha agonist, for example GW9578, GW-590735, K-111, LY-674, KRP-101, DRF-10945, LY-518674, or those as described in WO2001040207, WO2002096894, WO2005097076.

In one embodiment of the invention, the compound of the formula I is administered in combination with a mixed PPAR alpha/gamma agonist, for example naveglitazar, LY-510929, ONO-5129, E-3030, AVE 8042, AVE 8134, AVE 0847, CKD-501 (lobeglitazone sulfate), or as described in PCT/US 00/11833, PCT/US 00/11490, DE10142734.4 or in J. P. Berger et al., TRENDS in Pharmacological Sciences 28(5), 244-251, 2005.

In one embodiment of the invention, the compound of the formula I is administered in combination with a PPAR delta agonist, for example GW-501516, or as described in

WO2006059744, WO2006084176, WO2006029699, WO2007039172-WO2007039178.

In one embodiment, the compound of the formula I is administered in combination with metaglidasen or with MBX-2044 or other partial PPAR gamma agonists/antagonists In one embodiment of the invention, the compound of the formula I is administered in combination with a fibrate, for example fenofibrate, clofibrate, bezafibrate.

In one embodiment of the invention, the compound of the formula I is administered in combination with an MTP inhibitor, for example implitapide, BMS-201038, R-103757, AS-1552133, or as described in WO2005085226, WO2005121091, WO2006010423.

In one embodiment of the invention, the compound of the formula I is administered in combination with a CETP inhibitor, for example torcetrapib or JTT-705, or those as described in WO2006002342, WO2006010422, WO2006012093, WO2006073973, WO2006072362, WO2006097169, WO2007041494.

In one embodiment of the invention, the compound of the formula I is administered in combination with bile acid absorption inhibitors (see, for example, U.S. Pat. No. 6,245,744, U.S. Pat. No. 6,221,897 or WO00/61568), for example HMR 1741, or those as described in DE 10 2005 033099.1 and DE 10 2005 033100.9, WO2007009655-56.

In one embodiment of the invention, the compound of the formula I is administered in combination with a polymeric bile acid adsorber, for example cholestyramine, colesevelam.

In one embodiment of the invention, the compound of the formula I is administered in combination with an LDL receptor inducer (see U.S. Pat. No. 6,342,512), for example HMR1171, HMR1586, or those as described in WO2005097738.

In one embodiment of the invention, the compound of the formula I is administered in combination with an ABCA1 expression enhancer, as described, for example, in WO2006072393.

In a further embodiment of the invention, the compound of the formula I is administered in combination with an RNAi therapeutic agent which is directed to PCSK9 (proprotein convertase subtilisin/kexin type 9).

In one embodiment, the compound of the formula I is administered in combination with OMACOR® (omega-3 fatty acids; highly concentrated ethyl esters of eicosapentaenoic acid and of docosahexaenoic acid).

In one embodiment of the invention, the compound of the formula I is administered in combination with an ACAT inhibitor, for example avasimibe or SMP-797.

In one embodiment of the invention, the compound of the formula I is administered in combination with an antioxidant, for example OPC-14117, probucol, tocopherol, ascorbic acid, β-carotene or selenium.

In one embodiment of the invention, the compound of the formula I is administered in combination with a vitamin, for example vitamin B6 or vitamin B12.

In one embodiment of the invention, the compound of the formula I is administered in combination with a lipoprotein lipase modulator, for example ibrolipim (NO-1886).

In one embodiment of the invention, the compound of the formula I is administered in combination with an ATP-citrate lyase inhibitor, for example SB-204990.

In one embodiment of the invention, the compound of the formula I is administered in combination with a squalene synthetase inhibitor, for example BMS-188494, TAK-475, or as described in WO2005077907, JP2007022943.

In one embodiment of the invention, the compound of the formula I is administered in combination with a lipoprotein (a) antagonist, for example gemcabene (CI-1027).

In one embodiment of the invention, the compound of the formula I is administered in combination with an agonist of GPR109A (HM74A receptor agonists; NAR agonists (nicotinic acid receptor agonists), for example nicotinic acid or "extended release niacin" in conjunction with MK-0524A, or those compounds as described in WO2006045565, WO2006045564, WO2006069242, WO2006124490, WO2006113150, WO2007017261, WO2007017262, WO2007017265, WO2007015744, WO2007027532.

In another embodiment of the invention, the compound of the formula I is administered in combination with an agonist of GPR116, as described, for example, in WO2006067531, WO2006067532.

In one embodiment of the invention, the compound of the formula I is administered in combination with a lipase inhibitor, for example orlistat or cetilistat (ATL-962).

In one embodiment of the invention, the compound of the formula I is administered in combination with insulin.

In one embodiment, the compound of the formula I is administered in combination with a sulfonylurea, for example tolbutamide, glibenclamide, glipizide, gliclazide or glimepiride.

In one embodiment, the compound of the formula I is administered in combination with a substance which enhances insulin secretion, for example KCP-265 (WO2003097064), or those as described in WO2007026761.

In one embodiment, the compound of the formula I is administered in combination with agonists of the glucose-dependent insulinotropic receptor (GDIR), for example APD-668.

In one embodiment, the compound of the formula I is administered in combination with a biguanide, for example metformin.

In another embodiment, the compound of the formula I is administered in combination with a meglitinide, for example repaglinide, nateglinide or mitiglinide.

In a further embodiment, the compound of the formula I is administered with a combination of mitiglinide with a glitazone, e.g. pioglitazone hydrochloride.

In a further embodiment, the compound of the formula I is administered with a combination of mitiglinide with an alpha-glucosidase inhibitor.

In one embodiment, the compound of the formula I is administered in combination with a thiazolidinedione, for example troglitazone, ciglitazone, pioglitazone, rosiglitazone, or the compounds disclosed in WO 97/41097 of Dr. Reddy's Research Foundation, especially 5-[[4-[(3,4-dihydro-3-methyl-4-oxo-2-quinazolinylmethoxy]phenyl]methyl]-2,4-thiazolidinedione.

In one embodiment, the compound of the formula I is administered in combination with an α-glucosidase inhibitor, for example miglitol or acarbose.

In one embodiment, the compound of the formula I is administered in combination with an active ingredient which acts on the ATP-dependent potassium channel of the beta cells, for example tolbutamide, glibenclamide, glipizide, glimepiride or repaglinide.

In one embodiment, the compound of the formula I is administered in combination with more than one of the aforementioned compounds, for example in combination with a sulfonylurea and metformin, a sulfonylurea and acarbose, repaglinide and metformin, insulin and a sulfonylurea, insulin and metformin, insulin and troglitazone, insulin and lovastatin, etc.

In one embodiment, the compound of the formula I is administered in combination with an inhibitor of glycogen phosphorylase, for example PSN-357 or FR-258900, or those as described in WO2003084922, WO2004007455, WO2005073229-31, WO2005067932.

In one embodiment, the compound of the formula I is administered in combination with glucagon receptor antagonists, for example A-770077 or NNC-25-2504, or as described in WO2004100875, WO2005065680.

In one embodiment, the compound of the formula I is administered in combination with activators of glucokinase, for example LY-2121260 (WO2004063179), PSN-105, PSN-110, GKA-50, or those as described, for example, in WO2004072031, WO2004072066, WO2005080360, WO2005044801, WO2006016194, WO2006058923, WO2006112549, WO2006125972, WO2007017549, WO2007017649, WO2007007910, WO2007007040-42, WO2007006760-61, WO2007006814, WO2007007886, WO2007028135, WO2007031739, WO2007041365, WO2007041366, WO2007037534, WO2007043638, WO2007053345, WO2007051846, WO2007051845, WO2007053765, WO2007051847.

In one embodiment, the compound of the formula I is administered in combination with an inhibitor of gluconeogenesis, for example FR-225654.

In one embodiment, the compound of the formula I is administered in combination with inhibitors of fructose-1,6-bisphosphatase (FBPase), for example CS-917 (MB-06322) or MB-07803, or those as described in WO2006023515, WO2006104030, WO2007014619.

In one embodiment, the compound of the formula I is administered in combination with modulators of glucose transporter 4 (GLUT4), for example KST-48 (D.-O. Lee et al.: Arzneim.-Forsch. Drug Res. 54 (12), 835 (2004)).

In one embodiment, the compound of the formula I is administered in combination with inhibitors of glutamine: fructose-6-phosphate amidotransferase (GFAT), as described, for example, in WO2004101528.

In one embodiment, the compound of the formula I is administered in combination with inhibitors of dipeptidylpeptidase-IV (DPP-IV), for example vildagliptin (LAF-237), sitagliptin (MK-0431), sitagliptin phosphate, saxagliptin ((BMS-477118), GSK-823093, PSN-9301, SYR-322, SYR-619, TA-6666, TS-021, GRC-8200, GW-825964X, KRP-104, DP-893, ABT-341, ABT-279, or another salt thereof, or those compounds as described in WO2003074500, WO2003106456, WO2004037169, WO200450658, WO2005058901, WO2005012312, WO2005/012308, WO2006039325, WO2006058064, PCT/EP2005/007821, PCT/EP2005/008005, PCT/EP2005/008002, PCT/EP2005/008004, PCT/EP2005/008283, DE 10 2005 012874.2, DE 10 2005 012873.4, JP2006160733, WO2006071752, WO2006065826, WO2006078676, WO2006073167, WO2006068163, WO2006090915, WO2006104356, WO2006127530, WO2006111261, WO2007015767, WO2007024993, WO2007029086.

In one embodiment, the compound of the formula I is administered in combination with JANUMET™, a fixed combination of sitagliptin phosphate with metformin hydrochloride.

In one embodiment, the compound of the formula I is administered in combination with inhibitors of 11-beta-hydroxysteroid dehydrogenase 1 (11β-HSD1), for example BVT-2733, JNJ-25918646, INCB-13739, or those as described, for example, in WO200190090-94, WO200343999, WO2004112782, WO200344000, WO200344009, WO2004112779, WO2004113310, WO2004103980, WO2004112784, WO2003065983, WO2003104207, WO2003104208, WO2004106294, WO2004011410, WO2004033427, WO2004041264, WO2004037251, WO2004056744, WO2004058730, WO2004065351, WO2004089367, WO2004089380, WO2004089470-71, WO2004089896, WO2005016877, WO2005097759, WO2006010546, WO2006012227, WO2006012173, WO2006017542, WO2006034804, WO2006040329, WO2006051662, WO2006048750, WO2006049952, WO2006048331, WO2006050908, WO2006024627, WO2006040329, WO2006066109, WO2006074244, WO2006078006, WO2006106423, WO2006132436, WO2006134481, WO2006134467, WO2006135795, WO2006136502, WO2006138695, WO2006133926, WO2007003521, WO2007007688, US2007066584, WO2007047625, WO2007051811, WO2007051810.

In one embodiment, the compound of the formula I is administered in combination with inhibitors of protein-tyrosine phosphatase 1B (PTP1B), as described, for example, in WO200119830-31, WO200117516, WO2004506446, WO2005012295, WO2005116003, PCT/EP2005/005311, PCT/EP2005/005321, PCT/EP2005/007151, DE 10 2004 060542.4, WO2007009911, WO2007028145.

In one embodiment, the compound of the formula I is administered in combination with modulators of the sodium-dependent glucose transporter 1 or 2 (SGLT1, SGLT2), for example KGA-2727, T-1095, SGL-0010, AVE 2268, SAR7226 and sergliflozin, or as described, for example, in WO2004007517, WO200452903, WO200452902, PCT/EP2005/005959, WO2005085237, JP2004359630, WO2005121161, WO2006018150, WO2006035796, WO2006062224, WO2006058597, WO2006073197, WO2006080577, WO2006087997, WO2006108842, WO2007000445, WO2007014895 or by A. L. Handlon in Expert Opin. Ther. Patents (2005) 15(11), 1531-1540.

In one embodiment, the compound of the formula I is administered in combination with modulators of GPR40, as described, for example, in WO2007013689, WO2007033002.

In one embodiment, the compound of the formula I is administered in combination with modulators of GPR119b, as described, for example, in WO2004041274.

In one embodiment, the compound of the formula I is administered in combination with modulators of GPR119, as described, for example, in WO2005061489 (PSN-632408), WO2004065380, WO2007003960-62 and WO2007003964.

In a further embodiment, the compound of the formula I is administered in combination with modulators of GPR120.

In one embodiment, the compound of the formula I is administered in combination with inhibitors of hormone-sensitive lipase (HSL) and/or phospholipases, as described, for example, in WO2005073199, WO2006074957, WO2006087309, WO2006111321, WO2007042178.

In one embodiment, the compound of the formula I is administered in combination with inhibitors of acetyl-CoA carboxylase (ACC), for example those as described in WO199946262, WO200372197, WO2003072197, WO2005044814, WO2005108370, JP2006131559, WO2007011809, WO2007011811, WO2007013691.

In a further embodiment, the compound of the formula I is administered in combination with modulators of xanthine oxidoreductase (XOR).

In one embodiment, the compound of the formula I is administered in combination with an inhibitor of phosphoenolpyruvate carboxykinase (PEPCK), for example those as described in WO2004074288.

In one embodiment, the compound of the formula I is administered in combination with an inhibitor of glycogen synthase kinase-3 beta (GSK-3 beta), as described, for example, in US2005222220, WO2005085230, PCT/EP2005/005346, WO2003078403, WO2004022544, WO2003106410, WO2005058908, US2005038023, WO2005009997, US2005026984, WO2005000836, WO2004106343, EP1460075, WO2004014910, WO2003076442, WO2005087727, WO2004046117.

In one embodiment, the compound of the formula I is administered in combination with an inhibitor of serum/glucocorticoid-regulated kinase (SGK), as described, for example, in WO2006072354.

In one embodiment, the compound of the formula I is administered in combination with an agonist of the RUP3 receptor, as described, for example, in WO2007035355.

In one embodiment, the compound of the formula I is administered in combination with an inhibitor of protein kinase C beta (PKC beta), for example ruboxistaurin.

In another embodiment, the compound of the formula I is administered in combination with an activator of the gene which encodes the ataxia telangiectasia mutated (ATM) protein kinase, for example chloroquine.

In one embodiment, the compound of the formula I is administered in combination with an endothelin A receptor antagonist, for example avosentan (SPP-301).

In one embodiment, the compound of the formula I is administered in combination with inhibitors of "I-kappaB kinase" (IKK inhibitors), as described, for example, in WO2001000610, WO2001030774, WO2004022553, WO2005097129.

In one embodiment, the compound of the formula I is administered in combination with modulators of the glucocorticoid receptor (GR), as described, for example, in WO2005090336, WO2006071609, WO2006135826.

In a further embodiment, the compound of the formula I is employed in combination with CART modulators (see "Cocaine-amphetamine-regulated transcript influences energy metabolism, anxiety and gastric emptying in mice" Asakawa, A. et al.: Hormone and Metabolic Research (2001), 33(9), 554-558);

NPY antagonists, for example N-{4-[(4-aminoquinazolin-2-ylamino)methyl]cyclohexylmethyl}naphthalene-1-sulfonamide hydrochloride (CGP 71683A); NPY-5 receptor antagonists such as L-152804, or as described, for example, in WO2006001318;

NPY-4 receptor antagonists, as described, for example, in WO2007038942;

NPY-2 receptor antagonists, as described, for example, in WO2007038943;

peptide YY 3-36 (PYY3-36) or analogous compounds, for example CJC-1682 (PYY3-36 conjugated to human serum albumin via Cys34) or CJC-1643 (derivative of PYY3-36, which is conjugated to serum albumin in vivo) or those as described in WO2005080424, WO2006095166;

derivatives of the peptide obestatin as described by WO2006096847;

CB1R (cannabinoid receptor 1) antagonists (for example rimonabant, SR147778, SLV-319, AVE-1625, MK-0364 or salts thereof, or those compounds as described, for example, in EP 0656354, WO 00/15609, WO2001/64632, WO2001/64633, WO2001/64634, WO 02/076949, WO2005080345, WO2005080328, WO2005080343, WO2005075450, WO2005080357, WO200170700, WO2003026647-48, WO200302776, WO2003040107, WO2003007887, WO2003027069, U.S. Pat. No. 6,509,367, WO200132663, WO2003086288, WO2003087037, WO2004048317, WO2004058145, WO2003084930, WO2003084943, WO2004058744, WO2004013120, WO2004029204, WO2004035566, WO2004058249, WO2004058255, WO2004058727, WO2004069838, US20040214837, US20040214855, US20040214856, WO2004096209, WO2004096763, WO2004096794, WO2005000809, WO2004099157, US20040266845, WO2004110453, WO2004108728, WO2004000817, WO2005000820, US20050009870, WO200500974, WO2004111033-34, WO200411038-39, WO2005016286, WO2005007111, WO2005007628, US20050054679, WO2005027837, WO2005028456, WO2005063761-62, WO2005061509, WO2005077897, WO2006047516, WO2006060461, WO2006067428, WO2006067443, WO2006087480, WO2006087476, WO2006100208, WO2006106054, WO2006111849, WO2006113704, WO2007009705, WO2007017124, WO2007017126, WO2007018459, WO2007016460, WO2007020502, WO2007026215, WO2007028849, WO2007031720, WO2007031721, WO2007036945, WO2007038045, WO2007039740, US20070015810, WO2007046548, WO2007047737); cannabinoid receptor 1/cannabinoid receptor 2 (CB1/CB2) modulating compounds, as described, for example, in WO2007001939, WO2007044215, WO2007047737;

MC4 agonists (e.g. N-[2-(3a-benzyl-2-methyl-3-oxo-2,3,3a,4,6,7-hexahydropyrazolo[4,3-c]pyridin-5-yl)-1-(4-chlorophenyl)-2-oxoethyl]-1-amino-1,2,3,4-tetrahydronaphthalene-2-carboxamide (WO 01/91752)) or LB53280, LB53279, LB53278 or THIQ, MB243, RY764, CHIR-785, PT-141 or those as described in WO2005060985, WO2005009950, WO2004087159, WO2004078717, WO2004078716, WO2004024720, US20050124652, WO2005051391, WO2004112793, WOUS20050222014, US20050176728, US20050164914, US20050124636, US20050130988, US20040167201, WO2004005324, WO2004037797, WO2005042516, WO2005040109, WO2005030797, US20040224901, WO200501921, WO200509184, WO2005000339, EP1460069, WO2005047253, WO2005047251, WO2005118573, EP1538159, WO2004072076, WO2004072077, WO2006021655-57, WO2007009894, WO2007015162, WO2007041061, WO2007041052; orexin receptor antagonists (e.g. 1-(2-methylbenzoxazol-6-yl)-3-[1,5]naphthyridin-4-ylurea hydrochloride (SB-334867-A) or those as described, for example, in WO200196302, WO200185693, WO2004085403, WO2005075458, WO2006067224);

histamine H3 receptor agonists (e.g. 3-cyclohexyl-1-(4,4-dimethyl-1,4,6,7-tetrahydroimidazo[4,5-c]pyridin-5-yl) propan-1-one oxalic acid salt (WO 00/63208) or those as described in WO200064884, WO2005082893, WO2006107661, WO2007003804, WO2007016496, WO2007020213);

histamine H1/histamine H3 modulators, for example betahistine or its dihydrochloride;

CRF antagonists (e.g. [2-methyl-9-(2,4,6-trimethylphenyl)-9H-1,3,9-triazafluoren-4-yl]-dipropylamine (WO 00/66585));

CRF BP antagonists (e.g. urocortin);

urocortin agonists;

agonists of the beta-3 adrenoceptor, for example 1-(4-chloro-3-methanesulfonylmethylphenyl)-2-[2-(2,3-dimethyl-1H-indol-6-yloxy)ethylamino]ethanol hydrochloride (WO 01/83451) or solabegron (GW-427353) or N-5984 (KRP-204), or those as described in JP2006111553, WO2002038543, WO2007048840-843;

MSH (melanocyte-stimulating hormone) agonists;

MCH (melanine-concentrating hormone) receptor antagonists (for example NBI-845, A-761, A-665798, A-798, ATC-0175, T-226296, T-71, GW-803430 or those compounds as described in WO2005085200, WO2005019240, WO2004011438, WO2004012648, WO2003015769, WO2004072025, WO2005070898, WO2005070925, WO2004039780, WO2004092181, WO2003033476, WO2002006245, WO2002089729, WO2002002744, WO2003004027, FR2868780, WO2006010446, WO2006038680, WO2006044293, WO2006044174, JP2006176443, WO2006018280, WO2006018279, WO2006118320, WO2006130075, WO2007018248, WO2007012661, WO2007029847, WO2007024004, WO2007039462, WO2007042660, WO2007042668, WO2007042669, US2007093508, US2007093509, WO2007048802, JP2007091649);

CCK-A agonists (for example {2-[4-(4-chloro-2,5-dimethoxyphenyl)-5-(2-cyclohexylethyl)thiazol-2-ylcarbamoyl]-5,7-dimethylindol-1-yl}acetic acid trifluoroacetic acid salt (WO 99/15525) or SR-146131 (WO 0244150) or SSR-125180), or those as described in WO2005116034;

serotonin reuptake inhibitors (e.g. dexfenfluramine);

mixed serotonin/dopamine reuptake inhibitors (e.g. bupropion) or fixed combinations of bupropion with naltrexone;

mixed serotoninergic and noradrenergic compounds (e.g. WO 00/71549);

5-HT receptor agonists, e.g. 1-(3-ethylbenzofuran-7-yl)piperazine oxalic acid salt (WO 01/09111);

mixed dopamine/norepinephrine/acetylcholine reuptake inhibitors (e.g. tesofensine);

5-HT2C receptor agonists (for example lorcaserin hydrochloride (APD-356) or BVT-933 or those as described in WO200077010, WO200077001-02, WO2005019180, WO2003064423, WO200242304, WO2005035533, WO2005082859, WO2006077025, WO2006103511);

5-HT6 receptor modulators, for example E-6837 or BVT-74316, or those as described, for example, in WO2005058858, WO2007054257;

bombesin receptor agonists (BRS-3 agonists);

galanin receptor antagonists;

growth hormone (e.g. human growth hormone or AOD-9604);

growth hormone-releasing compounds (6-benzyloxy-1-(2-diisopropylaminoethylcarbamoyl)-3,4-dihydro-1H-isoquinoline-2-carboxylic acid tert-butyl ester (WO 01/85695));

growth hormone secretagogue receptor antagonists (ghrelin antagonists), for example A-778193 or those as described in WO2005030734;

TRH agonists (see, for example EP 0 462 884);

decoupling protein 2- or 3-modulators;

leptin agonists (see, for example, Lee, Daniel W.; Leinung, Matthew C.; Rozhavskaya-Arena, Marina; Grasso, Patricia. Leptin agonists as a potential approach to the treatment of obesity.

Drugs of the Future (2001), 26(9), 873-881);

DA agonists (bromocriptine, doprexin);

lipase/amylase inhibitors (e.g. WO 00/40569);

inhibitors of diacylglycerol O-acyltransferases (DGATs), for example BAY-74-4113 or as described, for example, in US2004/0224997, WO2004094618, WO200058491, WO2005044250, WO2005072740, JP2005206492, WO2005013907, WO2006004200, WO2006019020, WO2006064189, WO2006082952, WO2006120125, WO2006113919, WO2006134317, WO2007016538;

inhibitors of fatty acid synthase (FAS), for example C75 or those as described in WO2004005277;

inhibitors of stearoyl-CoA delta9 desaturase (SCD1), as described, for example, in WO2007009236, WO2007044085, WO2007046867, WO2007046868, WO20070501124; oxyntomodulin;

oleoyl-estrone;

or agonists or partial agonists of the thyroid hormone receptor (thyroid hormone receptor agonists), for example: KB-2115 or those as described in WO20058279, WO200172692, WO200194293, WO2003084915, WO2004018421, WO2005092316, WO2007003419, WO2007009913, WO2007039125.

In one embodiment, the further ingredient is varenicline tartrate, a partial agonist of the alpha 4-beta 2 nicotinic acetylcholine receptor.

In one embodiment, the further active ingredient is trodusquemine.

In one embodiment, the further active ingredient is a modulator of the enzyme SIRT1.

In one embodiment of the invention, the further active ingredient is leptin; see, for example, "Perspectives in the therapeutic use of leptin", Salvador, Javier; Gomez-Ambrosi, Javier; Fruhbeck, Gema, Expert Opinion on Pharmacotherapy (2001), 2(10), 1615-1622.

In one embodiment, the further active ingredient is dexamphetamine or amphetamine.

In one embodiment, the further active ingredient is fenfluramine or dexfenfluramine.

In another embodiment, the further active ingredient is sibutramine.

In one embodiment, the further active ingredient is mazindol or phentermine.

In one embodiment, the further active ingredient is a diphenylazetidinone derivative, as described, for example, in U.S. Pat. No. 6,992,067 or U.S. Pat. No. 7,205,290.

In one embodiment, the compound of the formula I is administered in combination with dietary fiber, preferably insoluble dietary fiber (see, for example, Carob/CAROMAX® (Zunft H J; et al., Carob pulp preparation for treatment of hypercholesterolemia, ADVANCES IN THERAPY (2001 September-October), 18(5), 230-6.) CAROMAX is a carob-containing product from Nutrinova, Nutrition Specialties &Food Ingredients GmbH, Industriepark Höchst, 65926 Frankfurt/Main)). The combination with CAROMAX® can be effected in one formulation, or by separate administration of compounds of the formula I and CAROMAX®. CAROMAX® can also be administered in the form of foods, for example in bakery products or muesli bars.

It will be appreciated that any suitable combination of the inventive compounds with one or more of the aforementioned compounds and optionally one or more further pharmacologically active substances is considered to fall within the scope of protection of the present invention.

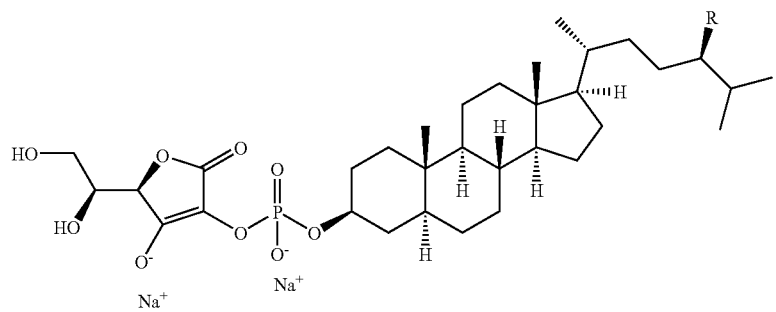
FM-VP4
R = CH₃; CH₂—CH₃
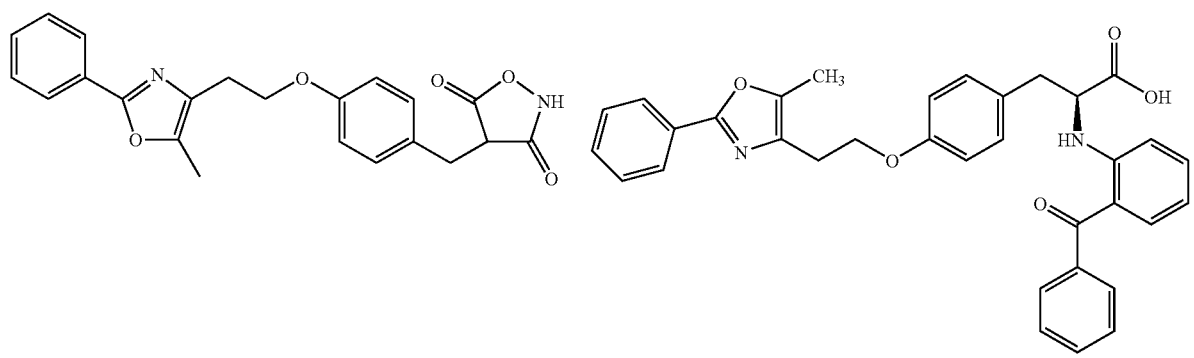
JTT-501
GI 262570
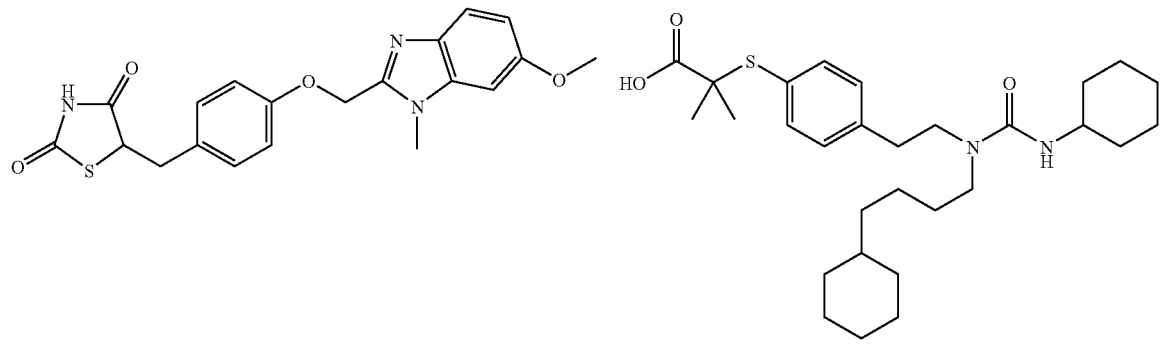
CS-011
Rivoglitazone
GW-9578
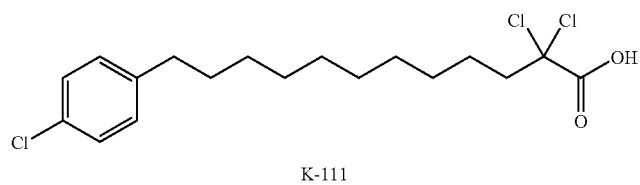
K-111
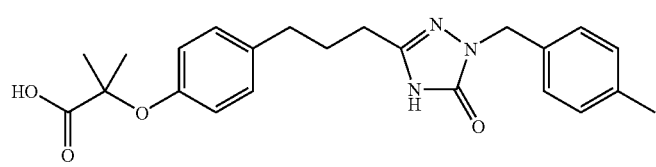
LY-674

-continued
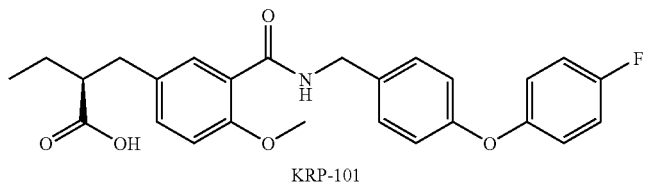
KRP-101
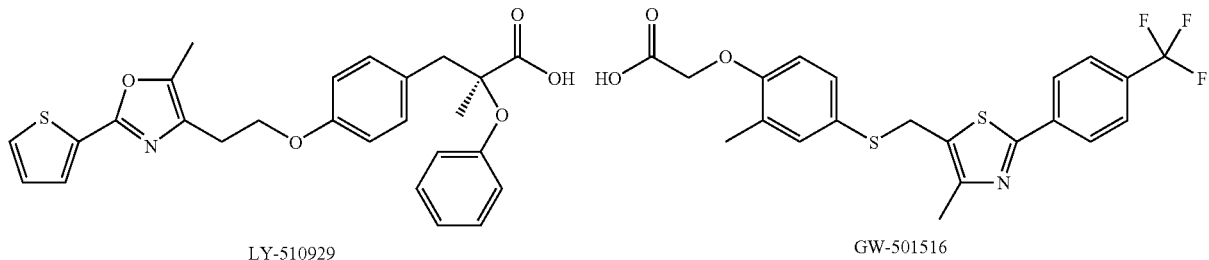
LY-510929
GW-501516
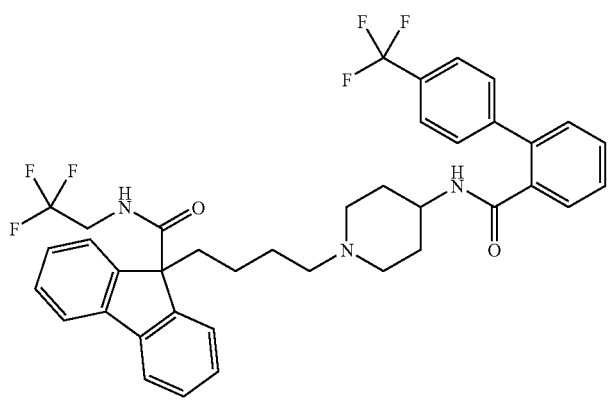
BMS-201038
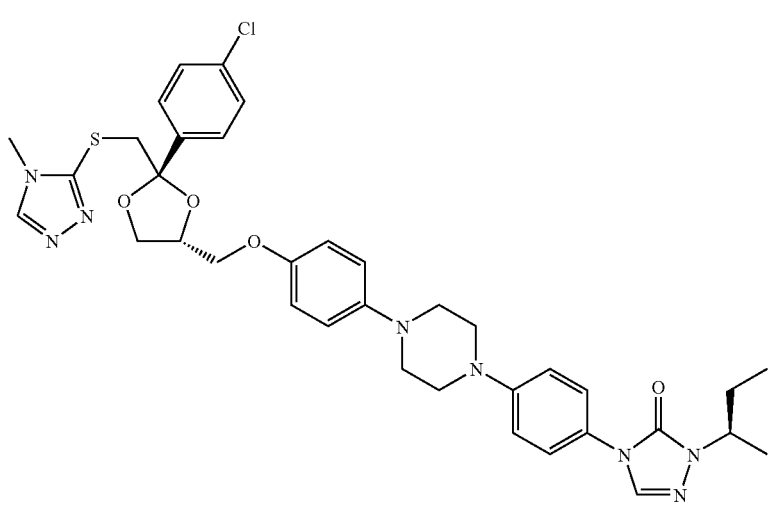
R-103757

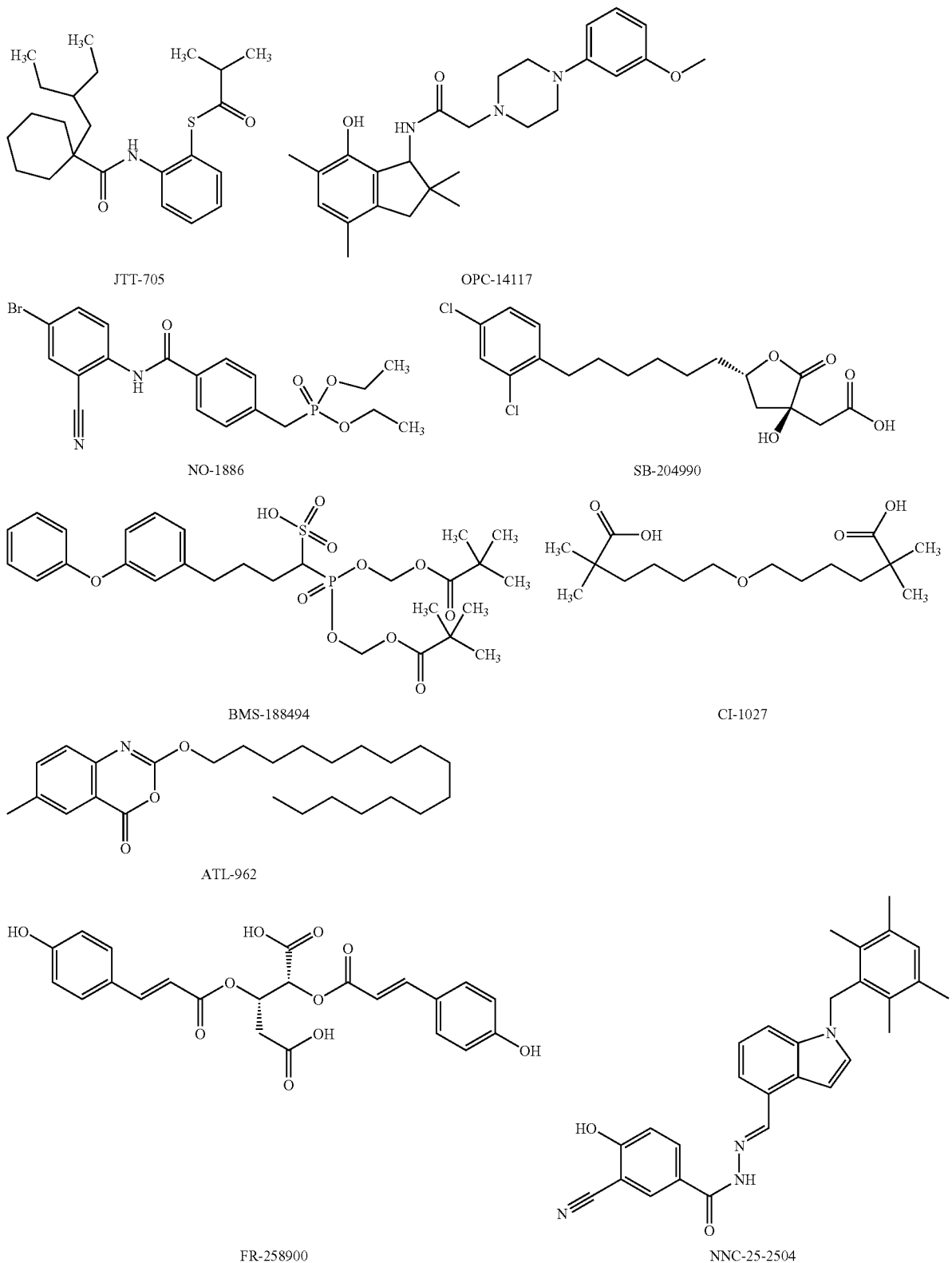

-continued
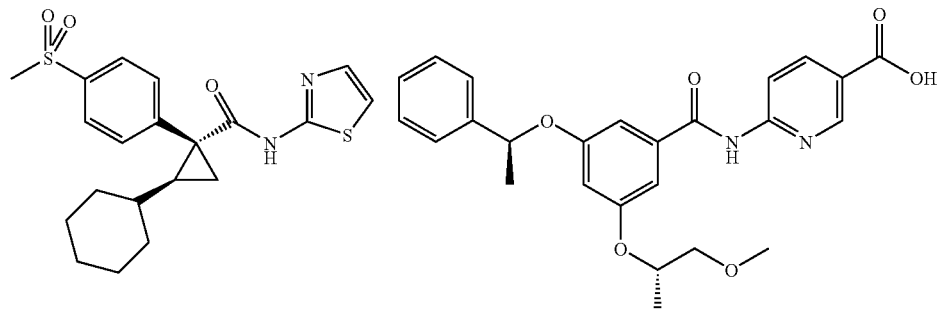
LY-2121260
GKA-50
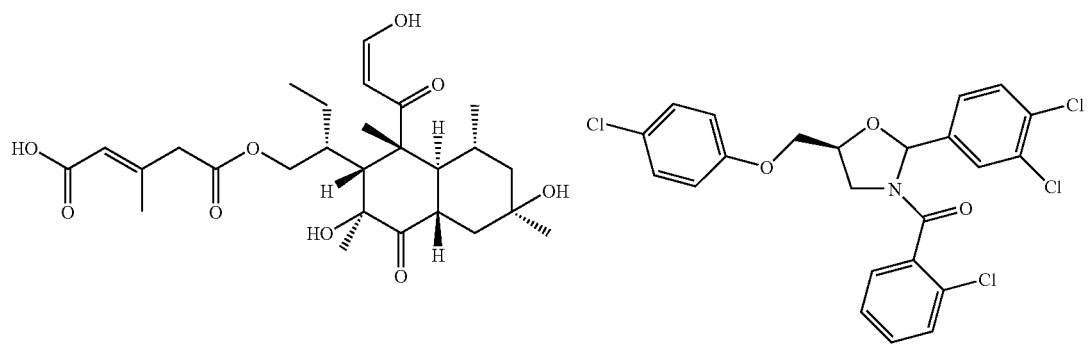
FR-225654
KST-48
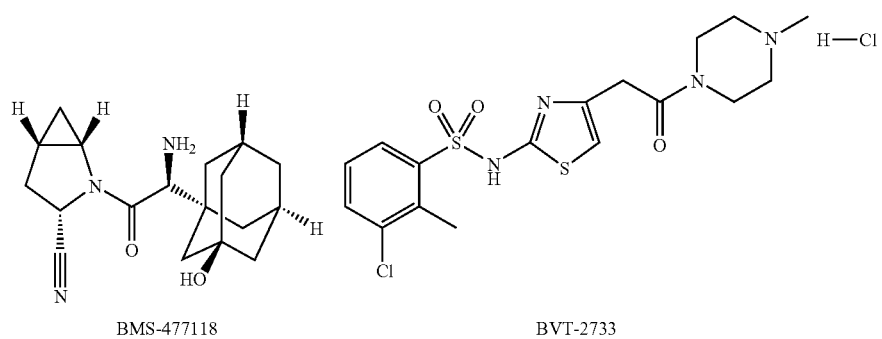
BMS-477118
BVT-2733
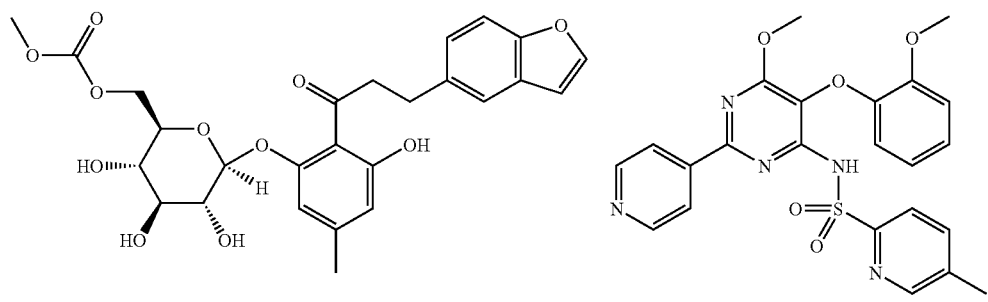
T-1095
SPP-301

-continued
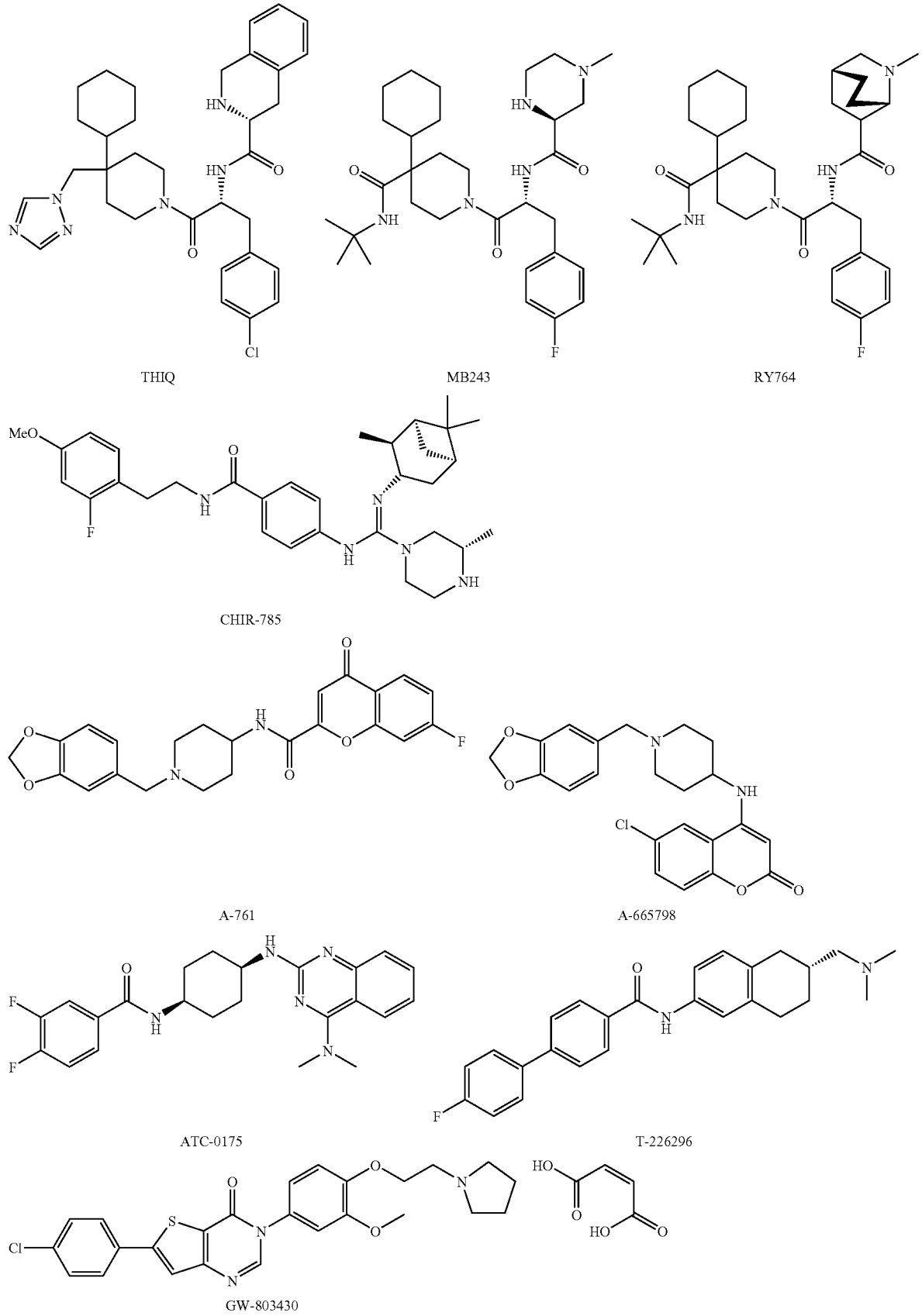

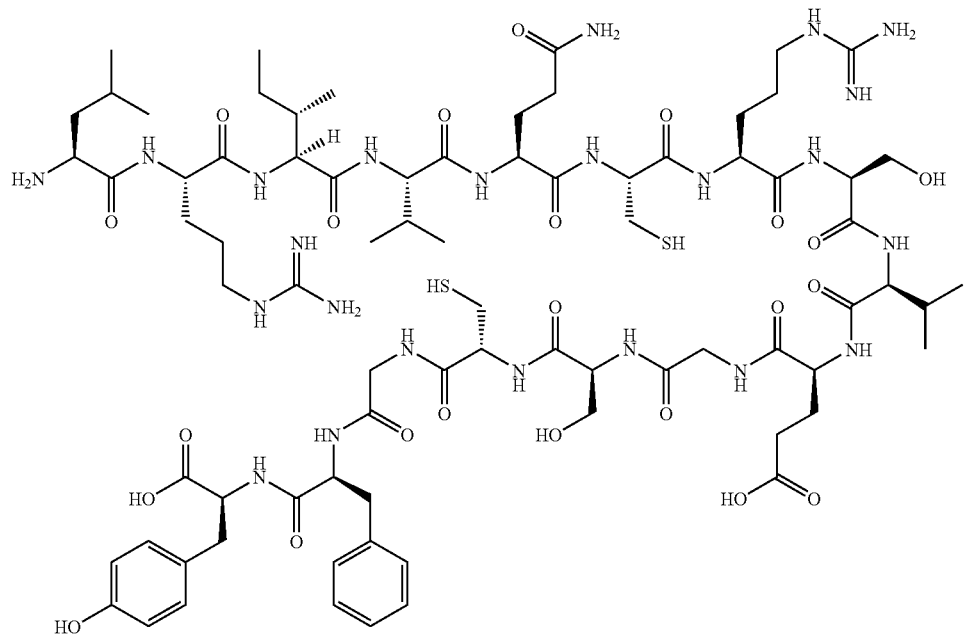
AOD-9604
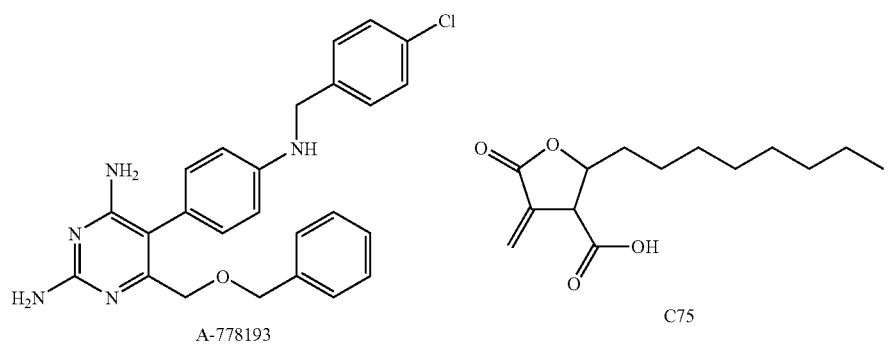
A-778193    C75
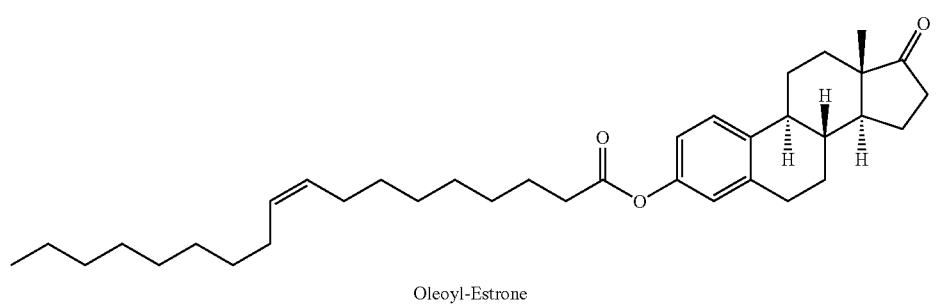
Oleoyl-Estrone
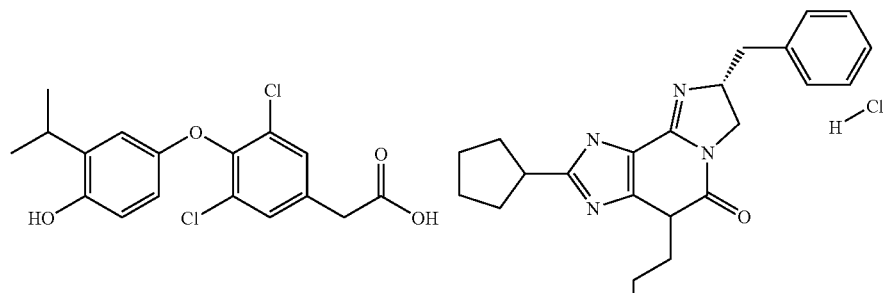
KB-2115    KCP-265

-continued
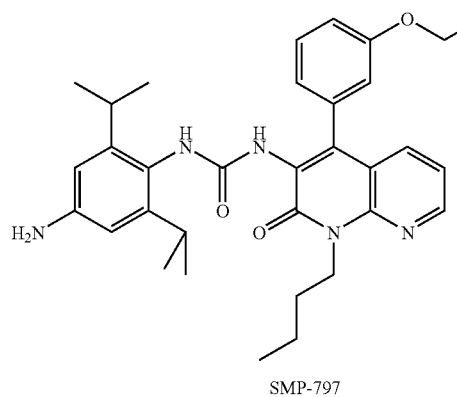
SMP-797
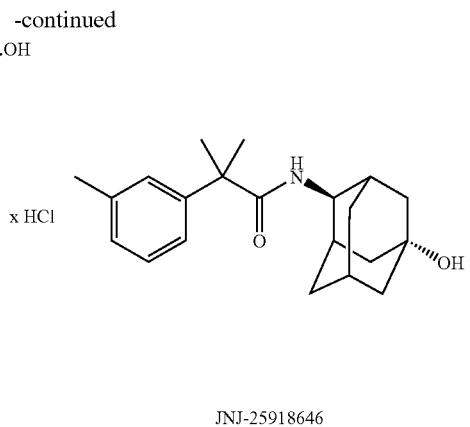
JNJ-25918646
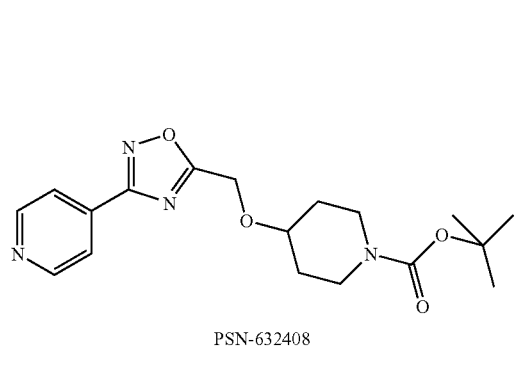
PSN-632408
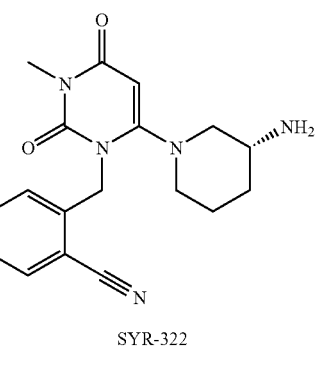
SYR-322
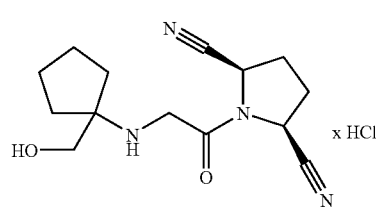
DP-893
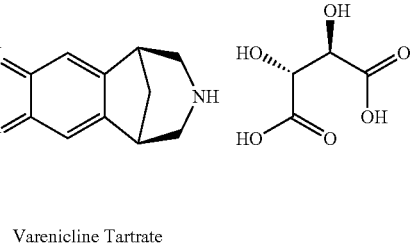
Varenicline Tartrate
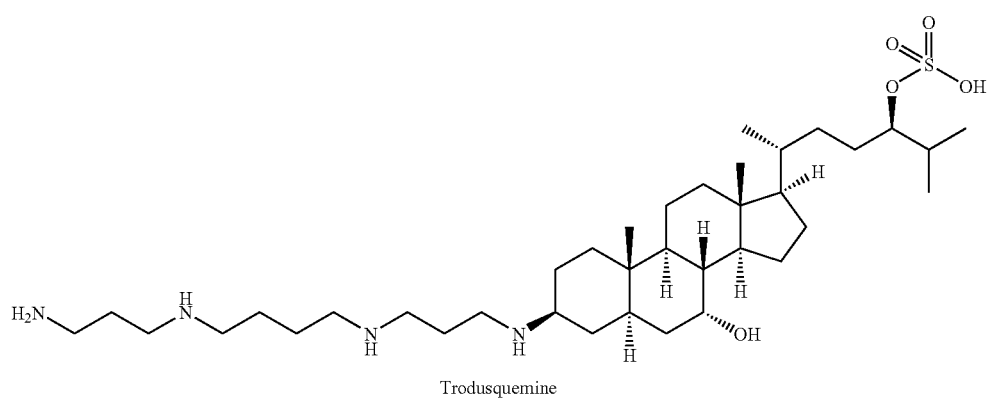
Trodusquemine
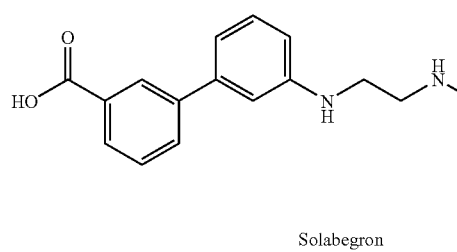
Solabegron
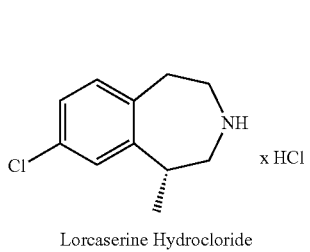
Lorcaserine Hydrochloride -continued
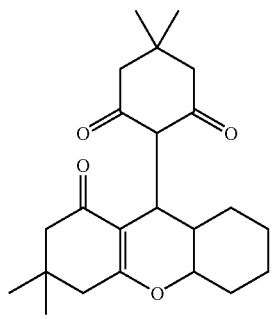
L-152804
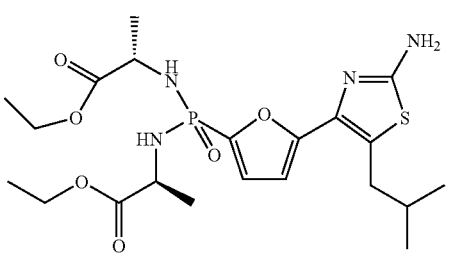
MB-06322
CS-917
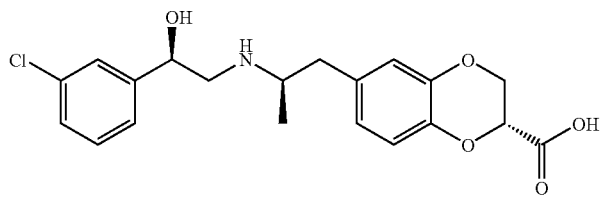
N-5984
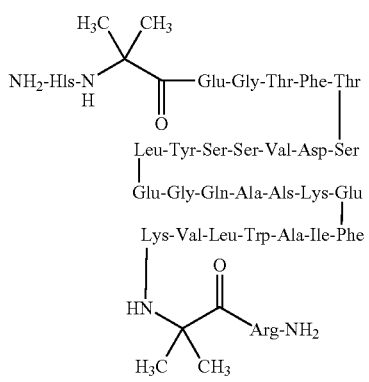
BIM-51077
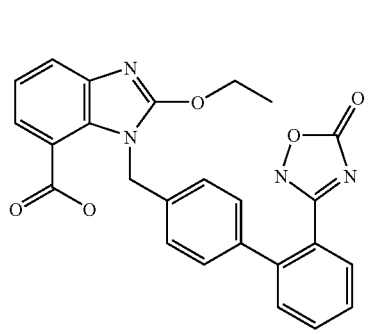
TAK-536
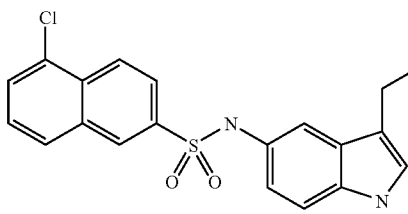
E-6837
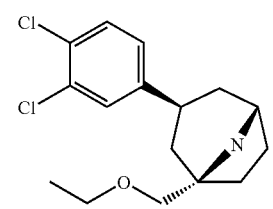
Tesofensine
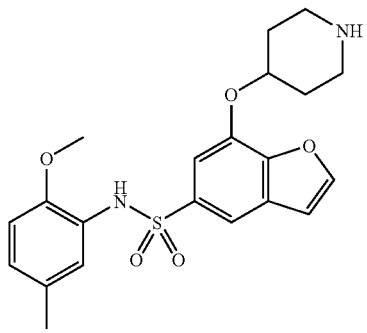
BVT-74316
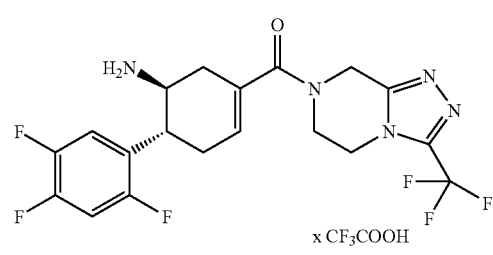
ABT-341

-continued
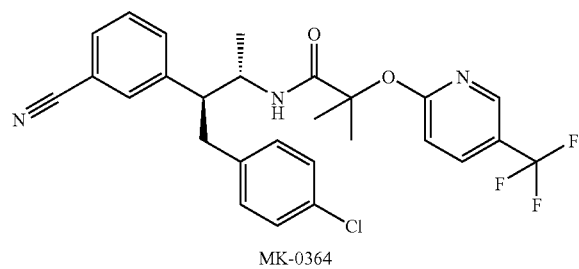
MK-0364
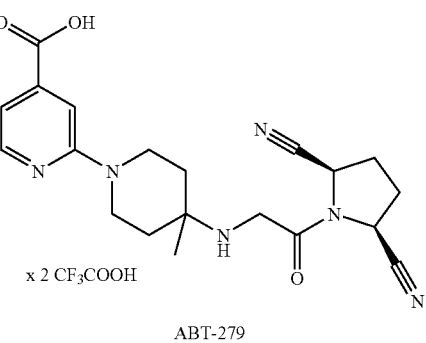
x 2 CF₃COOH
ABT-279
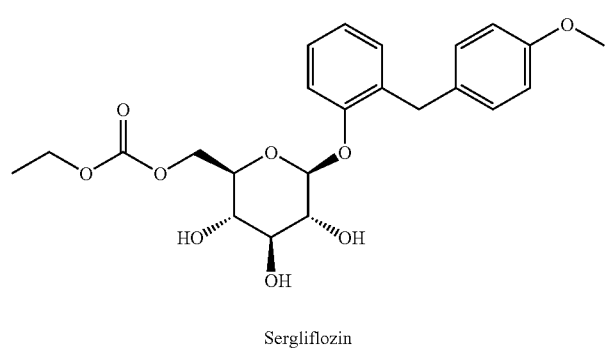
Sergliflozin
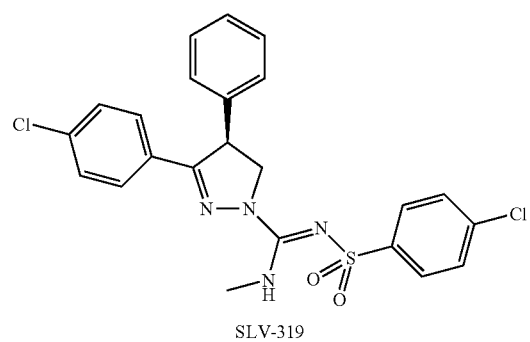
SLV-319
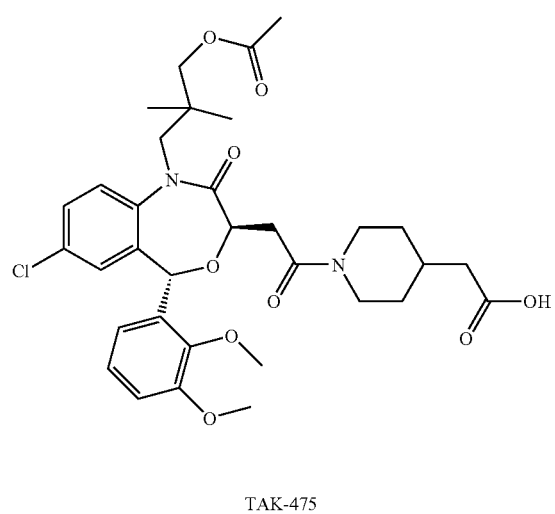
TAK-475
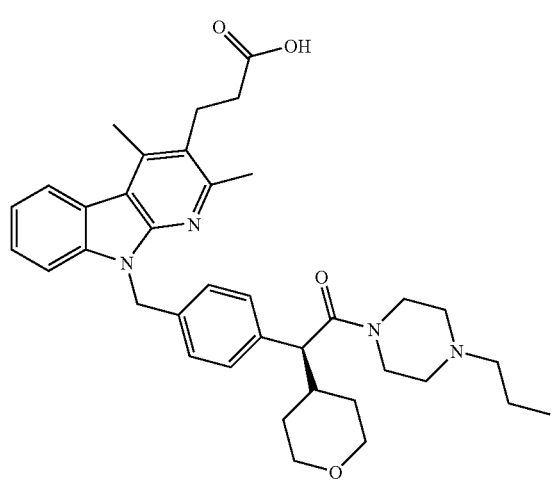
AS-1552133
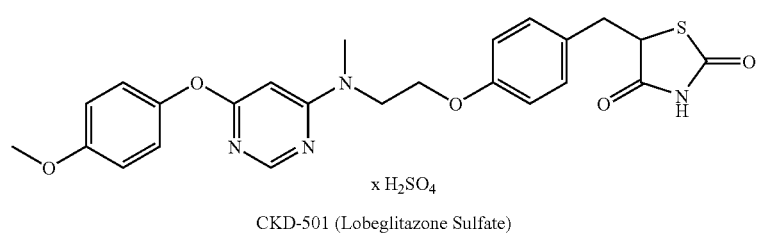
x H₂SO₄
CKD-501 (Lobeglitazone Sulfate)

Further suitable active ingredients for combination preparations are:

all antiepileptics specified in the Rote Liste 2006, Chapter 15;
all antihypertensives specified in the Rote Liste 2006, Chapter 17;
all hypotonics specified in the Rote Liste 2006, Chapter 19;
all anticoagulants specified in the Rote Liste 2006, Chapter 20;
all arteriosclerotic drugs specified in the Rote Liste 2006, Chapter 25;
all beta receptors, calcium channel blockers and inhibitors of the renin angiotensin system specified in the Rote Liste 2006, Chapter 27;
all diuretics and perfusion-promoting drugs specified in the Rote Liste 2006, Chapter 36 and 37;
all withdrawal drugs/drugs for the treatment of addictive disorders specified in the Rote Liste 2006, Chapter 39;
all coronary drugs and gastrointestinal drugs specified in the Rote Liste 2006, Chapter 55 and 60;
all migraine drugs, neuropathy preparations and Parkinson's drugs specified in the Rote Liste 2006, Chapter 61, 66 and 70.

The invention further provides processes for preparing the compounds of the general formula I, wherein the compounds of the formula I are obtained by proceeding analogously to the following reaction schemes:

Process "A":

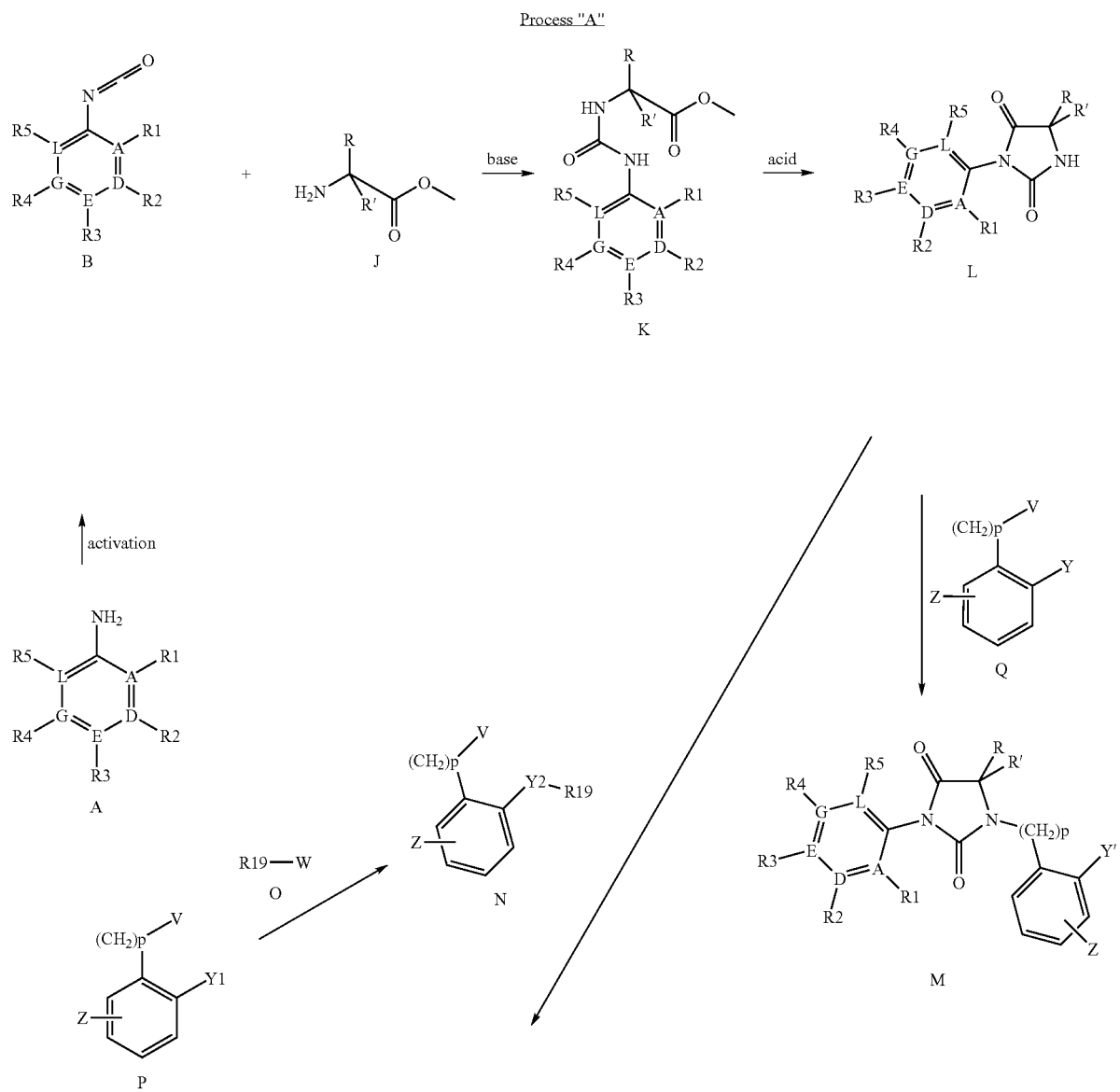

-continued

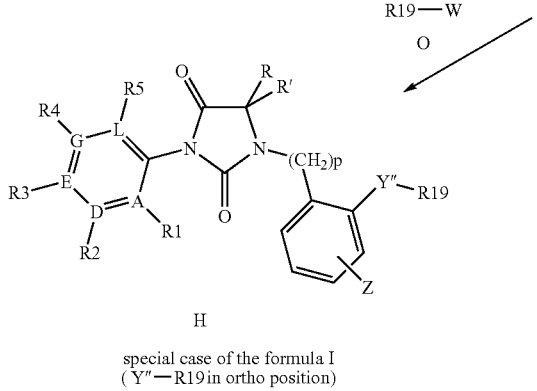

H
special case of the formula I
(Y"—R19 in ortho position)

In a first process "A", the procedure is to convert a suitably substituted aniline of the formula A in which the R1 to R5 radicals are present in protected form if necessary into an isocyanate of the formula B. This conversion can be performed, for example, with phosgene in toluene or with diphosgene or triphosgene. The isocyanate B is subsequently reacted with the methyl ester or another ester (e.g. tert-butyl) of the amino acid J in which R and R' are each as defined in formula I, or a salt of an ester of the amino acid J with addition of a base (e.g. triethylamine) to give a urea of the formula K. This urea can be ring-closed under basic or acidic conditions, preferably acidic conditions, to give the imidazolidine-2,4-dione of the formula L. The further conversion to a compound of the formula H, which is the ortho-substituted special case of a compound of the formula I, can, for example, be effected by alkylating it with a suitably substituted compound Q where Z may be one or more substituents as described above in formula I, and Y is either a halogen atom, preferably a bromine atom, or else a suitably protected amino function (e.g. isoindole-1,3-dion-2-yl or N=CH—N(CH$_3$)$_2$), and V is either also a halogen atom, preferably a chlorine or bromine atom, or else, for example, an O—SO$_2$—C$_6$H$_4$-4-CH$_3$ radical or an O—SO$_2$—CH$_3$ radical or an O—SO$_2$—CF$_3$ radical to obtain the compound M. M can be converted further under Buchwald-Hartwig conditions (e.g.: S. L. Buchwald et al.: Acc. Chem. Res. 1998, 31, 805; J. F. Hartwig et al.: J. Org. Chem. 1999, 64, 5575-5580; J. P. Wolfe et al.: J. Org. Chem. 2000, 65, 144-1157; M. D. Charles et al.: Org. Lett. 2005, 7, 3965-68) to compounds of the formula H. In M, Y' is defined as Br and NH$_2$ respectively when W is defined as NH$_2$ and Br respectively in the reactant O. Or the further conversion of the compound L to the compound H can be effected by alkylating L by reacting it with a compound of the formula N where V may be defined as just outlined, and where Y2 may be defined as NH or N-protecting groups. The compound N in turn may be obtained by reacting P in which V may be defined as described above and where Y1 is bromine or NH$_2$ with a possibly substituted R19-W compound O under, for example, Buchwald-Hartwig conditions. In this case, W is defined as NH$_2$ when Y1 is defined as Br and as Br when Y1 is defined as NH$_2$. R19 is defined as substituted or unsubstituted aryl, heteroaryl or bicyclic heteroaryl.

Any protecting groups present in compound H may be removed at the end and the Y" radical may, if required, be converted further by means of standard reactions of NH or N-protecting group according to NR17.

The formula H shown here constitutes a special case of the formula I in which the Y"—R19 radical in formula I is in the ortho position; this radical may, mutatis mutandis, also be present in the meta or para position.

One variant of process "A" is process "A'":

Process "A'"

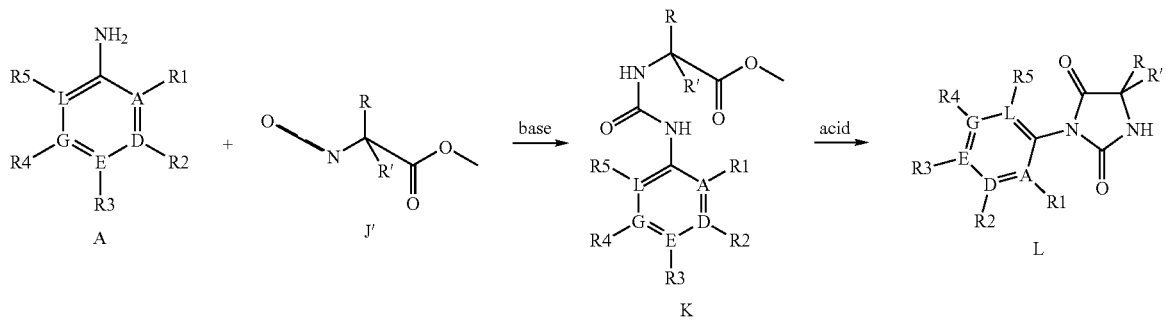

-continued
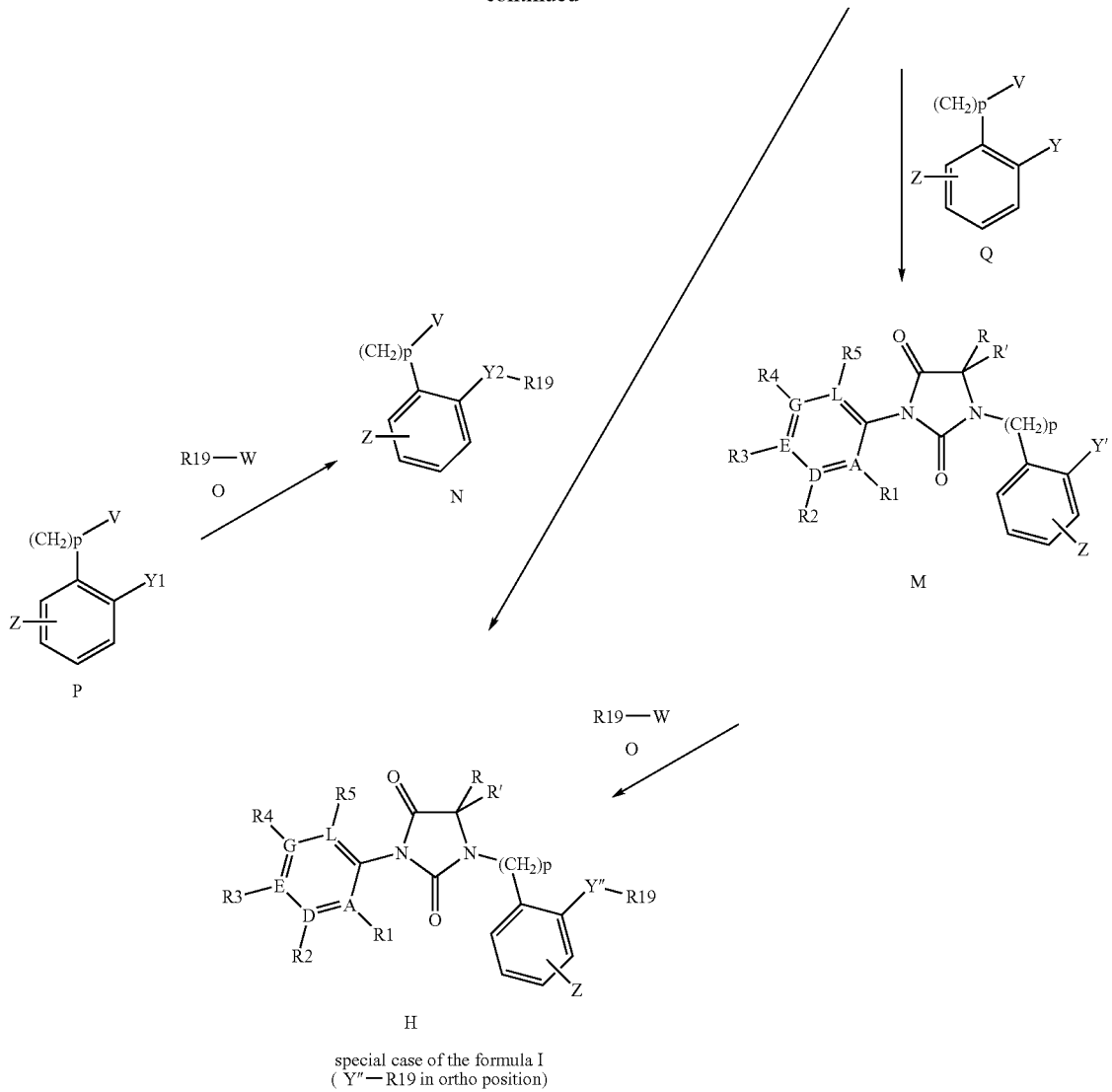
special case of the formula I
( Y″—R19 in ortho position)
In process "A'", the amine A is reacted with the isocyanate of the amino acid ester J' to form the compound K. The further steps may be effected as in process "A".
In another process "B"

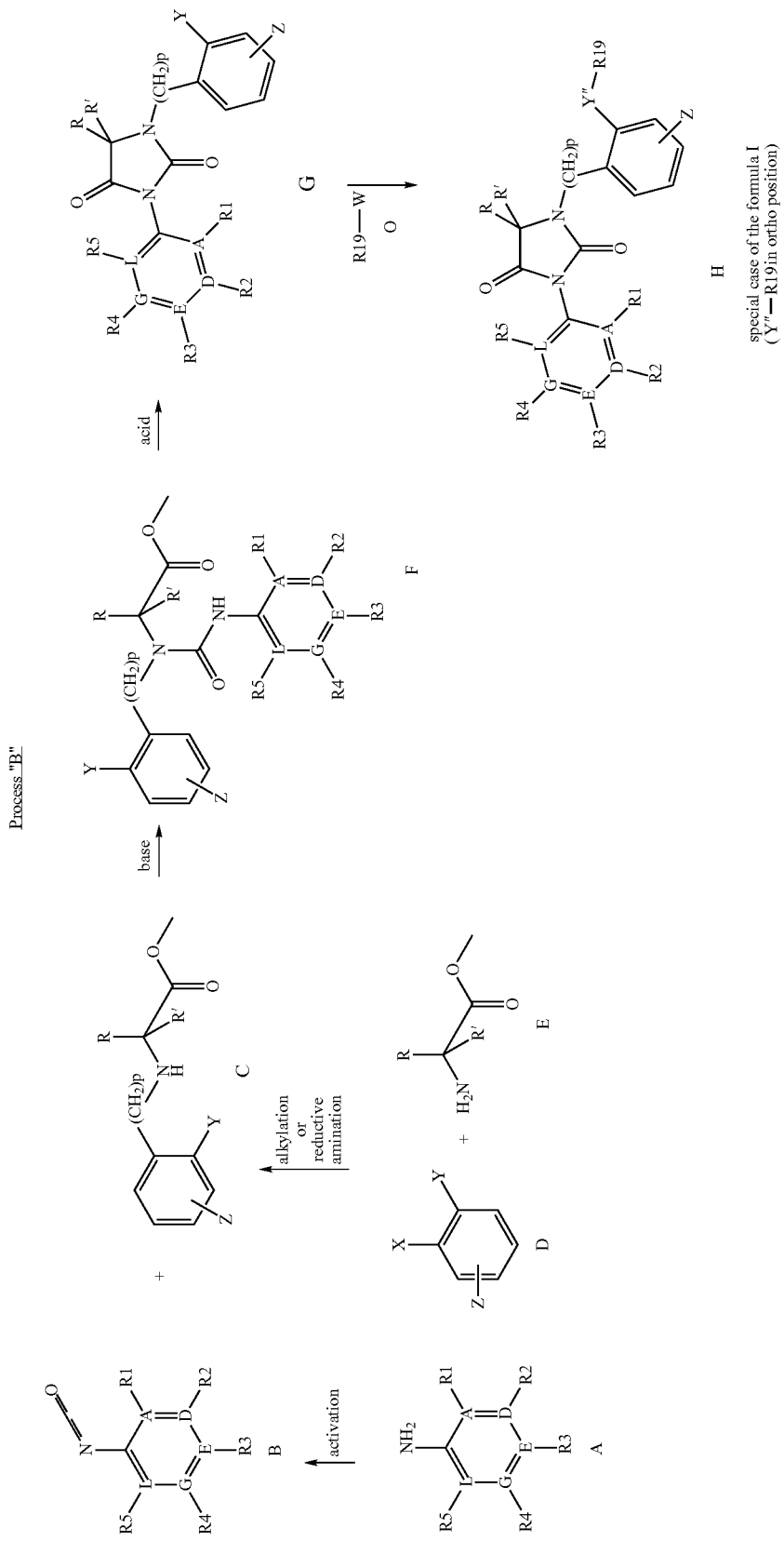

the isocyanate B is reacted with a suitably substituted amino acid ester derivative C in which the particular substituents are optionally provided with protecting groups, and where the methyl ester shown in the scheme is a nonlimiting example of an ester, and where Y is bromine or a protected amino function (e.g. N—CO—CH₃ or N=CH—N(CH₃)₂), with addition of a base (e.g. triethylamine) to give a urea of the formula F. The amino acid ester derivative C may be prepared from the compound D in which Z may be one or more substituents as described above in formula I, and where Y is bromine or a protected amino function and X is a (CH₂)ₚ—U moiety, in which U is defined as Cl, Br, I, O—SO₂—C₆H₄-4—CH₃, O—SO₂—CH₃ or O—SO₂—CF₃, with an amino acid ester of the formula E in which R and R' are each as defined in formula I under alkylating conditions. Alternatively, the compound of the formula C can be obtained by reductively aminating the aldehyde D (Z and Y as described above and X=(CH₂)ₚ—CHO) with the amino acid derivative E. The urea F can be ring-closed under basic or acidic conditions, preferably acidic conditions, to give the imidazolidine-2,4-dione of the formula G. Depending on whether Y in the compound of the formula G is bromine or NH₂, reaction with compounds of the formula O in which W is either NH₂ or bromine under Buchwald-Hartwig conditions prepares compounds of the formula H.

Any protecting groups present in the compound H may be removed at the end and the Y" radical can, if required, be reacted further by means of standard reactions of NH according to NR17.

The formula H shown here constitutes a special case of the formula I in which the Y"—R19 radical in formula I is in the ortho position; this radical may, mutatis mudandis, also be in the meta or para position.

In a further process (Process "C")

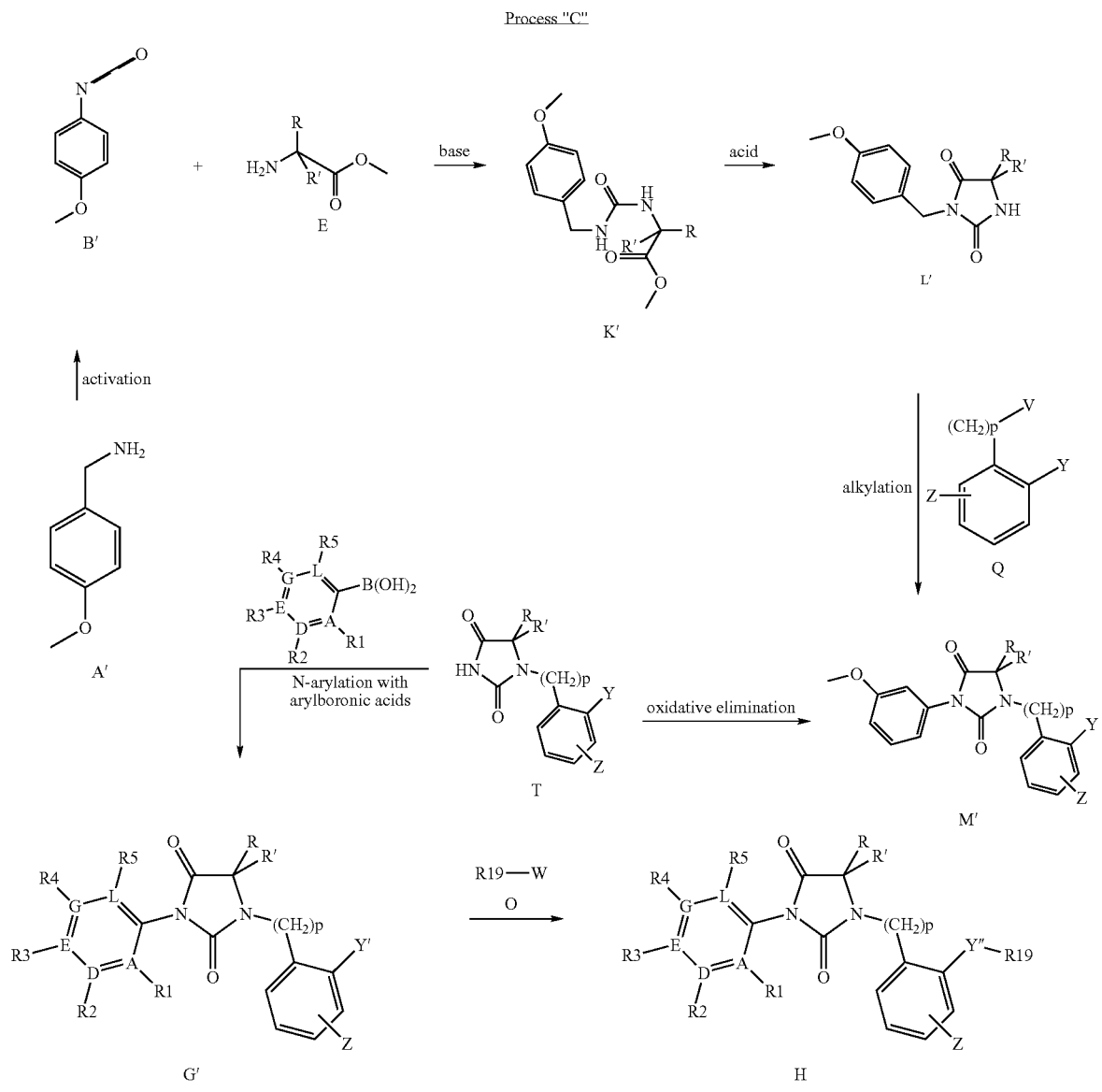

p-methoxybenzyl isocyanate B' is reacted with an amino acid ester, for example E, in which R and R' are each defined as specified in formula I under basic conditions to give the urea K'. The urea K' can be ring-closed under acidic or basic conditions, preferably acid conditions, to give the imidazolidine-2,4-dione of the formula L'. The compounds M' are obtained by reacting the compounds L' with the compounds Q under alkylating conditions. Z, V and Y in the compounds Q are each defined as specified in process "A". The p-methoxybenzyl group in the compounds M' can be eliminated oxidatively to obtain the compounds T. The N-arylation of the imide nitrogen atom in compounds of the formula T using arylboronic acids of the formula S, according to processes as described, for example, in J.-B. Lan et al.: SYNLETT 2004, 1095-1097 or D. M. T. Chan et al.: Tetrahedron Lett. 1998, 39, 2933-2936, affords compounds of the formula G'. Depending on whether Y' in the compound of the formula G' is bromine or $NH_2$, reaction with compounds of the formula O in which W is either $NH_2$ or bromine under Hartwig-Buchwald conditions can prepare compounds of the formula H. Any protecting groups present in compound H can be removed at the end and the Y" radical can, if required, be reacted further by means of standard reactions of NH according to NR17. The formula H shown here constitutes a special case of the formula I in which the Y"—R19 radical in formula I is present in the ortho position; this radical may, mutatis mudandis, also be present in the meta or para position.

A further process "D" finds use especially in the synthesis of alkyl-, cycloalkyl-, cycloalkenyl, arylalkylene-, heteroarylalkylene-, aryloxy-, heteroaryloxy, alkyloxy-, alkylthio-, cycloalkylthio-, arylthio-, heteroarylthio-, alkylcarbonyl-, cycloalkylcarbonyl-, arylcarbonyl-, heteroarylcarbonyl-, aryl- and heteroaryl-substituted N3-aryl- or N3-heteroaryl-substituted imidazolidine-2,4-diones.

an ester derivative thereof or an R2 trifluoroborate under conditions as described, for example, in J. Zhou and G. C. Fu, J. Am. Chem. Soc. 126 (2004) 1340-1341; F. Gonzáles-Bobes and G. C. Fu, J. Am. Chem. Soc. 128 (2006) 5360-5361; D. J. Wallace and C.-Y. Chen, Tetrahedron Letters 43 (2002) 6987-6990; T. E. Barder et al., J. Am. Chem. Soc. 127 (2005) 4685-4696; D. W. Old et al., J. Am. Chem. Soc. 120 (1998) 9722; T. E. Barder and St. L. Buchwald, Org. Lett. 6 (2004) 2649-2652. The further reaction of the compound A thus substituted by R2 can be effected as described for the process "A" and "B".

In process "D", the procedure may also be to react the compound A' where R2 is halogen, preferably chlorine or bromine, under palladium catalysis, with a diboron compound, e.g. bis(pinacolato)diboron, to give the aryl boronate of the formula A" where R2 is —B(O—C(CH$_3$)$_2$—C(CH$_3$)$_2$—O). In a further step, this compound can be reacted with an organohalogen compound R2-Hal to give compounds of the formula A in which R2 is, for example, cycloalkyl or aryl. The subsequent reactions to obtain the compounds of the formula H can in turn be effected according to process "A" or "B".

Compounds of the formula A in which R2 is —O/S-alkyl, —O/S-cycloalkyl, —O/S—CH$_2$-aryl, —O/S—CH$_2$-heteroaryl, —O/S-aryl, —O/S-heteroaryl can be prepared from compounds of the formula A' in which R2 is halogen, preferably bromine or chlorine, by reaction with the corresponding alcohols or phenols or mercaptans or mercaptoaryls and -heteroaryls and cesium carbonate under palladium or copper catalysis (see also R. Frlan and D. Kikelj; Synthesis 14 (2006) 2271-2285; A. V. Vorogushin et al., J. Am. Chem. Soc. 127 (2005) 8146-8149; F. Y. Kwong and St. L. Buchwald, Org. Lett. 4 (2002) 3517-3520).

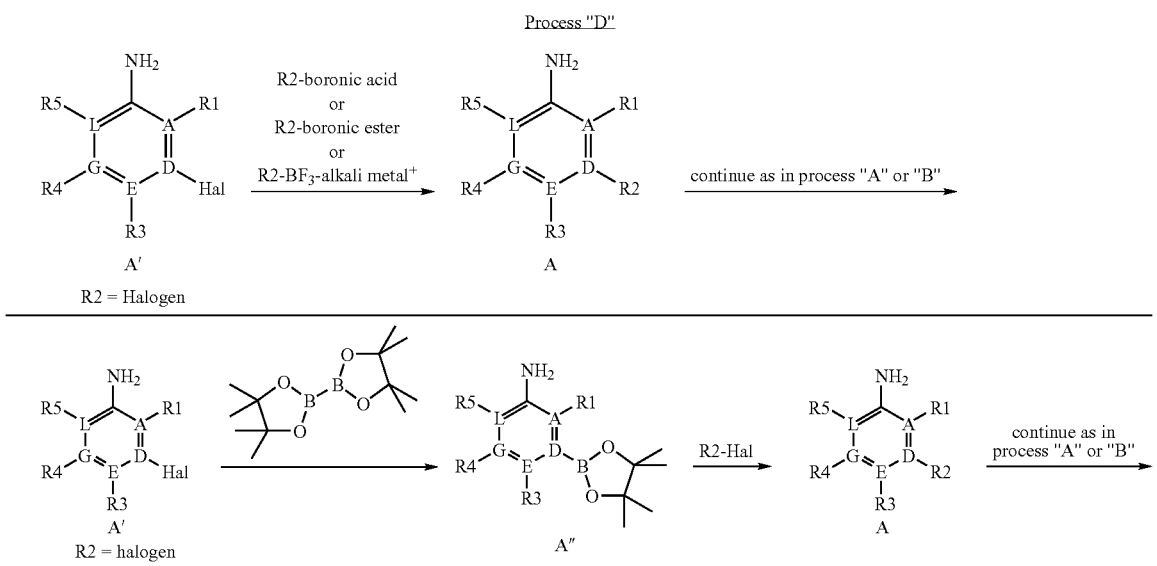

To prepare compounds in which, for example, R2=alkyl, cycloalkyl, cycloalkenyl, aryl or heteroaryl or another of the above-described radicals, the procedure may be to react a compound of the formula A' in which the amino function is optionally provided with a protecting group and R2 is halogen, preferably bromine or chlorine, with an alkyl-, cycloalkyl-, cycloalkenyl-, aryl- or heteroarylboronic acid or Compounds of the formula A in which R2 is —CH$_2$-aryl or —CH$_2$-heteroaryl may be obtained, for example, from compounds of the formula A" by reaction with halomethylaryls or halomethylheteroaryls where halogen is preferably bromine or chlorine under basic conditions and palladium catalysis (see also S. M. Nobre and A. L. Monteiro, Tetrahedron Letters 45 (2004) 8225-8228; S. Langle et al., Tetrahedron Letters 44 (2003) 9255-9258).

Compounds as obtainable via process "D" can also be obtained in a further process "E":
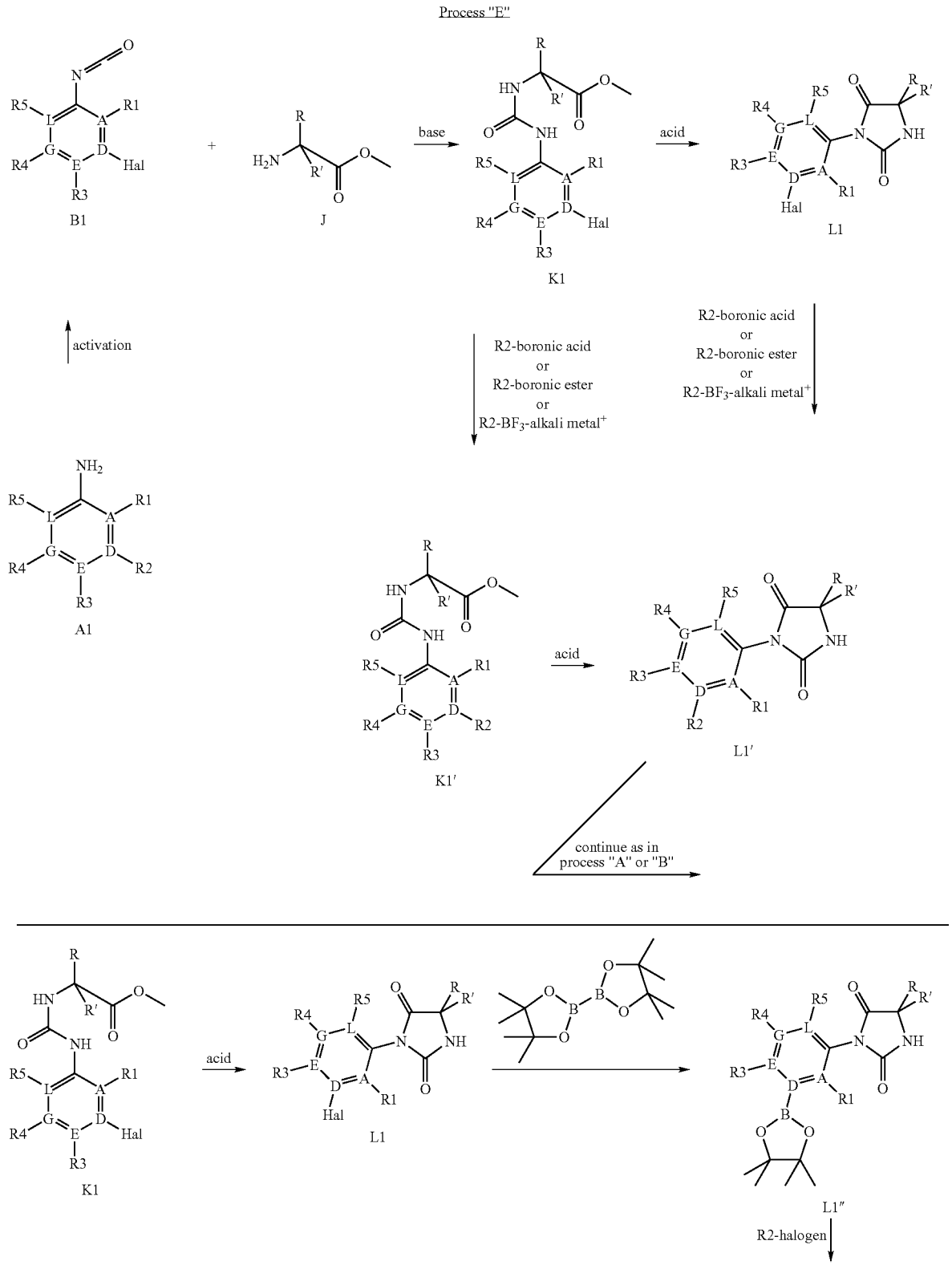

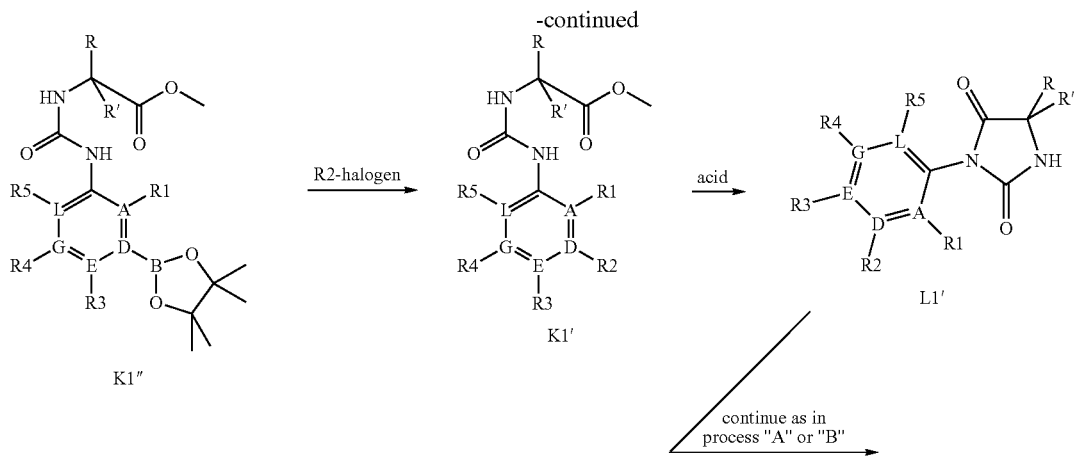

To prepare compounds in which, for example, R2=alkyl, cycloalkyl, cycloalkenyl, aryl or heteroaryl or another of the above-described radicals, the procedure may be to react a compound of the formula K1 or L1, which are obtained, for example, as described in process "A", and in which R2 is halogen, preferably bromine or chlorine, with an alkyl-, cycloalkyl-, cycloalkenyl-, aryl- or heteroarylboronic acid or an ester derivative thereof or an R2 trifluoroborate under conditions as described, for example, in J. Zhou and G. C. Fu, J. Am. Chem. Soc. 126 (2004) 1340-1341; F. Gonzáles-Bobes and G. C. Fu, J. Am. Chem. Soc. 128 (2006) 5360-5361; D. J. Wallace and C.-Y. Chen, Tetrahedron Letters 43 (2002) 6987-6990; T. E. Barder et al., J. Am. Chem. Soc. 127 (2005) 4685-4696; D. W. Old et al., J. Am. Chem. Soc. 120 (1998) 9722; T. E. Barder and St. L. Buchwald, Org. Lett. 6 (2004) 2649-2652. The further conversion of the compounds K1' and L1' thus substituted by R2 can be effected as described for process "A" and "B".

As described for process "D", the procedure in process "E" may also be to react the compounds K1 or L1 with a diboron compound, for example bis(pinacolato)diboron, to give the aryl boronate of the formula K1'' or L1'' where R2 is

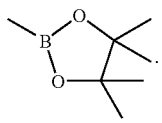

In a further step, these compounds can be reacted with an organohalogen compound R2-Hal to give compounds of the formula K1' or L1' in which R2 is, for example, cycloalkyl or aryl. The subsequent reaction to obtain the inventive compounds can be effected as described above for process "A" or "B".

The compounds with the further definitions of R2, which can be prepared by process "D", can also be prepared by process "E" by conversion of stages K1 or L1.

The examples which follow serve to further illustrate the invention without restricting it to the products and embodiments described in the examples.

General Experimental Methods:
$^1$H NMR:
The $^1$H NMR spectra were measured in deuterated dimethyl sulfoxide on a 500 MHz instrument (Bruker DRX 500) at 300 K. Data: δ in ppm, multiplicity (s for singlet, d for doublet, t for triplet, q for quartet, m for multiplet), xH (number of hydrogen atoms)

HPLC/MS:
The HPLC-MS measurements were performed on a Waters LCT instrument.

Column: YMC Jsphere 33×2 4 µm; gradient [A]: (acetonitrile+0.05% trifluoroacetic acid): (water+0.05% trifluoroacetic acid) 5:95 (0 minutes) to 95:5 (3 minutes); gradient [B]: (acetonitrile+0.05% trifluoroacetic acid): (water+0.05% trifluoroacetic acid) 5:95 (0 minutes) to 95:5 (2.5 minutes) to 95:5 (3.0 minutes); gradient [C]: (acetonitrile+0.05% trifluoroacetic acid): (water+0.05% trifluoroacetic acid) 5:95 (0 minutes) to 95:5 (3.4 minutes) to 95:5 (4.4 minutes); gradient [D]: (acetonitrile+0.05% trifluoroacetic acid) (water+0.05% trifluoroacetic acid) 2:98 (1 minute) to 95:5 (5 minutes) to 95:5 (6.25 minutes); gradient [E]: (acetonitrile+0.05% trifluoroacetic acid): (water+0.05% trifluoroacetic acid) 5:95 (0 minutes) to 5:95 (0.5 minutes) to 95:5 (3.5 minutes) to 95:5 (4.0 minutes); gradient [F]: column: YMC Jsphere ODS H80 20×2 mm, 4 µm; (water+0.05% trifluoroacetic acid): (acetonitrile+0.05% trifluoroacetic acid) 96:4 (0 minutes) to 5:95 (2 minutes) to 96:4 (2.4 minutes); detector: Tecan-LCT.

Chromatographic Purification Methods:
[RP1]: Flow rate: 30 ml/min; gradient: acetonitrile/water+ 0.1% trifluoroacetic acid; 30 min. column: XTerra C18 5 µm 30×100 mm; detection: MS (ESI), UV (DAD).

[RP2]: Flow rate: 150 ml/min; gradient: acetonitrile/water+0.1% trifluoroacetic acid; 20 min. column: XTerra C18 10 µm 50×250 mm; detection: MS (ESI), UV (DAD).

Example 1

4-[4,4-Dimethyl-2,5-dioxo-3-(2-phenylaminobenzyl) imidazolidin-1-yl]-2-trifluoromethylbenzonitrile

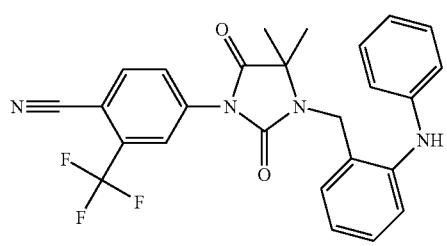

1) Preparation of 4-(4,4-dimethyl-2,5-dioxoimidazolidin-1-yl)-2-trifluoromethylbenzonitrile (1.1)

Compound 1.1 can be prepared by process "A". To this end, 14.74 g (79.21 mmol) of 4-amino-2-trifluoromethylbenzonitrile were dissolved in 200 ml of dry acetonitrile. This solution was added dropwise with stirring to a 20% solution, heated to 70° C., of phosgene in toluene and then stirred for 1 h. The cooled reaction solution was concentrated under reduced pressure, and the residue was taken up with toluene and concentrated again under reduced pressure. Finally, the residue was dissolved in 150 ml of dry acetonitrile and the solution was admixed with 15.5 g (79.21 mmol) of tert-butyl 2-amino-2-methylpropionate hydrochloride with stirring. 12.02 g (118.8 mmol) of triethylamine were slowly added dropwise to the reaction mixture which was then stirred at room temperature for 45 min. Thereafter, the mixture was admixed cautiously with 50 ml of concentrated hydrochloric acid and stirred at 70° C. for 1 h. The cooled reaction mixture was concentrated under reduced pressure and the residue was admixed with ethyl acetate and water. The organic phase was removed, washed with saturated sodium carbonate solution and then with water, dried over sodium sulfate, filtered and concentrated under reduced pressure. The residue was purified by chromatography on silica gel with 2:1 heptane/ethyl acetate. 21.2 g (90% yield) of 4-(4,4-dimethyl-2,5-dioxoimidazolidin-1-yl)-2-trifluoromethylbenzonitrile 1.1 with the melting point of 208-211° C. were obtained.

2) Preparation of 4-[3-(2-bromobenzyl)-4,4-dimethyl-2,5-dioxoimidazolidin-1-yl]-2-trifluoromethylbenzonitrile (1.2)

Compound 1.2 can be prepared by process "A". To this end, 21.2 g (71.32 mmol) of compound 1.1 and 17.83 g (71.32 mmol) of 2-bromobenzyl bromide were dissolved in 200 ml of dry acetonitrile, admixed with 12.32 g of potassium carbonate and stirred at room temperature for 5 h. For workup, the reaction mixture was admixed with water, the mixture was extracted by shaking with ethyl acetate, and the organic phase was dried over sodium sulfate, filtered and concentrated under reduced pressure. The residue was purified by chromatography on silica gel with 3:1 heptane/ethyl acetate. 28.5 g (86% yield) of 4-[3-(2-bromobenzyl)-4,4-dimethyl-2,5-dioxoimidazolidin-1-yl]-2-trifluoromethylbenzonitrile (1.2) with the melting point 56-58° C. were obtained.

3) Preparation of 4-[4,4-dimethyl-2,5-dioxo-3-(2-phenylaminobenzyl)imidazolidin-1-yl]-2-trifluoromethylbenzonitrile (1)

To prepare the compound of example 1, the procedure may be according to process "A". To this end, under an argon atmosphere, 49.98 mg (0.107 mmol) of compound 1.2, 14.98 mg (0.161 mmol) of aniline, 104.8 mg of cesium carbonate, 2.4 mg of palladium(II) acetate and 12.4 mg of 9,9-dimethyl-4,5-bis(diphenylphosphino)-xanthene were added successively to 20 ml of dry dioxane and the mixture was stirred at 80° C. for 8 h. The cooled reaction mixture was admixed with water and ethyl acetate, and the organic phase was removed, dried over sodium sulfate and concentrated under reduced pressure. The residue was purified by chromatography (method [RP1]). 45 mg (88% yield) of the compound of example 1 with molecular weight 478.16 ($C_{26}H_{21}F_3N_4O_2$) were obtained; retention time $R_t$=2.33 min. [B]; MS (ESI): 479.43 (MH$^+$).

The compounds of example 2, 4-{3-[2-(4-fluorophenylamino)benzyl]-4,4-dimethyl-2,5-dioxoimidazolidin-1-yl}-2-trifluoromethylbenzonitrile (molecular weight 496.15 ($C_{26}H_{20}F_4N_4O_2$); retention time $R_t$=2.25 min. [B]; MS (ESI): 497.28 (MH$^+$), and of examples 3, 4-{3-[2-(4-cyano-3-trifluoromethylphenylamino)benzyl]-4,4-dimethyl-2,5-dioxoimidazolidin-1-yl}-2-trifluoromethylbenzonitrile (molecular weight 571.14 ($C_{28}H_{19}F_6N_5O_2$); retention time $R_t$=2.17 min. [B]; MS (ESI): 572.38 (MH$^+$), 4, 4-{3-[2-(4-chlorophenylamino)benzyl]-4,4-dimethyl-2,5-dioxoimidazolidin-1-yl}-2-trifluoromethylbenzonitrile (molecular weight 512.12 ($C_{26}H_{20}ClF_3N_4O_2$); retention time $R_t$=2.35 min. [B]; MS (ESI): 513.01 (MH$^+$), 5, 4-{3-[2-(4-trifluoromethylphenylamino)benzyl]-4,4-dimethyl-2,5-dioxoimidazolidin-1-yl}-2-trifluoromethylbenzonitrile (molecular weight 546.14 ($C_{27}H_{20}F_6N_4O_2$); retention time $R_t$=2.34 min. [B]; MS (ESI): 547.09 (MH$^+$), 11, 4-{3-[2-(2,4-difluorophenylamino)benzyl]-4,4-dimethyl-2,5-dioxoimidazolidin-1-yl}-2-trifluoromethylbenzonitrile (molecular weight 514.14 ($C_{26}H_{19}F_5N_4O_2$); retention time $R_t$=2.32 min. [B]; MS (ESI): 515.17 (MH$^+$), 12, 4-{3-[2-(4-trifluoromethoxy-phenylamino)benzyl]-4,4-dimethyl-2,5-dioxoimidazolidin-1-yl}-2-trifluoromethylbenzonitrile (molecular weight 562.14 ($C_{27}H_{20}F_6N_4O_3$); Retention time $R_t$=2.46 min. [B]; MS (ESI): 563.15 (MH$^+$), 13, 4-{3-[2-(2,4-dichlorophenylamino)benzyl]-4,4-dimethyl-2,5-dioxoimidazolidin-1-yl}-2-trifluoromethylbenzonitrile (molecular weight 546.08 ($C_{26}H_{19}Cl_2F_3N_4O_2$); retention time $R_t$=2.52 min. [B]; MS (ESI): 547.14 (MH$^+$), 14, 4-{3-[2-(2-chloro-4-methylsulfonylphenylamino)benzyl]-4,4-dimethyl-2,5-dioxoimidazolidin-1-yl}-2-trifluoromethylbenzonitrile (molecular weight 590.10 ($C_{27}H_{22}ClF_3N_4O_4S$); retention time $R_t$=2.01 min. [B]; MS (ESI): 591.17 (MH$^+$), 20, 4-{3-[2-(3,4-dichlorophenylamino)benzyl]-4,4-dimethyl-2,5-dioxoimidazolidin-1-yl}-2-trifluoromethylbenzonitrile (molecular weight 546.08 ($C_{26}H_{19}Cl_2F_3N_4O_2$); retention time $R_t$=2.50 min. [B]; MS (ESI): 547.11 (MH$^+$), 21, 4-{3-[2-(2-chlorophenylamino)benzyl]-4,4-dimethyl-2,5-dioxoimidazolidin-1-yl}-2-trifluoromethylbenzonitrile (molecular weight 512.12 ($C_{26}H_{20}ClF_3N_4O_2$); retention time $R_t$=2.37 min. [B]; MS (ESI): 513.11 (MH$^+$), 22, 4-{3-[2-(3-chlorophenylamino)benzyl]-4,4-dimethyl-2,5-dioxoimidazolidin-1-yl}-2-trifluoromethylbenzonitrile (molecular weight 512.12 ($C_{26}H_{20}ClF_3N_4O_2$); retention time $R_t$=2.39 min. [B]; MS (ESI): 513.13 (MH$^+$), 26, 4-{3-[2-(4-pentafluorosulfanylphenylamino)benzyl]-4,4-dimethyl-2,5-dioxoimidazolidin-1-yl}-2-trifluoromethylbenzonitrile (molecular weight 604.11 ($C_{26}H_{20}F_8N_4O_2S$); retention time $R_t$=2.42 min. [B]; MS (ESI): 605.21 (MH$^+$), 27, 4-{3-[2-(4-methylsulfonylphenylamino)benzyl]-4,4-dimethyl-2,5-dioxoimidazolidin-1-yl}-2-trifluoromethylbenzonitrile (molecular weight 556.13 ($C_{27}H_{23}F_3N_4O_4S$); retention time $R_t$=1.92 min. [B]; MS (ESI): 557.23 (MH$^+$), 31, 4-{3-[2-(2,2-difluorobenzo[1,3]dioxol-4-ylamino)benzyl]-4,4-dimethyl-2,5-dioxoimidazolidin-1-yl}-2-trifluoromethylbenzonitrile (molecular weight 558.13 ($C_{27}H_{19}F_5N_4O_4$); retention time $R_t$=2.38 min. [B]; MS (ESI): 559.22 (MH$^+$), 32, 4-{3-[2-(2,2-difluorobenzo[1,3]dioxol-5-ylamino)benzyl]-4,4-dimethyl-2,5-dioxoimidazolidin-1-yl}-2-trifluoromethylbenzonitrile (molecular weight 558.13 ($C_{27}H_{19}F_5N_4O_4$); retention time $R_t$=2.42 min. [B]; MS (ESI): 559.20 (MH$^+$), 33, 4-{3-[2-(4-cyanophenylamino)benzyl]-4,4-dimethyl-2,5-dioxoimidazolidin-1-yl}-2-trifluoromethylbenzonitrile (molecular weight 503.15 ($C_{27}H_{20}F_3N_5O_2$); retention time $R_t$=2.09 min. [B]; MS (ESI): 545.28 (MH$^+$+CH$_3$CN), 34, 4-{3-[2-(3-trifluoromethylphenylamino)benzyl]-4,4-dimethyl-2,5-dioxoimidazolidin-1-yl}-2-trifluoromethylbenzonitrile (molecular weight 546.14 ($C_{27}H_{20}F_6N_4O_2$); retention time $R_t$=2.39 min. [B]; MS (ESI): 547.18 (MH$^+$), 44, 4-{3-[2-(2-fluorophenylamino)benzyl]-4,4-dimethyl-2,5-dioxoimidazolidin-1-yl}-2-trifluoromethylbenzonitrile (molecular weight 496.15 ($C_{26}H_{20}F_4N_4O_2$); retention time $R_t$=2.28 min. [B]; MS (ESI): 497.18 (MH$^+$), 45, 4-(4,4-dimethyl-2,5-dioxo-3-{2-[4-(piperidin-1-sulfonyl)phenylamino]benzyl}-imidazolidin-1-yl)-2-trifluoromethylbenzonitrile (molecular weight 625.19 ($C_{31}H_{30}F_3N_5O_4S$); retention time $R_t$=2.23 min. [B]; MS (ESI): 626.25 (MH$^+$), 46, 4-{2-[3-(4-cyano-3-trifluoromethylphenyl)-5,5-dimethyl-2,4-dioxoimidazolidin-1-ylmethyl]phenylamino}-N,N-dimethylbenzenesulfonamide (molecular weight 585.16 ($C_{28}H_{26}F_3N_5O_4S$); retention time $R_t$=2.05 min. [B]; MS (ESI): 586.19 (MH$^+$), 47, 4-(4,4-dimethyl-3-{2-[4-(morpholin-4-sulfonyl)phenylamino]benzyl}-2,5-dioxoimidazolidin-1-yl)-2-trifluoromethylbenzonitrile (molecular weight 627.17 ($C_{30}H_{28}F_3N_5O_5S$); retention time $R_t$=2.02 min. [B]; MS (ESI): 628.23 (MH$^+$), 53, 4-{3-[2-(2-cyano-4-fluorophenylamino)benzyl]-4,4-dimethyl-2,5-dioxoimidazolidin-1-yl}-2-trifluoromethylbenzonitrile (molecular weight 521.14 ($C_{27}H_{19}F_4N_5O_2$); retention time $R_t$=2.18 min. [B]; MS (ESI): 522.19 (MH$^+$), 60, methyl 4-{2-[3-(4-cyano-3-trifluoromethylphenyl)-5,5-dimethyl-2,4-dioxoimidazolidin-1-ylmethyl]phenylamino}benzoate (molecular weight 536.16 ($C_{28}H_{23}F_3N_4O_4$); retention time $R_t$=2.16 min. [B]; MS (ESI): 537.14 (MH$^+$), 67, 4-{3-[2-(4-methoxyphenylamino)benzyl]-4,4-dimethyl-2,5-dioxoimidazolidin-1-yl}-2-trifluoromethylbenzonitrile (molecular weight 508.17 ($C_{27}H_{23}F_3N_4O_3$); retention time $R_t$=2.29 min. [B]; MS (ESI): 509.22 (MH$^+$), 72, methyl 4-{2-[3-(4-cyano-3-trifluoromethylphenyl)-5,5-dimethyl-2,4-dioxoimidazolidin-1-ylmethyl]phenylamino}-3-fluorobenzoate (molecular weight 554.15 ($C_{28}H_{22}F_4N_4O_4$); retention time $R_t$=2.20 min. [B]; MS (ESI): 555.12 (MH$^+$), 73, 4-{3-[2-(2-fluoro-4-cyanophenylamino)benzyl]-4,4-dimethyl-2,5-dioxoimidazolidin-1-yl}-2-trifluoromethylbenzonitrile (molecular weight 521.14 ($C_{27}H_{19}F_4N_5O_2$); retention time $R_t$=2.11 min. [B]; MS (ESI): 522.13 (MH$^+$), 74, 4-{3-[2-(2-fluoro-4-methoxyphenylamino)benzyl]-4,4-dimethyl-2,5-dioxoimidazolidin-1-yl}-2-trifluoromethylbenzonitrile (molecular weight 526.16 ($C_{27}H_{22}F_4N_4O_3$); retention time $R_t$=2.28 min. [B]; MS (ESI): 527.10 (MH$^+$), 75, 4-{3-[2-(3,4-dimethoxyphenylamino)benzyl]-4,4-dimethyl-2,5-dioxoimidazolidin-1-yl}-2-trifluoromethylbenzonitrile (molecular weight 538.18 ($C_{28}H_{25}F_3N_4O_4$); retention time $R_t$=2.12 min. [B]; MS (ESI): 539.10 (MH$^+$), 76, 4-{3-[2-(4-benzyloxy-2-fluorophenylamino)benzyl]-4,4-dimethyl-2,5-dioxoimidazolidin-1-yl}-2-trifluoromethylbenzonitrile (molecular weight 602.19 ($C_{33}H_{26}F_4N_4O_3$); retention time $R_t$=2.52 min. [B]; MS (ESI): 603.14 (MH$^+$), 77, 4-{3-[2-(4-benzyloxyphenylamino)benzyl]-4,4-dimethyl-2,5-dioxoimidazolidin-1-yl}-2-trifluoromethylbenzonitrile (molecular weight 584.20 ($C_{33}H_{27}F_3N_4O_3$); retention time $R_t$=2.50 min. [B]; MS (ESI): 585.14 (MH$^+$), 78, 4-{3-[2-(4-cyanomethylphenylamino)benzyl]-4,4-dimethyl-2,5-dioxoimidazolidin-1-yl}-2-trifluoromethylbenzonitrile (molecular weight 517.17 ($C_{28}H_{22}F_3N_5O_2$); retention time $R_t$=2.10 min. [B]; MS (ESI): 518.15 (MH$^+$), 79, diethyl (4-{2-[3-(4-cyano-3-trifluoromethylphenyl)-5,5-dimethyl-2,4-dioxoimidazolidin-1-ylmethyl]phenylamino}phenyl)phosphonate (molecular weight 614.19 ($C_{30}H_{30}F_3N_4O_5P$); retention time $R_t$=2.00 min. [B]; MS (ESI): 615.10 (MH$^+$), 82, methyl (4-{2-[3-(4-cyano-3-trifluoromethylphenyl)-5,5-dimethyl-2,4-dioxoimidazolidin-1-ylmethyl]phenylamino}phenyl)acetate (molecular weight 550.18 ($C_{29}H_{25}F_3N_4O_4$); retention time $R_t$=2.18 min. [B]; MS (ESI): 551.14 (MH$^+$), 120, 4-{3-[2-(4-formylphenylamino)benzyl]-4,4-dimethyl-2,5-dioxoimidazolidin-1-yl}-2-trifluoromethylbenzonitrile (molecular weight 506.49 ($C_{27}H_{21}F_3N_4O3$); retention time $R_t$=2.02 min. [B]; MS (ESI): 507.11 (MH$^+$), 127, 4-{3-[2-(4-isopropoxyphenylamino)benzyl]-4,4-dimethyl-2,5-dioxoimidazolidin-1-yl}-2-trifluoromethylbenzonitrile (molecular weight 536.20 ($C_{29}H_{27}F_3N_4O_3$); retention time $R_t$=2.36 min. [B]; MS (ESI): 537.16 (MH$^+$), 145, methyl (4R,5S,6S)-6-(4-{2-[3-(4-cyano-3-trifluoromethylphenyl)-5,5-dimethyl-2,4-dioxoimidazolidin-1-ylmethyl]phenylamino}phenoxy)-4,5-dihydroxy-5,6-dihydro-4H-pyran-2-carboxylate ($^1$H NMR: 8.34, d, 1H, 8.25, s, 1H, 8.09, d, 1H, 7.42, m, 2H, 7.2, m, 1H, 7.12, m, 1H, 7.02, d, 2H, 6.92, m, 3H, 5.98, s, 1H, 5.65, s, 1H, 5.47, d, 1H, 4.6, s, 2H, 4.12, m, 1H, 3.71, s, 3H, 3.69, m, 1H, 1.4, s, 6H; molecular weight 566.19 ($C_{33}H_{29}F_3N_4O_8$); MS (ESI): 667.21 (MH$^+$), 197, methyl (4R,5S,6S)-4,5-diacetoxy-6-(4-{2-[3-(4-cyano-3-trifluoromethylphenyl)-5,5-dimethyl-2,4-dioxoimidazolidin-1-ylmethyl]phenylamino}phenoxy)-5,6-dihydro-4H-pyran-2-carboxylate ($^1$H NMR: 8.34, d, 1H, 8.23, s, 1H, 8.07, d, 1H, 7.49, s, 1H, 7.45, d, 1H, 7.21, t, 1H, 7.14, d, 1H, 6.99, d, 2H, 6.96, t, 1H, 6.91, d, 2H, 6.14, d, 1H, 5.91, d, 1H, 5.34, t, 1H, 5.21, t, 1H, 4.58, s, 2H, 3.74, s, 3H, 2.1, s, 6H, 1.38, s, 6H), were prepared like the compound of example 1 with the difference that, in the third stage of the synthesis, instead of aniline, 4-fluoroaniline (for 2),
4-cyano-3-trifluoromethylaniline (for 3),
4-chloroaniline (for 4),
4-trifluoromethylaniline (for 5),
2,4-difluoroaniline (for 11),
4-trifluoromethoxyaniline (for 12),
2,4-dichloroaniline (for 13),
2-chloro-4-methylsulfonylaniline (for 14),
3,4-dichloroaniline (for 20),
2-chloroaniline (for 21),
3-chloroaniline (for 22),
4-pentafluorosulfanylaniline (for 26; this compound has been prepared from 4-nitropentafluorosulfanylbenzene (CAS# 2613-27-6) by catalytic reduction with hydrogen and palladium on carbon (10%) in ethanol; analogous to the preparation of the isomeric compound 51.3),
4-methylsulfonylaniline (for 27),
2,2-difluorobenzo[1,3]dioxol-4-ylamine (for 31),
2,2-difluorobenzo[1,3]dioxol-5-ylamine (for 32),
4-cyanoaniline (for 33),
3-trifluoromethylaniline (for 34),
2-fluoroaniline (for 44),
4-(piperidine-1-sulfonyl)phenylamine (for 45),
4-amino-N,N-dimethylbenzenesulfonamide (for 46),
4-(morpholine-4-sulfonyl)phenylamine (for 47),
2-cyano-4-fluoroaniline (for 53), methyl 4-aminobenzoate (for 60),
4-methoxyaniline (for 67),
methyl 3-fluoro-4-aminobenzoate (for 72),
4-cyano-2-fluoroaniline (for 73),
2-fluoro-4-methoxyaniline (for 74),
3,4-dimethoxyaniline (for 75),
2-fluoro-4-benzyloxyaniline (for 76),
4-benzyloxyaniline (for 77),
(4-aminophenyl)acetonitrile (for 78),
diethyl (4-aminophenyl)phosphonate (for 79),
methyl (4-aminophenyl)acetate (for 82),
4-aminobenzaldehyde (for 120),
4-isopropoxyaniline (for 127),
methyl (2R,3R,4R,5S,6R)-3,4,5-triacetoxy-6-(4-aminophenoxy)tetrahydropyran-2-carboxylate (for 145 and 197).

Example 6

4-[3-(5-Methoxy-2-phenylaminobenzyl)-4,4-dimethyl-2,5-dioxoimidazolidin-1-yl]-2-trifluoromethylbenzonitrile

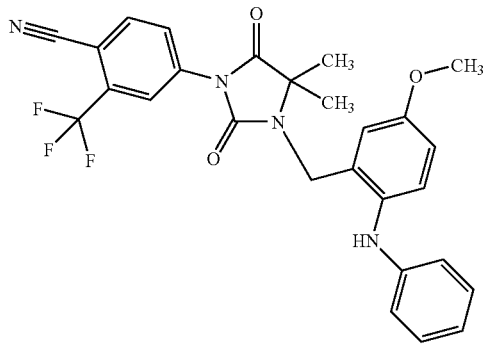

1) Preparation of 4-[3-(2-bromo-5-methoxybenzyl)-4,4-dimethyl-2,5-dioxoimidazolidin-1-yl]-2-trifluoromethylbenzonitrile 6.2

1.5 g (5.05 mmol) of compound 1.1 were reacted with 1.695 g (6.06 mmol) of 2-bromo-5-methoxybenzyl bromide and 2.06 g of cesium carbonate in 10 ml of acetonitrile, and worked up, as described in example 1, stage 2. 2.45 g (98% yield) of 4-[3-(2-bromo-5-methoxybenzyl)-4,4-dimethyl-2,5-dioxoimidazolidin-1-yl]-2-trifluoromethylbenzonitrile (6.2) were obtained. $^1$H NMR: 8.35, d, 1H, 8.25, s, 1H; 8.1, d, 1H, 7.55, d, 1H, 7.1, s, 1H, 6.88, d, 1H, 4.6, s, 2H, 3.76, s, 3H, 1.42, s, 6H.

2) Preparation of 4-[3-(5-methoxy-2-phenylaminobenzyl)-4,4-dimethyl-2,5-dioxoimidazolidin-1-yl]-2-trifluoromethylbenzonitrile 6

The further reaction with aniline to give the compound of example 6 was effected as described for example 1, stage 3. 4-[3-(5-Methoxy-2-phenylaminobenzyl)-4,4-dimethyl-2,5-dioxoimidazolidin-1-yl]-2-trifluoromethylbenzonitrile 6 was obtained (molecular weight 508.17 ($C_{27}H_{23}F_3N_4O_3$); retention time $R_t$=2.19 min. [B]; MS (ESI): 509.14 (MH$^+$).

The compounds of example 7, 4-{3-[2-(4-fluorophenylamino)-5-methoxybenzyl]-4,4-dimethyl-2,5-dioxoimidazolidin-1-yl}-2-trifluoromethylbenzonitrile (molecular weight 526.16 ($C_{27}H_{22}F_4N_4O_3$); retention time $R_t$=2.19 min. [B]; MS (ESI): 527.13 (MH$^+$), and of examples 8, 4-{3-[5-methoxy-2-(4-trifluoromethylphenylamino)benzyl]-4,4-dimethyl-2,5-dioxoimidazolidin-1-yl}-2-trifluoromethylbenzonitrile (molecular weight 576.15 ($C_{28}H_{22}F_6N_4O_3$); retention time $R_t$=2.30 min. [B]; MS (ESI): 577.15 (MH$^+$), 9, 4-{3-[2-(4-chlorophenylamino)-5-methoxybenzyl]-4,4-dimethyl-2,5-dioxoimidazolidin-1-yl}-2-trifluoromethylbenzonitrile (molecular weight 542.13 ($C_{27}H_{22}ClF_3N_4O_3$); retention time $R_t$=2.29 min. [B]; MS (ESI): 543.12 (MH$^+$), 10, 4-{3-[2-(4-cyano-3-trifluoromethylphenylamino)-5-methoxybenzyl]-4,4-dimethyl-2,5-dioxoimidazolidin-1-yl}-2-trifluoromethylbenzonitrile (molecular weight 601.15 ($C_{29}H_{21}F_6N_5O_3$); retention time $R_t$=2.12 min. [B]; MS ESI): 602.19 (MH$^+$)

were prepared like the compound of example 6 with the difference that, in the second stage of the synthesis, instead of aniline, 4-fluoroaniline (for 7),
4-trifluoromethylaniline (for 8),
4-chloroaniline (for 9),
4-cyano-3-trifluoromethylaniline (for 10)

was used.

Example 15

4-{3-[5-Fluoro-2-(4-fluorophenylamino)benzyl]-4,4-dimethyl-2,5-dioxoimidazolidin-1-yl}-2-trifluoromethylbenzonitrile

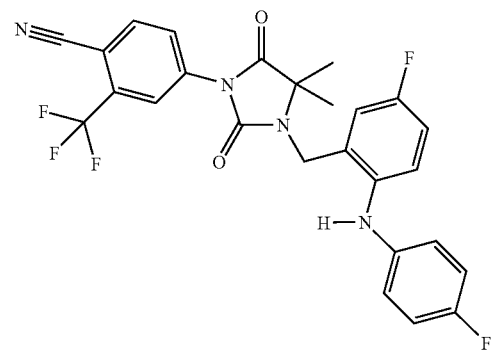

1) Preparation of 4-[3-(2-bromo-5-fluorobenzyl)-4,4-dimethyl-2,5-dioxoimidazolidin-1-yl]-2-trifluoromethylbenzonitrile 15.2

Compound 15.2 was prepared as described for example 6.2 by reacting compound 1.1 with 2-bromo-5-fluorobenzyl bromide. 4-[3-(2-Bromo-5-fluorobenzyl)-4,4-dimethyl-2,5-dioxoimidazolidin-1-yl]-2-trifluoromethylbenzonitrile was obtained in a yield of 95% (molecular weight 483.02 ($C_{20}H_{14}BrF_4N_3O_2$); retention time $R_t$=2.10 min. [B]; MS (ESI): 484.26 (MH$^+$)

2) Preparation of 4-{3-[5-fluoro-2-(4-fluorophenylamino)benzyl]-4,4-dimethyl-2,5-dioxoimidazolidin-1-yl}-2-trifluoromethylbenzonitrile 15

The further reaction with 4-fluoroaniline to give the compound of example 15 was effected as described for example 1, stage 3. 4-{3-[5-Fluoro-2-(4-fluorophenylamino)benzyl]-4,4-dimethyl-2,5-dioxoimidazolidin-1-yl}-2-trifluoromethylbenzonitrile 15 was obtained (molecular weight 514.14 ($C_{26}H_{19}F_5N_4O_2$); retention time $R_t$=2.28 min. [B]; MS (ESI): 515.21 (MH$^+$).

The compounds of example 16, 4-{3-[2-(4-chlorophenylamino)-5-fluorobenzyl]-4,4-dimethyl-2,5-dioxoimidazolidin-1-yl}-2-trifluoromethylbenzonitrile (molecular weight 530.11 ($C_{26}H_{19}ClF_4N_4O_2$); retention time $R_t$=2.38 min. [B]; MS (ESI): 531.21 (MH$^+$), and of example 18, 4-[3-(5-fluoro-2-phenylaminobenzyl)-4,4-dimethyl-2,5-dioxoimidazolidin-1-yl]-2-trifluoromethylbenzonitrile (molecular weight 496.15 ($C_{26}H_{20}F_4N_4O_2$); retention time $R_t$=2.28 min. [B]; MS (ESI): 497.20 (MH$^+$)

were prepared like the compound of example 15 with the difference that, in the second stage of the synthesis, instead of 4-fluoroaniline, 4-chloroaniline (for 16), aniline (for 18)

was used.

Example 17

4-{3-[2-(4-Fluorophenylamino)-5-trifluoromethylbenzyl]-4,4-dimethyl-2,5-dioxoimidazolidin-1-yl}-2-trifluoromethylbenzonitrile

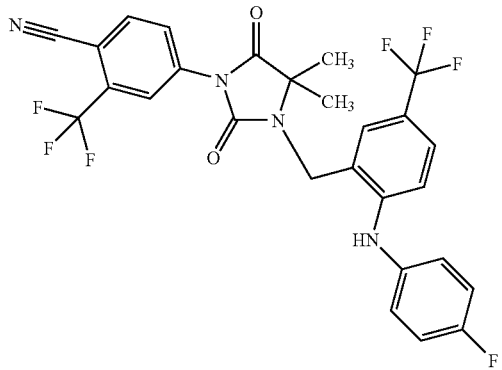

1) Preparation of 4-[3-(2-bromo-5-trifluoromethylbenzyl)-4,4-dimethyl-2,5-dioxoimidazolidin-1-yl]-2-trifluoromethylbenzonitrile 17.2

Compound 17.2 was prepared as described for example 6.2, by reacting compound 1.1 with 2-bromo-5-trifluoromethylbenzyl bromide. 4-[3-(2-Bromo-5-trifluoromethylbenzyl)-4,4-dimethyl-2,5-dioxoimidazolidin-1-yl]-2-trifluoromethylbenzonitrile was obtained in a yield of 96%. (Molecular weight 533.01 ($C_{21}H_{14}BrF_6N_3O_2$); retention time $R_t$=2.21 min. [B]; MS (ESI): 534.14 (MH$^+$)

2) Preparation of 4-{3-[2-(4-fluorophenylamino)-5-trifluoromethylbenzyl]-4,4-dimethyl-2,5-dioxoimidazolidin-1-yl}-2-trifluoromethylbenzonitrile 17

The further reaction with 4-fluoroaniline to give the compound of example 17 was effected as described for example 1, stage 3. 4-{3-[2-(4-Fluorophenylamino)-5-trifluoromethylbenzyl]-4,4-dimethyl-2,5-dioxoimidazolidin-1-yl}-2-trifluoromethylbenzonitrile 17 was obtained. (Molecular weight 564.13 ($C_{27}H_{19}F_7N_4O_2$); retention time $R_t$=3.13 min. [C]; MS (ESI): 565.17 (MH$^+$).

The compound of example 19, 4-{3-[2-(4-chlorophenylamino)-5-trifluoromethylbenzyl]-4,4-dimethyl-2,5-dioxoimidazolidin-1-yl}-2-trifluoromethylbenzonitrile (molecular weight 580.11 ($C_{27}H_{19}ClF_6N_4O_2$); retention time $R_t$=3.21 min. [C]; MS (ESI): 581.18 (MH$^+$) was prepared like the compound of example 17 with the difference that, in the second stage of the synthesis, instead of 4-fluoroaniline, 4-chloroaniline (for 19)

was used.

Example 109

Methyl 4-{5-chloro-2-[3-(4-cyano-3-trifluoromethylphenyl)-5,5-dimethyl-2,4-dioxoimidazolidin-1-ylmethyl]phenylamino}benzoate

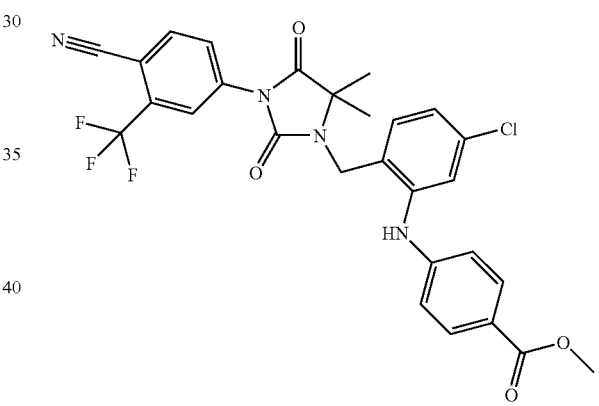

1) Preparation of 4-[3-(2-bromo-4-chlorobenzyl)-4,4-dimethyl-2,5-dioxoimidazolidin-1-yl]-2-trifluoromethylbenzonitrile 109.2

Compound 109.2 was prepared as described for example 1.2, by reacting compound 1.1, instead of 2-bromobenzyl bromide, with 2-bromo-1-bromomethyl-4-chlorobenzene (prepared by N-bromosuccinimide bromination from 2-bromo-4-chloro-1-methylbenzene; $^1$H NMR: 7.82, d, 1H; 7.65, s, 1H, 7.5, d, 1H, 4.72, s, 2H). 4-[3-(2-Bromo-4-chlorobenzyl)-4,4-dimethyl-2,5-dioxoimidazolidin-1-yl]-2-trifluoromethylbenzonitrile was obtained. (Molecular weight 498.99 ($C_{20}H_{14}BrClF_3N_3O_2$); retention time $R_t$=2.30 min. [B]; MS (ESI): 541.04 (MH$^+$+CH$_3$CN).

2) Methyl 4-{5-chloro-2-[3-(4-cyano-3-trifluoromethylphenyl)-5,5-dimethyl-2,4-dioxoimidazolidin-1-ylmethyl]phenylamino}benzoate 109

The further reaction with methyl 4-aminobenzoate to give the compound of example 109 was effected as described for example 1, stage 3. Methyl 4-{5-chloro-2-[3-(4-cyano-3-trifluoromethylphenyl)-5,5-dimethyl-2,4-dioxoimidazolidin-1-ylmethyl]phenylamino}benzoate 109 was obtained. (Molecular weight 570.12 ($C_{28}H_{22}ClF_3N_4O_4$); retention time $R_t$=2.30 min. [B]; MS (ESI): 571.21 ($MH^+$).

The compound of example 123, tert-butyl 4-{5-chloro-2-[3-(4-cyano-3-trifluoromethylphenyl)-5,5-dimethyl-2,4-dioxoimidazolidin-1-ylmethyl]phenylamino}benzoate [(molecular weight 612.17 ($C_{31}H_{28}ClF_3N_4O_4$); $^1$H NMR: 8.38, s, 1H, 8.35, d, 1H, 8.2, s, 1H, 8.07, d, 1H; 7.8, d, 2H, 7.57, d, 1H, 7.3, s, 1H, 7.18, d, 1H, 6.9, d, 2H, 4.56, s, 2H, 1.52, s, 9H, 1.39, s, 6H)]

was prepared like the compound of example 109 with the difference that, in the second stage of the synthesis, instead of methyl 4-aminobenzoate,
tert-butyl 4-aminobenzoate was used.

Example 110

Methyl 4-{2-[3-(4-cyano-3-trifluoromethylphenyl)-5,5-dimethyl-2,4-dioxoimidazolidin-1-ylmethyl]-5-methoxyphenylamino}benzoate

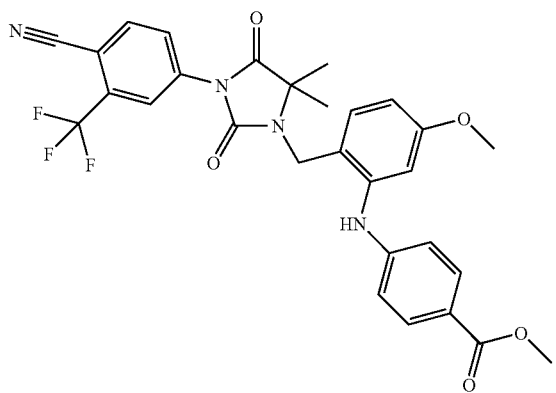

1) Preparation of 4-[3-(2-bromo-4-methoxybenzyl)-4,4-dimethyl-2,5-dioxoimidazolidin-1-yl]-2-trifluoromethylbenzonitrile 110.2

Compound 110.2 was prepared as described for example 1.2, by reacting compound 1.1, instead of with 2-bromobenzyl bromide, with 2-bromo-1-bromomethyl-4-methoxybenzene (prepared by N-bromosuccinimide bromination from 2-bromo-4-methoxy-1-methylbenzene; $^1$H NMR: 7.56, d, 1H, 7.23, s, 1H, 7.0, d, 1H, 4.74, s, 2H; 3.8, s, 3H). 4-[3-(2-Bromo-4-methoxybenzyl)-4,4-dimethyl-2,5-dioxoimidazolidin-1-yl]-2-trifluoromethylbenzonitrile was obtained. (Molecular weight 495.04 ($C_{21}H_{17}BrF_3N_3O_3$); $^1$H NMR: 8.38, d, 1H, 8.25, s, 1H, 8.1, d, 1H, 7.5, d, 1H, 7.22, s, 1H, 6.95, d, 1H, 4.6, s, 2H, 3.79, s, 3H, 1.4, s, 6H.

2) Methyl 4-{2-[3-(4-cyano-3-trifluoromethylphenyl)-5,5-dimethyl-2,4-dioxoimidazolidin-1-ylmethyl]-5-methoxyphenylamino}benzoate 110

The further reaction with methyl 4-aminobenzoate to give the compound of example 110 was effected as described for example 1, stage 3. Methyl 4-{2-[3-(4-cyano-3-trifluoromethylphenyl)-5,5-dimethyl-2,4-dioxoimidazolidin-1-ylmethyl]-5-methoxyphenylamino}benzoate 110 was obtained. (Molecular weight 566.17 ($C_{29}H_{25}F_3N_4O_5$); retention time $R_t$=2.17 min. [B]; MS (ESI): 567.22 ($MH^+$).

The compound of example 124, tert-butyl 4-{2-[3-(4-cyano-3-trifluoromethylphenyl)-5,5-dimethyl-2,4-dioxoimidazolidin-1-ylmethyl]-5-methoxyphenylamino}benzoate [(molecular weight 608.22 ($C_{32}H_{31}F_3N_4O_5$); retention time $R_t$=2.37 min. [B]; MS (ESI): 553.14 ($MH^+-C_4H_6$)]

was prepared like the compound of example 110 with the difference that, in the second stage of the synthesis, instead of methyl 4-aminobenzoate, tert-butyl 4-aminobenzoate was used.

Example 111

Methyl 4-{2-[3-(4-cyano-3-trifluoromethylphenyl)-5,5-dimethyl-2,4-dioxoimidazolidin-1-ylmethyl]-5-fluorophenylamino}benzoate

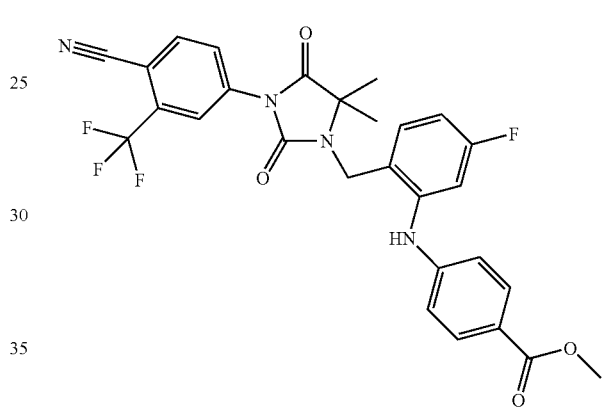

1) Preparation of 4-[3-(2-bromo-4-fluorobenzyl)-4,4-dimethyl-2,5-dioxoimidazolidin-1-yl]-2-trifluoromethylbenzonitrile 111.2

Compound 111.2 was prepared as described for example 1.2, by reacting compound 1.1, instead of with 2-bromobenzyl bromide, with 2-bromo-1-bromomethyl-4-chlorobenzene (prepared by free-radical bromination from 2-bromo-4-fluoro-1-methylbenzene with N-bromosuccinimide in tetrachloromethane; $^1$H NMR: 7.7, m, 1H, 7.65, d, 1H, 7.3, m, 1H, 4.75, s, 2H). (Molecular weight 483.02 ($C_{20}H_{14}BrF_4N_3O_3$); $^1$H NMR: 8.37, d, 1H, 8.25, s, 1H, 8.1, d, 1H, 7.65, m, 2H, 7.27, m, 1H, 4.62, s, 2H, 1.41, s, 6H).

2) Methyl 4-{2-[3-(4-cyano-3-trifluoromethylphenyl)-5,5-dimethyl-2,4-dioxoimidazolidin-1-ylmethyl]-5-fluorophenylamino}benzoate 111

The further reaction with methyl 4-aminobenzoate to give the compound of example 111 was effected as described for example 1, stage 3. Methyl 4-{2-[3-(4-cyano-3-trifluoromethylphenyl)-5,5-dimethyl-2,4-dioxoimidazolidin-1-ylmethyl]-5-fluorophenylamino}benzoate 111 was obtained. (Molecular weight 554.15 ($C_{28}H_{22}F_4N_4O_4$); retention time $R_t$=2.21 min. [B]; MS (ESI): 555.22 ($MH^+$)).

The compound of example 125, tert-butyl 4-{2-[3-(4-cyano-3-trifluoromethylphenyl)-5,5-dimethyl-2,4-dioxoimidazolidin-1-ylmethyl]-5-fluorophenylamino}benzoate [(molecular weight 596.20 ($C_{31}H_{28}F_4N_4O_4$); retention time $R_t$=2.42 min. [B]; MS (ESI): 541.14 ($MH^+–C_4H_6$)]

was prepared like the compound of example 111 with the difference that, in the second stage of the synthesis, instead of methyl 4-aminobenzoate, tert-butyl 4-aminobenzoate was used.

In an analogous manner, by reaction of 111.2 with methyl 6-aminonicotinate, the compound of example 265 (methyl 6-{2-[3-(4-cyano-3-trifluoromethylphenyl)-5,5-dimethyl-2,4-dioxoimidazolidin-1-ylmethyl]-5-fluorophenylamino}nicotinate (as the salt with trifluoroacetic acid)) was obtained.

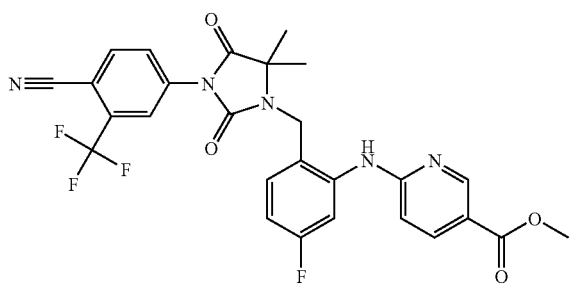

Molecular weight 555.15 ($C_{27}H_{21}F_4N_4O_4$); retention time $R_t$=2.81 min. [E]; MS (ESI): 556.03 ($MH^+$).

Example 126 tert-Butyl 4-{5-cyano-2-[3-(4-cyano-3-trifluoromethylphenyl)-5,5-dimethyl-2,4-dioxoimidazolidin-1-ylmethyl]phenylamino}benzoate

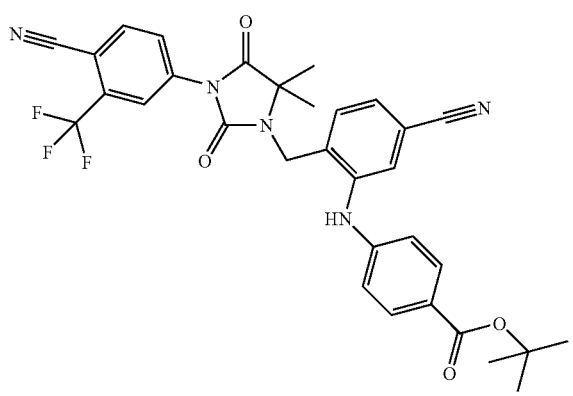

1) Preparation of 4-[3-(2-bromo-4-cyanobenzyl)-4,4-dimethyl-2,5-dioxoimidazolidin-1-yl]-2-trifluoromethylbenzonitrile 126.2

Compound 126.2 was prepared as described for example 1.2 by reacting compound 1.1, instead of with 2-bromobenzyl bromide, with 2-bromo-1-bromomethyl-4-cyanobenzene (prepared by N-bromosuccinimide bromination from 3-bromo-4-benzonitrile; $^1$H NMR: 8.25, s, 1H, 7.9, d, 1H, 7.81, d, 1H, 4.78, s, 3H). (Molecular weight 490.02 ($C_{21}H_{14}BrF_3N_4O_2$); $^1$H NMR: 8.35, d, 1H, 8.25, m, 2H, 8.1, d, 1H, 7.88, d, 1H, 7.78, d, 1H, 4.68, s, 2H, 1.49, s, 6H.

2) tert-Butyl 4-{5-cyano-2-[3-(4-cyano-3-trifluoromethylphenyl)-5,5-dimethyl-2,4-dioxoimidazolidin-1-ylmethyl]phenylamino}benzoate 126

The further reaction with tert-butyl 4-aminobenzoate to give the compound of example 126 was effected as described for example 1, stage 3. tert-Butyl 4-{5-cyano-2-[3-(4-cyano-3-trifluoromethylphenyl)-5,5-dimethyl-2,4-dioxoimidazolidin-1-ylmethyl]phenylamino}benzoate 126 was obtained. (Molecular weight 603.20 ($C_{32}H_{28}F_3N_5O_4$); retention time $R_t$=2.28 min. [B]; MS (ESI): 548.16 ($MH^+–C_4H_8$)).

Example 146 tert-Butyl 4-{2-[3-(4-cyano-3-trifluoromethylphenyl)-5,5-dimethyl-2,4-dioxoimidazolidin-1-ylmethyl]-5-dimethylsulfamoylphenylamino}benzoate

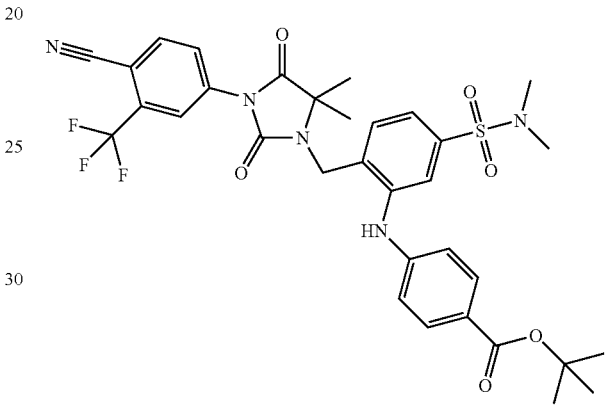

1) Preparation of 3-bromo-4-[3-(4-cyano-3-trifluoromethylphenyl)-5,5-dimethyl-2,4-dioxoimidazolidin-1-ylmethyl]-N,N-dimethylbenzenesulfonamide 146.2

Compound 146.2 was prepared as described for example 1.2, by reacting compound 1.1, instead of with 2-bromobenzyl bromide, with 3-bromo-4-bromomethyl-N,N-dimethylbenzenesulfonamide (146.3, prepared by reacting 3-bromo-4,N,N-trimethylbenzenesulfonamide with N-bromosuccinimide and N,N'-azobis(2-methylpropionitrile) in tetrachloromethane). 3-Bromo-4-[3-(4-cyano-3-trifluoromethylphenyl)-5,5-dimethyl-2,4-dioxoimidazolidin-1-ylmethyl]-N,N-dimethylbenzenesulfonamide was obtained. (Molecular weight 572.03 ($C_{22}H_{20}BrF_3N_4O_4S$); retention time $R_t$=2.38 min. [B]; MS (ESI): 573.25 ($MH^+$).

2) tert-Butyl 4-{2-[3-(4-cyano-3-trifluoromethylphenyl)-5,5-dimethyl-2,4-dioxoimidazolidin-1-ylmethyl]-5-dimethylsulfamoylphenylamino}benzoate 146

The further reaction with tert-butyl 4-aminobenzoate to give the compound of example 146 was effected analogously to the manner described for example 1, stage 3. tert-Butyl 4-{2-[3-(4-cyano-3-trifluoromethylphenyl)-5,5-dimethyl-2,4-dioxoimidazolidin-1-ylmethyl]-5-dimethylsulfamoylphenylamino}benzoate 146 was obtained. (Molecular weight 685.21 ($C_{33}H_{34}F_3N_5O_6S$); retention time $R_t$=2.85 min. [C]; MS (ESI): 630.18 ($MH^+–C_4H_8$)).

Example 23

3-(4-Fluoro-3-trifluoromethylphenyl)-5,5-dimethyl-1-(2-phenylaminobenzyl)imidazolidin-2,4-dione

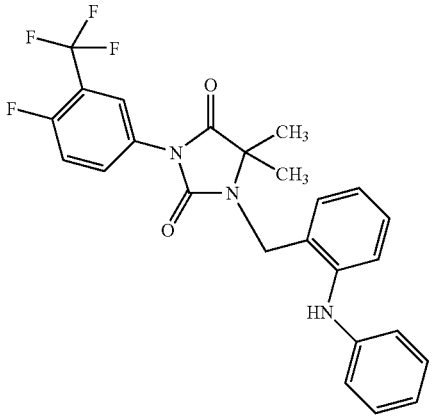

1) Preparation of 3-(4-fluoro-3-trifluoromethylphenyl)-5,5-dimethylimidazolidin-2,4-dione (23.1)

Compound 23.1 can be prepared by process "A". To this end, 1.5 g (9.76 mmol) of methyl 2-amino-2-methylpropionate hydrochloride were suspended in 20 ml of dry tetrahydrofuran, and admixed with 1.38 ml (9.76 mmol) of triethylamine and 2 g (9.76 mmol) of 1-fluoro-4-isocyanato-2-trifluoromethylbenzene. The mixture was stirred at 70° C. for 1 h, then allowed to cool somewhat, 10 ml of concentrated hydrochloric acid were added and the mixture was stirred at 70° C. for 2 h. The cooled reaction mixture was admixed with ethyl acetate and water; the organic phase was removed, dried over sodium sulfate, filtered and concentrated under reduced pressure. The residue was purified by chromatography (method [RP2]) and, after dissolving in ethyl acetate, drying the solution, concentrating under reduced pressure and redissolving in dichloromethane, was crystallized with n-heptane. 2.8 g of 3-(4-fluoro-3-trifluoromethylphenyl)-5,5-dimethylimidazolidine-2,4-dione (23.1) with the melting point of 111-114° C. were obtained.

Molecular weight 290.06 ($C_{12}H_{10}F_4N_2O_2$); retention time $R_t$=1.55 min. [B]; MS (ESI): 291.27 (MH$^+$).

2) Preparation of 1-(2-bromobenzyl)-3-(4-fluoro-3-trifluoromethylphenyl)-5,5-dimethylimidazolidine-2,4-dione (23.2)

Compounds 23.2 can be prepared by process "A". To this end, compound 23.1, analogously to the method as described for the preparation of 1.2, was reacted with 2-bromobenzyl bromide. 1-(2-Bromobenzyl)-3-(4-fluoro-3-trifluoromethylphenyl)-5,5-dimethylimidazolidine-2,4-dione was obtained in a yield of 93%. Molecular weight 458.02 ($C_{19}H_{15}BrF_4N_2O_2$); retention time $R_t$=2.80 min. [C]; MS (ESI): 459.04 (MH$^+$).

3) Preparation of 3-(4-fluoro-3-trifluoromethylphenyl)-5,5-dimethyl-1-(2-phenylaminobenzyl)imidazolidine-2,4-dione 23

To prepare the compound of example 23, the procedure may be according to process "A". Analogously to the method for example 1, stage 3, compound 23.2 was reacted with aniline. Compounds 23 was obtained in a yield of 81%. Molecular weight 471.14 ($C_{25}H_{21}F_4N_3O_2$); retention time $R_t$=2.34 min. [B]; MS (ESI): 472.11 (MH$^+$).

The compounds of example 24, 1-[2-(4-fluorophenylamino)benzyl]-3-(4-fluoro-3-trifluoromethylphenyl)-5,5-dimethylimidazolidine-2,4-dione, (molecular weight 489.14 ($C_{25}H_{20}F_5N_3O_2$); retention time $R_t$=2.34 min. [B]; MS (ESI): 490.11 (MH$^+$);

and of examples 25, 1-[2-(4-chlorophenylamino)benzyl]-3-(4-fluoro-3-trifluoromethylphenyl)-5,5-dimethylimidazolidine-2,4-dione (molecular weight 505.11 ($C_{25}H_{20}ClF_4N_3O_2$); retention time $R_t$=2.45 min. [B]; MS (ESI): 506.11 (MH$^+$);

52, 1-[2-(2,4-difluorophenylamino)benzyl]-3-(4-fluoro-3-trifluoromethylphenyl)-5,5-dimethylimidazolidine-2,4-dione, (molecular weight 507.13 ($C_{25}H_{19}F_6N_3O_2$); retention time $R_t$=2.34 min. [B]; MS (ESI): 507.98 (MH$^+$), 134, 4-{2-[3-(4-fluoro-3-trifluoromethylphenyl)-5,5-dimethyl-2,4-dioxoimidazolidin-1-ylmethyl]phenylamino}benzonitrile, (molecular weight 496.15 ($C_{26}H_{20}F_4N_4O_2$); retention time $R_t$=2.14 min. [B]; MS (ESI): 497.18 (MH$^+$)

were prepared like the compound of example 23 with the difference that, in the third stage of the synthesis, instead of aniline, 4-fluoroaniline (for 24),
4-chloroaniline (for 25),
2,4-difluoroaniline (for 52),
4-aminobenzonitrile (for 134) was used.

Example 28

4-[2,4-Dioxo-1-(2-phenylaminobenzyl)-1,3-diazaspiro[4.5]dec-3-yl]-2-trifluoromethylbenzonitrile

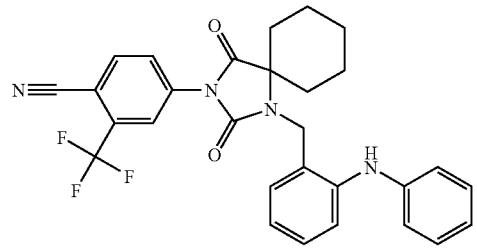

1) Preparation of 4-(2,4-dioxo-1,3-diazaspiro[4.5]dec-3-yl)-2-trifluoromethylbenzonitrile (28.1)

Compound 28.1 can be prepared by process "A". To this end, 5.3 ml of phosgene solution (20% in toluene) were initially charged under argon atmosphere. At 75° C., a solution of 4-cyano-3-trifluoromethylaniline in 15 ml of dry acetonitrile was slowly added dropwise. After the addition had ended, the mixture was stirred at 75° C. for another 90 min. The mixture was concentrated under reduced pressure. The residue was then taken up repeatedly in toluene and concentrated again under reduced pressure. Finally, the residue was dissolved in 15 ml of dry tetrahydrofuran, admixed with 0.72 g of 1-amino-1-cyclohexanecarboxylic acid and dropwise with 1.05 ml of triethylamine, and the mixture was stirred at room temperature for 2 h. After standing overnight at room temperature, the reaction mixture was admixed with 5 ml of concentrated hydrochloric acid and stirred under reflux for 2 h. The cooled reaction mixture was admixed with saturated sodium hydrogencarbonate solution and extracted with ethyl acetate. The organic phase was dried over magnesium sulfate, filtered and concentrated under reduced pressure. 0.62 g of 4-(2,4-dioxo-1,3-diazaspiro[4.5]dec-3-yl)-2-trifluoromethylbenzonitrile (28.1) was obtained. $^1$H NMR: 9.21, s, 1H, 8.30, d, 1H, 8.19, s, 1H, 8.02, d, 1H, 1.8-1.5, m, 9H, 1.4-1.25, m, 1H.

2) Preparation of 4-[1-(2-bromobenzyl)-2,4-dioxo-1,3-diazaspiro[4.5]dec-3-yl]-2-trifluoromethylbenzonitrile (28.2)

Compound 28.2 can be prepared by process "A". To this end, compound 28.1 was reacted with 2-bromobenzyl bromide as described in example 1.2. Compound 28.2 was obtained in a yield of 98%. $^1$H NMR: 8.45, d, 1H, 8.26, s, 1H, 8.10, d, 1H, 7.7-7.25, m, 4H, 4.6, s, 2H, 2.1-1.55, m, 9H, 1.2, m, 1H.

3) Preparation of 4-[2,4-dioxo-1-(2-phenylaminobenzyl)-1,3-diazaspiro[4.5]dec-3-yl]-2-trifluoromethylbenzonitrile (28)

To prepare the compound of example 28, the procedure may be according to process "A". Analogously to the process described in example 1.2, 28.2 and aniline were reacted. 28: Molecular weight 518.19 ($C_{29}H_{25}F_3N_4O_2$); retention time $R_t$=3.19 min. [C]; MS (ESI): 519.24 (MH$^+$).

Example 29

4-[4,4-Dimethyl-2,5-dioxo-3-(3-phenylaminobenzyl)imidazolidin-1-yl]-2-trifluoromethylbenzonitrile

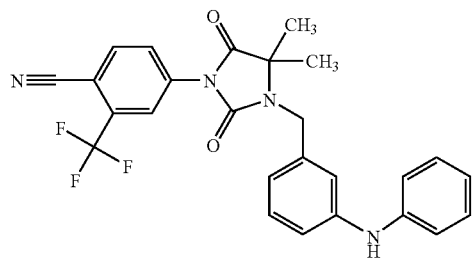

The compound of example 29 was obtained analogously to the procedure for the compound of example 1, by reacting compound 1.1, instead of with 2-bromobenzyl bromide, with 3-bromobenzyl bromide to give compounds 29.2 ($^1$H NMR: 8.35, d, 1H, 8.25, s, 1H, 8.10, d, 1H, 7.7, s, 1H, 7.5, m, 2H, 7.3, t, 1H, 4.6, s, 2H, 1.4, s, 6H). 29.2 was reacted in a further step as described in example 1, stage 3 with aniline to give the compound of example 29. Molecular weight 478.16 ($C_{26}H_{21}F_3N_4O_2$); retention time $R_t$=2.53 min. [B]; MS (ESI): 479.48 (MH$^+$).

Example 30

4-[4,4-Dimethyl-2,5-dioxo-3-(4-phenylaminobenzyl)imidazolidin-1-yl]-2-trifluoromethylbenzonitrile

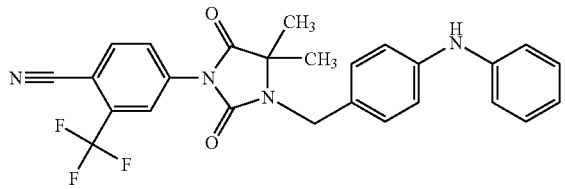

The compound of example 30 was obtained analogously to the procedure for the compound of example 1, by reacting compound 1.1, instead of with 2-bromobenzyl bromide, with 4-bromobenzyl bromide to give compound 30.2 ($^1$H NMR: 8.35, d, 1H; 8.25, s, 1H, 8.10, d, 1H, 7.55, d, 2H, 7.4, d, 2H, 4.6, s, 2H, 1.4, s, 6H). 30.2 was, in a further step as described in example 1, stage 3, reacted with aniline to give the compound of example 30. Molecular weight 478.16 ($C_{26}H_{21}F_3N_4O_2$); retention time $R_t$=2.54 min. [B]; MS (ESI): 479.41 (MH$^+$).

Example 35

4-{3-[2,4-Dichloro-6-(4-fluorophenylamino)benzyl]-4,4-dimethyl-2,5-dioxoimidazolidin-1-yl}-2-trifluoromethylbenzonitrile

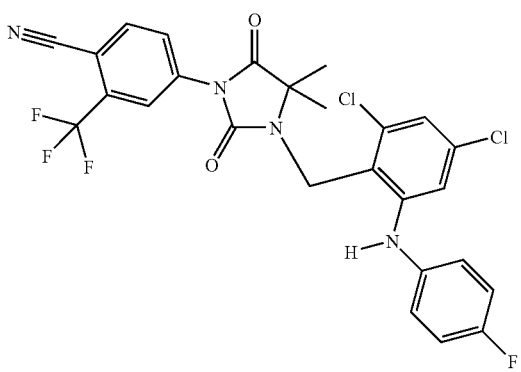

Preparation of 2-bromo-4,6-dichlorobenzyl bromide 35.3

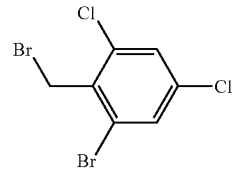

a) 2-Bromo-4,6-dichlorobenzoic acid 35.5

4.85 ml of tert-butyl nitrite were added dropwise at 0° C. to a suspension of 6.5 g of copper(II) bromide in 100 ml of dry acetonitrile. Within 5 minutes, 5 g of 2-amino-4,6-dichlorobenzoic acid were added in portions to this dark green solution. The mixture was stirred at 0° C. for 2 h, then allowed to warm to room temperature and stirred overnight. The mixture was concentrated under reduced pressure to about half the volume; 70 ml of 1 N hydrochloric acid were added and the mixture was extracted with 60 ml of diisopropyl ether. The organic phase was admixed with 70 ml of 2 N sodium hydroxide solution. The water phase was removed and adjusted to a pH of 2 with hydrochloric acid. The aqueous phase was extracted by shaking with diisopropyl ether, and the organic phase was dried over magnesium sulfate, filtered and concentrated under reduced pressure. 2-Bromo-4,6-dichlorobenzoic acid 35.5 was obtained. $^1$H NMR: 14.2, s, 1H, 7.9, d, 1H, 7.8, d, 1H.

b) (2-Bromo-4,6-dichlorophenyl)methanol 35.4

2.5 g of the acid 35.5 were dissolved in 25 ml of dry tetrahydrofuran and admixed dropwise at 0° C. with 9.26 ml of a 1 molar solution of lithium aluminum hydride in tetrahydrofuran with stirring. The reaction mixture was stirred at 0° C. for another 30 min and at room temperature for 2 h. For workup, the mixture was adjusted to pH 2 with 2.5 N sulfuric acid with cooling and admixed with ethyl acetate and water. The organic phase was removed, dried over magnesium sulfate and concentrated under reduced pressure. (2-Bromo-4,6-dichlorophenyl)methanol 35.4 was obtained and was used in the next stage without further purification.

c) 2-Bromo-4,6-dichlorobenzyl bromide 35.3

3.1 g of the benzyl alcohol 35.4 were dissolved in 40 ml of dry dichloromethane and admixed dropwise at 5° C. with a solution of 0.455 ml of phosphorus tribromide in 10 ml of dichloromethane. The reaction mixture was stirred overnight and then neutralized with 5 ml of a saturated aqueous sodium carbonate solution. The organic phase was removed, dried over magnesium sulfate, filtered and concentrated under reduced pressure. The residue was purified by column chromatography on silica gel with n-heptane as the eluent. 2-Bromo-4,6-dichlorobenzyl bromide 35.3 was obtained.

$^1$H NMR: 7.9, s, 1H; 7.8, s, 1H, 4.75, s, 2H.

1) Preparation of 4-[3-(2-bromo-4,6-dichlorobenzyl)-4,4-dimethyl-2,5-dioxoimidazolidin-1-yl]-2-trifluoromethylbenzonitrile 35.2

Compound 35.2 was prepared as described for example 6.2, by reacting compound 1.1 with 2-bromo-4,6-dichlorobenzyl bromide 35.3. 4-[3-(2-Bromo-4,6-dichlorobenzyl)-4,4-dimethyl-2,5-dioxoimidazolidin-1-yl]-2-trifluoromethylbenzonitrile was obtained in a yield of 83%. $^1$H NMR: 8.35, d, 1H, 8.2, s, 1H, 8.05, d, 1H, 7.9, s, 1H; 7.8, s, 1H; 4.9, s, 2H, 1.35, s, 6H.

2) Preparation of 4-{3-[2,4-dichloro-6-(4-fluorophenylamino)benzyl]-4,4-dimethyl-2,5-dioxoimidazolidin-1-yl}-2-trifluoromethylbenzonitrile 35

The further reaction with 4-fluoroaniline to give the compound of example 35 was effected as described for example 1, stage 3. 4-{3-[2,4-Dichloro-6-(4-fluorophenylamino)benzyl]-4,4-dimethyl-2,5-dioxoimidazolidin-1-yl}-2-trifluoromethylbenzonitrile 35 was obtained. (Molecular weight 564.07 ($C_{26}H_{18}Cl_2F_4N_4O_2$); retention time $R_t$=2.98 min. [B]; MS (ESI): 606.23 ($MH^+$+$CH_3CN$).

The compound of example 36, 4-{3-[2,4-dichloro-6-(2,4-difluorophenylamino)benzyl]-4,4-dimethyl-2,5-dioxoimidazolidin-1-yl}-2-trifluoromethylbenzonitrile (molecular weight 582.06 ($C_{26}H_{17}Cl_2F_5N_4O_2$); retention time $R_t$=2.98 min. [B]; MS (ESI): 583.32 ($MH^+$), and of example 37, 4-{3-[2,4-dichloro-6-(4-chlorophenylamino)benzyl]-4,4-dimethyl-2,5-dioxoimidazolidin-1-yl}-2-trifluoromethylbenzonitrile (molecular weight 580.04 ($C_{26}H_{18}Cl_3F_3N_4O_2$); retention time $R_t$=3.09 min. [B]; MS (ESI): 581.32 ($MH^+$), and of example 104, methyl 4-{3,5-dichloro-2-[3-(4-cyano-3-trifluoromethylphenyl)-5,5-dimethyl-2,4-dioxoimidazolidin-1-ylmethyl]phenylamino}benzoate (molecular weight 604.08 ($C_{28}H_{21}Cl_2F_3N_4O_4$); retention time $R_t$=2.52 min. [B]; MS (ESI): 605.17 ($MH^+$), was prepared like the compound of example 35 with the difference that, in the second stage of the synthesis, instead of 4-fluoroaniline, 2,4-difluoroaniline (for 36),
4-chloroaniline (for 37),
methyl 4-aminobenzoate (for 104) was used.

Example 38

4-{3-[3,5-Dichloro-2-(4-fluorophenylamino)benzyl]-4,4-dimethyl-2,5-dioxoimidazolidin-1-yl}-2-trifluoromethylbenzonitrile

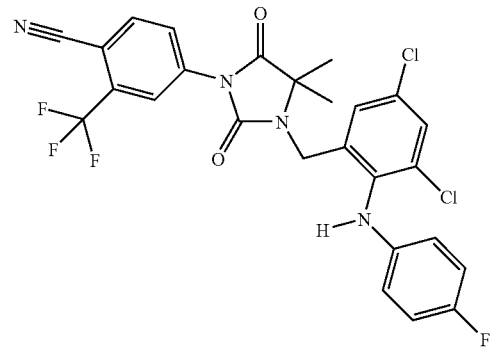

Preparation of 2-bromo-3,5-dichlorobenzyl bromide 38.3

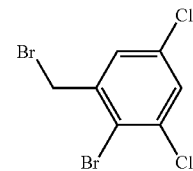

2-Bromo-3,5-dichlorobenzyl bromide 38.3 was prepared in the same way as 2-bromo-4,6-dichlorobenzyl bromide 35.3, but starting from 3,5-dichloroanthranilic acid via 2-bromo-3,5-dichlorobenzoic acid 38.5 and (2-bromo-3,5-dichlorophenyl)methanol 38.4. 2-Bromo-3,5-dichlorobenzyl bromide 38.3: $^1$H NMR: 7.8, s, 1H, 7.55, s, 1H, 4.75, s, 2H.

1) Preparation of 4-[3-(2-bromo-3,5-dichlorobenzyl)-4,4-dimethyl-2,5-dioxoimidazolidin-1-yl]-2-trifluoromethylbenzonitrile 38.2

Compound 38.2 was prepared as described for example 6.2, by reacting compound 1.1 with 2-bromo-3,5-dichlorobenzyl bromide. 4-[3-(2-Bromo-3,5-dichlorobenzyl)-4,4-dimethyl-2,5-dioxoimidazolidin-1-yl]-2-trifluoromethylbenzonitrile was obtained in a yield of 55%. $^1$H NMR: 8.35, d, 1H, 8.25, s, 1H, 8.1, d, 1H, 7.7, s, 1H, 7.65, s, 1H; 4.65, s, 2H, 1.45, s, 6H.

2) Preparation of 4-{3-[3,5-dichloro-2-(4-fluorophenylamino)benzyl]-4,4-dimethyl-2,5-dioxoimidazolidin-1-yl}-2-trifluoromethylbenzonitrile 38

The further reaction with 4-fluoroaniline to give the compound of example 38 was effected as described for example 1, stage 3. 4-{3-[3,5-Dichloro-2-(4-fluorophenylamino)benzyl]-4,4-dimethyl-2,5-dioxoimidazolidin-1-yl}-2-trifluoromethylbenzonitrile 38 was obtained. (Molecular weight 564.07 (C$_{26}$H$_{18}$Cl$_2$F$_4$N$_4$O$_2$); retention time R$_t$=2.37 min. [B]; MS (ESI): 565.17 (MH$^+$)).

The compound of example 39, 4-{3-[3,5-dichloro-6-(2,4-difluorophenylamino)benzyl]-4,4-dimethyl-2,5-dioxoimidazolidin-1-yl}-2-trifluoromethylbenzonitrile (molecular weight 582.06 (C$_{26}$H$_{17}$Cl$_2$F$_5$N$_4$O$_2$); retention time R$_t$=2.42 min. [B]; MS (ESI): 583.16 (MH$^+$)), and of example 40, 4-{3-[3,5-dichloro-6-(4-chlorophenylamino)benzyl]-4,4-dimethyl-2,5-dioxoimidazolidin-1-yl}-2-trifluoromethylbenzonitrile (molecular weight 580.04 (C$_{26}$H$_{18}$Cl$_3$F$_3$N$_4$O$_2$); retention time R$_t$=2.47 min. [B]; MS (ESI): 581.14 (MH$^+$)), were prepared like the compound of example 38 with the difference that, in the second stage of the synthesis, instead of 4-fluoroaniline, 2,4-difluoroaniline (for 39),
4-chloroaniline (for 40) was used.

Example 41

4-{3-[5-Chloro-2-(4-fluorophenylamino)benzyl]-4,4-dimethyl-2,5-dioxoimidazolidin-1-yl}-2-trifluoromethylbenzonitrile

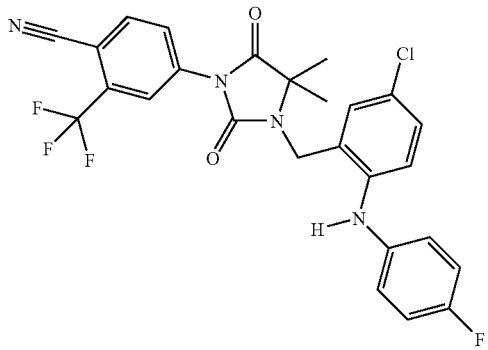

1) Preparation of 4-[3-(2-bromo-5-chlorobenzyl)-4,4-dimethyl-2,5-dioxoimidazolidin-1-yl]-2-trifluoromethylbenzonitrile 41.2

Compound 41.2 was prepared as described for example 6.2, by reacting compound 1.1 with 2-bromo-5-chlorobenzyl bromide (prepared from 2-bromo-5-chlorobenzoic acid by reaction with lithium aluminum hydride and reaction of the benzyl alcohol thus obtained with phosphorus tribromide). 4-[3-(2-Bromo-5-chlorobenzyl)-4,4-dimethyl-2,5-dioxoimidazolidin-1-yl]-2-trifluoromethylbenzonitrile was obtained in a yield of 64%. $^1$H NMR: 8.35, d, 1H, 8.25, s, 1H, 8.1, d, 1H, 7.65, m, 2H, 7.33, d, 1H, 4.6, s, 2H, 1.45, s, 6H.

2) Preparation of 4-{3-[5-chloro-2-(4-fluorophenylamino)benzyl]-4,4-dimethyl-2,5-dioxoimidazolidin-1-yl}-2-trifluoromethylbenzonitrile 41

The further reaction with 4-fluoroaniline to give the compound of example 41 was effected as described for example 1, stage 3. 4-{3-[5-Chloro-2-(4-fluorophenylamino)benzyl]-4,4-dimethyl-2,5-dioxoimidazolidin-1-yl}-2-trifluoromethylbenzonitrile 41 was obtained. (Molecular weight 530.11 (C$_{26}$H$_{19}$ClF$_4$N$_4$O$_2$); retention time R$_t$=2.37 min. [B]; MS (ESI): 531.17 (MH$^+$)).

The compound of example 42, 4-{3-[5-chloro-6-(2,4-difluorophenylamino)benzyl]-4,4-dimethyl-2,5-dioxoimidazolidin-1-yl}-2-trifluoromethylbenzonitrile (molecular weight 548.10 (C$_{26}$H$_{18}$ClF$_5$N$_4$O$_2$); retention time R$_t$=2.38 min. [B]; MS (ESI): 549.17 (MH$^+$)), and of example 43, 4-{3-[5-chloro-6-(4-chlorophenylamino)benzyl]-4,4-dimethyl-2,5-dioxoimidazolidin-1-yl}-2-trifluoromethylbenzonitrile (molecular weight 546.08 (C$_{26}$H$_{19}$Cl$_2$F$_3$N$_4$O$_2$); retention time R$_t$=2.48 min. [B]; MS (ESI): 547.15 (MH$^+$)), were prepared like the compound of example 41 with the difference that, in the second stage of the synthesis, instead of 4-fluoroaniline, 2,4-difluoroaniline (for 42),
4-chloroaniline (for 43) was used.

Example 48

4-{3-[2,5-Bis(4-chlorophenylamino)benzyl]-4,4-dimethyl-2,5-dioxoimidazolidin-1-yl}-2-trifluoromethylbenzonitrile

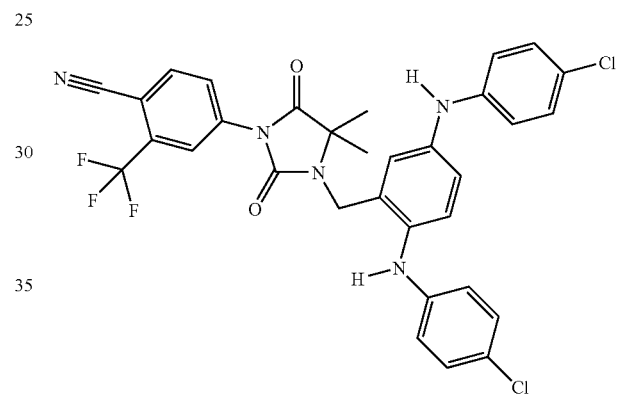

In the preparation of the compound of example 43 (40% yield), the compound of example 48 was obtained as a further product in 23% yield. Molecular weight 637.12 (C$_{32}$H$_{24}$Cl$_2$F$_3$N$_5$O$_2$); retention time R$_t$=2.58 min. [B]; MS (ESI): 638.20 (MH$^+$).

Example 49

1-[2-(2,4-Difluorophenylamino)benzyl]-5,5-dimethyl-3-(4-phenoxyphenyl)imidazolidine-2,4-dione

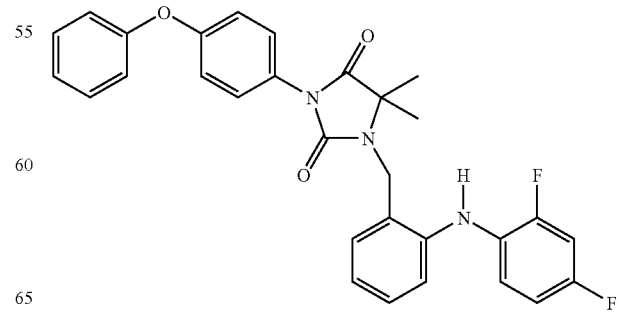

1) Preparation of 5,5-dimethyl-3-(4-phenoxyphenyl) imidazolidine-2,4-dione (49.1)

Compound 49.1 can be prepared by process "A". To this end, 7.8 g of tert-butyl 2-amino-2-methylpropionate hydrochloride were suspended at room temperature in 100 ml of dry tetrahydrofuran, and admixed with 8.9 g of 4-phenoxyphenyl isocyanate and 8.4 ml of triethylamine, and the mixture was stirred at room temperature for 2 h. Thereafter, 20 ml of concentrated hydrochloric acid were added and the mixture was stirred under reflux for a further 2 h. The cooled reaction mixture was admixed with water and ethyl acetate; the organic phase was washed with saturated sodium hydrogencarbonate solution and then with concentrated sodium chloride solution, dried over magnesium sulfate, filtered and concentrated under reduced pressure. The residue was stirred with diisopropyl ether, filtered off with suction, washed with more diisopropyl ether and dried. 49.1 was obtained with the melting point of 165° C. in a yield of 97%. Molecular weight 296.11 ($C_{17}H_{16}N_2O_3$); retention time $R_t$=1.95 min.; MS (ESI): 297.42 (MH$^+$).

2) Preparation of 1-(2-bromobenzyl)-5,5-dimethyl-3-(4-phenoxyphenyl)imidazolidine-2,4-dione (49.2)

Compound 49.2 can be prepared by process "A". To this end, compound 49.1 was reacted with 2-bromobenzyl bromide as described in example 1.2. Compound 49.2 was obtained in a yield of 98%. Molecular weight 464.07 ($C_{24}H_{21}BrN_2O_3$); retention time $R_t$=2.58 min. [B]; MS (ESI): 465.33 (MH$^+$).

3) Preparation of 1-[2-(2,4-difluorophenylamino) benzyl]-5,5-dimethyl-3-(4-phenoxyphenyl)imidazolidine-2,4-dione (49)

To prepare the compound of example 49, the procedure may be according to process "A". Analogously to the process described in example 1.2, 49.2 and 2,4-difluoroaniline were reacted. 49: Molecular weight 513.18 ($C_{30}H_{25}F_2N_3O_3$); retention time $R_t$=2.41 min. [B]; MS (ESI): 514.23 (MH$^+$).

Example 50

3-[4-(4-Chlorophenoxy)-3-trifluoromethylphenyl]-1-[2-(2,4-difluorophenylamino)benzyl]-5,5-dimethylimidazolidine-2,4-dione

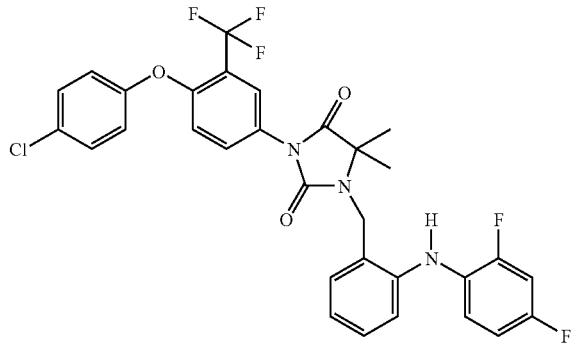

1) Preparation of 3-[4-(4-chlorophenoxy)-3-trifluoromethylphenyl]-5,5-dimethylimidazolidine-2,4-dione (50.1)

Compound 50.1 can be prepared by process "A". To this end, 0.51 g of di(N-succinimidyl) carbonate was initially charged at room temperature in 15 ml of dry acetonitrile and admixed slowly (1 h) with a solution of 0.29 g of 4-(4-chlorophenoxy)-3-trifluoromethylphenylamine in 10 ml of dry acetonitrile. The reaction mixture was stirred at room temperature overnight. The reaction mixture was concentrated under reduced pressure; the residue was stirred with ethyl acetate and cooled in an ice bath, and the precipitate was filtered off. The filtrate was washed with 1 N hydrochloric acid and then with saturated sodium hydrogencarbonate solution, dried over magnesium sulfate, filtered and concentrated under reduced pressure. For further processing, the crude product (2,5-dioxopyrrolidin-1-yl [4-(4-chlorophenoxy)-3-trifluoromethylphenyl]carbamate) was dissolved in 10 ml of dry acetonitrile at room temperature and admixed successively with 0.15 g of methyl 2-amino-2-methylpropionate hydrochloride and 0.14 ml of triethylamine, and stirred under reflux for 2 h. Thereafter, 2 ml of concentrated hydrochloric acid were slowly added dropwise and the reaction mixture was subsequently stirred under reflux for 2 h. The cooled reaction mixture was admixed cautiously with saturated sodium hydrogencarbonate solution with stirring and extracted by shaking with ethyl acetate, and the organic phase was dried over magnesium sulfate, filtered and concentrated under reduced pressure. The residue was purified by chromatography (silica gel; 98/2 dichloromethane/methanol) to obtain 3-[4-(4-chlorophenoxy)-3-trifluoromethylphenyl]-5-dimethylimidazolidine-2,4-dione in a 53% yield. $^1$H NMR: 8.62, s, 1H, 7.9, d, 1H, 7.7, dd, 1H, 7.5, m, 2H, 7.15, m, 3H, 1.4, s, 6H.

2) Preparation of 1-(2-bromobenzyl)-3-[4-(4-chlorophenoxy)-3-trifluoromethylphenyl]-5,5-dimethylimidazolidine-2,4-dione (50.2)

Compound 50.2 can be prepared by process "A". To this end, compound 50.1 was reacted with 2-bromobenzyl bromide as described in example 1.2. Compound 50.2 was obtained in a yield of 97%.

Molecular weight 566.02 ($C_{25}H_{19}BrClF_3N_2O_3$); retention time $R_t$=2.86 min. [B]; MS (ESI): 608.16 (MH$^+$+CH$_3$CN).

3) Preparation of 3-[4-(4-chlorophenoxy)-3-trifluoromethylphenyl]-1-[2-(2,4-difluorophenylamino) benzyl]-5,5-dimethylimidazolidine-2,4-dione (50)

To prepare the compound of example 50, the procedure may be according to process "A". Analogously to the process described in example 1.2, 50.2 and 2,4-difluoroaniline were reacted. 50: Molecular weight 615.13 ($C_{31}H_{23}ClF_5N_3O_3$); retention time $R_t$=2.99 min. [B]; MS (ESI): 616.26 (MH$^+$).

Example 51

4-{3-[2-(2,4-Difluorophenylamino)benzyl]-4,4-dimethyl-2,5-dioxoimidazolidin-1-yl}-2-pentafluorosulfanylbenzonitrile

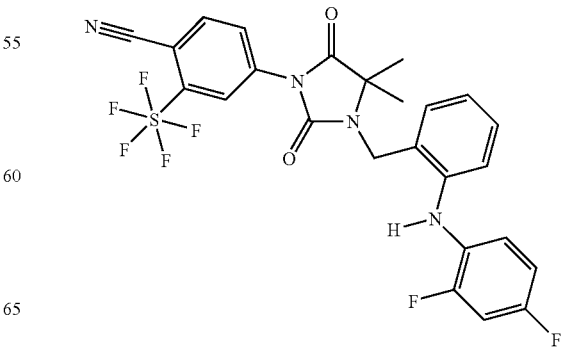

A) Preparation of 4-amino-2-pentafluorosulfanylbenzonitrile 51.9

1) 3-Pentafluorosulfanylphenylamine 51.3

2 g (8 mmol) of 3-nitropentafluorosulfanylbenzene (CAS # 2613-26-5) were dissolved in 20 ml of ethanol, admixed with 0.1 g of palladium on carbon (10%) and hydrogenated at 5.5 bar until the hydrogen uptake had ended. Subsequently, the reaction mixture was filtered and concentrated under reduced pressure. Molecular weight 219.01 ($C_6H_6F_5NS$); retention time $R_f$=1.74 min. [C]; MS (ESI): 261.07 ($MH^+ + CH_3CN$).

2) 2-(3-Pentafluorosulfanylphenyl)isoindole-1,3-dione 51.4

1.5 g (6.84 mmol) of 3-pentafluorosulfanylphenylamine 51.3 were suspended with 1.01 g (6.84 mmol) of phthalic anhydride in 4 ml of acetic acid and boiled under reflux for 2 h. The cooled reaction mixture was admixed with 40 ml of water, treated in an ultrasound bath for 30 min and filtered. The residue was washed with water and then with a little ethanol, and dried under reduced pressure. 2-(3-Pentafluorosulfanylphenyl)isoindole-1,3-dione 51.4 with the melting point of 188-190° C. was obtained.

3) 2-(4-Nitro-3-pentafluorosulfanylphenyl)isoindole-1,3-dione 51.5 and 2-(2-nitro-5-pentafluorosulfanylphenyl)isoindole-1,3-dione 51.6

1 g (2.863 mmol) of 2-(3-pentafluorosulfanylphenyl)isoindole-1,3-dione 51.4 was dissolved at 0° C. in 3.29 ml of concentrated nitric acid, and the mixture was stirred at 0° C. for 2 h. Thereafter, the mixture was left to stand overnight at room temperature. The reaction solution was added to 50 g of ice-water and the mixture was stirred for 1 h; thereafter, the precipitate was filtered off with suction, washed with water, dried and purified by chromatography on silica gel with toluene as the eluent. 2-(4-Nitro-3-pentafluorosulfanylphenyl)isoindole-1,3-dione 51.5 with the melting point of 200-203° C. and 2-(2-nitro-5-pentafluorosulfanylphenyl)isoindole-1,3-dione 51.6 with the melting point of 175-177° C. were obtained in a ratio of 1:2.

4) 2-(4-Amino-3-pentafluorosulfanylphenyl)isoindole-1,3-dione 51.7

1.94 g (4.92 mmol) of 2-(4-nitro-3-pentafluorosulfanylphenyl)isoindole-1,3-dione 51.5 were dissolved in 20 ml of methanol, admixed with 53 mg of 10% palladium on activated carbon and hydrogenated at room temperature at a hydrogen pressure of 5 bar. After the reaction had ended, the mixture was filtered from the catalyst and the filtrate was concentrated. The residue was stirred in a mixture of dichloromethane and n-heptane, filtered with suction and dried under reduced pressure. 2-(4-Amino-3-pentafluorosulfanylphenyl)isoindole-1,3-dione 51.7 with the melting point of 176-178° C. was obtained.

5) 4-(1,3-Dioxo-1,3-dihydroisoindol-2-yl)-2-pentafluorosulfanylbenzonitrile 51.8

0.46 ml (8.24 mmol) of semiconcentrated sulfuric acid was slowly added dropwise at 0° C. to a solution of 1 g (2.74 mmol) of 2-(4-amino-3-pentafluorosulfanylphenyl)isoindole-1,3-dione 51.7 in acetic acid. The mixture was stirred at 0° C. for 10 min; thereafter, a solution of 189.4 mg of sodium nitrite in 2 ml of water was slowly added dropwise with stirring, and the resulting solution was stirred at 0° C. for 30 min. This solution was finally added dropwise to a solution, cooled to 0° C., of 246 mg (2.74 mmol) of copper(I) cyanide and 536 mg (8.23 mmol) of potassium cyanide in 5 ml of water. The reaction mixture was stirred at 0° C. for 30 min and then at room temperature for another 3 h. After the reaction had ended, the mixture was added to water and the aqueous phase was extracted by shaking twice with ethyl acetate. The organic phase was dried over magnesium sulfate and filtered, the filtrate was concentrated and the residue was purified by chromatography on silica gel first with toluene and then with 20/1 toluene/ethyl acetate. 4-(1,3-Dioxo-1,3-dihydroisoindol-2-yl)-2-pentafluorosulfanylbenzonitrile 51.8 was obtained. $^1$H NMR: 8.4, m, 2H, 8.1-7.95, m, 5H.

6) 4-Amino-2-pentafluorosulfanylbenzonitrile 51.9 and N-(4-cyano-3-pentafluorosulfanylphenyl)phthalamide ethyl ester 51.10

610 mg (1.63 mmol) of 4-(1,3-dioxo-1,3-dihydroisoindol-2-yl)-2-pentafluorosulfanylbenzonitrile 51.8 were dissolved in 30 ml of ethanol and admixed with 100 mg (1.956 mmol) of hydrazine hydrate (100%). The mixture was stirred at room temperature overnight. Thereafter, the mixture was concentrated under reduced pressure and the residue was purified by chromatography (preparative HPLC; Purospher STAR RP-18e (10 μm); eluent: acetonitrile/water (0.5% trifluoroacetic acid) 5/95→95/5 [45 min.]). 4-Amino-2-pentafluorosulfanylbenzonitrile 51.9 ($^1$H NMR: 7.65, s, 1H, 7.2, s, 1H, 6.8, m, 3H) and N-(4-cyano-3-pentafluorosulfanylphenyl)phthalamide ethyl ester 51.10 ($^1$H NMR: 11.3, s, 1H, 8.6, s, 1H, 8.2, d, 1H, 8.1, d, 1H, 7.95, d, 1H, 7.75, m, 1H, 7.7, m, 2H, 4.2, q, 2H, 1.15, t, 3H) were obtained.

B) Preparation of 4-{3-[2-(2,4-difluorophenylamino)benzyl]-4,4-dimethyl-2,5-dioxoimidazolidin-1-yl}-2-pentafluorosulfanylbenzonitrile 51

1) 4-(4,4-Dimethyl-2,5-dioxoimidazolidin-1-yl)-2-pentafluorosulfanylbenzonitrile 51.1

To prepare compound 51.1, the procedure may be according to process "A". 505 mg of amine 51.9 and 227.1 mg of triphosgene were dissolved in 15 ml of dry tetrahydrofuran. At 0° C., over 30 minutes, 0.864 ml of triethylamine in 2.5 ml of tetrahydrofuran was added dropwise and then the mixture was stirred at 5° C. for a further 10 minutes. 404.7 mg of the hydrochloride of tert-butyl 2-amino-2-methylpropionate were added, and the mixture was allowed to warm to room temperature and stirred at room temperature for a further 2 h. The reaction mixture was admixed with 2.5 ml of concentrated hydrochloric acid and stirred at room temperature for a further 2 h. For workup, the mixture was admixed with water and ethyl acetate, and the organic phase was removed, washed with saturated sodium chloride solution, dried over magnesium sulfate, filtered and concentrated under reduced pressure. The chromatographic purification was effected according to method [RP1]. The product-containing fractions were concentrated under reduced pressure, the residue was extracted by repeated shaking with dichloromethane, and the organic phase was dried over magnesium sulfate and concentrated under reduced pressure. 51.1 was obtained in 41% yield. $^1$H NMR: 8.85, s, 1H, 8.4, s, 1H, 8.3, d, 1H, 8.02, d, 1H, 1.4, s, 6H.

2) Preparation of 4-[3-(2-Bromobenzyl)-4,4-dimethyl-2,5-dioxoimidazolidin-1-yl]-2-pentafluorosulfanylbenzonitrile 51.2

Compound 51.2 was prepared as described for example 6.2, by reacting compound 51.1 with 2-bromobenzyl bromide. 4-[3-(2-Bromobenzyl)-4,4-dimethyl-2,5-dioxoimidazolidin-1-yl]-2-pentafluorosulfanylbenzonitrile was obtained in a yield of 71%. $^1$H NMR: 8.45, s, 1H, 8.35, d, 1H, 8.1, d, 1H, 7.65, d, 1H, 7.58, d, 1H, 7.4, t, 1H, 7.25, t, 1H, 4.65, s, 2H, 1.45, s, 6H.

3) Preparation of 4-{3-[2-(2,4-difluorophenylamino)benzyl]-4,4-dimethyl-2,5-dioxoimidazolidin-1-yl}-2-pentafluorosulfanylbenzonitrile 51

The further reaction with 2,4-difluoroaniline to give the compound of example 51 was effected as described for example 1, stage 3. 4-{3-[2-(2,4-Difluorophenylamino)benzyl]-4,4-dimethyl-2,5-dioxoimidazolidin-1-yl}-2-pentafluorosulfanylbenzonitrile 51 was obtained. Molecular weight 572.11 ($C_{25}H_{19}F_7N_4O_2S$); retention time $R_t$=2.36 min. [B]; MS (ESI): 573.13 (MH$^+$); $^1$H NMR: 8.42, s, 1H, 8.35, d, 1H, 8.08, d, 1H, 7.45, d, 1H, 7.41, s, 1H, 7.26, t, 1H, 7.2, t, 1H, 6.9, m, 3H, 4.6, s, 2H, 1.4, s, 6H.

Example 55

4-{3-[2-(4-Fluorophenylamino)-4-trifluoromethylbenzyl]-4,4-dimethyl-2,5-dioxoimidazolidin-1-yl}-2-trifluoromethylbenzonitrile

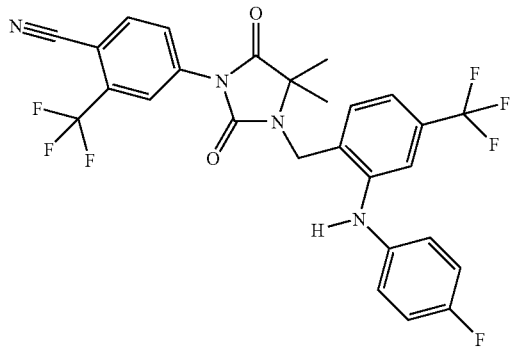

1) Preparation of 4-[3-(2-bromo-4-trifluoromethylbenzyl)-4,4-dimethyl-2,5-dioxoimidazolidin-1-yl]-2-trifluoromethylbenzonitrile 55.2

Compound 55.2 was prepared as described for example 6.2, by reacting compound 1.1 with 2-bromo-4-trifluoromethylbenzyl bromide. 4-[3-(2-Bromo-4-trifluoromethylbenzyl)-4,4-dimethyl-2,5-dioxoimidazolidin-1-yl]-2-trifluoromethylbenzonitrile was obtained in a yield of 78%. $^1$H NMR: 8.36, d, 1H, 8.25, s, 1H, 8.1, d, 1H, 8.05, s, 1H; 7.85, d, 1H, 7.73, d, 1H, 4.7, s, 2H, 1.48, s, 6H.

2) Preparation of 4-{3-[2-(4-Fluorophenylamino)-4-trifluoromethylbenzyl]-4,4-dimethyl-2,5-dioxoimidazolidin-1-yl}-2-trifluoromethylbenzonitrile 55

The further reaction with 4-fluoroaniline to give the compound of example 55 was effected as described for example 1, stage 3. 4-{3-[2-(4-Fluorophenylamino)-4-trifluoromethylbenzyl]-4,4-dimethyl-2,5-dioxoimidazolidin-1-yl}-2-trifluoromethylbenzonitrile 55 was obtained. Molecular weight 564.13 ($C_{27}H_{19}F_7N_4O_2$); retention time $R_t$=2.40 min. [B]; MS (ESI): 565.09 (MH$^+$).

The compound of example 56, 4-{3-[2-(2,4-difluorophenylamino)-4-trifluoromethylbenzyl]-4,4-dimethyl-2,5-dioxoimidazolidin-1-yl}-2-trifluoromethylbenzonitrile (molecular weight 582.13 ($C_{27}H_{18}F_8N_4O_2$); retention time $R_t$=2.40 min. [B]; MS (ESI): 583.07 (MH$^+$)), of example 57, 4-{3-[2-(4-chlorophenylamino)-4-trifluoromethylbenzyl]-4,4-dimethyl-2,5-dioxoimidazolidin-1-yl}-2-trifluoromethylbenzonitrile (molecular weight 580.11 ($C_{27}H_{19}ClF_6N_4O_2$); retention time $R_t$=2.51 min. [B]; MS (ESI): 581.06 (MH$^+$)), of example 106, methyl 4-{2-[3-(4-cyano-3-trifluoromethylphenyl)-5,5-dimethyl-2,4-dioxoimidazolidin-1-ylmethyl]-5-trifluoromethylphenylamino}benzoate (molecular weight 604.15 ($C_{29}H_{22}F_6N_4O_4$); retention time $R_t$=2.31 min. [B]; MS (ESI): 605.21 (MH$^+$)), of example 122, tert-butyl 4-{2-[3-(4-cyano-3-trifluoromethylphenyl)-5,5-dimethyl-2,4-dioxoimidazolidin-1-ylmethyl]-5-trifluoromethylphenylamino}benzoate (molecular weight 646.20 ($C_{32}H_{28}F_6N_4O_4$); retention time $R_t$=2.50 min. [B]; MS (ESI): 591.14 (MH$^+$−$C_4H_8$)), and of example 165, ethyl 4-{2-[3-(4-cyano-3-trifluoromethylphenyl)-5,5-dimethyl-2,4-dioxoimidazolidin-1-ylmethyl]-5-trifluoromethylphenylamino}benzoate (molecular weight 618.17 ($C_{30}H_{24}F_6N_4O_4$); retention time $R_t$=2.38 min. [B]; MS (ESI): 619.15 (MH$^+$))

were prepared like the compound of example 55 with the difference that, in the second stage of the synthesis, instead of 4-fluoroaniline, 2,4-difluoroaniline (for 56), 4-chloroaniline (for 57), methyl 4-aminobenzoate (for 106), tert-butyl 4-aminobenzoate (for 122), ethyl 4-aminobenzoate (for 165) was used.

Example 58

2-{2-[3-(4-Cyano-3-trifluoromethylphenyl)-5,5-dimethyl-2,4-dioxoimidazolidin-1-ylmethyl]phenylamino}-5-fluorobenzamide

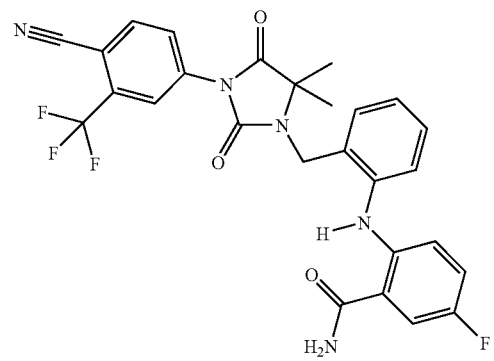

150 mg (0.288 mmol) of the compound of example 53 were dissolved in 1.5 ml of dichloromethane. At 5° C., 19.5 mg of tetrabutylammonium hydrogensulfate, 180 mg of sodium hydroxide in 0.133 ml of water and 0.148 ml of hydrogen peroxide (30%) were added. The mixture was warmed to room temperature and stirred for 2 h. Thereafter, another 148 µl of hydrogen peroxide were added and the mixture was stirred for a further 2 hours. Thereafter, another 148 µl of hydrogen peroxide were added and the mixture was stirred for 2 further hours. For workup, a little water and dichloromethane were added to the reaction mixture, and the organic phase was removed and purified by chromatography (method [RP1]). 2-{2-[3-(4-Cyano-3-trifluoromethylphenyl)-5,5-dimethyl-2,4-dioxoimidazolidin-1-ylmethyl]phenylamino}-5-fluorobenzamide 58 was obtained in a yield of 52%. Molecular weight 539.15 ($C_{27}H_{21}F_4N_5O_3$); retention time $R_t$=2.04 min. [B]; MS (ESI): 540.06 (MH$^+$).

The compound of example 54 4-{3-[2-(4-cyanophenylamino)benzyl]-4,4-dimethyl-2,5-dioxoimidazolidin-1-yl}-2-trifluoromethylbenzamide was prepared analogously using compound 33. Molecular weight 521.16 ($C_{27}H_{22}F_3N_5O_3$); retention time $R_t$=1.72 min. [B]; MS (ESI): 522.10 (MH$^+$).

Example 59

4-{4,4-Dimethyl-3-[2-(methylphenylamino)benzyl]-2,5-dioxoimidazolidin-1-yl}-2-trifluoromethylbenzonitrile

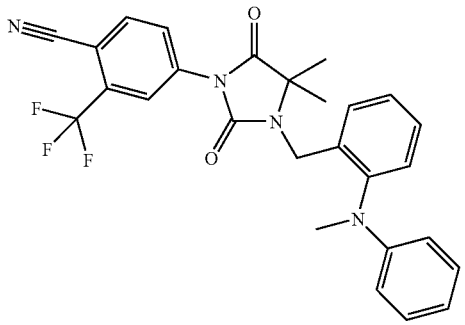

53 mg of the compound of example 1 were dissolved in 1.1 ml of acetonitrile. 10.4 mg of sodium cyanoborohydride were added to this solution. Subsequently, 0.18 ml of a 37% formalin solution and 0.05 ml of glacial acetic acid were added dropwise. The mixture was stirred at room temperature for 2 h; thereafter and another 2 h later, the same amounts of sodium cyanoborohydride and formalin solution were once again added dropwise. For workup, the mixture was filtered through a silica gel cartridge and the filtrate was concentrated under reduced pressure and purified by chromatography (method [RP1]). 4-{4,4-Dimethyl-3-[2-(methylphenylamino)benzyl]-2,5-dioxoimidazolidin-1-yl}-2-trifluoromethylbenzonitrile 59 was obtained in a yield of 60%. Molecular weight 492.17 ($C_{27}H_{23}F_3N_4O_2$); retention time $R_t$=2.33 min. [B]; MS (ESI): 493.05 (MH$^+$).

Example 61

4-{4,4-Dimethyl-2,5-dioxo-3-[2-(pyridin-4-ylamino)benzyl]imidazolidin-1-yl}-2-trifluoromethylbenzonitrile; trifluoroacetic acid salt

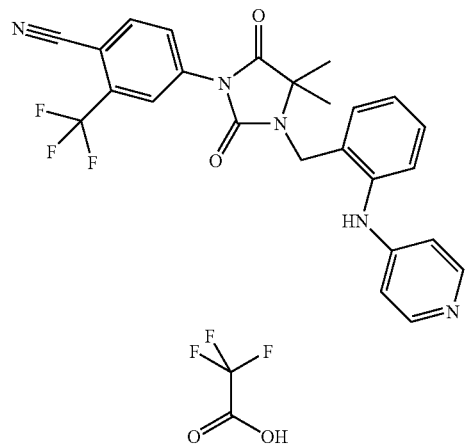

1) Preparation of 4-[3-(2-aminobenzyl)-4,4-dimethyl-2,5-dioxoimidazolidin-1-yl]-2-trifluoromethylbenzonitrile 61.2

The compound of example 61.2 can be prepared by process "A". 370 mg (0.794 mmol) of the compound of example 1.2 were admixed under an argon atmosphere with 2.8 ml of dry dioxane with 216 mg of benzophenone imine, 776 mg of cesium carbonate, 9 mg of palladium(II) acetate and 46 mg of 9,9-dimethyl-4,5-bis(diphenylphosphino)xanthene. The mixture was stirred at 95° C. for 6 h; 7.5 ml of 1 N hydrochloric acid were added to the cooled reaction mixture. The mixture was stirred at room temperature for 10 min and neutralized with aqueous sodium hydroxide solution. For workup, the reaction mixture was extracted by shaking 3x with dichloromethane, and the organic phase was dried over magnesium sulfate, filtered and concentrated under reduced pressure. The residue was purified by chromatography (method [RP2]). 4-[3-(2-Aminobenzyl)-4,4-dimethyl-2,5-dioxoimidazolidin-1-yl]-2-trifluoromethylbenzonitrile 61.2 was obtained in 78% yield. Molecular weight 402.13 ($C_{20}H_{17}F_3N_4O_2$); retention time $R_t$=1.61 min. [B]; MS (ESI): 403.06 (MH$^+$).

2) Preparation of 4-{4,4-Dimethyl-2,5-dioxo-3-[2-(pyridin-4-ylamino)benzyl]-imidazolidin-1-yl}-2-trifluoromethylbenzonitrile; trifluoroacetic acid salt 61

The compound of example 61 can be prepared by process "A". 50 mg (0.124 mmol) of the compound of example 61.2 were admixed with 1 ml of dry toluene under an argon atmosphere with 30 mg of 4-bromopyridine, 30 mg of sodium tert-butoxide, 5.7 mg of tris(dibenzylideneacetone)dipalladium(0) and 7.7 mg of (R)-(+)-2,2'-bis(diphenylphosphino)-1,1'-binaphthyl. The mixture was stirred at 90° C. for 8 h. For workup, the reaction mixture was filtered through a silica gel cartridge and the filtrate was concentrated under reduced pressure. The residue was purified by chromatography (method [RP1]). The trifluoroacetic acid salt of 4-{4,4-dimethyl-2,5-dioxo-3-[2-(pyridin-4-ylamino)benzyl]imidazolidin-1-yl}-2-trifluoromethylbenzonitrile 61 was obtained. Molecular weight 479.15 (free base) ($C_{25}H_{20}F_3N_5O_2$); retention time $R_t$=1.41 min. [B]; MS (ESI): 480.13 (MH$^+$).

The compound of example 83, 4-{3-[2-(6-methoxypyridin-3-ylamino)benzyl]-4,4-dimethyl-2,5-dioxoimidazolidin-1-yl}-2-trifluoromethylbenzonitrile (molecular weight 509.16 ($C_{26}H_{22}F_3N_5O_3$); retention time $R_t$=1.97 min. [B]; MS (ESI): 510.08 (MH$^+$)), of example 84, 4-(4,4-dimethyl-3-{2-[4-(morpholin-4-sulfonyl)-3-trifluoromethylphenylamino]benzyl}-2,5-dioxoimidazolidin-1-yl)-2-trifluoromethylbenzonitrile (molecular weight 695.16 ($C_{31}H_{27}F_6N_5O_5S$); retention time $R_t$=2.51 min. [B]; MS (ESI): 696.15 (MH$^+$)), of example 85, 4-{3-[2-(2-fluoro-4-trifluoromethoxyphenylamino)benzyl]-4,4-dimethyl-2,5-dioxoimidazolidin-1-yl}-2-trifluoromethylbenzonitrile (molecular weight 580.13 ($C_{27}H_{19}F_7N_4O_3$); retention time $R_t$=2.45 min. [B]; MS (ESI): 581.07 (MH$^+$)), of example 86, 4-{2-[3-(4-cyano-3-trifluoromethylphenyl)-5,5-dimethyl-2,4-dioxoimidazolidin-1-ylmethyl]phenylamino}-N-(2-hydroxyethyl)benzenesulfonamide (molecular weight 601.16 ($C_{28}H_{26}F_3N_5O_5S$); retention time $R_t$=2.17 min. [C]; MS (ESI): 602.24 (MH$^+$)), of example 87, methyl 2-{2-[3-(4-cyano-3-trifluoromethylphenyl)-5,5-dimethyl-2,4-dioxoimidazolidin-1-ylmethyl]phenylamino}benzoate (molecular weight 536.16 ($C_{28}H_{23}F_3N_4O_4$); retention time $R_t$=2.44 min. [B]; MS (ESI): 527.10 (MH$^+$)), of example 88, methyl 3-{2-[3-(4-cyano-3-trifluoromethylphenyl)-5,5-dimethyl-2,4-dioxoimidazolidin-1-ylmethyl]phenylamino}benzoate (molecular weight 536.16 ($C_{28}H_{23}F_3N_4O_4$); retention time $R_t$=2.25 min. [B]; MS (ESI): 537.11 (MH$^+$)), of example 89, dimethyl 4-{2-[3-(4-cyano-3-trifluoromethylphenyl)-5,5-dimethyl-2,4-dioxoimidazolidin-1-ylmethyl]phenylamino}isophthalate (molecular weight 594.17 ($C_{30}H_{25}F_3N_4O_6$); retention time $R_t$=2.33 min. [B]; MS (ESI): 595.13 (MH$^+$)), of example 90, methyl 5-{2-[3-(4-cyano-3-trifluoromethylphenyl)-5,5-dimethyl-2,4-dioxoimidazolidin-1-ylmethyl]phenylamino}pyridine-2-carboxylate (molecular weight 537.16 ($C_{27}H_{22}F_3N_5O_4$); retention time $R_t$=1.76 min. [B]; MS (ESI): 538.08 (MH$^+$)), of example 91, 4-{4,4-dimethyl-2,5-dioxo-3-[2-(6-trifluoromethylpyridin-3-ylamino)benzyl]-imidazolidin-1-yl}-2-trifluoromethylbenzonitrile trifluoroacetic acid salt (molecular weight 547.14 (free base) ($C_{26}H_{19}F_6N_5O_2$); retention time $R_t$=2.18 min. [B]; MS (ESI): 548.06 (MH$^+$), of example 96, methyl 2-{2-[3-(4-cyano-3-trifluoromethylphenyl)-5,5-dimethyl-2,4-dioxoimidazolidin-1-ylmethyl]phenylamino}-5-fluorobenzoate (molecular weight 554.15 ($C_{28}H_{22}F_4N_4O_4$); retention time $R_t$=2.42 min. [B]; MS (ESI): 555.22 (MH$^+$), of example 112, 4-{4,4-dimethyl-3-[2-(4-nitrophenylamino)benzyl]-2,5-dioxoimidazolidin-1-yl}-2-trifluoromethylbenzonitrile (molecular weight 523.14 ($C_{26}H_{20}F_3N_5O_4$); retention time $R_t$=2.66 min. [C]; MS (ESI): 524.33 (MH$^+$), of example 113, after acidic hydrolysis of the Schiff base, 4-{3-[2-(4-aminophenylamino)benzyl]-4,4-dimethyl-2,5-dioxoimidazolidin-1-yl}-2-trifluoromethylbenzonitrile (molecular weight 493.17 ($C_{26}H_{22}F_3N_5O_2$); retention time $R_t$=1.48 min. [B]; MS (ESI): 494.14 (MH$^+$), of example 128, 4-{4,4-dimethyl-2,5-dioxo-3-[2-(4-phenoxyphenylamino)benzyl]-imidazolidin-1-yl}-2-trifluoromethylbenzonitrile (molecular weight 570.18 ($C_{32}H_{25}F_3N_4O_3$); retention time $R_t$=2.44 min. [B]; MS (ESI): 571.17 (MH$^+$), of example 129, methyl 5-{2-[3-(4-cyano-3-trifluoromethylphenyl)-5,5-dimethyl-2,4-dioxoimidazolidin-1-ylmethyl]phenylamino}-2-methoxybenzoate (molecular weight 566.17 ($C_{29}H_{25}F_3N_4O_5$); retention time $R_t$=2.08 min. [B]; MS (ESI): 567.17 (MH$^+$), of example 138, ethyl (4-{2-[3-(4-cyano-3-trifluoromethylphenyl)-5,5-dimethyl-2,4-dioxoimidazolidin-1-ylmethyl]phenylamino}phenoxy)acetate (molecular weight 580.19 ($C_{30}H_{27}F_3N_4O_5$); retention time $R_t$=2.19 min. [B]; MS (ESI): 581.14 (MH$^+$), of example 140, methyl 4-{2-[3-(4-cyano-3-trifluoromethylphenyl)-5,5-dimethyl-2,4-dioxoimidazolidin-1-ylmethyl]phenylamino}-2-methoxybenzoate (molecular weight 566.17 ($C_{29}H_{25}F_3N_4O_5$); retention time $R_t$=2.03 min. [B]; MS (ESI): 567.15 (MH$^+$), of example 141,

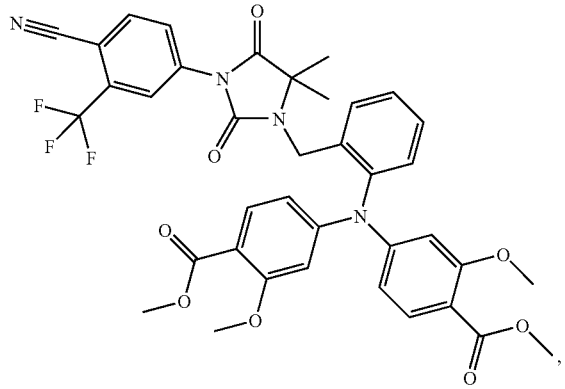

(molecular weight 730.22 ($C_{38}H_{33}F_3N_4O_8$); retention time $R_t$=2.19 min. [B]; MS (ESI): 731.19 (MH$^+$), of example 142, 4-{4,4-dimethyl-3-[2-(2-methyl-4-oxo-4H-1,3-benzodioxin-6-ylamino)benzyl]-2,5-dioxoimidazolidin-1-yl}-2-trifluoromethylbenzonitrile (molecular weight 564.16 ($C_{29}H_{23}F_3N_4O_5$); retention time $R_t$=2.15 min. [B]; MS (ESI): 565.15 (MH$^+$), of example 150, dimethyl 2-{2-[3-(4-cyano-3-trifluoromethylphenyl)-5,5-dimethyl-2,4-dioxoimidazolidin-1-ylmethyl]phenylamino}terephthalate (molecular weight 594.17 ($C_{30}H_{25}F_3N_4O_6$); retention time $R_t$=2.29 min. [B]; MS (ESI): 595.23 (MH$^+$), of example 151, 4-{2-[3-(4-cyano-3-trifluoromethylphenyl)-5,5-dimethyl-2,4-dioxoimidazolidin-1-ylmethyl]phenylamino}-N-ethylbenzenesulfonamide (molecular weight 585.16 ($C_{28}H_{26}F_3N_5O_4S$); retention time $R_t$=2.03 min. [B]; MS (ESI): 586.25 (MH$^+$), of example 152, 3-{2-[3-(4-cyano-3-trifluoromethylphenyl)-5,5-dimethyl-2,4-dioxoimidazolidin-1-ylmethyl]phenylamino}-N-[1-dimethylaminomethylidene]benzenesulfonamide (molecular weight 612.17 ($C_{29}H_{27}F_3N_6O_4S$); retention time $R_t$=1.97 min. [B];

MS (ESI): 613.27 (MH$^+$), of example 179, 4-{3-[2-(6-methoxypyridazin-3-ylamino)benzyl]-4,4-dimethyl-2,5-dioxoimidazolidin-1-yl}-2-trifluoromethylbenzonitrile salt with trifluoroacetic acid (free base: molecular weight 510.16 ($C_{25}H_{21}F_3N_6O_3$); retention time $R_t$=1.45 min. [B]; MS (ESI): 511.30 (MH$^+$)), of example 180, 4-{3-[2-(2-methoxypyrimidin-5-ylamino)benzyl]-4,4-dimethyl-2,5-dioxoimidazolidin-1-yl}-2-trifluoromethylbenzonitrile salt with trifluoroacetic acid (free base: molecular weight 510.16 ($C_{25}H_{21}F_3N_6O_3$); retention time $R_t$=1.94 min. [B]; MS (ESI): 511.31 (MH$^+$)), of example 181, 4-{4,4-dimethyl-3-[2-(3-methylpyridin-4-ylamino)benzyl]-2,5-dioxoimidazolidin-1-yl}-2-trifluoromethylbenzonitrile salt with trifluoroacetic acid (free base: molecular weight 493.17 ($C_{26}H_{22}F_3N_6O_2$); retention time $R_t$=1.44 min. [B]; MS (ESI): 494.31 (MH$^+$)), of example 199, 4-{3-[2-(2,2-dimethyl-4-oxo-4H-benzo[1,3]dioxin-7-ylamino)benzyl]-4,4-dimethyl-2,5-dioxoimidazolidin-1-yl}-2-trifluoromethylbenzonitrile (molecular weight 578.17 ($C_{30}H_{25}F_3N_4O_5$); retention time $R_t$=2.11 min. [B]; MS (ESI): 579.19 (MH$^+$)), of example 200, 4-{4,4-dimethyl-2,5-dioxo-3-[2-(3-oxo-1,3-dihydroisobenzofuran-5-ylamino)benzyl]imidazolidin-1-yl}-2-trifluoromethylbenzonitrile (molecular weight 534.15 ($C_{28}H_{21}F_3N_4O_4$); retention time $R_t$=2.47 min. [C]; MS (ESI): 535.26 (MH$^+$)), of example 201, 4-{4,4-dimethyl-2,5-dioxo-3-[2-(1-oxo-1,3-dihydroisobenzofuran-5-ylamino)benzyl]imidazolidin-1-yl}-2-trifluoromethylbenzonitrile (molecular weight 534.15 ($C_{28}H_{21}F_3N_4O_4$); retention time $R_t$=2.33 min. [B]; MS (ESI): 535.19 (MH$^+$)), of example 202, tert-butyl 6-{2-[3-(4-cyano-3-trifluoromethylphenyl)-5,5-dimethyl-2,4-dioxoimidazolidin-1-ylmethyl]phenylamino}naphthalene-2-carboxylate (molecular weight 628.22 ($C_{35}H_{31}F_3N_4O_4$); retention time $R_t$=3.27 min. [C]; MS (ESI): 629.50 (MH$^+$)), of example 208, 4-{3-[2-(2,4-di-tert-butoxypyrimidin-5-ylamino)benzyl]-4,4-dimethyl-2,5-dioxoimidazolidin-1-yl}-2-trifluoromethylbenzonitrile (molecular weight 624.26 ($C_{32}H_{35}F_3N_6O_4$); retention time $R_t$=1.92 min. [B]; MS (ESI): 625.39 (MH$^+$)), of example 211, tert-butyl 5-{2-[3-(4-cyano-3-trifluoromethylphenyl)-5,5-dimethyl-2,4-dioxoimidazolidin-1-ylmethyl]phenylamino}-2-methoxybenzoate (molecular weight 608.22 ($C_{32}H_{31}F_3N_4O_5$); retention time $R_t$=2.37 min. [B]; MS (ESI): 553.22 (MH$^+$–$C_4H_8$))

were obtained like the compound of example 61 by reacting compound 61.2 with 5-bromo-2-methoxypyridine (for 83), 4-(4-bromo-2-trifluoromethylbenzenesulfonyl)morpholine (for 84; prepared by reacting 4-bromo-2-trifluoromethylbenzenesulfonyl chloride with morpholine and potassium carbonate in acetonitrile at room temperature: $^1$H NMR: 8.22, s, 1H, 8.15, d, 1H, 8.0, d, 1H, 3.65, m, 4H, 3.15, m, 4H), 1-bromo-2-fluoro-4-(trifluoromethoxy)benzene (for 85),
4-bromo-N-(2-hydroxyethyl)benzenesulfonamide (for 86),
methyl 2-bromobenzoate (for 87),
methyl 3-bromobenzoate (for 88),
dimethyl 4-bromoisophthalate (for 89),
methyl 5-bromopyridine-2-carboxylate (for 90),
5-bromo-2-trifluoromethylpyridine (for 91),
methyl 2-bromo-5-fluorobenzoate (for 96; the methyl ester was obtained by reacting 2-bromo-5-fluorobenzoic acid with methanol under catalysis with sulfuric acid: $^1$H NMR: 7.8, m, 1H, 7.65, m, 1H, 7.4, m, 1H, 3.85, s, 3H),
1-bromo-4-nitrobenzene (for 112),
(4-bromophenyl)[1-phenylmethylidene]amine (for 113; the Schiff base was obtained by reacting 4-bromophenylamine with benzaldehyde: $^1$H NMR: 8.65, s, 1H, 7.95, d, 2H, 7.61-7.5, m, 5H, 7.25, d, 2H),
1-bromo-4-phenoxybenzene (for 128),
methyl 5-bromo-2-methoxybenzoate (for 129),
ethyl (4-bromophenoxy)acetate (for 138),
methyl 4-bromo-2-methoxybenzoate (for 140 and 141),
6-bromo-2-methylbenzo[1,3]dioxin-4-one (for 142),
dimethyl 2-bromoterephthalate (for 150),
4-bromo-N-ethylbenzenesulfonamide (for 151),
3-bromo-N-[1-dimethylaminomethylidene]benzenesulfonamide (prepared from 3-bromobenzenesulfonamide with dimethylformamide dimethyl acetal (molecular weight 289.97 ($C_9H_{11}BrN_2O_2S$); retention time $R_t$=1.64 min. [B]; MS (ESI): 291.03/293.05 (MH$^+$)) analogously to the process as described below for the 4-bromo isomer 68.3) for 152),
3-chloro-6-methoxypyridazine (for 179),
5-bromo-2-methoxypyrimidine (for 180),
4-bromo-3-methylpyridine (for 181),
7-bromo-2,2-dimethylbenzo[1,3]dioxin-4-one (for 199),
6-bromo-3H-isobenzofuran-1-one (for 200),
5-bromo-3H-isobenzofuran-1-one (for 201),
tert-butyl 6-bromonaphthalene-2-carboxylate (prepared from the corresponding carboxylic acid by reacting thionyl chloride and the lithium salt of tert-butanol) (for 202),
5-bromo-2,4-di-tert-butoxypyrimidine (for 208),
tert-butyl 5-bromo-2-methoxybenzoate (for 211; prepared from 5-bromo-2-methoxybenzoic acid by reacting thionyl chloride and the lithium salt of tert-butanol).

In analogous manner, the compounds of examples 260 (4-{3-[4-fluoro-2-(6-methoxypyridin-3-ylamino)benzyl]-4,4-dimethyl-2,5-dioxoimidazolidin-1-yl}-2-trifluoromethylbenzonitrile; molecular weight 527.15 ($C_{26}H_{21}F_4N_5O_3$); retention time $R_t$=2.80 min. [D]; MS (ESI): 528.21 (MH$^+$)), 261 (4-{3-[4-fluoro-2-(2-methoxypyrimidin-5-ylamino)benzyl]-4,4-dimethyl-2,5-dioxoimidazolidin-1-yl}-2-trifluoromethylbenzonitrile; molecular weight 528.15 ($C_{25}H_{20}F_4N_6O_3$); retention time $R_t$=2.66 min. [D]; MS (ESI): 529.23 (MH$^+$)), 263 (4-{2-[3-(4-cyano-3-trifluoromethylphenyl)-5,5-dimethyl-2,4-dioxoimidazolidin-1-ylmethyl]-5-fluorophenylamino}benzenesulfonamide, molecular weight 575.12 ($C_{26}H_{21}F_4N_5O_4S$); retention time $R_t$=2.54 min. [D]; MS (ESI): 576.20 (MH$^+$), by acidic hydrolysis of 4-{2-[3-(4-cyano-3-trifluoromethylphenyl)-5,5-dimethyl-2,4-dioxoimidazolidin-1-ylmethyl]-5-fluorophenylamino}-N-[1-dimethylaminomethylidene]benzenesulfonamide (262), 271 (4-{3-[2-(1H-benzimidazol-5-ylamino)-4-fluorobenzyl]-4,4-dimethyl-2,5-dioxoimidazolidin-1-yl}-2-trifluoromethylbenzonitrile ($^1$H NMR: 14.2, s, broad, 1H, 9.22, s, 1H, 8.35, d, 1H, 8.21, s, 1H, 8.13, s, 1H, 8.07, d, 1H, 7.71, d, 1H, 7.58, t, 1H, 7.23, m, 2H, 7.05, d, 1H, 6.85, t, 1H, 4.6, s, 2H, 1.4, s, 6H), were obtained from the compound 4-[3-(2-amino-4-fluorobenzyl)-4,4-dimethyl-2,5-dioxoimidazolidin-1-yl]-2-trifluoromethylbenzonitrile (260.1; see below for preparation) by reaction with
5-bromo-2-methoxypyridine (for 260),
5-bromo-2-methoxypyrimidine (for 261),
4-bromo-N-[1-dimethylaminomethylidene]benzenesulfonamide 68.3 (for 262 and 263),
tert-butyl 5/6-bromobenzimidazole-1-carboxylate (for 271; tert-butyl 5/6-bromobenzimidazole-1-carboxylate (271.1) was prepared by 4-dimethylaminopyridine-catalyzed reaction of 5-bromo-1H-benzimidazole with di-tert-butyl pyrocarbonate in acetonitrile, molecular weight 296.01 ($C_{12}H_{13}BrN_2O_2$); retention time $R_t$=2.65 min. [E]; MS (ESI): 297.08 (MH$^+$)).

Example 62

4-{4,4-{2-[3-(4-Cyano-3-trifluoromethylphenyl)-5,5-dimethyl-2,4-dioxoimidazolidin-1-ylmethyl]phenylamino}benzoic acid

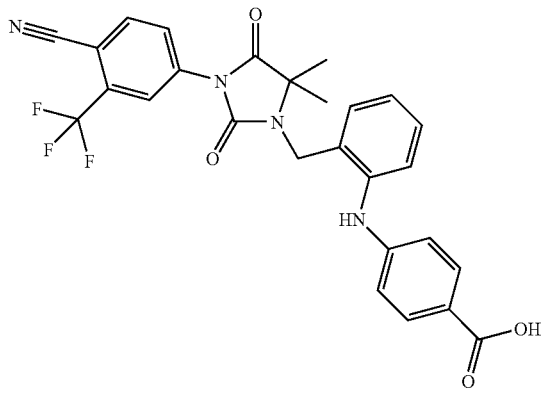

64 mg of the compound of example 60 were dissolved in 0.32 ml of dioxane (warm), admixed with 0.36 ml of concentrated hydrochloric acid and stirred at 75° C. for 1 h. For workup, the reaction mixture was admixed with a little acetonitrile and purified by chromatography (method [RP1]). After freeze-drying, 4-{4,4-{2-[3-(4-cyano-3-trifluoromethylphenyl)-5,5-dimethyl-2,4-dioxoimidazolidin-1-ylmethyl]phenylamino}benzoic acid 62 was obtained. Molecular weight 522.15 ($C_{27}H_{21}F_3N_4O_4$); retention time $R_t$=1.88 min. [B]; MS (ESI): 523.16 (MH$^+$).

In the same way, compounds 80, 92, 118, 119, 130, 131, 132, 133, 156, 159, 166 168 169 227 228 209, 210, 212 were obtained from their esters 72 82 115 117 124 123 126 125 192 194, 195, 193, 196, 225, 226, 202, 203, 211:

80: 4-{2-[3-(4-cyano-3-trifluoromethylphenyl)-5,5-dimethyl-2,4-dioxoimidazolidin-1-ylmethyl]phenylamino}-3-fluorobenzoic acid; $^1$H NMR: 12.6, s, 1H, 8.32, d, 1H, 8.2, s (broad), 2H, 8.03, d, 1H, 7.6, m, 3H, 7.35, t, 1H, 7.25, m, 2H, 6.7, t, 1H, 4.58, s, 2H, 1.35, s, 6H.

92: (4-{2-[3-(4-cyano-3-trifluoromethylphenyl)-5,5-dimethyl-2,4-dioxoimidazolidin-1-ylmethyl]phenylamino}phenyl)acetic acid; molecular weight 536.16 ($C_{28}H_{23}F_3N_4O_4$);
retention time $R_t$=1.95 min. [B]; MS (ESI): 537.26 (MH$^+$).

118: 4-{2-[5,5-dimethyl-3-(4-methylsulfanyl-3-trifluoromethylphenyl)-2,4-dioxoimidazolidin-1-ylmethyl]phenylamino}benzoic acid; molecular weight 543.14 ($C_{27}H_{24}F_3N_3O_4S$); retention time $R_t$=2.38 min. [C]; MS (ESI): 544.30 (MH$^+$).

119: 4-{2-[3-(4-methanesulfonyl-3-trifluoromethylphenyl)-5,5-dimethyl-2,4-dioxoimidazolidin-1-ylmethyl]phenylamino}benzoic acid; molecular weight 575.13 ($C_{27}H_{24}F_3N_3O_6S$); retention time $R_t$=2.17 min. [C]; MS (ESI): 576.13 (MH$^+$).

130: 4-{2-[3-(4-cyano-3-trifluoromethylphenyl)-5,5-dimethyl-2,4-dioxoimidazolidin-1-ylmethyl]-5-methoxyphenylamino}benzoic acid; molecular weight 552.16 ($C_{28}H_{23}F_3N_4O_5$);
retention time $R_t$=1.91 min. [B]; MS (ESI): 553.15 (MH$^+$).

131: 4-{5-chloro-2-[3-(4-cyano-3-trifluoromethylphenyl)-5,5-dimethyl-2,4-dioxoimidazolidin-1-ylmethyl]phenylamino}benzoic acid; molecular weight 556.11 ($C_{27}H_{20}ClF_3N_4O_4$); retention time $R_t$=2.00 min. [B]; MS (ESI): 556.11 (MH$^+$).

132: 4-{5-cyano-2-[3-(4-cyano-3-trifluoromethylphenyl)-5,5-dimethyl-2,4-dioxoimidazolidin-1-ylmethyl]phenylamino}benzoic acid; molecular weight 547.14 ($C_{28}H_{20}F_3N_5O_4$); retention time $R_t$=1.86 min. [B]; MS (ESI): 548.14 (MH$^+$).

133: 4-{2-[3-(4-cyano-3-trifluoromethylphenyl)-5,5-dimethyl-2,4-dioxoimidazolidin-1-ylmethyl]-5-fluorophenylamino}benzoic acid; molecular weight 540.14 ($C_{27}H_{20}F_4N_4O_4$);
retention time $R_t$=1.96 min. [B]; MS (ESI): 541.14 (MH$^+$).

156: 4-{5-fluoro-2-[3-(4-fluoro-3-trifluoromethylphenyl)-5,5-dimethyl-2,4-dioxoimidazolidin-1-ylmethyl]phenylamino}benzoic acid; molecular weight 533.13 ($C_{26}H_{20}F_5N_3O_4$); retention time $R_t$=2.00 min. [B]; MS (ESI): 534.25 (MH$^+$).

159: 4-{2-[3-(4-cyano-3-cyclopropylphenyl)-5,5-dimethyl-2,4-dioxoimidazolidin-1-ylmethyl]-5-fluorophenylamino}benzoic acid; molecular weight 512.18 ($C_{29}H_{25}FN_4O_4$); retention time $R_t$=1.94 min. [B]; MS (ESI): 513.24 (MH$^+$).

166: 4-{2-[3-(4-cyano-3-methylphenyl)-5,5-dimethyl-2,4-dioxoimidazolidin-1-ylmethyl]-5-fluorophenylamino}benzoic acid; molecular weight 486.17 ($C_{27}H_{23}FN_4O_4$); retention time $R_t$=1.85 min. [B]; MS (ESI): 487.31 (MH$^+$).

168: 4-{2-[3-(2-tert-butylpyridin-4-yl)-5,5-dimethyl-2,4-dioxoimidazolidin-1-ylmethyl]-5-fluorophenylamino}benzoic acid×HCl; molecular weight (free acid) 504.21 ($C_{28}H_{29}FN_4O_4$);
retention time $R_t$=1.50 min. [B]; MS (ESI): 505.18 (MH$^+$).

169: 4-{2-[3-(3-tert-butyl-4-cyanophenyl)-5,5-dimethyl-2,4-dioxoimidazolidin-1-ylmethyl]-5-fluorophenylamino}benzoic acid; molecular weight 528.21 ($C_{30}H_{29}FN_4O_4$); retention time $R_t$=2.06 min. [B]; MS (ESI): 529.16 (MH$^+$).

227: 4-{2-[3-(6-cyanobiphenyl-3-yl)-5,5-dimethyl-2,4-dioxoimidazolidin-1-ylmethyl]-5-fluorophenylamino}benzoic acid; molecular weight 548.18 ($C_{32}H_{25}FN_4O_4$); retention time $R_t$=1.96 min. [B]; MS (ESI): 549.23 (MH$^+$).

228: 4-{2-[3-(4'-chloro-6-cyanobiphenyl-3-yl)-5,5-dimethyl-2,4-dioxoimidazolidin-1-ylmethyl]-5-fluorophenylamino}benzoic acid; molecular weight 582.14 ($C_{32}H_{24}ClFN_4O_4$); retention time $R_t$=2.06 min. [B]; MS (ESI): 583.19 (MH$^+$).

209: 6-{2-[3-(4-cyano-3-trifluoromethylphenyl)-5,5-dimethyl-2,4-dioxoimidazolidin-1-ylmethyl]phenylamino}naphthalene-2-carboxylic acid; molecular weight 572.16 ($C_{31}H_{23}F_3N_4O_4$); retention time $R_t$=2.54 min. [C]; MS (ESI): 573.41 (MH$^+$).

210: 4'-{2-[3-(4-cyano-3-trifluoromethylphenyl)-5,5-dimethyl-2,4-dioxoimidazolidin-1-ylmethyl]phenylamino}biphenyl-4-carboxylic acid; molecular weight 598.18 ($C_{33}H_{25}F_3N_4O_4$); retention time $R_t$=2.52 min. [B]; MS (ES$^-$): 597.10 (M–H$^+$).

212: 5-{2-[3-(4-cyano-3-trifluoromethylphenyl)-5,5-dimethyl-2,4-dioxoimidazolidin-1-ylmethyl]phenylamino}-2-methoxybenzoic acid; molecular weight 552.16 ($C_{28}H_{23}F_3N_4O_5$); retention time $R_t$=1.94 min. [B]; MS (ESI): 553.23 (MH$^+$).

In the same way, except using hydrobromic acid in glacial acetic acid, the compounds 99, 100, 101, 108 were obtained from their esters 87, 88, 89, 96:

99: 2-{2-[3-(4-cyano-3-trifluoromethylphenyl)-5,5-dimethyl-2,4-dioxoimidazolidin-1-ylmethyl]phenylamino}benzoic acid; molecular weight 522.15 ($C_{27}H_{21}F_3N_4O_4$); retention time $R_t$=2.12 min. [B]; MS (ESI): 523.11 (MH$^+$).

100: 3-{2-[3-(4-cyano-3-trifluoromethylphenyl)-5,5-dimethyl-2,4-dioxoimidazolidin-1-ylmethyl]phenylamino}benzoic acid; molecular weight 522.15 ($C_{27}H_{21}F_3N_4O_4$); retention time $R_t$=1.94 min. [B]; MS (ESI): 523.11 (MH$^+$).

101: 4-{2-[3-(4-cyano-3-trifluoromethylphenyl)-5,5-dimethyl-2,4-dioxoimidazolidin-1-ylmethyl]phenylamino}isophthalic acid; molecular weight 566.14 ($C_{28}H_{21}F_3N_4O_6$); retention time $R_t$=1.79 min. [B]; MS (ESI): 567.12 (MH$^+$).

108: 2-{2-[3-(4-cyano-3-trifluoromethylphenyl)-5,5-dimethyl-2,4-dioxoimidazolidin-1-ylmethyl]phenylamino}-5-fluorobenzoic acid; molecular weight 540.14 ($C_{27}H_{20}F_3N_4O_4$);

retention time $R_t$=2.12 min. [B]; MS (ESI): 541.22 (MH$^+$).

In the same way, compounds 102 and 103 were also obtained from the ester 90, and compounds 105 and 107 from esters 104 and 106:

102: 5-{2-[3-(4-cyano-3-trifluoromethylphenyl)-5,5-dimethyl-2,4-dioxoimidazolidin-1-ylmethyl]phenylamino}pyridine-2-carboxylic acid; molecular weight 523.14 ($C_{26}H_{20}F_3N_5O_4$);

retention time $R_t$=1.52 min. [B]; MS (ESI): 524.09 (MH$^+$).

103: 5-{4-bromo-2-[3-(4-cyano-3-trifluoromethylphenyl)-5,5-dimethyl-2,4-dioxoimidazolidin-1-ylmethyl]phenylamino}pyridine-2-carboxylic acid; molecular weight 601.05 ($C_{26}H_{19}BrF_3N_5O_4$); retention time $R_t$=1.68 min. [B]; MS (ESI): 602.01 (MH$^+$).

105: 4-{3,5-dichloro-2-[3-(4-cyano-3-trifluoromethylphenyl)-5,5-dimethyl-2,4-dioxoimidazolidin-1-ylmethyl]phenylamino}benzoic acid; molecular weight 590.07 ($C_{27}H_{19}Cl_2F_3N_4O_4$); retention time $R_t$=2.18 min. [B]; MS (ESI): 591.12 (MH$^+$).

107: 4-{2-[3-(4-cyano-3-trifluoromethylphenyl)-5,5-dimethyl-2,4-dioxoimidazolidin-1-ylmethyl]-5-trifluoromethylphenylamino}benzoic acid; molecular weight 590.13 ($C_{28}H_{20}F_6N_4O_4$); retention time $R_t$=2.00 min. [B]; MS (ESI): 591.20 (MH$^+$).

Example 63

2-tert-Butyl-4-[4,4-dimethyl-2,5-dioxo-3-(2-phenylaminobenzyl)imidazolidin-1-yl]benzonitrile

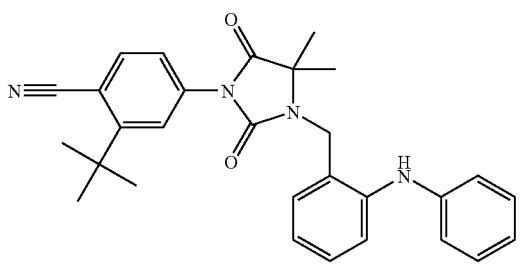

1) 2-tert-Butyl-4-nitrobenzonitrile 63.3

1.1 g of 2-tert-butyl-4-nitrophenylamine were dissolved in 5 ml of glacial acetic acid and admixed with 2 ml of 30% sulfuric acid with ice cooling. Within 30 minutes, 460 mg of sodium nitrite were added slowly at 0° C. and the mixture was then stirred at 0° C. for 5 h. The solution was filtered and added dropwise to a solution at 75° C. of 1.9 g of potassium cyanide and 1.3 g of copper cyanide in 20 ml of water. The mixture was stirred at 75° C. for another 1 h. The cooled reaction mixture was filtered off with suction and washed with water. The residue was stirred in methanol and filtered, and the filtrate was concentrated under reduced pressure. The residue was purified by chromatography on silica gel with 80/20 n-heptane/ethyl acetate. 63.3 was obtained in 61% yield. $^1$H NMR: 8.25-8.15, m, 3H, 1.51, s, 9H.

2) Preparation of 4-amino-2-tert-butylbenzonitrile 63.4

0.6 g of the compound of example 63.3 was suspended at room temperature in 19.4 ml of hydriodic acid (57%) and stirred at 80° C. for 4 h. The cooled reaction mixture was taken up in ethyl acetate and washed successively and cautiously with saturated sodium thiosulfate solution, saturated sodium hydrogencarbonate solution and saturated sodium chloride solution, dried over magnesium sulfate, filtered and concentrated under reduced pressure. The residue was purified by chromatography on silica gel with 70/30 n-heptane/ethyl acetate. 63.4 was obtained in 88% yield. Molecular weight 174.11 ($C_{11}H_{14}N_2$); retention time $R_t$=1.89 min. [B]; MS (ESI): 175.22 (MH$^+$).

3) Preparation of 2-tert-butyl-4-(4,4-dimethyl-2,5-dioxoimidazolidin-1-yl)benzonitrile 63.1

To prepare compound 63.1, the procedure may be according to process "A". To this end, a flask was initially charged with 2.5 ml of a 20% solution of phosgene in toluene under an argon atmosphere. 0.45 g of the compound of example 63.4 dissolved in 10 ml of acetonitrile was slowly added dropwise to this solution and then the mixture was stirred at 75° C. for 90 minutes. The cooled reaction mixture was concentrated under reduced pressure, admixed with toluene and concentrated again. The residue was dissolved in 10 ml of dry tetrahydrofuran and the solution was admixed with 0.36 g of methyl 2-amino-2-methylpropionate hydrochloride. 0.5 ml of triethylamine was slowly added to this mixture which was then stirred at room temperature for 2 h. After adding 2.4 ml of concentrated hydrochloric acid, the mixture was stirred under reflux for 2 h. For workup, the cooled reaction mixture was admixed cautiously with saturated sodium hydrogencarbonate solution and extracted with ethyl acetate. The organic extracts were dried over magnesium sulfate, filtered and concentrated under reduced pressure. The residue was purified by chromatography on silica gel with 70/30 n-heptane/ethyl acetate. Compound 63.1 was obtained in 76% yield. Molecular weight 285.14 ($C_{16}H_{19}N_3O_2$); retention time $R_t$=1.88 min. [B]; MS (ES$^-$): 284.50 ((M-H)$^+$).

4) Preparation of 4-[3-(2-bromobenzyl)-4,4-dimethyl-2,5-dioxoimidazolidin-1-yl]-2-tert-butylbenzonitrile 63.2

Compound 63.2 was prepared as described for example 6.2, by reacting compound 63.1 with 2-bromobenzyl bromide. 4-[3-(2-Bromobenzyl)-4,4-dimethyl-2,5-dioxoimidazolidin-1-yl]-2-tert-butylbenzonitrile was obtained in a yield of 98%. Molecular weight 453.10 ($C_{23}H_{24}Br_3N_3O_2$); retention time $R_t$=2.65 min. [B]; MS (ESI): 454.38 (MH$^+$).

5) Preparation of 2-tert-butyl-4-[4,4-dimethyl-2,5-dioxo-3-(2-phenylaminobenzyl)-imidazolidin-1-yl]benzonitrile 63

The further reaction with aniline to give the compound of example 63 was effected as described for example 1, stage 3. 2-tert-Butyl-4-[4,4-dimethyl-2,5-dioxo-3-(2-phenylaminobenzyl)imidazolidin-1-yl]benzonitrile 63 was obtained. Molecular weight 466.23 ($C_{29}H_{30}N_4O_2$); retention time $R_t$=3.09 min. [C]; MS (ESI): 467.29 (MH$^+$).

The compound of example 64, 2-tert-butyl-4-{3-[2-(2,4-difluorophenylamino)benzyl]-4,4-dimethyl-2,5-dioxoimidazolidin-1-yl}benzonitrile (molecular weight 502.21 ($C_{29}H_{28}F_2N_4O_2$); retention time $R_t$=2.81 min. [B]; MS (ESI): 503.45 (MH$^+$)), was obtained analogously to the compound of example 63 by reacting the compound 63.2 with 2,4-difluoroaniline.

The compound of example 157, methyl 4-{2-[3-(3-tert-butyl-4-cyanophenyl)-5,5-dimethyl-2,4-dioxoimidazolidin-1-ylmethyl]-5-fluorophenylamino}benzoate was obtained in an analogous manner. To this end, 63.1 was reacted with 2-bromo-1-bromomethyl-4-fluorobenzene to give 4-[3-(2-bromo-4-fluorobenzyl)-4,4-dimethyl-2,5-dioxoimidazolidin-1-yl]-2-tert-butylbenzonitrile (157.2; molecular weight 471.09 ($C_{23}H_{23}BrFN_3O_2$); retention time $R_t$=2.31 min. [B]; MS (ESI): 472.24 (MH$^+$)). The reaction of methyl 4-aminobenzoate with 157.2 under conditions as described above gave rise to the compound of example 157; molecular weight 542.23 ($C_{31}H_{31}FN_4O_4$); retention time $R_t$=2.31 min. [B]; MS (ESI): 543.31 (MH$^+$).

In an analogous manner, reaction of 157.2 with tert-butyl 4-aminobenzoate afforded compound 196 (tert-butyl 4-{2-[3-(3-tert-butyl-4-cyanophenyl)-5,5-dimethyl-2,4-dioxoimidazolidin-1-ylmethyl]-5-fluorophenylamino}benzoate; molecular weight 584.27 ($C_{34}H_{37}FN_4O_4$); retention time $R_t$=2.60 min. [B]; MS (ESI): 529.18 (MH$^+$–$C_4H_8$)).

In an analogous manner, reaction of 157.2 with 2,4-difluoroaniline afforded compounds 221 (2-tert-butyl-4-{3-[2-(2,4-difluorophenylamino)-4-fluorobenzyl]-4,4-dimethyl-2,5-dioxoimidazolidin-1-yl}benzonitrile; molecular weight 520.20 ($C_{29}H_{27}F_3N_4O_2$); retention time $R_t$=2.80 min. [B]; MS (ESI): 521.23 (MH$^+$)).

Example 65

5,5-Dimethyl-1-(2-phenylaminobenzyl)-3-(2-trifluoromethylpyridin-4-yl)imidazolidine-2,4-dione

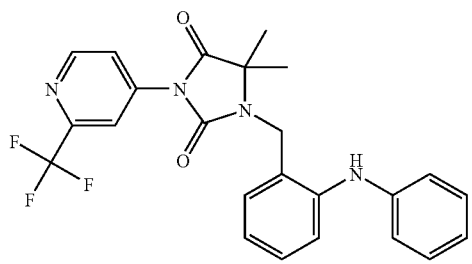

1) 2-(Trifluoromethyl)pyridine N-oxide 65.3

5.1 g (35 mmol) of trifluoromethylpyridine were dissolved at room temperature in 100 ml of dry dichloromethane, admixed with 17.3 g of m-chloroperbenzoic acid and stirred at room temperature for 72 h. Thereafter, the mixture was admixed with 1 N sodium hydroxide solution and extracted four times with dichloromethane; the combined organic phases were dried over magnesium sulfate, filtered and concentrated under reduced pressure. The crude product was taken up in water, stirred and filtered, and the filtrate was concentrated under reduced pressure. 65.3 was obtained in 47% yield. $^1$H NMR: 8.46, d, 1H, 7.96, d, 1H, 7.7, m, 1H, 7.5, m, 1H.

2) 4-Nitro-2-trifluoromethylpyridine N-oxide 65.4

2.66 g of the compound of example 65.3 were initially charged in 8.5 ml of concentrated sulfuric acid at 0° C.; subsequently, at 0° C., the nitrating acid (13.3 ml of fuming nitric acid and 8.5 ml of concentrated sulfuric acid) was slowly added dropwise. Subsequently, the reaction mixture was stirred at 120° C. for 4 h. The reaction mixture was cooled and poured onto ice-water and neutralized cautiously with potassium carbonate. The mixture was extracted with dichloromethane, dried over magnesium sulfate, filtered and concentrated under reduced pressure. The residue was purified by chromatography on silica gel with 70/30 n-heptane/ethyl acetate. Compound 65.4 was obtained in 26% yield. $^1$H NMR: 8.69, d, 1H, 8.59, d, 1H, 8.5, m, 1H.

3) 2-Trifluoromethylpyridin-4-ylamine 65.5

0.86 g of the compound of example 65.4 was dissolved at room temperature in 50 ml of dry ethanol and admixed under argon with 88 mg of palladium/carbon (10%) catalyst, and hydrogenated at room temperature and 5 bar for 3 h. The reaction mixture was filtered with suction through a depth filter and washed with ethanol, and the filtrate was concentrated under reduced pressure. The residue was purified by chromatography on silica gel with 95/5 dichloromethane/methanol. Compound 65.5 was obtained in 88% yield. $^1$H NMR: 8.10, d, 1H; 6.9, s, 1H, 6.65, d, 1H, 6.52, s, 2H.

4) Methyl 2-methyl-2-[3-(2-trifluoromethylpyridin-4-yl)ureido]propionate 65.6

3.8 ml of a solution of phosgene in toluene (20%) were initially charged under argon. At 75° C., 0.58 g of compound 65.5 dissolved in 20 ml of dry acetonitrile was slowly added dropwise; the mixture was then stirred at 80° C. for 4 h. The mixture was repeatedly concentrated with toluene under reduced pressure. The residue was dissolved in 20 ml of dry tetrahydrofuran and admixed with 0.55 g of methyl aminoisobutyrate hydrochloride. 0.76 ml of triethylamine was slowly added dropwise to this mixture which was then stirred at room temperature for 4 h and then left to stand overnight. The reaction mixture was admixed with water and extracted with ethyl acetate. The organic phase was dried over magnesium sulfate, filtered and concentrated under reduced pressure. The residue was purified by chromatography on silica gel with 95/5 dichloromethane/methanol. The urea 65.6 was obtained in 59% yield. Molecular weight 305.09 ($C_{12}H_{14}F_3N_3O_3$); retention time $R_t$=1.66 min. [B]; MS (ESI): 306.44 (MH$^+$).

5) 5,5-Dimethyl-3-(2-trifluoromethylpyridin-4-yl)imidazolidine-2,4-dione 65.1

0.52 g of compound 65.6 was dissolved at room temperature in 15 ml of dry tetrahydrofuran, admixed with 1.7 ml of concentrated hydrochloric acid and stirred at 80° C. for 4 h. The mixture was cooled, taken up in ethyl acetate and washed with saturated sodium hydrogencarbonate solution, dried over magnesium sulfate, filtered and concentrated under reduced pressure. The residue was purified by chromatography on silica gel with 95/5 dichloromethane/methanol. Compound 65.1 was obtained in quantitative yield. Molecular weight 273.07 ($C_{11}H_{10}F_3N_3O_2$); retention time $R_t$=1.62 min. [B]; MS (ESI): 274.33 (MH$^+$).

6) 1-(2-Bromobenzyl)-5,5-dimethyl-3-(2-trifluoromethylpyridin-4-yl)imidazolidine-2,4-dione 65.2

0.18 g of compound 65.1 was dissolved at room temperature in 10 ml of dry acetonitrile, admixed with 0.18 g of 2-bromobenzyl bromide and 0.24 g of cesium carbonate and stirred at room temperature for 4 h and then left to stand overnight. The reaction mixture was concentrated under reduced pressure, and the residue was taken up in water and extracted with dichloromethane. The organic phase was dried over magnesium sulfate, filtered and concentrated under reduced pressure. 65.2 was obtained in 89% yield. Molecular weight 441.03 ($C_{18}H_{15}BrF_3N_3O_2$); retention time $R_t$=2.45 min. [B]; MS (ESI): 442.29 (MH$^+$).

7) 5,5-Dimethyl-1-(2-phenylaminobenzyl)-3-(2-trifluoromethylpyridin-4-yl)-imidazolidine-2,4-dione 65

The further reaction with aniline to give the compound of example 65 was effected as described for example 1, stage 3. 5,5-Dimethyl-1-(2-phenylaminobenzyl)-3-(2-trifluoromethylpyridin-4-yl)imidazolidine-2,4-dione 65 was obtained. Molecular weight 454.16 ($C_{24}H_{21}F_3N_4O_2$); retention time $R_t$=2.25 min. [B]; MS (ESI): 455.19 (MH$^+$).

The compound of example 66, 1-[2-(2,4-difluorophenylamino)benzyl]-5,5-dimethyl-3-(2-trifluoromethylpyridin-4-yl)imidazolidine-2,4-dione (molecular weight 490.14 ($C_{24}H_{19}F_5N_4O_2$); retention time $R_t$=2.27 min. [B]; MS (ESI): 491.16 (MH$^+$)), was obtained analogously to the compound of example 65 by reacting compound 65.2 with 2,4-difluoroaniline.

Example 68

5,5-4-{2-[3-(4-Cyano-3-trifluoromethylphenyl)-5,5-dimethyl-2,4-dioxoimidazolidin-1-ylmethyl] phenylamino}benzene sulfonamide

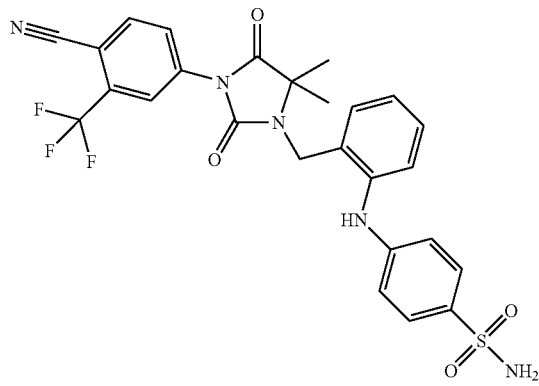

1) Alternative synthesis of 4-[3-(2-aminobenzyl)-4,4-dimethyl-2,5-dioxoimidazolidin-1-yl]-2-trifluoromethylbenzonitrile 61.2

The compound of example 61.2 can also be prepared by another route according to process "A":

a) tert-Butyl (2-bromomethylphenyl)carbamate 68.1

1.3 g of tert-butyl (2-hydroxymethylphenyl)carbamate were dissolved in 20 ml of dichloromethane; at 5° C., a solution of 630 mg of phosphorus tribromide in 5 ml of DCM was then added dropwise. The reaction mixture was subsequently stirred at 5° C. for 2 h. For workup, the mixture was admixed cautiously with solid sodium hydrogencarbonate and 1 ml of water, stirred at 5° C. for 30 min, filtered through a cartridge and concentrated under reduced pressure. tert-Butyl (2-bromomethylphenyl)carbamate was obtained in a 67% yield. $^1$H NMR: 8.71, s, 1H, 7.45, d, 1H, 7.42, d, 1H, 7.3, t, 1H, 7.1, t, 1H; 4.78, 2, 2H, 1.45, s, 9H.

b) tert-Butyl {2-[3-(4-cyano-3-trifluoromethylphenyl)-5,5-dimethyl-2,4-dioxoimidazolidin-1-ylmethyl] phenyl}carbamate 68.2

1.1 g of 4-(4,4-dimethyl-2,5-dioxoimidazolidin-1-yl)-2-trifluoromethylbenzonitrile 1.1 and 1.1 g of compound 68.1 were dissolved in 11 ml of dry acetonitrile, admixed with 1.5 g of cesium carbonate and stirred at room temperature for 5 h. For workup, the reaction mixture was admixed with water and extracted by shaking with ethyl acetate. The organic phase was dried over sodium sulfate, filtered and concentrated under reduced pressure. The residue was purified by chromatography (method [RP2]). The fractions comprising the desired product were freed of acetonitrile by distillation; the aqueous residue was neutralized with saturated sodium hydrogencarbonate solution, extracted by shaking with dichloromethane, dried over sodium sulfate, filtered and concentrated under reduced pressure. tert-Butyl {2-[3-(4-cyano-3-trifluoromethylphenyl)-5,5-dimethyl-2,4-dioxoimidazolidin-1-ylmethyl]phenyl}carbamate 68.2 was obtained. $^1$H NMR: 8.81, s, 1H, 8.25, d, 1H, 8.23, s, 1H, 8.08, d, 1H, 7.41, d, 1H, 7.3, d, 1H, 7.22, t, 1H, 7.12, t, 1H, 4.55, s, 2H, 1.45, s, 9H, 1.35, s, 6H.

c) 4-[3-(2-Aminobenzyl)-4,4-dimethyl-2,5-dioxoimidazolidin-1-yl]-2-trifluoromethylbenzonitrile hydrochloride (salt of 61.2)

0.369 g of compound 68.2 were dissolved in 3.7 ml of ethyl acetate and admixed with 1.47 ml of a 2 molar solution of HCl in diethyl ether, and stirred at room temperature for 24 h. 4 equivalents in each case of ethereal HCl solution were added twice more and the solution was left to stand for 24 h each time. For workup, the reaction mixture was concentrated under reduced pressure, and the residue was dissolved in acetonitrile/water and freeze-dried. 4-[3-(2-Aminobenzyl)-4, 4-dimethyl-2,5-dioxoimidazolidin-1-yl]-2-trifluoromethylbenzonitrile hydrochloride was obtained in quantitative yield. Molecular weight (free base) 402.13 ($C_{20}H_{17}F_3N_4O_2$); retention time $R_t$=1.59 min. [B]; MS (ESI): 403.14 (MH$^+$).

2) Preparation of 4-bromo-N-[1-dimethylaminomethylidene]benzenesulfonamide 68.3

0.325 g of 4-bromobenzenesulfonamide was admixed with 0.82 g of dimethylformamide dimethyl acetal in 1.6 ml of dry dimethylformamide and stirred at room temperature for 90 min. For workup, the reaction mixture was admixed with 10 ml of water, and the precipitate was filtered off with suction, filtered and dried under reduced pressure. 4-Bromo-N-[1- dimethylaminomethylidene]benzenesulfonamide was obtained in a yield of 85%. Molecular weight 289.97 ($C_9H_{11}BrN_2O_2S$); retention time $R_t$=1.3 min. [B]; MS (ESI): 290.96 ($MH^+$).

3) Preparation of 4-{2-[3-(4-cyano-3-trifluoromethylphenyl)-5,5-dimethyl-2,4-dioxoimidazolidin-1-ylmethyl]phenylamino}-N-[1-dimethylaminomethylidene]-benzenesulfonamide 68.4

Analogously to the procedure as described for example 61, the free base from 68.1.c was reacted with compound 68.3. 4-{2-[3-(4-Cyano-3-trifluoromethylphenyl)-5,5-dimethyl-2,4-dioxoimidazolidin-1-ylmethyl]phenylamino}-N-[1-dimethylaminomethylidene]benzenesulfonamide was obtained in a yield of 94%. Molecular weight 612.17 ($C_{29}H_{27}F_3N_6O_4S$); retention time $R_t$=2.37 min. [C]; MS (ESI): 613.24 ($MH^+$).

4) 5,5-4-{2-[3-(4-Cyano-3-trifluoromethylphenyl)-5,5-dimethyl-2,4-dioxoimidazolidin-1-ylmethyl]phenylamino}benzenesulfonamide 68

0.143 g of compound 68.4 was dissolved in 2.3 ml of ethanol, admixed with 1.15 ml of concentrated hydrochloric acid and stirred under reflux for 2 h. The cooled reaction mixture was neutralized cautiously with solid sodium hydrogencarbonate and concentrated under reduced pressure. The residue was admixed with water and extracted by shaking three times with ethyl acetate, and the organic phases were dried over magnesium sulfate, filtered and concentrated under reduced pressure. The residue was purified by chromatography (method [RP1]). 5,5-4-{2-[3-(4-Cyano-3-trifluoromethylphenyl)-5,5-dimethyl-2,4-dioxoimidazolidin-1-ylmethyl]phenylamino}benzenesulfonamide was obtained in 64% yield. Molecular weight 557.13 ($C_{26}H_{22}F_3N_5O_4S$); retention time $R_t$=1.85 min. [B]; MS (ESI): 558.28 ($MH^+$).

Compound 81 (4-{2-[3-(4-cyano-3-trifluoromethylphenyl)-5,5-dimethyl-2,4-dioxoimidazolidin-1-ylmethyl]phenylamino}-3-fluorobenzenesulfonamide (molecular weight 575.12 ($C_{26}H_{21}F_4N_5O_4S$); retention time $R_t$=1.87 min. [B]; MS (ESI): 576.11 ($MH^+$)) was obtained by the process just described via 4-{2-[3-(4-cyano-3-trifluoromethylphenyl)-5,5-dimethyl-2,4-dioxoimidazolidin-1-ylmethyl]phenylamino}-N-[1-dimethylaminomethylidene]-3-fluorobenzenesulfonamide 81.1, molecular weight 630.16 ($C_{29}H_{26}F_4N_6O_4S$); retention time $R_t$=1.92 min. [B]; MS (ESI): 631.11 ($MH^+$), which had been obtained from 4-bromo-N-[1-dimethylaminomethylidene]-3-fluorobenzenesulfonamide 81.2 and the free base from 68.1.c.

Compound 98 4-{2-[3-(4-cyano-3-trifluoromethylphenyl)-5,5-dimethyl-2,4-dioxoimidazolidin-1-ylmethyl]phenylamino}-2,5-difluorobenzenesulfonamide (molecular weight 593.11 ($C_{26}H_{20}F_5N_5O_4S$); retention time $R_t$=1.88 min. [B]; MS (ESI): 594.18 ($MH^+$)) was obtained by the process just described via 4-{2-[3-(4-cyano-3-trifluoromethylphenyl)-5,5-dimethyl-2,4-dioxoimidazolidin-1-ylmethyl]phenylamino}-N-[1-dimethylamino-methylidene]-2,5-difluorobenzenesulfonamide 98.1, molecular weight 648.15 ($C_{29}H_{25}F_5N_6O_4S$); retention time $R_t$=1.95 min. [B]; MS (ESI): 649.08 ($MH^+$), which had been obtained from 4-bromo-N-[1-dimethylaminomethylidene]-2,5-difluorobenzenesulfonamide 98.2 and the free base from 68.1.c.

Example 69

5,5-4-{5-[4,4-Dimethyl-2,5-dioxo-3-(2-phenylaminobenzyl)imidazolidin-1-yl]pyridine-2-carbonitrile

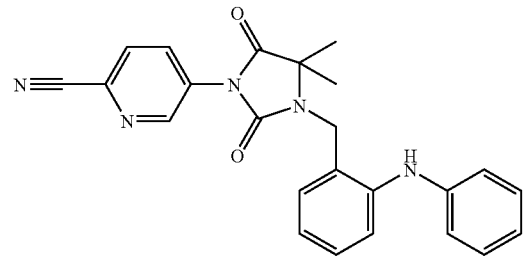

1) Preparation of methyl 2-[3-(6-cyanopyridin-3-yl)ureido]-2-methylpropionate 69.3

3.8 ml of a solution of phosgene in toluene (20%) was initially charged under argon; at 75° C., 0.43 g of 5-amino-2-cyanopyridine in 20 ml of dry acetonitrile was slowly added dropwise and then the mixture was stirred at 80° C. for 4 h. The cooled mixture was concentrated under reduced pressure, admixed with toluene and concentrated again under reduced pressure. The residue was dissolved in 20 ml of dry tetrahydrofuran and admixed with 0.55 g of 2-amino-2-methylpropionate hydrochloride; with stirring, 0.76 ml of triethylamine were slowly added dropwise and the mixture was then stirred at room temperature for 8 h. For workup, the mixture was admixed with water and then extracted with ethyl acetate. The organic phase was dried over magnesium sulfate, filtered and concentrated under reduced pressure. Methyl 2-[3-(6-cyanopyridin-3-yl)ureido]-2-methylpropionate was obtained in quantitative yield. Molecular weight 262.10 ($C_{12}H_{14}N_4O_3$); retention time $R_t$=1.6 min. [B]; MS (ESI): 263.49 ($MH^+$).

2) Preparation of 5-(4,4-dimethyl-2,5-dioxoimidazolidin-1-yl)pyridine-2-carbonitrile 69.1

0.94 g of the urea 69.3 was dissolved at room temperature in 20 ml of dry tetrahydrofuran, admixed with 3.6 ml of concentrated hydrochloric acid and stirred at 80° C. for 3 h. The cooled reaction mixture was taken up in ethyl acetate and washed with saturated sodium hydrogencarbonate solution, dried over magnesium sulfate, filtered and concentrated under reduced pressure. The crude product was stirred with methyl tert-butyl ether, filtered off with suction, washed and dried. 5-(4,4-Dimethyl-2,5-dioxoimidazolidin-1-yl)pyridine-2-carbonitrile was obtained in a yield of 52%. Molecular weight 230.08 ($C_{11}H_{10}N_4O_2$); retention time $R_t$=1.31 min. [B]; MS (ESI): 231.24 ($MH^+$), 3) Preparation of 5-[3-(2-bromobenzyl)-4,4-dimethyl-2,5-dioxoimidazolidin-1-yl]-pyridine-2-carbonitrile 69.2

Compound 69.2 was obtained as described for example 1, stage 2 by reaction of 69.1 with 1-bromo-2-bromomethylbenzene. Molecular weight 398.03 ($C_{18}H_{15}BrN_4O_2$); retention time $R_t$=2.24 min. [B]; MS (ESI): 399.32 ($MH^+$).

4) 5,5-4-{5-[4,4-Dimethyl-2,5-dioxo-3-(2-phenylaminobenzyl)imidazolidin-1-yl]-pyridine-2-carbonitrile 69

The compound of example 69, molecular weight 411.16 ($C_{24}H_{21}N_5O_2$); retention time $R_t$=2.04 min. [B]; MS (ESI): 412.37 (MH$^+$), was obtained analogously to the compound of example 1, stage 3 by reaction with aniline.

The compound of example 70, 5-{3-[2-(2,4-difluorophenylamino)benzyl]-4,4-dimethyl-2,5-dioxoimidazolidin-1-yl}pyridine-2-carbonitrile (molecular weight 447.37 ($C_{24}H_{19}F_2N_5O_2$); retention time $R_t$=2.07 min. [B]; MS (ESI): 448.40 (MH$^+$)), was obtained analogously to the compound of 69 by reacting compound 69.2 with 2,4-difluoroaniline.

Example 71

5,5-1-[2-(2,4-Dichlorophenylamino)benzyl]-3-(2-ethoxypyridin-4-yl)-5,5-dimethylimidazolidine-2,4-dione

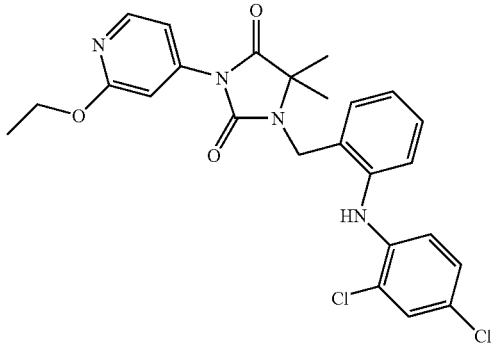

1) Preparation of tert-butyl 2-[3-(2-ethoxypyridin-4-yl)ureido]-2-methylpropionate 71.3

When, as described in the preparation of 69.3, 2-ethoxy-4-aminopyridine was used instead of 5-amino-2-cyanopyridine and the tert-butyl ester instead of the methyl ester of 2-amino-2-methylpropionic acid, tert-butyl 2-[3-(2-ethoxypyridin-4-yl)ureido]-2-methylpropionate was obtained. Molecular weight 323.18 ($C_{16}H_{25}N_3O_4$); retention time $R_t$=1.28 min. [B]; MS (ESI): 324.16 (MH$^+$).

2) Preparation of 3-(2-ethoxypyridin-4-yl)-5,5-dimethylimidazolidine-2,4-dione 71.1

Under conditions as described for the preparation of 69.1, compound 71.1 was also obtained. Molecular weight 249.11 ($C_{12}H_{15}N_3O_3$); retention time $R_t$=1.06 min. [B];
MS (ESI): 250.08 (MH$^+$).

3) Preparation of 1-(2-bromobenzyl)-3-(2-ethoxypyridin-4-yl)-5,5-dimethylimidazolidine-2,4-dione 71.2

Compound 71.2 was obtained as described for example 1, stage 2 by reaction of 71.1 with 1-bromo-2-bromomethylbenzene. Molecular weight 417.06 ($C_{19}H_{20}BrN_3O_3$); retention time $R_t$=21.97 min. [B]; MS (ESI): 418.10 (MH$^+$).

4) 5,5-1-[2-(2,4-Dichlorophenylamino)benzyl]-3-(2-ethoxypyridin-4-yl)-5,5-dimethylimidazolidine-2,4-dione 71

The compound of example 71, molecular weight 498.12 ($C_{25}H_{24}Cl_2N_4O_3$); retention time $R_t$=2.84 min. [B]; MS (ESI): 499.40 (MH$^+$), was obtained analogously to the compound of example 1, stage 3 by reaction with 2,4-dichloroaniline.

Example 93 and 94

Monoethyl (4-{2-[3-(4-cyano-3-trifluoromethylphenyl)-5,5-dimethyl-2,4-dioxoimidazolidin-1-ylmethyl]phenylamino}phenyl)phosphonate 93 and (4-{2-[3-(4-cyano-3-trifluoromethylphenyl)-5,5-dimethyl-2,4-dioxoimidazolidin-1-ylmethyl]phenylamino}phenyl)phosphonic acid 94

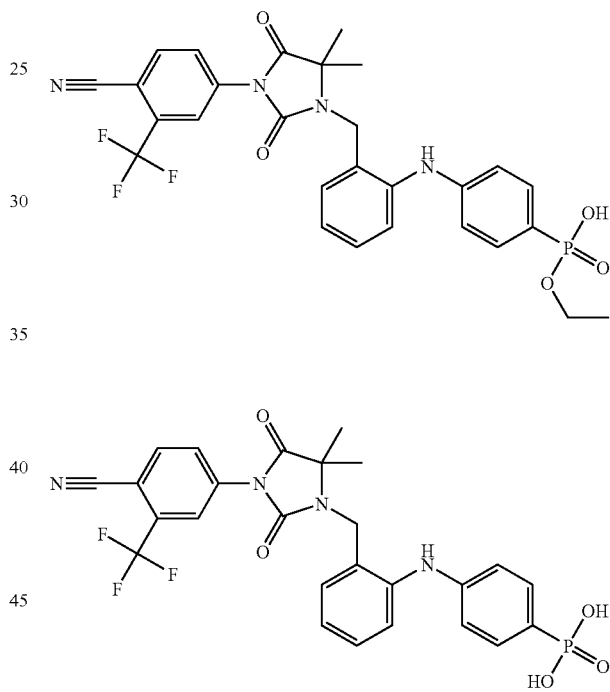

0.17 g of the compound of example 79 was dissolved at room temperature in 3 ml of dry dioxane, admixed with 0.23 ml of concentrated hydrochloric acid and stirred at 80° C. for 4 h. Thereafter, another 0.43 ml of concentrated hydrochloric acid was added and the mixture was stirred at 80° C. for a further 8 h. The cooled reaction mixture was concentrated under reduced pressure and the residue was purified by chromatography (method [RP1]). The monoester 93 and the phosphonic acid 94 were obtained.

93: Molecular weight 586.15 ($C_{28}H_{26}F_3N_4O_5P$); retention time $R_t$=1.75 min. [B]; MS (ESI): 587.10 (MH$^+$).

94: Molecular weight 558.12 ($C_{26}H_{22}F_3N_4O_5P$); retention time $R_t$=1.92 min. [C]; MS (ESI): 559.26 (MH$^+$).

Example 95

4-{3-[2-(4-Amino-3-fluorophenylamino)benzyl]-4,4-dimethyl-2,5-dioxoimidazolidin-1-yl}-2-trifluoromethylbenzonitrile

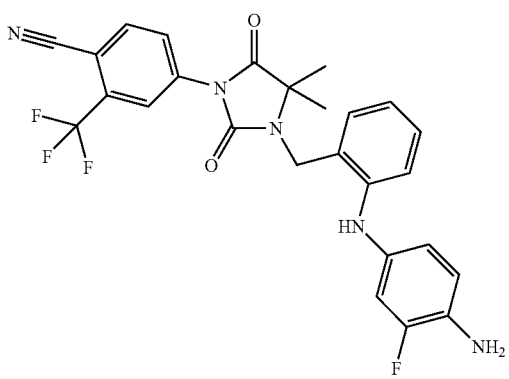

1) Preparation of N'-(2-fluoro-4-nitrophenyl)-N,N-dimethylformamidine 95.1

5 g of 2-fluoro-4-nitroaniline were dissolved in 35 ml of dry dimethylformamide, admixed at room temperature with 19.90 g of dimethylformamide dimethyl acetal and stirred for 90 min. For workup, 250 ml of water were added to the reaction mixture, and the precipitate was filtered off with suction, washed with water and dried. N'-(2-Fluoro-4-nitrophenyl)-N,N-dimethylformamidine was obtained in a yield of 85%. Molecular weight 211.07 ($C_9H_{10}FN_3O_2$); retention time $R_t$=0.49 min. [B]; MS (ESI): 212.03 (MH$^+$).

2) Preparation of N'-(4-amino-2-fluorophenyl)-N,N-dimethylformamidine 95.2

5.37 g of compound 95.1 were dissolved in 110 ml of methanol. 747 mg of Raney nickel were added, and then the mixture was hydrogenated at 5 bar until the hydrogen uptake had ended. For workup, the catalyst was filtered off and the filtrate was largely concentrated under reduced pressure. The product was precipitated by adding water, filtered and washed with a little water. The filtrate was extracted repeatedly with a mixture of 4:1 dichloromethane and isopropanol. The extract was concentrated under reduced pressure and dried. N'-(4-Amino-2-fluorophenyl)-N,N-dimethylformamidine was obtained in 83% yield. Molecular weight 181.10 ($C_9H_{12}FN_3$); retention time $R_t$=0.15 min. [B]; MS (ESI): 182.10 (MH$^+$).

3) Preparation of N'-(4-{2-[3-(4-cyano-3-trifluoromethylphenyl)-5,5-dimethyl-2,4-dioxoimidazolidin-1-ylmethyl]phenylamino}-2-fluorophenyl)-N,N-dimethylformamidine 95.3

The further reaction of compound 95.2 with compound 1.2 to give the compound of example 95.3 was effected as described for example 1, stage 3. N'-(4-{2-[3-(4-Cyano-3-trifluoromethylphenyl)-5,5-dimethyl-2,4-dioxoimidazolidin-1-ylmethyl]phenylamino}-2-fluorophenyl)-N,N-dimethylformamidine was obtained. Molecular weight 566.20 ($C_{29}H_{26}F_4N_6O_2$); retention time $R_t$=1.55 min. [B]; MS (ESI): 567.10 (MH$^+$).

4) 4-{3-[2-(4-Amino-3-fluorophenylamino)benzyl]-4,4-dimethyl-2,5-dioxoimidazolidin-1-yl}-2-trifluoromethylbenzonitrile 95

520 mg of compound 95.3 were dissolved in a mixture of tert-butanol/water (10 ml), admixed with 30 mg of palladium hydroxide and hydrogenated at 60° C. and 6 bar. 4-{3-[2-(4-Amino-3-fluorophenylamino)benzyl]-4,4-dimethyl-2,5-dioxoimidazolidin-1-yl}-2-trifluoromethylbenzonitrile was obtained.

Molecular weight 511.16 ($C_{26}H_{21}F_4N_5O_2$); retention time $R_t$=1.58 min. [B]; MS (ESI): 512.26 (MH$^+$).

Example 97

2-(4-{2-[3-(4-Cyano-3-trifluoromethylphenyl)-5,5-dimethyl-2,4-dioxoimidazolidin-1-ylmethyl]phenylamino}phenyl)acetamide

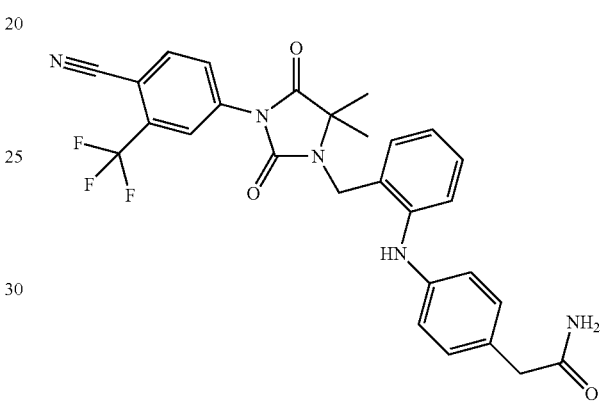

265 mg of compound 78 were dissolved in 0.56 ml of glacial acetic acid and admixed with 0.44 ml of hydrobromic acid (33% in acetic acid). The mixture was stirred at 75° C. for 2 h, and the next day at 100° C. for a further 8 h. The cooled solution was admixed with water, concentrated under reduced pressure and purified by chromatography (method [RP1]). 97 was obtained in 42% yield. Molecular weight 535.18 ($C_{28}H_{24}F_3N_5O_3$); retention time $R_t$=2.18 min. [C]; MS (ESI): 536.21 (MH$^+$).

Example 113

4-{3-[2-(4-Aminophenylamino)benzyl]-4,4-dimethyl-2,5-dioxoimidazolidin-1-yl}-2-trifluoromethylbenzonitrile

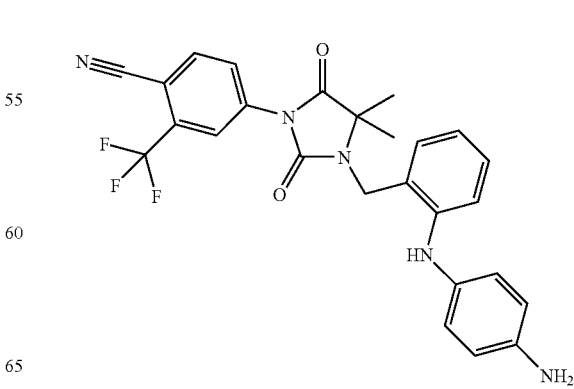

can be obtained not only via the hydrolysis of the corresponding benzylidene compound (as described above), but also by reduction of the nitro compound 112 with Raney nickel and hydrogen in a mixture of methanol and dichloromethane. $^1$H NMR: 8.35, d, 1H; 8.8.24, s, 1H, 8.07, d, 1H, 7.33, d, 1H, 7.08, t, 1H, 6.96, s, 1H, 6.83, s, 1H, 6.79, d, 2H, 6.72, t, 1H, 6.57, d, 2H, 4.8, s, 2H, 4.59, s, 2H, 1.41, s, 6H.

Example 114

1-[2-(2,4-Difluorophenylamino)benzyl]-3-(4-methanesulfinyl-3-trifluoromethylphenyl)-5,5-dimethylimidazolidine-2,4-dione

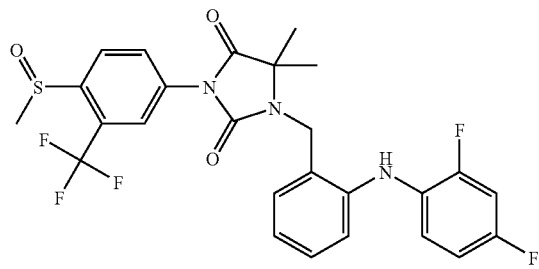

1) Preparation of 5,5-dimethyl-3-(4-methylsulfanyl-3-trifluoromethylphenyl)-imidazolidine-2,4-dione (114.1)

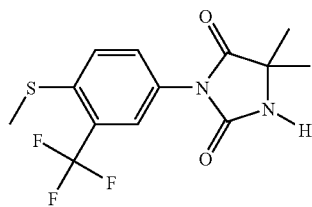

Compound 114.1 can be prepared by process "A". To this end, 1.04 g of 4-methylsulfanyl-3-trifluoromethylphenylamine were dissolved in 25 ml of dry acetonitrile. This solution was added dropwise with stirring to a 20% solution, heated to 70° C., of phosgene in toluene, and then stirred at 80° C. for 2 h. The cooled reaction solution was concentrated under reduced pressure, and the residue was taken up with toluene and concentrated again under reduced pressure. Finally, the residue was dissolved in 25 ml of dry tetrahydrofuran and the solution was admixed with stirring with 0.88 g of tert-butyl 2-amino-2-methylpropionate hydrochloride. 1.05 ml of triethylamine were slowly added dropwise to the reaction mixture which was then stirred at room temperature for 4 h. The reaction mixture was admixed with water and extracted with ethyl acetate. The organic phase was dried over magnesium sulfate, filtered and concentrated. tert-Butyl 2-methyl-2-[3-(4-methylsulfanyl-3-trifluoromethylphenyl) ureido]propionate (molecular weight 392.13 ($C_{17}H_{23}F_3N_2O_3S$); retention time $R_t$=2.40 min. [B]; MS (ESI): 337.26 (MH$^+$–$C_4H_8$)) was obtained. The urea was dissolved in 20 ml of tetrahydrofuran, admixed with 4.9 ml of concentrated hydrochloric acid and stirred at 80° C. for 2 h. The cooled reaction mixture was concentrated under reduced pressure and the residue was admixed with ethyl acetate and water. The organic phase was removed, washed with saturated sodium hydrogen-carbonate solution and then with water, dried over sodium sulfate, filtered and concentrated under reduced pressure. The residue was purified by chromatography on silica gel with 96/4 dichloromethane/methanol. 21.2 g (90% yield) of 5,5-dimethyl-3-(4-methylsulfanyl-3-trifluoromethylphenyl)imidazolidin-2,4-dione 114.1 were obtained. Molecular weight 318.06 ($C_{13}H_{13}F_3N_2O_2S$); retention time $R_t$=1.93 min. [B]; MS (ES–): 317.07 (M–H$^+$).

2) Preparation of 3-(4-methanesulfinyl-3-trifluoromethylphenyl)-5,5-dimethylimidazolidine-2,4-dione (114.1a)

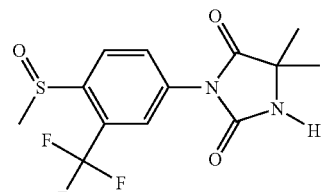

470 mg of sodium periodate were dissolved in 5 ml of water and admixed slowly with 640 mg of 114.1, dissolved in 10 ml of tetrahydrofuran, with ice bath cooling. The mixture was stirred at room temperature overnight. Another 210 mg of sodium periodate were added and the mixture was stirred for a further 8 h. Thereafter, the reaction mixture was admixed with water and extracted with ethyl acetate. The organic phase was dried over magnesium sulfate, filtered and concentrated under reduced pressure. The chromatographic purification (silica gel; 96/4 dichloromethane/methanol) afforded 3-(4-methanesulfinyl-3-trifluoromethylphenyl)-5,5-dimethylimidazolidine-2,4-dione (114.1a). Molecular weight 334.05 ($C_{13}H_{13}F_3N_2O_3S$); retention time $R_t$=1.69 min. [B]; MS (ES$^-$): 335.19 (M–H$^+$).

3) Preparation of 1-(2-bromobenzyl)-3-(4-methanesulfinyl-3-trifluoromethylphenyl)-5,5-dimethylimidazolidine-2,4-dione (114.2)

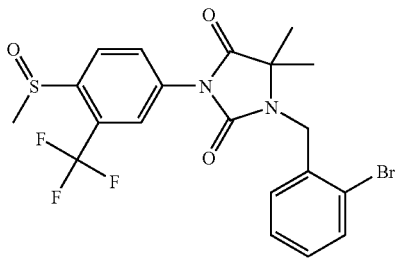

Compound 114.2 was prepared by the method as described for compound 1.2. To this end, 114.1a was reacted with 2-bromobenzyl bromide in acetonitrile with potassium carbonate. 1-(2-Bromobenzyl)-3-(4-methanesulfinyl-3-trifluoromethylphenyl)-5,5-dimethylimidazolidine-2,4-dione with the molecular weight of 502.01 ($C_{20}H_{18}BrF_3N_2O_3S$); retention time $R_t$=2.24 min. [B]; MS (ESI): 503.21 (MH$^+$) was obtained.

4) Preparation of 1-[2-(2,4-difluorophenylamino)benzyl]-3-(4-methanesulfinyl-3-trifluoromethylphenyl)-5,5-dimethylimidazolidine-2,4-dione (114)

The reaction of 114.2 with 2,4-difluoroaniline under conditions as described for the preparation of compound 1 afforded 114. Molecular weight 551.13 ($C_{26}H_{22}F_5N_3O_3S$); retention time $R_t$=2.06 min. [B]; MS (ESI): 552.17 (MH$^+$).

Example 115

Methyl 4-{2-[5,5-dimethyl-3-(4-methylsulfanyl-3-trifluoromethylphenyl)-2,4-dioxoimidazolidin-1-ylmethyl]phenylamino}benzoate

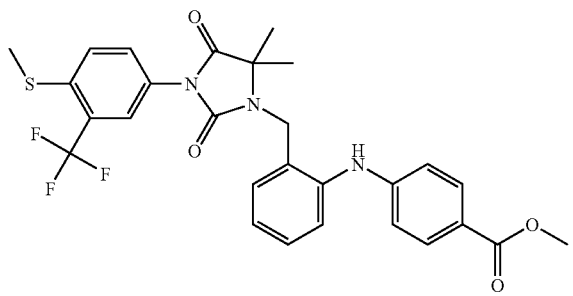

The reaction of 114.1 with 2-bromobenzyl bromide afforded 1-(2-bromobenzyl)-5,5-dimethyl-3-(4-methylsulfanyl-3-trifluoromethylphenyl)imidazolidine-2,4-dione (115.2). The further reaction with methyl 4-aminobenzoate under conditions as described for the preparation of compound I afforded methyl 4-{2-[5,5-dimethyl-3-(4-methylsulfanyl-3-trifluoromethylphenyl)-2,4-dioxoimidazolidin-1-ylmethyl]phenylamino}benzoate; molecular weight 557.15 ($C_{28}H_{26}F_3N_3O_4S$); retention time $R_t$=2.22 min. [B]; MS (ESI): 558.21 (MH$^+$).

In an analogous manner, 116 (methyl 4-{2-[3-(4-methanesulfinyl-3-trifluoromethylphenyl)-5,5-dimethyl-2,4-dioxoimidazolidin-1-ylmethyl]phenylamino}benzoate) was obtained from 114.2 with methyl 4-aminobenzoate; molecular weight 573.15 ($C_{28}H_{26}F_3N_3O_5S$); retention time $R_t$=1.91 min. [B]; MS (ESI): 574.19 (MH$^+$).

The compound of example 117, methyl 4-{2-[3-(4-methanesulfonyl-3-trifluoromethylphenyl)-5,5-dimethyl-2,4-dioxoimidazolidin-1-ylmethyl]phenylamino}benzoate (molecular weight 589.14 ($C_{28}H_{26}F_3N_3O_6S$); retention time $R_t$=2.47 min. [C]; MS (ESI): 590.06 (MH$^+$)) was obtained by reaction of methyl 4-aminobenzoate ester with 1-(2-bromobenzyl)-3-(4-methanesulfonyl-3-trifluoromethylphenyl)-5,5-dimethylimidazolidine-2,4-dione (117.2). 117.2 was obtainable by reaction of 2-bromobenzyl bromide with 3-(4-methanesulfonyl-3-trifluoromethylphenyl)-5,5-dimethylimidazolidine-2,4-dione (117.1).

117.1 ($^1$H NMR: 8.8, s, 1H, 8.37, d, 1H, 8.2, s, 1H, 5.1, d, 1H, 3.32, s, 3H, 1.42, s, 6H) was obtained from 114.1 by oxidation with meta-chloroperbenzoic acid.

Example 121

4-{3-[2-(4-Aminophenylamino)benzyl]-4,4-dimethyl-2,5-dioxoimidazolidin-1-yl}-2-trifluoromethylbenzonitrile trifluoroacetic acid

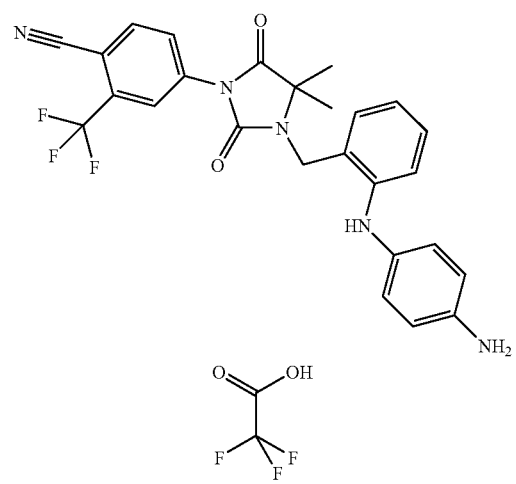

The trifluoroacetic acid salt 121 was obtained by reaction of the free amine 113 with trifluoroacetic acid in acetonitrile.
$^1$H NMR: 9.3, s (broad), 2H, 8.35, d, 1H, 8.21, s, 1H, 8.05, d, 1H, 7.8, s, 1H, 7.5, d, 1H, 7.28, t, 1H, 7.2, d, 1H, 7.12, d, 2H, 7.08, t, 1H;
6.9, d, 2H, 4.56, s, 2H, 1.35, s, 6H.

Example 135

4-{3-[2-(4-Hydroxyphenylamino)benzyl]-4,4-dimethyl-2,5-dioxoimidazolidin-1-yl}-2-trifluoromethylbenzonitrile

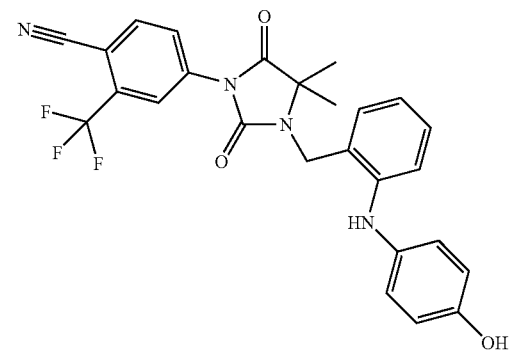

110 mg of compound 127 were dissolved in 3.3 ml of dry dichloromethane and admixed dropwise at −10° C. with 1.025 ml of boron trichloride solution (1 molar in xylene) with stirring. The mixture was stirred at −10° C. for 2 h, then warmed to 0° C. and stirred at 0° C. for a further hour. Another 5 equivalents of boron trichloride solution were added dropwise and the mixture was stirred at 0° C. for 1 h. Finally, another 5 equivalents of boron trifluoride solution were added dropwise and the mixture was stirred at 0° C. for another hour. The reaction mixture was admixed with 1.1 ml of methanol, stirred for 30 min and then concentrated three times with methanol under reduced pressure. The residue was purified by chromatography (method [RP1]) and afforded 4-{3-[2-(4-hydroxyphenylamino)benzyl]-4,4-dimethyl-2,5-dioxoimidazolidin-1-yl}-2-trifluoromethylbenzonitrile. Molecular weight 494.15 ($C_{26}H_{21}F_3N_4O_3$); retention time $R_t$=2.50 min. [C]; MS (ESI): 495.33 (MH$^+$).

Example 136

4-{2-[3-(4-Cyano-3-trifluoromethylphenyl)-5,5-dimethyl-2,4-dioxoimidazolidin-1-ylmethyl]phenylamino}benzamide

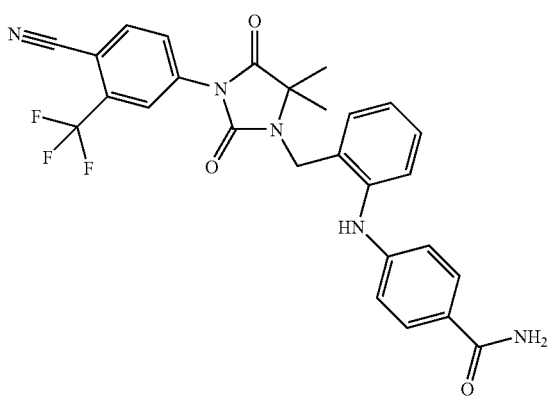

1) Preparation of 4-(3-{2-[4-(benzotriazole-1-carbonyl)phenylamino]benzyl}-4,4-dimethyl-2,5-dioxoimidazolidin-1-yl)-2-trifluoromethylbenzonitrile 136.1

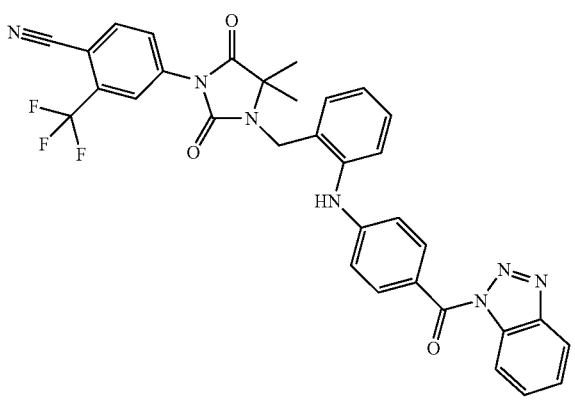

550.2 mg of the acid 62, 207.7 mg of 1-methanesulfonyl-1H-benzotriazole (A. R. Katritzky et al.: J. Org. Chem. 2005, 70, 9191-9197) and 0.205 ml of triethylamine were dissolved in 5.5 ml of dry tetrahydrofuran and stirred at reflux temperature for 6 hours. One further equivalent of benzotriazole derivative and triethylamine was added and the mixture was stirred at reflux temperature overnight. The next day, the cooled reaction mixture was concentrated under reduced pressure, taken up with 10 ml of dichloromethane and extracted by shaking twice with water, and the organic phase was removed, dried over magnesium sulfate, filtered and concentrated under reduced pressure. The residue was purified by chromatography (silica gel; ⅑ to ½ n-heptane/ethyl acetate). 4-(3-{2-[4-(Benzotriazole-1-carbonyl)phenylamino]benzyl}-4,4-dimethyl-2,5-dioxoimidazolidin-1-yl)-2-trifluoromethylbenzonitrile was obtained. Molecular weight 623.18 ($C_{33}H_{24}F_3N_7O_3$); retention time $R_t$=2.75 min. [B]; MS (ES−): 622.14 (M−H$^+$).

2) Preparation of 4-{2-[3-(4-cyano-3-trifluoromethylphenyl)-5,5-dimethyl-2,4-dioxoimidazolidin-1-ylmethyl]phenylamino}benzamide 136

430.3 mg of compound 136.1 were dissolved in 2.5 ml of dry tetrahydrofuran and admixed with 0.2 ml of a solution of ammonia in tetrahydrofuran (7 N in methanol). The solution stood at room temperature for 3 days, and was then concentrated under reduced pressure and purified by chromatography (method [RP1]). 4-{2-[3-(4-Cyano-3-trifluoromethylphenyl)-5,5-dimethyl-2,4-dioxoimidazolidin-1-ylmethyl]phenylamino}benzamide 136 was obtained. Molecular weight 521.16 ($C_{27}H_{22}F_3N_5O_3$);

retention time $R_t$=1.75 min. [B]; MS (ESI): 522.19 (MH$^+$).

The compounds of examples 137, 4-{2-[3-(4-cyano-3-trifluoromethylphenyl)-5,5-dimethyl-2,4-dioxoimidazolidin-1-ylmethyl]phenylamino}-N-(2-hydroxy-1-hydroxymethylethyl)benzamide (molecular weight 595.20 ($C_{30}H_{28}F_3N_5O_5$); retention time $R_t$=1.64 min. [B]; MS (ESI): 596.22 (MH$^+$)), 149, 4-{2-[3-(4-cyano-3-trifluoromethylphenyl)-5,5-dimethyl-2,4-dioxoimidazolidin-1-ylmethyl]phenylamino}-N-(2-hydroxyethyl)benzamide (molecular weight 565.19 ($C_{29}H_{26}F_3N_5O_4$); retention time $R_t$=1.74 min. [B]; MS (ESI): 566.27 (MH$^+$)), 161, N-carbamoylmethyl-4-{2-[3-(4-cyano-3-trifluoromethylphenyl)-5,5-dimethyl-2,4-dioxoimidazolidin-1-ylmethyl]phenylamino}benzamide (molecular weight 578.18 ($C_{29}H_{25}F_3N_6O_4$); retention time $R_t$=1.69 min. [B]; MS (ESI): 579.16 (MH$^+$)), 162, tert-butyl 2-(4-{2-[3-(4-cyano-3-trifluoromethylphenyl)-5,5-dimethyl-2,4-dioxoimidazolidin-1-ylmethyl]phenylamino}benzoylamino)-2-methylpropionate (molecular weight 663.26 ($C_{35}H_{36}F_3N_5O_5$); retention time $R_t$=2.26 min. [B]; MS (ESI): 664.39 (MH$^+$)), 163, 4-(4,4-dimethyl-2,5-dioxo-3-{2-[4-(piperidine-1-carbonyl)phenylamino]benzyl}-imidazolidin-1-yl)-2-trifluoromethylbenzonitrile (molecular weight 589.62 ($C_{32}H_{30}F_3N_5O_3$);

retention time $R_t$=2.14 min. [B]; MS (ESI): 590.18 (MH$^+$)), were obtained as described for 136 from 136.1 by reaction with 2-aminopropane-1,3-diol (for 137), 2-aminoethanol (for 149), 2-aminoacetamide (for 161), tert-butyl 2-amino-2-methylpropionate (for 162), piperidine (for 163)

and diisopropylethylamine.

Example 143

4-{2-[3-(4-Fluoro-3-trifluoromethylphenyl)-5,5-dimethyl-2,4-dioxoimidazolidin-1-ylmethyl]phenylamino}-N-hydroxybenzamidine hydrochloride

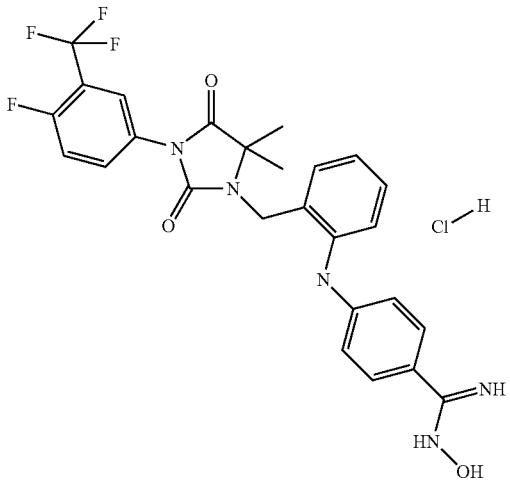

250 mg of the compound of example 134 were dissolved in 2.5 ml of ethanol and admixed successively with 70 mg of hydroxylamine hydrochloride and 102 mg of triethylamine. The mixture was stirred at 65° C. for 2 h. For workup, the reaction mixture was admixed with water and extracted by shaking twice with ethyl acetate. The organic phase was dried over magnesium sulfate and purified by chromatography (method [RP1]). The product-containing fractions were freeze-dried, dissolved in a little ethyl acetate and acidified with 2 N hydrochloric acid in ether. The reaction mixture was concentrated under reduced pressure, and the residue was dissolved in a mixture of water and acetonitrile and freeze-dried again. The hydrochloride of 4-{2-[3-(4-fluoro-3-trifluoromethylphenyl)-5,5-dimethyl-2,4-dioxoimidazolidin-1-ylmethyl]phenylamino}-N-hydroxybenzamidine was obtained, molecular weight 29.17 ($C_{26}H_{23}F_4N_5O_3$); retention time $R_t$=1.51 min. [B]; MS (ESI): 530.13 (MH$^+$).

Example 144

4-{2-[3-(4-Fluoro-3-trifluoromethylphenyl)-5,5-dimethyl-2,4-dioxoimidazolidin-1-ylmethyl]phenylamino}benzamidine hydrochloride

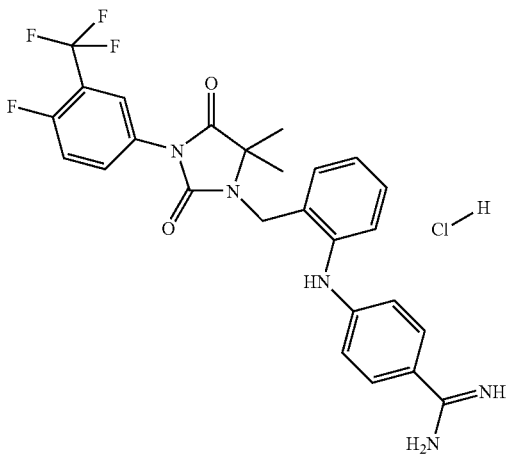

The compound of example 144 was obtained from 134 after conversion to the imidate and reaction with ammonia and subsequent reaction with hydrochloric acid. Free base: Molecular weight 513.17 ($C_{26}H_{23}F_4N_5O_2$); retention time $R_t$=1.52 min. [B]; MS (ESI): 514.24 (MH$^+$).

Alternatively, compound 144 can be obtained by hydrogenation of 143 under pressure (5 bar, 10% Pd on activated carbon, methanol, 20 h).

Example 148

N-(4-{2-[3-(4-Cyano-3-trifluoromethylphenyl)-5,5-dimethyl-2,4-dioxoimidazolidin-1-ylmethyl]phenylamino}phenyl)acetamide

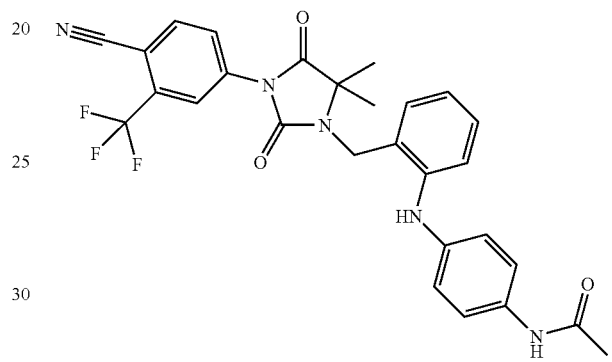

The compound of example 148 was obtained by reaction of 113 with acetyl chloride and sodium hydrogencarbonate in acetonitrile. Molecular weight 535.18 ($C_{28}H_{24}F_3N_5O_3$); retention time $R_t$=1.92 min. [B]; MS (ESI): 536.27 (MH$^+$).

Example 153

3-{2-[3-(4-Cyano-3-trifluoromethylphenyl)-5,5-dimethyl-2,4-dioxoimidazolidin-1-ylmethyl]phenylamino}benzenesulfonamide

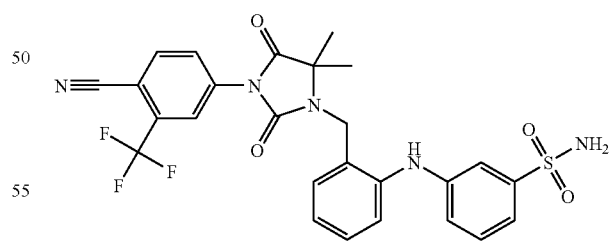

The compound of example 153 was prepared as described for example 68 by eliminating the dimethylaminomethylidene protecting group with hydrochloric acid. 3-{2-[3-(4-Cyano-3-trifluoromethylphenyl)-5,5-dimethyl-2,4-dioxoimidazolidin-1-ylmethyl]phenylamino}benzenesulfonamide was obtained (molecular weight 5577.13 ($C_{26}H_{22}F_3N_5O_4S$); retention time $R_t$=1.91 min. [B]; MS (ESI): 558.26 (MH$^+$)).

Example 154

Methyl 4-{5-fluoro-2-[3-(4-fluoro-3-trifluoromethylphenyl)-5,5-dimethyl-2,4-dioxoimidazolidin-1-ylmethyl]phenylamino}benzoate

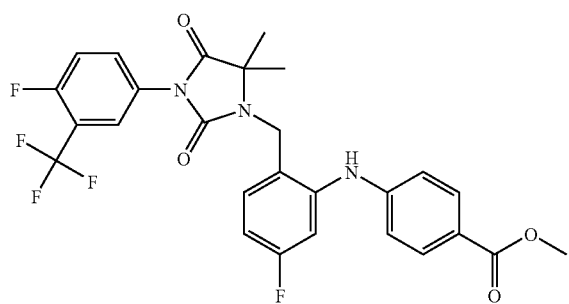

1) Preparation of 1-(2-bromo-4-fluorobenzyl)-3-(4-fluoro-3-trifluoromethylphenyl)-5,5-dimethylimidazolidine-2,4-dione 154.2

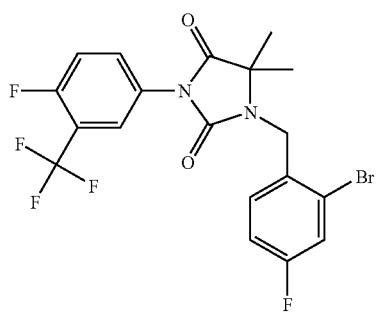

The title compound was prepared by reacting 23.1 with 2-bromo-1-bromomethyl-4-fluorobenzene under conditions as described above for 1.2. $^1$H NMR: 7.98, m, 1H; 7.9, m, 1H; 7.7-7.6, m, 3H; 7.26, m, 1H; 4.6, s, 2H, 1.4, s, 6H.

2) Preparation of methyl 4-{5-fluoro-2-[3-(4-fluoro-3-trifluoromethylphenyl)-5,5-dimethyl-2,4-dioxoimidazolidin-1-ylmethyl]phenylamino}benzoate 154

The further reaction of 154.2 with methyl 4-aminobenzoate was effected under conditions as described above for the preparation of example 1, stage 3. 154 with the molecular weight of 547.15 ($C_{27}H_{22}F_5N_3O_4$) was obtained; retention time $R_t$=2.27 min. [B]; MS (ESI): 548.26 (MH$^+$).

The compound of example 192, tert-butyl 4-{5-fluoro-2-[3-(4-fluoro-3-trifluoromethylphenyl)-5,5-dimethyl-2,4-dioxoimidazolidin-1-ylmethyl]phenylamino}benzoate was obtained in an analogous manner using tert-butyl 4-aminobenzoate. Molecular weight 589.20 ($C_{30}H_{28}F_5N_3O_4$); retention time $R_t$=2.56 min. [B]; MS (ESI): 534.23 (MH$^+$–$C_4H_8$).

The compound of example 247, methyl 5-{5-fluoro-2-[3-(4-fluoro-3-trifluoromethylphenyl)-5,5-dimethyl-2,4-dioxoimidazolidin-1-ylmethyl]phenylamino}-2-methoxybenzoate was obtained in an analogous manner using methyl 5-bromo-2-methoxybenzoate. Molecular weight 577.16 ($C_{28}H_{24}F_5N_3O_5$); retention time $R_t$=2.21 min. [B]; MS (ESI): 578.17 (MH$^+$).

Example 155

1-Methyl 2-{2-[3-(4-cyano-3-trifluoromethylphenyl)-5,5-dimethyl-2,4-dioxoimidazolidin-1-ylmethyl]phenylamino}terephthalate

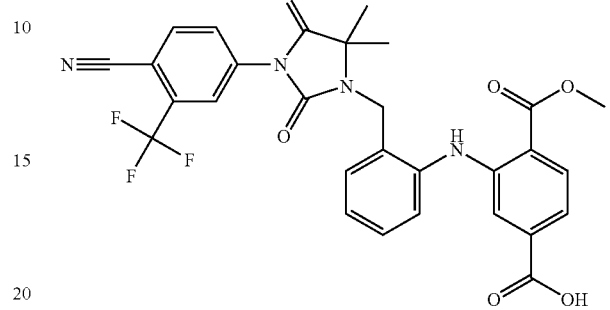

0.2 g of compound 150 was dissolved at room temperature in 5 ml of dry dioxane, admixed with 0.25 ml of hydrobromic acid (62%) and stirred at 80° C. for 30 h. The cooled reaction mixture was concentrated under reduced pressure and purified by chromatography (method [RP1]). The monomethyl ester 1-methyl 2-{2-[3-(4-cyano-3-trifluoromethylphenyl)-5,5-dimethyl-2,4-dioxoimidazolidin-1-ylmethyl]phenylamino}terephthalate was obtained. $^1$H NMR: 13.15, s, 1H, 9.2, s, 1H, 8.25, d, 1H; 8.17, s, 1H, 8.05, d, 1H, 7.97, d, 1H, 7.62, d, 1H, 7.4, m, 3H, 7.28, m, 2H, 4.6, s, 2H; 3.8, s, 3H, 1.35, s, 6H.

Example 158

Methyl 4-{2-[3-(4-cyano-3-cyclopropylphenyl)-5,5-dimethyl-2,4-dioxoimidazolidin-1-ylmethyl]-5-fluorophenylamino}benzoate

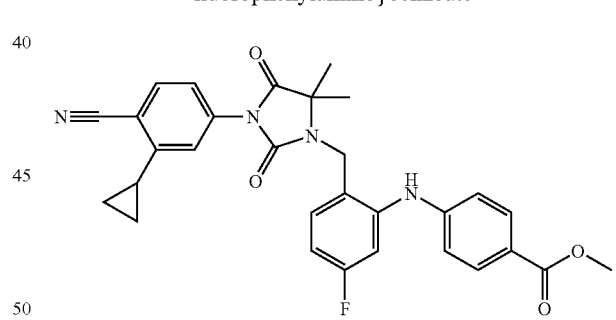

1) Preparation of 4-amino-2-cyclopropylbenzonitrile (158.3)

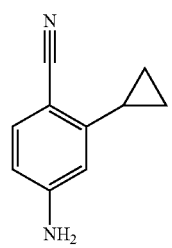

269 mg of palladium acetate were added under an argon atmosphere to a suspension of 916 mg of 2-chloro-4-aminobenzonitrile, 773 mg of cyclopropylboronic acid, 5.094 g of potassium phosphate and 673 mg of tricyclohexylphosphine in a mixture of 10.5 ml of toluene and 1.74 ml of water. The mixture was stirred at 80° C. overnight. The cooled reaction mixture was admixed with water and ethyl acetate and filtered, and the filtrate was extracted three times with a mixture of ethyl acetate with toluene. The organic phases were dried over magnesium sulfate, filtered and concentrated under reduced pressure. The residue was purified by chromatography (method [PR1]) and afforded 4-amino-2-cyclopropylbenzonitrile. $^1$H NMR: 7.3, d, 1H; 6.4, d, 1H, 6.1, d, 1H, 4.0, s (broad), 2H, 2.0, m, 1H, 1.0, m, 2H, 0.65, m, 2H.

2) Preparation of 2-cyclopropyl-4-(4,4-dimethyl-2,5-dioxoimidazolidin-1-yl)benzonitrile (158.1)

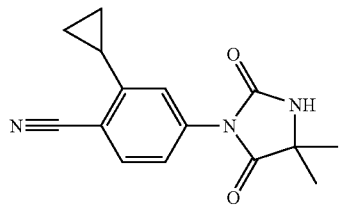

Compound 158.1 was prepared by the process as described for 1.1 by reaction of 158.3 with tert-butyl 2-amino-2-methylpropionate hydrochloride and phosgene (solution in toluene). Molecular weight 269.11 ($C_{15}H_{15}N_3O_2$); retention time $R_t$=1.43 min. [B]; MS (ESI): 270.18 (MH$^+$).

3) Preparation of 4-[3-(2-bromo-4-fluorobenzyl)-4,4-dimethyl-2,5-dioxoimidazolidin-1-yl]-2-cyclopropyl-benzonitrile (158.2)

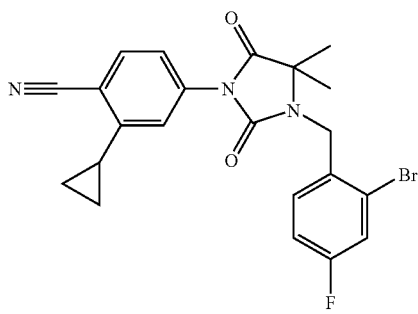

Under conditions as described for the preparation of 1.2, compound 158.1 was reacted with 2-bromo-1-bromomethyl-4-fluorobenzene and afforded 158.2. Molecular weight 455.06 ($C_{22}H_{19}BrFN_3O_2$); retention time $R_t$=2.15 min. [B]; MS (ESI): 456.02 (MH$^+$).

4) Preparation of methyl 4-{2-[3-(4-cyano-3-cyclopropylphenyl)-5,5-dimethyl-2,4-dioxoimidazolidin-1-ylmethyl]-5-fluorophenylamino}benzoate (158)

The further reaction of 158.2 with methyl 4-aminobenzoate was effected under conditions as described above for the preparation of example 1, stage 3. 158 with the molecular weight of 526.20 ($C_{30}H_{27}F_4N_4O_4$) was obtained; retention time $R_t$=2.19 min. [B]; MS (ESI): 527.28 (MH$^+$).

The compound of example 194 (tert-butyl 4-{2-[3-(4-cyano-3-cyclopropylphenyl)-5,5-dimethyl-2,4-dioxoimidazolidin-1-ylmethyl]-5-fluorophenylamino}benzoate was obtained in an analogous manner by reaction of 158.2 with tert-butyl 4-aminobenzoate. Molecular weight 568.24 ($C_{33}H_{33}FN_4O_4$); retention time $R_t$=2.49 min. [B]; MS (ESI): 513.26 (MH$^+$–$C_4H_8$).

Example 160

Methyl 4-{2-[3-(4-cyano-3-methylphenyl)-5,5-dimethyl-2,4-dioxoimidazolidin-1-ylmethyl]-5-fluorophenylamino}benzoate

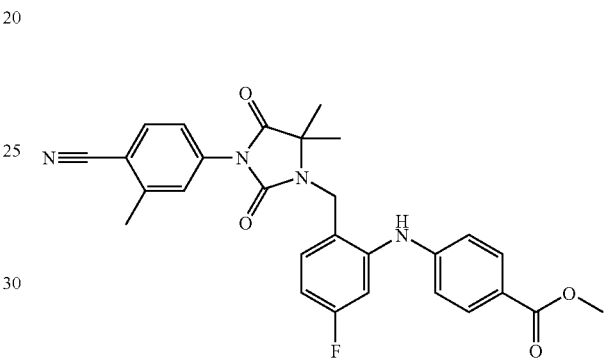

In the synthesis of the compound of example 160, the procedure was as in the preparation of the compound of example 158: 2-methyl-4-nitrobenzonitrile was reduced with hydriodic acid (analogously to the procedure for the synthesis of compound 63.4) to 4-amino-2-methylbenzonitrile (160.3; $^1$H NMR: 7.3, d, 1H, 6.48, s, 1H, 6.42, d, 1H, 6.02, s, 2H; 227, s, 3H). The aniline 160.3 was converted with standard methods using tert-butyl 2-amino-2-methylpropionate hydrochloride and phosgene (solution in toluene) to compound 160.1 (4-(4,4-dimethyl-2,5-dioxoimidazolidin-1-yl)-2-methylbenzonitrile; $^1$H NMR: 8.7, s, 1H, 7.88, d, 1H, 7.55, s, 1H; 7.44, d, 1H, 1.4, s, 3H), which was in turn reacted with 2-bromo-1-bromomethyl-4-fluorobenzene to give 160.2 (4-[3-(2-bromo-4-fluorobenzyl)-4,4-dimethyl-2,5-dioxoimidazolidin-1-yl]-2-methylbenzonitrile; molecular weight 429.04 ($C_{20}H_{17}BrFN_3O_2$); retention time $R_t$=2.08 min. [B]; MS (ESI): 430.05 (MH$^+$)). The reaction of 160.2 with methyl 4-aminobenzoate gave the title compound 160. Molecular weight 500.18 ($C_{28}H_{25}FN_4O_4$); retention time $R_t$=2.14 min. [B]; MS (ESI): 501.23 (MH$^+$).

The compound of example 195 (tert-butyl 4-{2-[3-(4-cyano-3-methylphenyl)-5,5-dimethyl-2,4-dioxoimidazolidin-1-ylmethyl]-5-fluorophenylamino}benzoate) was obtained in an analogous manner by reacting 160.2 with tert-butyl 4-aminobenzoate. Molecular weight 542.23 ($C_{31}H_{31}FN_4O_4$); retention time $R_t$=2.40 min. [B]; MS (ESI): 487.21 (MH$^+$–$C_4H_8$).

Example 167

Methyl 4-{2-[3-(2-tert-butylpyridin-4-yl)-5,5-dimethyl-2,4-dioxoimidazolidin-1-ylmethyl]-5-fluorophenylamino}benzoate ·HCl·trifluoroacetic acid

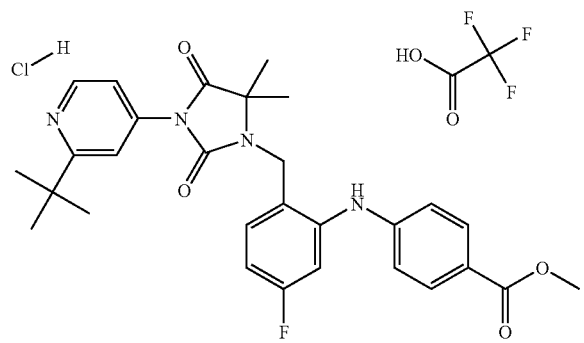

The compound of example 167 was obtained via the sequence of 2-tert-butylpyridin-4-ylamine→3-(2-tert-butylpyridin-4-yl)-5,5-dimethylimidazolidine-2,4-dione 167.1 (molecular weight 261.14 ($C_{14}H_{19}N_3O_2$); retention time $R_t$=0.91 min. [B]; MS (ESI):

262.19 (MH$^+$)) →1-(2-bromo-4-fluorobenzyl)-3-(2-tert-butylpyridin-4-yl)-5,5-dimethylimidazolidine-2,4-dione 167.2 (molecular weight 447.09 ($C_{21}H_{23}BrFN_3O_2$);

retention time $R_t$=1.59 min. [B]; MS (ESI): 448.07 (MH$^+$))→methyl 4-{2-[3-(2-tertbutylpyridin-4-yl)-5,5-dimethyl-2,4-dioxoimidazolidin-1-ylmethyl]-5-fluorophenylamino}benzoate ·HCl ·trifluoroacetic acid 167 (free base: molecular weight 518.23 ($C_{29}H_{31}FN_4O_4$); retention time $R_t$=1.68 min. [B]; MS (ESI): 519.18 (MH$^+$)).

The compound of example 193, the tert-butyl ester corresponding to compound 167, was prepared in an analogous manner using tert-butyl 4-aminobenzoate. Molecular weight 560.27 ($C_{32}H_{37}FN_4O_4$); retention time $R_t$=1.94 min. [B]; MS (ESI): 561.35 (MH$^+$).

Example 170

4-{5-Fluoro-2-[3-(4-fluoro-3-trifluoromethylphenyl)-5,5-dimethyl-2,4-dioxoimidazolidin-1-ylmethyl]phenylamino}-N-((2S,3R,4R,5R)-2,3,4,5,6-pentahydroxyhexyl)benzamide

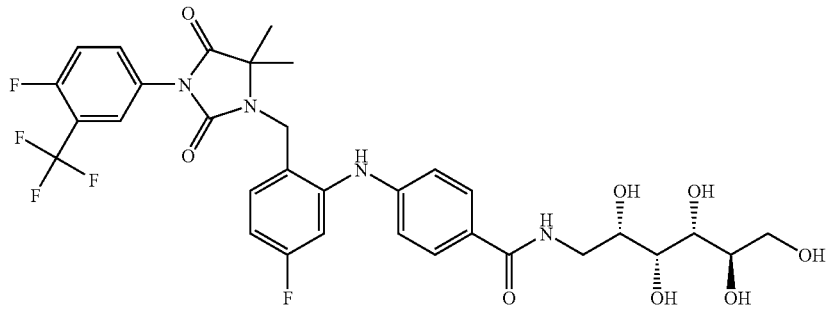

The compound of example 170 was prepared by reacting 156 with N-(3-dimethylaminopropyl)-N'-ethylcarbodiimide hydrochloride, 1-hydroxybenzotriazole, ethyldiisopropylamine and D-glucamine in dimethylformamide. 4-{5-Fluoro-2-[3-(4-fluoro-3-trifluoromethylphenyl)-5,5-dimethyl-2,4-dioxoimidazolidin-1-yl-methyl]phenylamino}-N-((2S,3R,4R,5R)-2,3,4,5,6-pentahydroxyhexyl)benzamide was obtained; molecular weight 696.22 ($C_{32}H_{33}F_5N_4O_8$); retention time $R_t$=1.86 min.

[C]; MS (ESI): 697.33 (MH$^+$).

Example 164

2-(4-{2-[3-(4-Cyano-3-trifluoromethylphenyl)-5,5-dimethyl-2,4-dioxoimidazolidin-1-ylmethyl] phenylamino}benzoylamino)ethanesulfonic acid

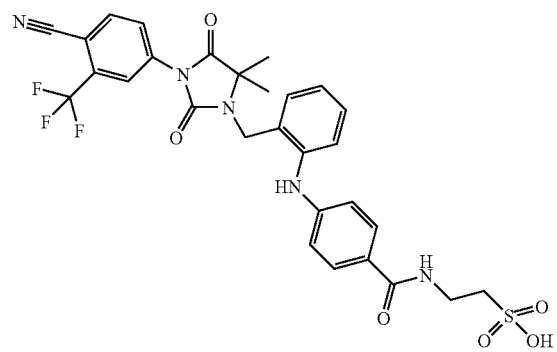

In an analogous manner, except using the compound of example 62 and taurine, the compound of example 164, 2-(4-{2-[3-(4-cyano-3-trifluoromethylphenyl)-5,5-dimethyl-2,4-dioxoimidazolidin-1-ylmethyl] phenylamino}benzoylamino)ethane-sulfonic acid (molecular weight 629.15 ($C_{29}H_{26}F_3N_5O_6S$); retention time $R_t$=1.63 min. [B]; MS (ESI): 630.25 (MH$^+$)), was obtained.

Example 171

1-{4-Fluoro-2-[4-(4-hydroxypiperidine-1-carbonyl)phenylamino]benzyl}-3-(4-fluoro-3-trifluoromethylphenyl)-5,5-dimethylimidazolidine-2,4-dione

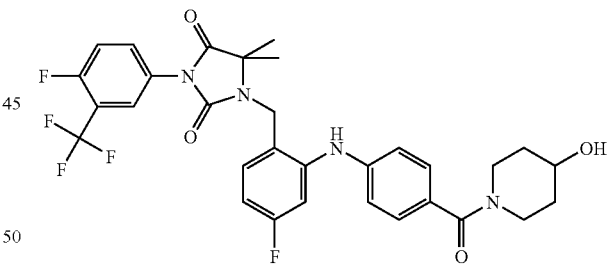

In an analogous manner and using the compound of example 156 with piperidin-4-ol, the compound of example 171, 1-{4-fluoro-2-[4-(4-hydroxypiperidin-1-carbonyl)phenylamino]benzyl}-3-(4-fluoro-3-trifluoromethylphenyl)-5,5-dimethylimidazolidine-2,4-dione (molecular weight 616.21 ($C_{31}H_{29}F_5N_4O_4$); retention time $R_t$=2.18 min. [C]; MS (ESI): 617.24 (MH$^+$)), was obtained.

Example 172

1-{4-Fluoro-2-[4-(piperazine-1-carbonyl)phenylamino]benzyl}-3-(4-fluoro-3-trifluoromethylphenyl)-5,5-dimethylimidazolidine-2,4-dione, salt with hydrochloric acid

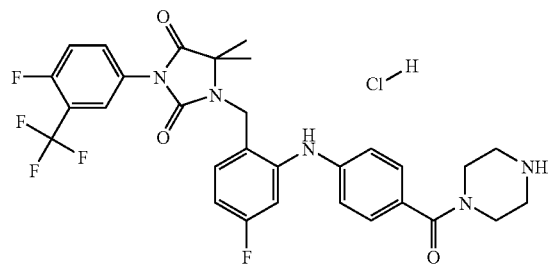

The compound of example 172 was prepared as described for 170, with the difference that the amine component used, instead of D-glucamine, was piperazine, and the amide was subsequently converted to the hydrochloride with hydrochloric acid in dioxane. Molecular weight (free base) 601.21 ($C_{30}H_{28}F_5N_5O_3$); retention time $R_t$=1.71 min. [C]; MS (ESI): 602.25 (MH$^+$).

Example 173

4-{2-[3-(4-Cyano-3-trifluoromethylphenyl)-5,5-dimethyl-2,4-dioxoimidazolidin-1-ylmethyl]phenylamino}-N-(3-methanesulfonylpropyl)benzamide

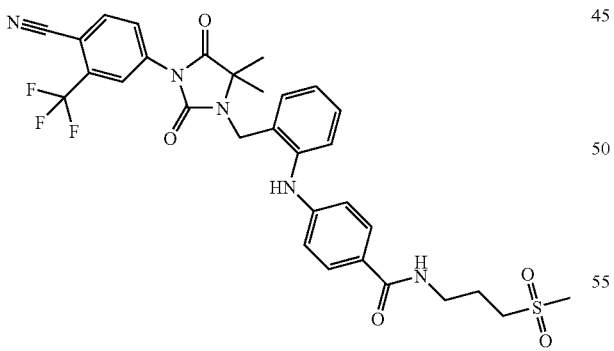

In an analogous manner and using the compound of example 62 and 3-methanesulfonylpropylamine, the compound of example 173, 4-{2-[3-(4-cyano-3-trifluoromethylphenyl)-5,5-dimethyl-2,4-dioxoimidazolidin-1-ylmethyl]phenylamino}-N-(3-methanesulfonylpropyl)benzamide (molecular weight 641.19 ($C_{31}H_{30}F_3N_5O_5S$); retention time $R_t$=1.79 min. [B]; MS (ESI): 642.18 (MH$^+$)), was prepared.

Example 174

4-{2-[3-(4-Cyano-3-trifluoromethylphenyl)-5,5-dimethyl-2,4-dioxoimidazolidin-1-ylmethyl]phenylamino}-N-piperidin-1-ylbenzamide

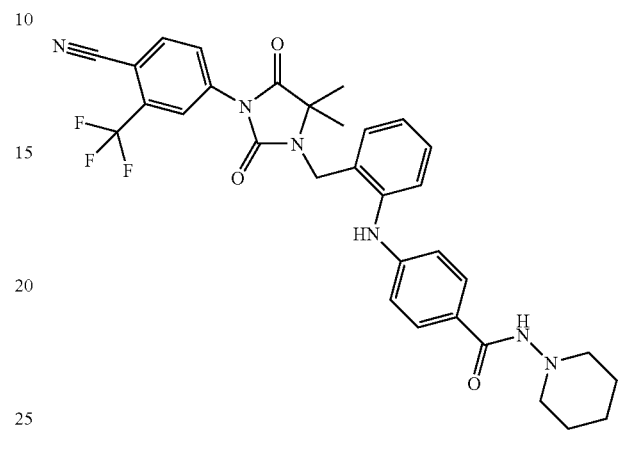

100 mg of the compound of example 62 were dissolved in 2.5 ml of dimethylformamide and admixed successively with 45.9 mg of N-(3-dimethylaminopropyl)-N'-ethylcarbodiimide hydrochloride, 36.6 mg of 1-hydroxybenzotriazole and 30.9 mg of ethyldiisopropylamine, and stirred at room temperature for 30 minutes. Thereafter, 0.031 ml of N-aminopiperidine was added and the mixture was stirred for a further 6 h. For workup, the reaction mixture was concentrated under reduced pressure and purified by chromatography (method [RP1]). 4-{2-[3-(4-Cyano-3-trifluoromethylphenyl)-5,5-dimethyl-2,4-dioxoimidazolidin-1-ylmethyl]phenylamino}-N-piperidin-1-ylbenzamide was obtained; molecular weight 604.24 ($C_{32}H_{31}F_3N_6O_3$); retention time $R_t$=1.60 min. [B]; MS (ESI): 605.24 (MH$^+$).

Example 237

(R)-1-(4-{2-[3-(4-Cyano-3-trifluoromethylphenyl)-5,5-dimethyl-2,4-dioxoimidazolidin-1-ylmethyl]-5-fluorophenylamino}benzoyl)pyrrolidine-2-carbonitrile

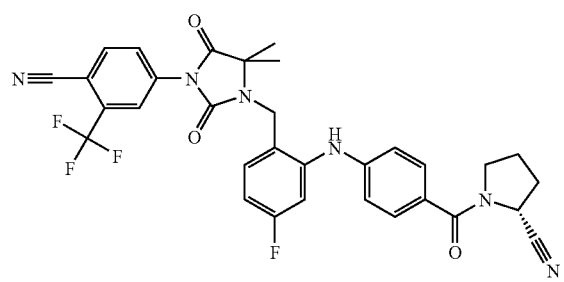

In an analogous manner, except using the compound of example 133 and (R)-pyrrolidine-2-carbonitrile, the compound of example 237, (R)-1-(4-{2-[3-(4-cyano-3-trifluoromethylphenyl)-5,5-dimethyl-2,4-dioxoimidazolidin-1-ylmethyl]-5-fluorophenylamino}benzoyl)pyrrolidine-2-carbonitrile (molecular weight 618.20 ($C_{32}H_{26}F_4N_6O_3$); retention time $R_t$=2.01 min. [B]; MS (ESI): 619.22 (MH$^+$)), was prepared.

Example 175

N-(4-{2-[3-(4-Cyano-3-trifluoromethylphenyl)-5,5-dimethyl-2,4-dioxoimidazolidin-1-ylmethyl]phenylamino}phenyl)methanesulfonamide

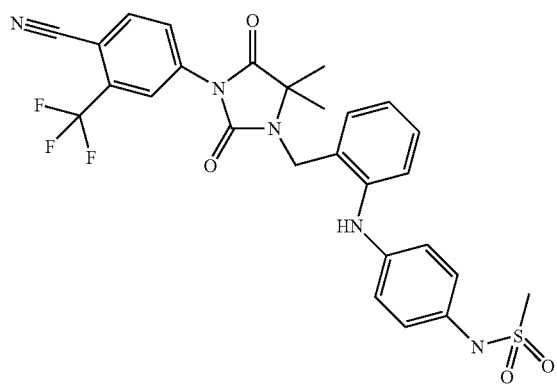

The compound of example 175 was obtained by reacting 113 with methanesulfonyl chloride and sodium hydrogencarbonate in acetonitrile. Molecular weight 571.15 ($C_{27}H_{24}F_3N_5O_4S$); retention time $R_t$=1.95 min. [B]; MS (ESI): 572.24 (MH$^+$).

As a further reaction product, the compound of example 176,

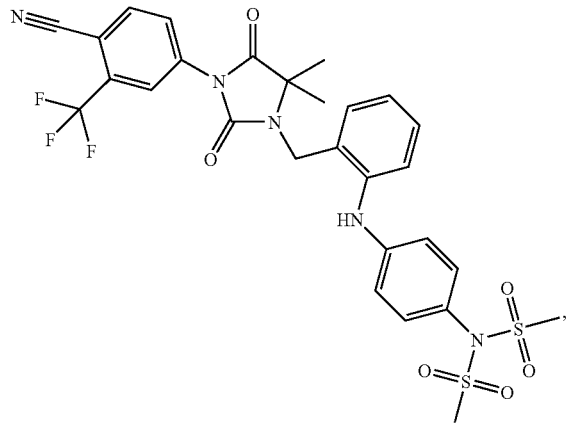

was obtained. Molecular weight 649.12 ($C_{28}H_{26}F_3N_5O_6S_2$); retention time $R_t$=2.06 min. [B]; MS (ESI): 650.26 (MH$^+$).

Example 177

Methyl (4-{2-[3-(4-cyano-3-trifluoromethylphenyl)-5,5-dimethyl-2,4-dioxoimidazolidin-1-ylmethyl]phenylamino}phenylamino)acetate

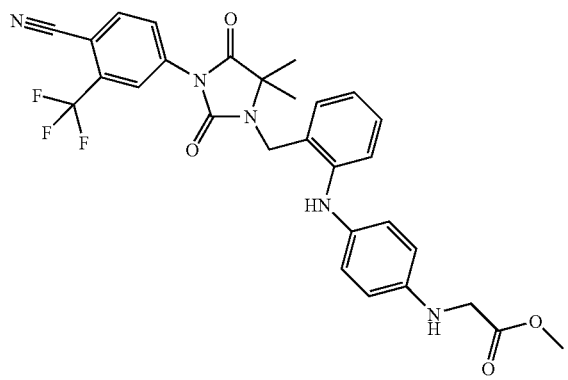

The compound of example 177 was obtained by reacting 113 with methyl bromoacetate and sodium hydrogencarbonate in acetonitrile. Molecular weight 565.19 ($C_{29}H_{26}F_3N_5O_4$); retention time $R_t$=1.96 min. [B]; MS (ESI): 566.29 (MH$^+$).

As a further reaction product, the compound of example 178, methyl [(4-{2-[3-(4-cyano-3-trifluoromethylphenyl)-5,5-dimethyl-2,4-dioxoimidazolidin-1-yl-methyl]phenylamino}phenyl)methoxycarbonylmethylamino]acetate

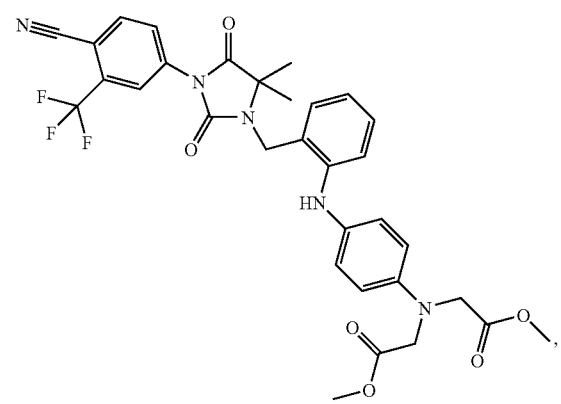

was obtained. Molecular weight 637.21 ($C_{32}H_{30}F_3N_5O_6$); retention time $R_t$=2.14 min. [B]; MS (ESI): 638.31 (MH$^+$).

Example 182

(4-{2-[3-(4-Cyano-3-trifluoromethylphenyl)-5,5-dimethyl-2,4-dioxoimidazolidin-1-ylmethyl]phenylamino}phenoxy)acetic acid

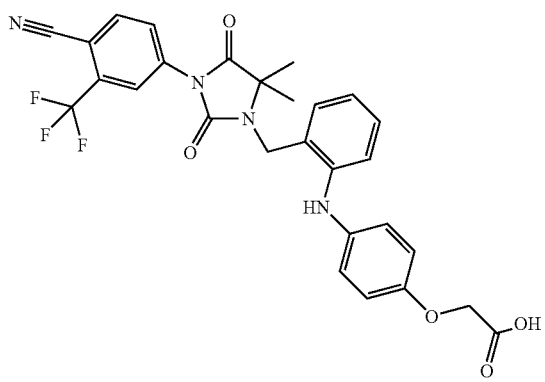

The compound of example 182 was obtained by reacting 191 with 4 N hydrochloric acid in dioxane. Molecular weight 552.16 ($C_{28}H_{23}F_3N_4O_5$); retention time $R_t$=1.93 min. [B]; MS (ESI): 553.17 ($MH^+$).

Example 183

3-(4-Carboxyphenylamino)-4-[3-(4-cyano-3-trifluoromethylphenyl)-5,5-dimethyl-2,4-dioxoimidazolidin-1-ylmethyl]benzoic acid

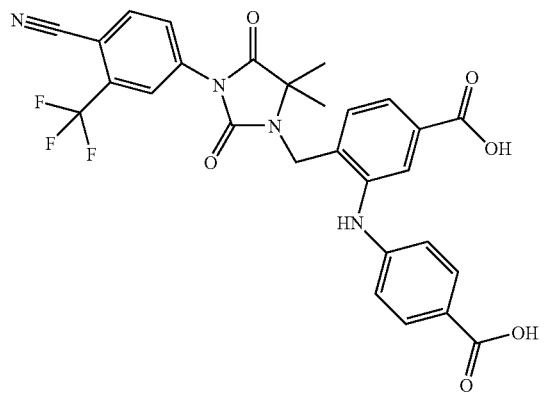

1) Preparation of tert-butyl 3-bromo-4-methylbenzoate (183.1)

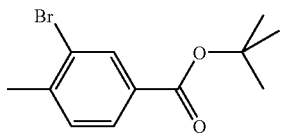

2 g of 3-bromo-4-methylbenzoic acid were suspended in 9.4 g of thionyl chloride and stirred at 60° C. for 2 h. The cooled reaction mixture was concentrated under reduced pressure, taken up in 20 ml of acetonitrile, admixed with 887 mg of lithium tert-butoxide and stirred at room temperature for 20 h. For workup, the reaction mixture was admixed with ethyl acetate and water. The organic phase was removed, dried over magnesium sulfate, filtered and concentrated under reduced pressure. The residue was purified by chromatography (silica gel; n-heptane) and afforded tert-butyl 3-bromo-4-methylbenzoate. $^1$H NMR: 8.0, s, 1H; 7.8, d, 1H, 7.5, d, 1H, 2.4, s, 3H, 1.55, s, 9H.

2) Preparation of tert-butyl 3-bromo-4-bromomethylbenzoate (183.2)

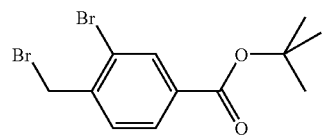

The free-radical bromination of compound 183.1 with N-bromosuccinimide and dibenzoyl peroxide in chlorobenzene at 120° C. afforded 183.2, tert-butyl 3-bromo-4-bromomethylbenzoate. $^1$H NMR: 8.06, s, 1H, 7.9, d, 1H, 7.75, d, 1H, 4.78, s, 2H; 1.55, s, 9H.

3) Preparation of tert-butyl 3-bromo-4-[3-(4-cyano-3-trifluoromethylphenyl)-5,5-dimethyl-2,4-dioxoimidazolidin-1-ylmethyl]benzoate (183.3)

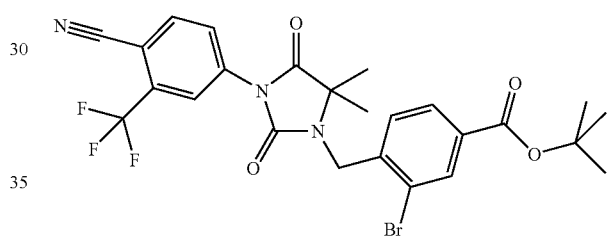

Under conditions as described for the preparation of the compound of Example 6.2, compound 1.1 was reacted with 183.2 to give 183.3. $^1$H NMR: 8.35, d, 1H, 8.25, s, 1H, 8.1, d, 1H, 8.09, s, 1H, 7.88, d, 1H, 7.7, d, 2H, 4.69, s, 2H, 1.55, s, 9H, 1.43, s, 6H.

4) Preparation of tert-butyl 3-(4-tert-butoxycarbonylphenylamino)-4-[3-(4-cyano-3-trifluoromethylphenyl)-5,5-dimethyl-2,4-dioxoimidazolidin-1-ylmethyl]benzoate (214)

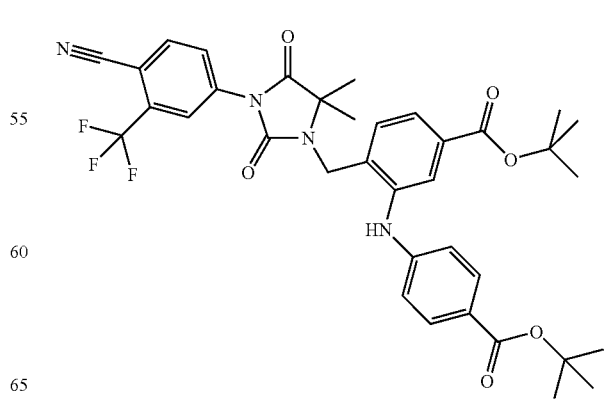

Under conditions as described above for the preparation of compound 126, 214 was obtained by reaction of 183.3 with tert-butyl 4-aminobenzoate. Molecular weight 678.26 ($C_{36}H_{37}F_3N_4O_6$); retention time $R_t$=2.62 min. [B]; MS (ESI): 623.20 ($MH^+-C_4H_8$).

5) 3-(4-Carboxyphenylamino)-4-[3-(4-cyano-3-trifluoromethylphenyl)-5,5-dimethyl-2,4-dioxoimidazolidin-1-ylmethyl]benzoic acid 183

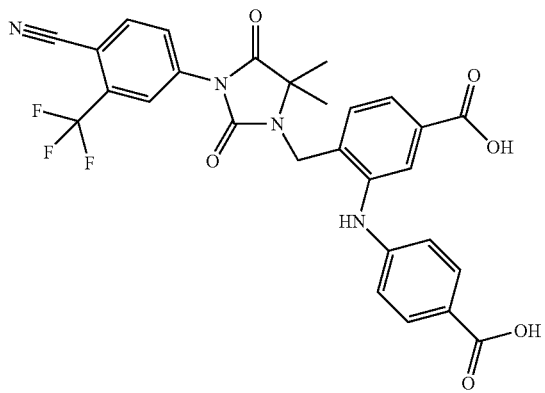

The ester cleavage of 214 to form 183 was undertaken as described above for Example 62. 183: molecular weight 566.14 ($C_{28}H_{21}F_3N_4O_6$); retention time $R_t$=1.69 min. [B]; MS (ESI): 567.17 ($MH^+$).

The compounds of Examples 185, 220, 187, 188 and 189 were prepared in a similar sequence:

185: 4-[3-(4-cyano-3-trifluoromethylphenyl)-5,5-dimethyl-2,4-dioxoimidazolidin-1-ylmethyl]-3-(4-trifluoromethylphenylamino)benzoic acid (molecular weight 590.13 ($C_{28}H_{20}F_6N_4O_4$); retention time $R_t$=2.04 min. [B]; MS (ESI): 591.15 ($MH^+$) via the sequence of 183.3→tert-butyl 4-[3-(4-cyano-3-trifluoromethylphenyl)-5,5-dimethyl-2,4-dioxoimidazolidin-1-ylmethyl]-3-(4-trifluoromethylphenylamino)benzoate (215, molecular weight 646.20 ($C_{32}H_{28}F_6N_4O_4$); retention time $R_t$=2.55 min. [B]; MS (ESI): 647.23 ($MH^+$))→185;

220: 4-[3-(4-cyano-3-trifluoromethylphenyl)-5,5-dimethyl-2,4-dioxoimidazolidin-1-ylmethyl]-3-(4-fluorophenylamino)benzoic acid (molecular weight 540.14 ($C_{27}H_{20}F_4N_4O_4$); retention time $R_t$=1.95 min. [B]; MS (ESI): 541.15 ($MH^+$) via the sequence of 183.3→tert-butyl 4-[3-(4-cyano-3-trifluoromethylphenyl)-5,5-dimethyl-2,4-dioxoimidazolidin-1-ylmethyl]-3-(4-fluorophenylamino)benzoate (216, molecular weight 596.20 ($C_{31}H_{28}F_4N_4O_4$);

retention time $R_t$=2.46 min. [B]; MS (ESI): 597.19 ($MH^+$))→220;

187: 4-(4-carboxyphenylamino)-3-[3-(4-cyano-3-trifluoromethylphenyl)-5,5-dimethyl-2,4-dioxoimidazolidin-1-ylmethyl]benzoic acid (molecular weight 566.14 ($C_{28}H_{21}F_3N_4O_6$);

retention time $R_t$=1.68 min. [B]; MS (ESI): 567.17 ($MH^+$) via the sequence of 187.1 (tert-butyl 4-bromo-3-methylbenzoate, $^1$H NMR: 7.85, s, 1H, 7.72, d, 1H, 7.62, d, 1H, 2.4, s, 3H, 1.53, s, 9H)→187.2 (tert-butyl 4-bromo-3-bromomethylbenzoate, $^1$H NMR: 8.12, s, 1H, 7.8, d, 1H, 7.75, d, 1H, 4.8, s, 2H, 1.56, s, 9H) →187.3 (tert-butyl 4-bromo-3-[3-(4-cyano-3-trifluoromethylphenyl)-5,5-dimethyl-2,4-dioxoimidazolidin-1-ylmethyl]benzoate, molecular weight 565.08 ($C_{25}H_{23}BrF_3N_3O_4$); retention time $R_t$=3.03 min. [C]; MS (ESI): 566.14 ($MH^+$))→217 (tert-butyl 4-(4-tert-butoxycarbonylphenylamino)-3-[3-(4-cyano-3-trifluoromethylphenyl)-5,5-dimethyl-2,4-dioxoimidazolidin-1-ylmethyl]benzoate; molecular weight 678.26 ($C_{36}H_{37}F_3N_4O_6$); retention time $R_t$=2.67 min. [B]; MS (ESI): 623.23 ($MH^+-C_4H_8$))→187 (compounds 187.1, 187.2, 187.3 and 217 are isomers of compounds 183.1, 183.2, 183.3 and 214 and were prepared by the process described there);

188: 3-[3-(4-cyano-3-trifluoromethylphenyl)-5,5-dimethyl-2,4-dioxoimidazolidin-1-ylmethyl]-4-(4-trifluoromethylphenylamino)benzoic acid (molecular weight 590.13 ($C_{28}H_{20}F_6N_4O_4$); retention time $R_t$=2.09 min. [B]; MS (ESI): 591.17 ($MH^+$) via the sequence of 187.3→tert-butyl 3-[3-(4-cyano-3-trifluoromethylphenyl)-5,5-dimethyl-2,4-dioxoimidazolidin-1-ylmethyl]-4-(4-trifluoromethylphenylamino)benzoate (218, (molecular weight 646.20 ($C_{32}H_{28}F_6N_4O_4$); retention time $R_t$=2.59 min. [B]; MS (ESI): 591.16 ($MH^+-C_4H_8$))→188;

189: 3-[3-(4-cyano-3-trifluoromethylphenyl)-5,5-dimethyl-2,4-dioxoimidazolidin-1-ylmethyl]-4-(4-fluorophenylamino)benzoic acid (molecular weight 540.14 ($C_{27}H_{20}F_4N_4O_4$);

retention time $R_t$=1.98 min. [B]; MS (ESI): 541.16 ($MH^+$) via the sequence of 187.3→tert-butyl 3-[3-(4-cyano-3-trifluoromethylphenyl)-5,5-dimethyl-2,4-dioxoimidazolidin-1-ylmethyl]-4-(4-fluorophenylamino)benzoate (219, (molecular weight 596.20 ($C_{31}H_{28}F_4N_4O_4$);

retention time $R_t$=2.49 min. [B]; MS (ESI): 541.16 ($MH^+-C_4H_8$))→189.

Example 184

4-{2-[3-(4-Cyano-3-trifluoromethylphenyl)-5,5-dimethyl-2,4-dioxoimidazolidin-1-ylmethyl]-5-trifluoromethylphenylamino}benzoic acid sodium salt

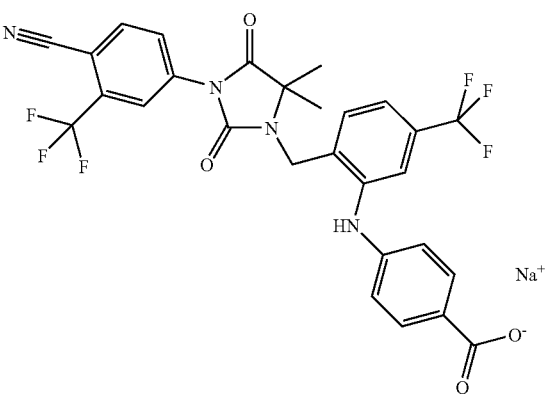

The sodium salt of the acid 107 was obtained by adding solid sodium hydrogencarbonate to a solution of the acid in a mixture of water and acetonitrile, and the mixture was stirred at room temperature for 30 min. Excess sodium hydrogencarbonate was removed by adding AMBERLITE™ IPR-64H$^+$ form (weakly acidic). After filtration through a syringe filter and freeze-drying, 184 was obtained;

¹H NMR: 8.35, d, 1H, 8.24, s, 1H, 8.1, d, 2H, 8.0, s, 1H, 7.79, d, 2H, 7.7, d, 1H, 7.44, s, 1H, 7.26, 1H, 6.9, d, 2H, 4.62, s, 2H, 1.42, s, 6H.

Example 190

4-{2-[3-(4-Cyano-3-methylphenyl)-5,5-dimethyl-2,4-dioxoimidazolidin-1-ylmethyl]-5-fluorophenylamino}benzamide

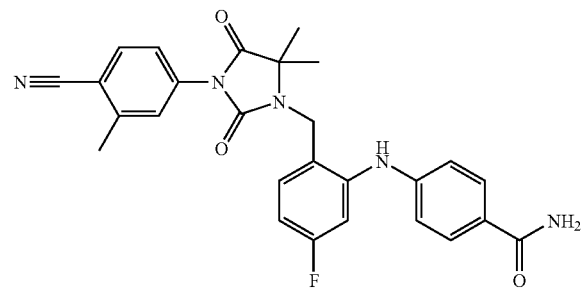

The compound of Example 190 was prepared as described for 170, with the difference that the acid component used was the compound 166 and the amine component used was ammonia (concentrated aqueous solution). Molecular weight 485.18 ($C_{27}H_{24}FN_5O_3$); retention time $R_t$=1.68 min. [B]; MS (ESI): 486.22 (MH⁺).

Example 191 tert-Butyl (4-{2-[3-(4-cyano-3-trifluoromethylphenyl)-5,5-dimethyl-2,4-dioxoimidazolidin-1-ylmethyl]phenylamino}phenoxy)acetate

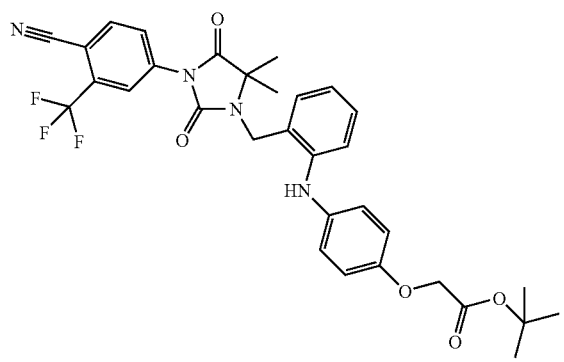

The compound of Example 191 was obtained by reaction of 135 with tert-butyl bromoacetate and cesium carbonate in acetonitrile. Molecular weight 608.22 ($C_{32}H_{31}F_3N_4O_5$); retention time $R_t$=3.04 min. [C]; MS (ESI): 609.25 (MH⁺).

Example 198

4-{3-[2-(6-Hydroxypyridazin-3-ylamino)benzyl]-4,4-dimethyl-2,5-dioxoimidazolidin-1-yl}-2-trifluoromethylbenzonitrile trifluoroacetic acid

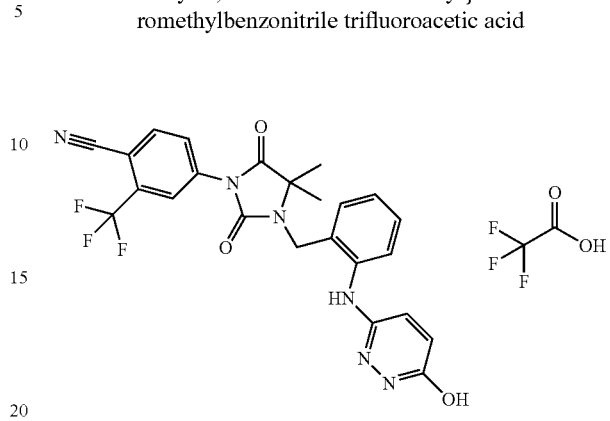

275 mg of the compound of Example 179 were dissolved in 10 ml of dry acetonitrile, admixed with 219 mg of potassium iodide and 169 µl of trimethylsilyl chloride and heated to 85° C. for 4 h. The cooled reaction mixture was concentrated under reduced pressure and the residue was admixed with ethyl acetate and water. The organic phase was purified by chromatography (method [RP1]) and afforded 4-{3-[2-(6-hydroxypyridazin-3-ylamino)benzyl]-4,4-dimethyl-2,5-dioxoimidazolidin-1-yl}-2-trifluoromethylbenzonitrile as the salt with trifluoroacetic acid. Molecular weight 496.14 ($C_{24}H_{19}F_3N_6O_3$); retention time $R_t$=1.63 min. [C]; MS (ESI): 497.16 (MH⁺).

Example 204

1-[4-Fluoro-2-(8-oxo-5,6,7,8-tetrahydronaphthalen-2-ylamino)benzyl]-3-(4-fluoro-3-trifluoromethylphenyl)-5,5-dimethylimidazolidine-2,4-dione

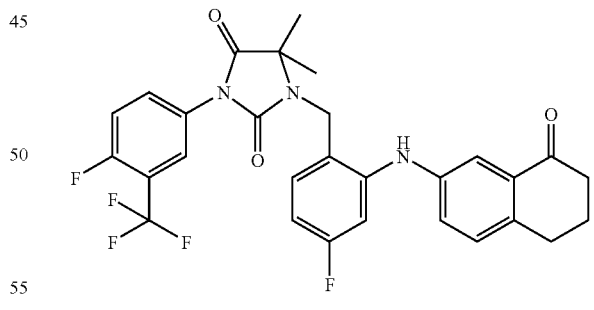

1) Preparation of 1-(2-amino-4-fluorobenzyl)-3-(4-fluoro-3-trifluoromethylphenyl)-5,5-dimethylimidazolidine-2,4-dione (204.2)

Analogously to the process as described for the preparation of compound 61.2, 204.2 was obtained by reaction of 154.2 with benzophenone imine. Molecular weight 413.11 ($C_{19}H_{16}F_5N_3O_2$); retention time $R_t$=2.45 min. [C]; MS (ESI): 414.23 (MH⁺).

2) Preparation of 1-[4-fluoro-2-(8-oxo-5,6,7,8-tetrahydronaphthalen-2-ylamino)-benzyl]-3-(4-fluoro-3-trifluoromethylphenyl)-5,5-dimethylimidazolidine-2,4-dione (204)

The reaction of 204.2 with 7-bromo-3,4-dihydro-2H-naphthalen-1-one under conditions as described for the preparation of the compound of Example 61 afforded 1-[4-fluoro-2-(8-oxo-5,6,7,8-tetrahydronaphthalen-2-ylamino)benzyl]-3-(4-fluoro-3-trifluoromethylphenyl)-5,5-dimethylimidazolidine-2,4-dione (204). Molecular weight 557.17 ($C_{29}H_{24}F_5N_3O_2$); retention time $R_t$=2.33 min. [B]; MS (ESI): 558.25 (MH$^+$).

The compounds of Example 205, 1-[4-fluoro-2-(3-oxoindan-5-ylamino)benzyl]-3-(4-fluoro-3-trifluoromethylphenyl)-5,5-dimethylimidazolidine-2,4-dione (molecular weight 543.15 ($C_{28}H_{22}F_5N_3O_3$); retention time $R_t$=2.09 min. [B]; MS (ESI): 544.24 (MH$^+$)), of Example 206, 1-[4-fluoro-2-(1-oxoindan-5-ylamino)benzyl]-3-(4-fluoro-3-trifluoromethylphenyl)-5,5-dimethylimidazolidine-2,4-dione (molecular weight 543.15 ($C_{28}H_{22}F_5N_3O_3$); retention time $R_t$=2.07 min. [B]; MS (ESI): 544.23 (MH$^+$)), of Example 207, 1-[2-(2,2-dimethyl-4-oxochroman-6-ylamino)-4-fluorobenzyl]-3-(4-fluoro-3-trifluoromethylphenyl)-5,5-dimethylimidazolidine-2,4-dione (molecular weight 587.18 ($C_{30}H_{26}F_5N_3O_4$); retention time $R_t$=2.38 min. [B]; MS (ESI): 588.25 (MH$^+$)), of Example 213, 1-[4-fluoro-2-(4-methanesulfonylphenylamino)benzyl]-3-(4-fluoro-3-trifluoromethylphenyl)-5,5-dimethylimidazolidine-2,4-dione (molecular weight 567.12 ($C_{26}H_{22}F_5N_3O_4S$); retention time $R_t$=2.00 min. [B]; MS (ESI): 568.10 (MH$^+$)), of Example 222, 3-{5-fluoro-2-[3-(4-fluoro-3-trifluoromethylphenyl)-5,5-dimethyl-2,4-dioxoimidazolidin-1-ylmethyl]phenylamino}benzenesulfonamide HCl salt, molecular weight (free base) 568.12 ($C_{25}H_{21}F_5N_4O_4S$); retention time $R_t$=2.39 min. [C]; MS (ESI): 569.41 (MH$^+$), prepared by hydrochloric acid hydrolysis of N-[1-dimethylaminomethylidene]-3-{5-fluoro-2-[3-(4-fluoro-3-trifluoromethylphenyl)-5,5-dimethyl-2,4-dioxoimidazolidin-1-ylmethyl]phenylamino}benzenesulfonamide (222.1, molecular weight 623.16 ($C_{28}H_{26}F_5N_5O_4S$); retention time $R_t$=2.48 min. [C]; MS (ESI): 624.33 (MH$^+$)), of Example 230, 4-{5-fluoro-2-[3-(4-fluoro-3-trifluoromethylphenyl)-5,5-dimethyl-2,4-dioxoimidazolidin-1-ylmethyl]phenylamino}benzenesulfonamide, molecular weight 568.12 ($C_{25}H_{21}F_5N_4O_4S$); retention time $R_t$=1.88 min. [B]; MS (ESI): 569.31 (MH$^+$), prepared by hydrochloric acid hydrolysis of N-[1-dimethylaminomethylidene]-4-{5-fluoro-2-[3-(4-fluoro-3-trifluoromethylphenyl)-5,5-dimethyl-2,4-dioxoimidazolidin-1-ylmethyl]phenylamino}-benzenesulfonamide (230.1, molecular weight 623.16 ($C_{28}H_{26}F_5N_5O_4S$); retention time $R_t$=1.95 min. [B]; MS (ESI): 624.05 (MH$^+$)), of Example 239, 1-[4-fluoro-2-(4-oxochroman-6-ylamino)benzyl]-3-(4-fluoro-3-trifluoromethylphenyl)-5,5-dimethylimidazolidine-2,4-dione, molecular weight 559.15 ($C_{28}H_{22}F_5N_3O_4$); retention time $R_t$=2.19 min. [B]; MS (ESI): 560.22 (MH$^+$) were obtained under conditions as described for the preparation of the compound of Example 204 by reaction of compound 204.2 with 6-bromoindan-1-one (for 205), 5-bromoindan-1-one (for 206), 6-bromo-2,2-dimethylchroman-4-one (for 207), 1-bromo-4-methanesulfonylbenzene (for 213), 3-bromo-N-[1-dimethylaminomethylidene]benzenesulfonamide (prepared by reaction of 3-bromobenzenesulfonamide with dimethylformamide dimethyl acetal for 222.1 and 222), 4-bromo-N-[1-dimethylaminomethylidene]benzenesulfonamide (prepared by reaction of 4-bromobenzenesulfonamide with dimethylformamide dimethyl acetal for 230.1 and 230), 6-bromochroman-4-one (for 239, using, as a catalyst, [1,3-bis(2,6-diisopropylphenyl)-imidazol-2-ylidene](3-chloropyridyl)palladium(II) dichloride and, as a base, cesium carbonate).

Example 210

4'-{2-[3-(4-Cyano-3-trifluoromethylphenyl)-5,5-dimethyl-2,4-dioxoimidazolidin-1-ylmethyl]phenylamino}biphenyl-4-carboxylic acid

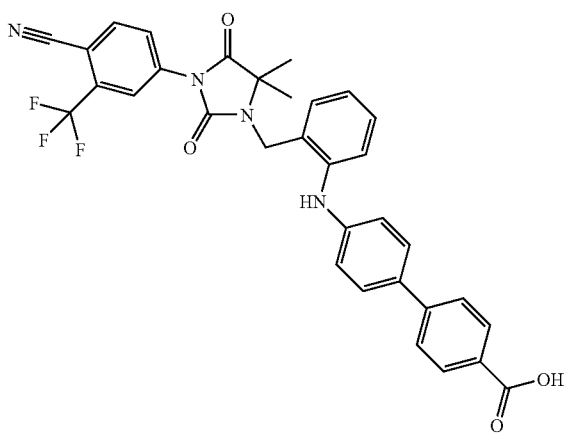

1) Preparation of tert-butyl 4'-bromobiphenyl-4-carboxylate (210.1)

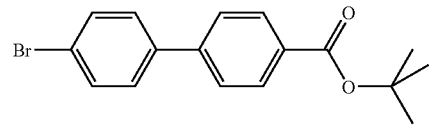

Compound 210.1 was prepared as described for the preparation of 183.1 from 4'-bromobiphenyl-4-carboxylic acid, thionyl chloride and lithium tert-butoxide.

$^1$H NMR: 7.99, d, 2H, 7.8, d, 2H, 7.7, s, 4H, 1.57, s, 9H.

2) Preparation of tert-butyl 4'-{2-[3-(4-cyano-3-trifluoromethylphenyl)-5,5-dimethyl-2,4-dioxoimidazolidin-1-ylmethyl]phenylamino}biphenyl-4-carboxylate (203)

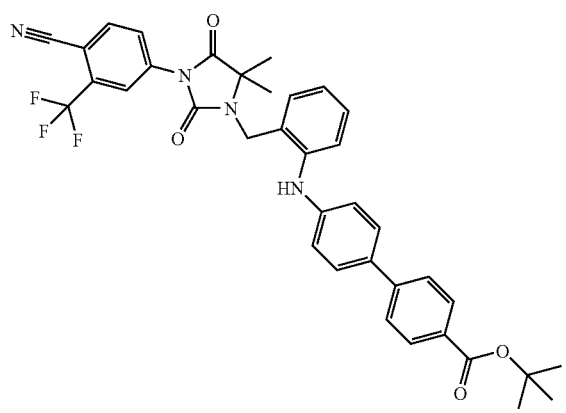

Under conditions as described for the preparation of the compound of Example 61, compound 61.2 was reacted with 210.1 to give 203. Molecular weight 654.24 ($C_{37}H_{33}F_3N_4O_4$); retention time $R_t$=3.43 min. [C]; MS (ESI): 655.51 (MH$^+$).

3) Preparation of 4'-{2-[3-(4-cyano-3-trifluoromethylphenyl)-5,5-dimethyl-2,4-dioxoimidazolidin-1-ylmethyl]phenylamino}biphenyl-4-carboxylic acid (210)

Compound 210 was obtained by acidic hydrolysis of ester 203 (analogously to the method in the preparation of 62). Molecular weight 598.18 ($C_{33}H_{25}F_3N_4O_4$); retention time $R_t$=2.52 min. [B]; MS (ES−): 597.10 (M−H$^+$).

Example 223

Methyl (4-{2-[4-{2-[3-(6-cyanobiphenyl-3-yl)-5,5-dimethyl-2,4-dioxoimidazolidin-1-ylmethyl]-5-fluorophenylamino}benzoate

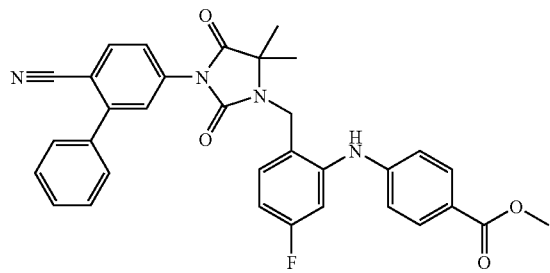

1) Preparation of 5-aminobiphenyl-2-carbonitrile (223.3)

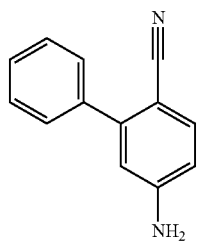

534 mg of phenylboronic acid, 79 mg of palladium(II) acetate, 287 mg of 2-dicyclohexylphosphino-2',6'-dimethoxybiphenyl, 1.486 g of potassium phosphate ($K_3PO_4$) and 305 mg of 2-chloro-4-aminobenzonitrile were suspended in 7 ml of toluene and stirred at 80° C. under an argon atmosphere for 12 h. The cooled reaction mixture was admixed with water and ethyl acetate and filtered. The filtrate was extracted three times with a mixture of ethyl acetate and toluene. The organic phases were removed, dried over magnesium sulfate, filtered and concentrated under reduced pressure. $^1$H NMR: 7.52-7.42, m, 6H, 6.63, m, 2H, 6.25, s (broad), 2H.

2) Preparation of 5-(4,4-dimethyl-2,5-dioxoimidazolidin-1-yl)biphenyl-2-carbonitrile (223.1)

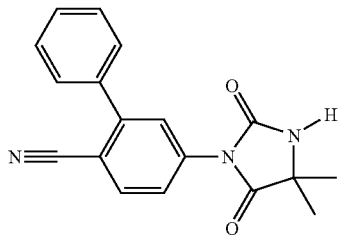

Compound 223.1 was prepared by the process as described for 1.1 by reaction of 223.3 with tert-butyl 2-amino-2-methylpropionate hydrochloride and phosgene (solution in toluene). $^1$H NMR: 8.73, s, 1H; 8.09, d, 1H, 7.75, s, 1H, 7.69, d, 1H, 7.62-7.5, m, 5H, 1.42, s, 6H.

3) Preparation of 5-[3-(2-bromo-4-fluorobenzyl)-4,4-dimethyl-2,5-dioxoimidazolidin-1-yl]biphenyl-2-carbonitrile (223.2)

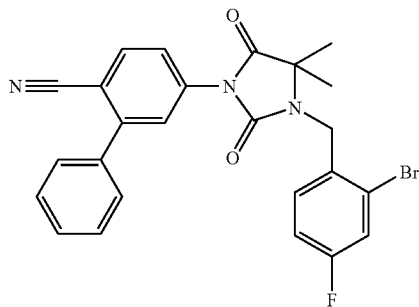

Under conditions as described for the preparation of 1.2, compound 223.1 was reacted with 2-bromo-1-bromomethyl-4-fluorobenzene and afforded 223.2. Molecular weight 491.06 ($C_{25}H_{19}BrFN_3O_2$); retention time $R_t$=2.68 min. [B]; MS (ESI): 492.31 (MH$^+$).

4) Preparation of methyl (4-{2-[4-{2-[3-(6-cyanobiphenyl-3-yl)-5,5-dimethyl-2,4-dioxoimidazolidin-1-ylmethyl]-5-fluorophenylamino}benzoate (223)

The further reaction of 223.2 with methyl 4-aminobenzoate was effected under conditions as described above for the preparation of Example 1, stage 3. 223 with the molecular weight of 562.20 ($C_{33}H_{27}FN_4O_4$) was obtained; retention time $R_t$=2.87 min. [C]; MS (ESI): 563.29 (MH$^+$).

The compound of Example 225 (tert-butyl 4-{2-[3-(6-cyanobiphenyl-3-yl)-5,5-dimethyl-2,4-dioxoimidazolidin-1-ylmethyl]-5-fluorophenylamino}benzoate, molecular weight 604.24 ($C_{36}H_{33}FN_4O_4$); retention time $R_t$=3.22 min. [C]; MS (ESI): 605.36 (MH$^+$)), was obtained in an analogous manner from 223.2 with tert-butyl 4-aminobenzoate.

The compound of Example 224 (methyl 4-{2-[3-(4'-chloro-6-cyanobiphenyl-3-yl)-5,5-dimethyl-2,4-dioxoimidazolidin-1-ylmethyl]-5-fluorophenylamino}benzoate, molecular weight 596.16 ($C_{33}H_{26}ClFN_4O_4$); retention time $R_t$=3.03 min. [C]; MS (ESI): 597.16 (MH$^+$)), was obtained in an analogous manner via the sequence of 5-amino-4'-chlorobiphenyl-2-carbonitrile (224.3, $^1$H NMR: 7.59-7.49, m, 5H, 6.63, m, 2H, 6.3, s (broad), 2H)→4'-chloro-5-(4,4-dimethyl-2,5-dioxoimidazolidin-1-yl)biphenyl-2-carbonitrile (224.1, $^1$HNMR: 8.75, s, 1H, 8.09, d, 1H, 7.76, s, 1H, 7.7, d, 1H, 7.62, m, 4H, 1.42, s, 6H)→5-[3-(2-bromo-4-fluorobenzyl)-4,4-dimethyl-2,5-dioxoimidazolidin-1-yl]-4'-chlorobiphenyl-2-carbonitrile (224.2, $^1$H NMR: 8.12, d, 1H, 7.82, s, 1H, 7.78, d, 1H, 7.69-7.6, m, 6H, 7.28, t, 1H, 4.61, s, 2H, 1.4, s, 6H)→224.

The compound of Example 226 (tert-butyl 4-{2-[3-(4'-chloro-6-cyanobiphenyl-3-yl)-5,5-dimethyl-2,4-dioxoimidazolidin-1-ylmethyl]-5-fluorophenylamino}benzoate, $^1$H NMR: 8.39, s, 1H, 8.1, d, 1H, 7.8-7.52, m, 9H, 7.1, d, 1H, 6.94, m, 3H, 4.55, s, 2H, 1.51, s, 9H, 1.35, s, 6H) was obtained in an analogous manner from 224.2 with tert-butyl 4-aminobenzoate.

Example 229

Dimethyl 2-(4-{2-[3-(4-cyano-3-trifluoromethylphenyl)-5,5-dimethyl-2,4-dioxoimidazolidin-1-ylmethyl]phenylamino}phenyl)malonate

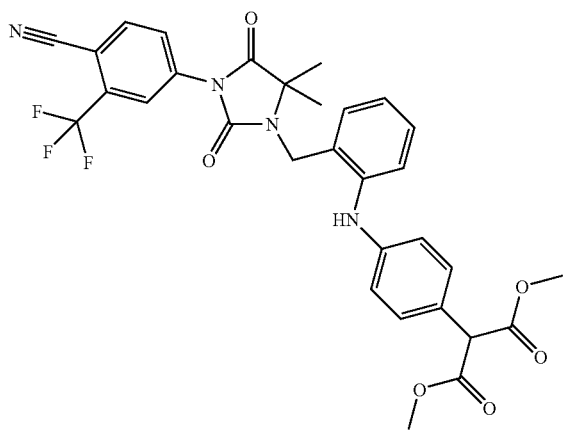

1) Preparation of dimethyl 2-(4-nitrophenyl)malonate (229.1)

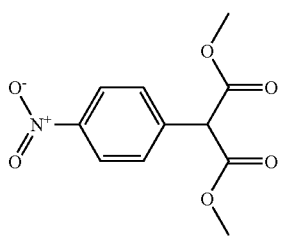

2.0 g of dimethyl malonate, 3.36 g of 1-bromo-4-nitrobenzene, 9.64 g of potassium phosphate, 85 mg of palladium(II) acetate and 394 mg of 9,9-dimethyl-4,5-bis(diphenylphosphino)xanthene were dissolved under an argon atmosphere in 25 ml of dry dioxane and stirred at 90° C. for 8 h. For workup, the reaction mixture was filtered through a cartridge and the filtrate was concentrated under reduced pressure. The residue was purified by chromatography (silica gel; n-heptane/15-35% ethyl acetate). Dimethyl 2-(4-nitrophenyl)malonate (229.1) was obtained. Molecular weight 253.05 ($C_{11}H_{11}NO_6$); retention time $R_t$=1.88 min. [B]; MS (ESI): 254.03 (MH$^+$).

2) Preparation of dimethyl 2-(4-aminophenyl)malonate hydrochloride (229.2)

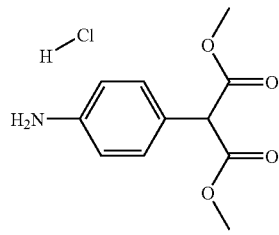

349 mg of compound 229.1 were hydrogenated in methanol with addition of palladium on carbon (10%) until the hydrogen uptake had ended. The filtered crude product was purified by chromatography (method [RP1]). The product-containing fractions were concentrated under reduced pressure, and the residue was dissolved in ethyl acetate, admixed with hydrochloric acid and concentrated under reduced pressure. The residue thus obtained was dissolved in a mixture of acetonitrile and water and the solution was freeze-dried. The hydrochloride of dimethyl 2-(4-aminophenyl)malonate 229.2 was obtained. Molecular weight 223.08 ($C_{11}H_{13}NO_4$); retention time $R_t$=0.52 min. [B]; MS (ESI): 224.17 (MH$^+$).

3) Preparation of dimethyl 2-(4-{2-[3-(4-cyano-3-trifluoromethylphenyl)-5,5-dimethyl-2,4-dioxoimidazolidin-1-ylmethyl]phenylamino}phenyl)malonate (229)

229 was obtained by reacting compound 229.2 with compound 1.2 under conditions as described for the preparation of compound 1. Molecular weight 608.18 ($C_{31}H_{27}F_3N_4O_6$); retention time $R_t$=2.14 min. [B]; MS (ESI): 609.13 (MH$^+$).

The corresponding di-tert-butyl ester 235 was obtained via the analogous sequence of 235.1 (di-tert-butyl 2-(4-nitrophenyl)malonate; $^1$H NMR: 8.24, d, 2H, 7.68, d, 2H, 4.97, s, 1H, 1.41, s, 18H)→235.2 (di-tert-butyl 2-(4-aminophenyl)malonate hydrochloride; molecular weight (free base) 307.17 ($C_{17}H_{25}NO_4$); retention time $R_t$=1.53 min. [C]; MS (ESI): 252.24 (MH$^+$–$C_4H_8$))→235 (di-tert-butyl 2-(4-{2-[3-(4-cyano-3-trifluoromethylphenyl)-5,5-dimethyl-2,4-dioxoimidazolidin-1-ylmethyl]phenylamino}phenyl)malonate; molecular weight 692.28 ($C_{37}H_{39}F_3N_4O_6$); retention time $R_t$=2.59 min. [B]; MS (ESI): 637.22 (MH$^+$–$C_4H_8$)).

Example 231

Dimethyl 2-(4-{2-[3-(4-cyano-3-trifluoromethylphenyl)-5,5-dimethyl-2,4-dioxoimidazolidin-1-ylmethyl]phenylamino}phenyl)-2-methylmalonate

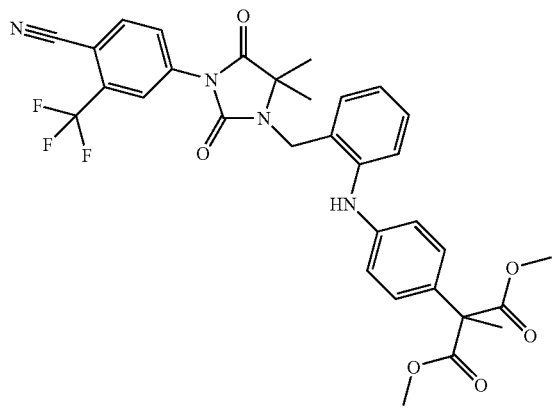

1) Preparation of dimethyl 2-methyl-2-(4-nitrophenyl)malonate (231.1)

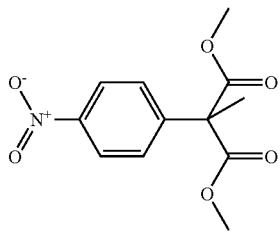

640 mg of compound 229.1 were dissolved in 12 ml of dry tetrahydrofuran and admixed with 138 mg of sodium hydride (60% in mineral oil). The mixture was stirred at room temperature for one hour, then a solution of 393 µl of methyl iodide in 5 ml of dry tetrahydrofuran was added dropwise and the resulting mixture was stirred at room temperature overnight. For workup, the reaction mixture was admixed cautiously with water and ethyl acetate. The organic phase was removed, dried over magnesium sulfate, filtered and concentrated under reduced pressure. The residue was purified by chromatography (silica gel; n-heptane/0-10% ethyl acetate). Dimethyl 2-methyl-2-(4-nitrophenyl)malonate (231.1) was obtained; $^1$H NMR: 8.22, d, 2H, 7.61, d, 2H, 3.71, s, 6H, 1.82, s, 3H.

2) Preparation of dimethyl 2-(4-aminophenyl)-2-methylmalonate hydrochloride (231.2)

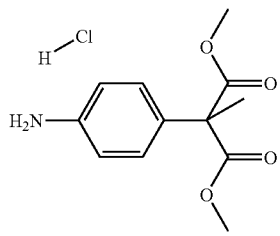

231.2 was obtained as described above for the preparation of 229.1. Molecular weight 237.10 ($C_{12}H_{15}NO_4$); retention time $R_t$=0.80 min. [C]; MS (ESI): 238.21 (MH$^+$).

3) Preparation of dimethyl 2-(4-{2-[3-(4-cyano-3-trifluoromethylphenyl)-5,5-dimethyl-2,4-dioxoimidazolidin-1-ylmethyl]phenylamino}phenyl)-2-methylmalonate (231)

231 was obtained by reacting compound 231.2 with compound 1.2 under conditions as described for the preparation of compound 1. Molecular weight 622.20 ($C_{32}H_{29}F_3N_4O_6$); retention time $R_t$=2.20 min. [B]; MS (ESI): 623.29 (MH$^+$).

The corresponding di-tert-butyl ester 236 was obtained via the analogous sequence of 236.1 (di-tert-butyl 2-methyl-2-(4-nitrophenyl)malonate; $^1$H NMR: 8.22, d, 2H, 7.64, d, 2H, 1.71, s, 3H, 1.41, s, 18H)→236.2 (di-tert-butyl 2-(4-aminophenyl)-2-methylmalonate hydrochloride; molecular weight (free base) 321.19 ($C_{18}H_{27}NO_4$); retention time $R_t$=1.61 min. [C]; MS (ESI): 322.21 (MH$^+$))→236 (di-tert-butyl 2-(4-{2-[3-(4-cyano-3-trifluoromethylphenyl)-5,5-dimethyl-2,4-dioxoimidazolidin-1-ylmethyl]phenylamino}phenyl)-2-methylmalonate; molecular weight 706.29 ($C_{38}H_{41}F_3N_4O_6$); retention time $R_t$=2.66 min. [B]; MS (ESI): 707.38 (MH$^+$)).

Example 232

Dimethyl 2-(4-{2-[3-(4-cyano-3-trifluoromethylphenyl)-5,5-dimethyl-2,4-dioxoimidazolidin-1-ylmethyl]phenylamino}benzyl)malonate

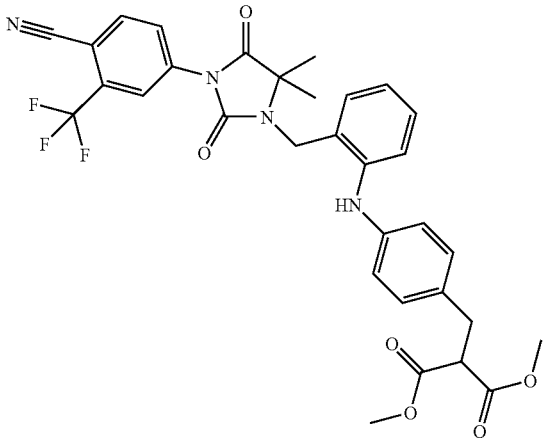

1) Preparation of dimethyl 2-methyl-2-(4-nitrophenyl)malonate (232.1)

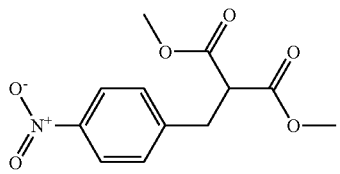

The alkylation of dimethyl malonate with 4-nitrobenzyl bromide under conditions as described for the preparation of compound 231.1 afforded dimethyl 2-methyl-2-(4-nitrophenyl)malonate. Molecular weight 267.07 ($C_{12}H_{13}NO_6$); retention time $R_t$=1.97 min. [B]; MS (ESI): 268.05 (MH$^+$).

2) Preparation of dimethyl 2-(4-aminobenzyl)malonate hydrochloride (232.2)

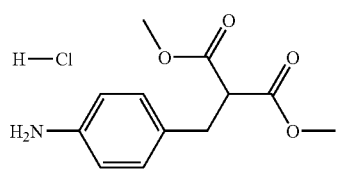

232.2 was obtained as described above for the preparation of 229.1. Molecular weight 237.10 ($C_{12}H_{15}NO_4$); retention time $R_t$=0.70 min. [C]; MS (ESI): 238.22 (MH$^+$).

3) Preparation of dimethyl 2-(4-{2-[3-(4-cyano-3-trifluoromethylphenyl)-5,5-dimethyl-2,4-dioxoimidazolidin-1-ylmethyl]phenylamino}benzyl)malonate (232)

232 was obtained by reacting compound 232.2 with compound 1.2 under conditions as described for the preparation of compound I. Molecular weight 622.20 ($C_{32}H_{29}F_3N_4O_6$); retention time $R_t$=2.21 min. [B]; MS (ESI): 623.21 (MH$^+$).

Example 233

2-(4-{2-[3-(4-Cyano-3-trifluoromethylphenyl)-5,5-dimethyl-2,4-dioxoimidazolidin-1-ylmethyl]phenylamino}phenyl)-2-methylmalonic acid

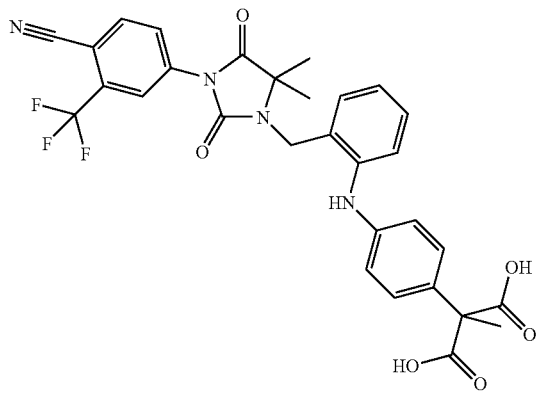

The ester 236 was, as described for the preparation of the compound of Example 62, admixed with hydrochloric acid in dioxane and afforded the acid 233. Molecular weight 594.17 ($C_{30}H_{25}F_3N_4O_6$); retention time $R_t$=1.83 min. [B]; MS (ESI): 595.33 (MH$^+$).

The compound of Example 234 (2-(4-{2-[3-(4-cyano-3-trifluoromethylphenyl)-5,5-dimethyl-2,4-dioxoimidazolidin-1-ylmethyl]phenylamino}benzyl)malonic acid) was obtained in an analogous manner from compound 232. $^1$H NMR: ~12.85, s (very broad), 2H, 8.32, d, 1H, 8.22, s, 1H, 8.06, d, 1H, 7.55, s, 1H, 7.45, d, 1H, 7.21, m, 2H, 7.08, d, 2H, 6.98, m, 1H, 6.81, d, 2H, 4.59, s, 2H, 3.55-3.3, broad water signal, 2.92, s (broad), 2H, 1.38, s, 6H.

The compound of Example 238 (2-(4-{2-[3-(4-cyano-3-trifluoromethylphenyl)-5,5-dimethyl-2,4-dioxoimidazolidin-1-ylmethyl]phenylamino}phenyl)malonic acid) was obtained in an analogous manner from compound 235. Molecular weight 580.15 ($C_{29}H_{23}F_3N_4O_6$); retention time $R_t$=1.78 min. [B]; MS (ESI): 581.17 (MH$^+$). As a further product, the phenylacetic acid derivative 92 ((4-{2-[3-(4-cyano-3-trifluoromethylphenyl)-5,5-dimethyl-2,4-dioxoimidazolidin-1-ylmethyl]phenylamino}phenyl)acetic acid) was obtained.

Example 240

N-(4-{5-Fluoro-2-[3-(4-fluoro-3-trifluoromethylphenyl)-5,5-dimethyl-2,4-dioxoimidazolidin-1-ylmethyl]phenylamino}phenyl)methanesulfonamide

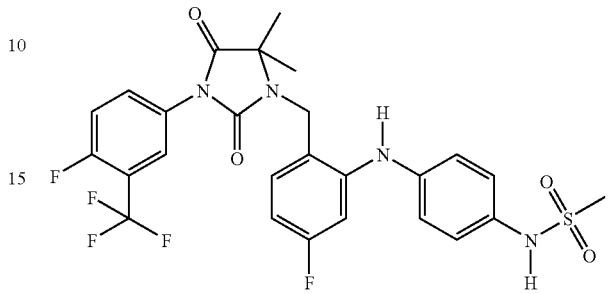

1) Preparation of 1-[2-(4-aminophenylamino)-4-fluorobenzyl]-3-(4-fluoro-3-trifluoromethylphenyl)-5,5-dimethylimidazolidine-2,4-dione (240.1)

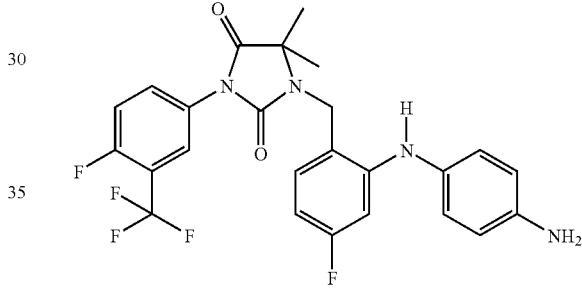

Compound 240.1 was prepared like compound 113, but with the difference that, instead of the aniline 61.2, the aniline 204.2 was reacted with the Schiff base (4-bromophenyl)[1-phenylmethylidene]amine. The subsequent hydrogenolysis afforded 1-[2-(4-aminophenylamino)-4-fluorobenzyl]-3-(4-fluoro-3-trifluoromethylphenyl)-5,5-dimethylimidazolidine-2,4-dione. Molecular weight 504.15 ($C_{25}H_{21}F_5N_4O_2$); retention time $R_t$=1.81 min. [C]; MS (ESI): 505.15 (MH$^+$).

2) Preparation of N-(4-{5-fluoro-2-[3-(4-fluoro-3-trifluoromethylphenyl)-5,5-dimethyl-2,4-dioxoimidazolidin-1-ylmethyl]phenylamino}phenyl)methanesulfonamide (240)

150 mg of compound 240.1 were dissolved in 5 ml of acetonitrile and admixed with 145 mg of cesium carbonate and 41 mg of methanesulfonyl chloride. Subsequently, the mixture was stirred at 60° C. for 6 h; the next day, a further 1.2 equivalents of methanesulfonyl chloride were added and the mixture was stirred at 60° C. for a further 8 h. For workup, the reaction mixture was filtered, the filtrate was concentrated under reduced pressure and the residue was purified by chromatography (method [RP1]). N-(4-{5-Fluoro-2-[3-(4-fluoro-3-trifluoromethylphenyl)-5,5-dimethyl-2,4-dioxoimidazolidin-1-ylmethyl]phenylamino}phenyl)methanesulfonamide was obtained. Molecular weight 582.13 ($C_{26}H_{23}F_5N_4O_4S$); retention time $R_t$=3.88 min. [C]; MS (ESI): 583.14 (MH$^+$).

As a further product,

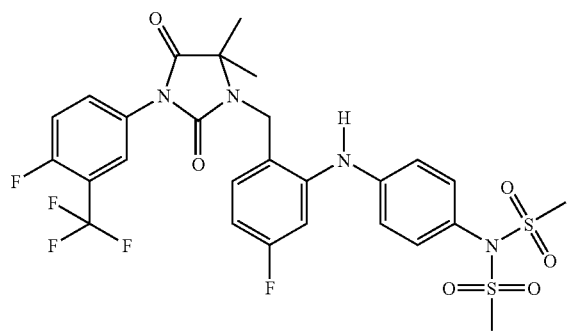

(241) was obtained. Molecular weight 660.11 ($C_{27}H_{25}F_5N_4O_6S_2$); retention time $R_t$=2.49 min. [B]; MS (ES−): 659.03 (M−H+).

Example 243

4-2-[3-(4-Cyano-3-trifluoromethylphenyl)-5,5-dimethyl-2,4-dioxoimidazolidin-1-ylmethyl]phenylamino}-2-hydroxybenzoic acid

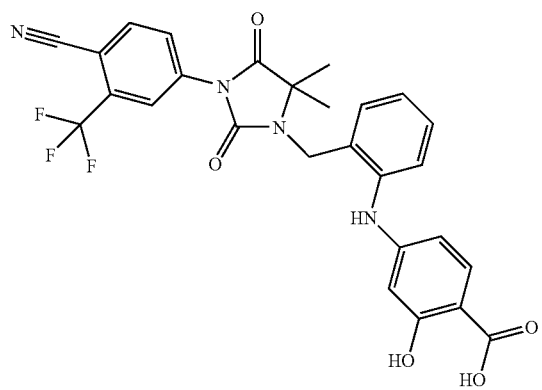

115 mg of the compound of Example 199 were dissolved in 1.5 ml of dioxane, admixed with 0.5 ml of 4N hydrochloric acid in dioxane and left to stand at room temperature for four days. For workup, the reaction mixture was concentrated under reduced pressure, and the residue was taken up with acetonitrile and water and then freeze-dried. 243 with the molecular weight of 538.14 ($C_{27}H_{21}F_3N_4O_5$) was obtained; retention time $R_t$=1.96 min. [B]; MS (ESI): 539.12 (MH+).

Example 244

1-[2-(2,2-Dimethyl-4-oxo-4H-benzo[1,3]dioxin-6-ylamino)-4-fluorobenzyl]-3-(4-fluoro-3-trifluoromethylphenyl)-5,5-dimethylimidazolidine-2,4-dione

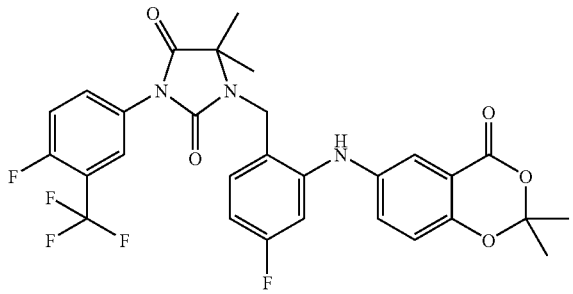

1) Preparation of 6-bromo-2,2-dimethylbenzo[1,3]dioxin-4-one (244.1)

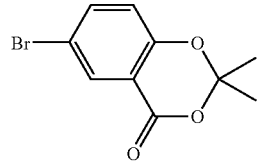

5 g of 5-bromosalicylic acid were heated under reflux with 6.7 g of acetone in a mixture of 25 ml of trifluoroacetic acid with 5 ml of trifluoroacetic anhydride for 5 h. For workup, the reaction mixture was concentrated under reduced pressure. The residue was neutralized with sodium hydrogencarbonate solution and extracted repeatedly with diethyl ether. The organic phase was dried over magnesium sulfate, filtered and concentrated under reduced pressure. The residue was purified by chromatography (silica gel; 9/1 n-heptane/ethyl acetate). 244.1 was obtained.

$^1$H NMR: 7.98, s, 1H, 7.88, d, 1H, 7.13, d, 1H, 1.7, s, 6H.

2) Preparation of 1-[2-(2,2-dimethyl-4-oxo-4H-benzo[1,3]dioxin-6-ylamino)-4-fluorobenzyl]-3-(4-fluoro-3-trifluoromethylphenyl)-5,5-dimethylimidazolidine-2,4-dione (244)

The reaction of 204.2 with 6-bromo-2,2-dimethylbenzo[1,3]dioxin-4-one (244.1) under conditions as described for the preparation of the compound of Example 61 afforded 1-[2-(2,2-dimethyl-4-oxo-4H-benzo[1,3]dioxin-6-ylamino)-4-fluorobenzyl]-3-(4-fluoro-3-trifluoromethylphenyl)-5,5-dimethylimidazolidine-2,4-dione (244). Molecular weight 589.16 ($C_{29}H_{24}F_5N_3O_5$); retention time $R_t$=2.32 min. [B]; MS (ESI): 590.17 (MH+).

Example 245

5-{5-Fluoro-2-[3-(4-fluoro-3-trifluoromethylphenyl)-5,5-dimethyl-2,4-dioxoimidazolidin-1-ylmethyl]phenylamino}-2-hydroxybenzoic acid

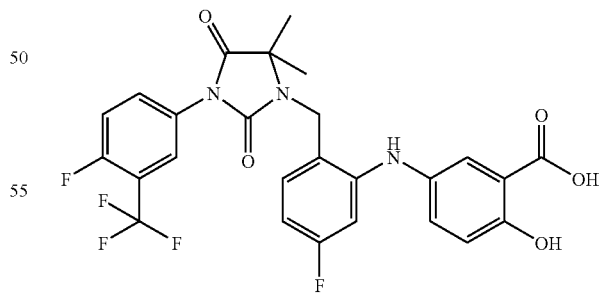

The hydrolysis of compound 244 to compound 245 was effected under conditions as described above for the preparation of 243 from 199. 5-{5-Fluoro-2-[3-(4-fluoro-3-trifluoromethylphenyl)-5,5-dimethyl-2,4-dioxoimidazolidin-1-ylmethyl]phenylamino}-2-hydroxybenzoic acid (245) was obtained. Molecular weight 549.13 ($C_{26}H_{20}F_5N_3O_5$); retention time $R_t$=2.06 min. [B]; MS (ESI): 550.13 (MH+).

Example 246

4-{3-[2-(2,4-Dihydroxypyrimidin-5-ylamino)benzyl]-4,4-dimethyl-2,5-dioxoimidazolidin-1-yl}-2-trifluoromethylbenzonitrile

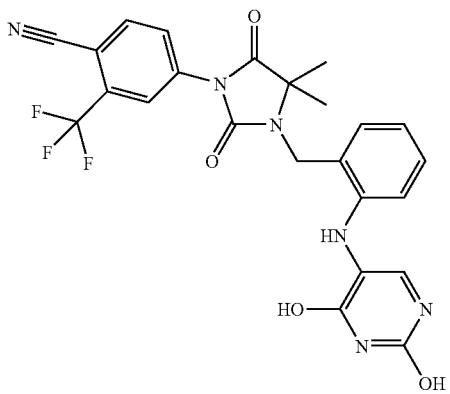

The acidic hydrolysis (4N hydrochloric acid in dioxane) of compound 208 afforded compound 246. Molecular weight 512.14 ($C_{24}H_{19}F_3N_6O_4$); retention time $R_t$=1.62 min. [B]; MS (ESI): 513.11 (MH$^+$).

Example 248

5-{5-Fluoro-2-[3-(4-fluoro-3-trifluoromethylphenyl)-5,5-dimethyl-2,4-dioxoimidazolidin-1-ylmethyl]phenylamino}-2-methoxybenzoic acid

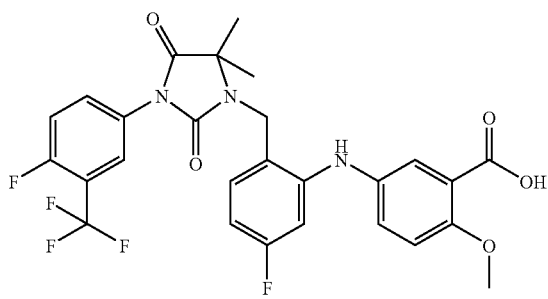

140 mg of the ester 247 were dissolved in 4 ml of dry tetrahydrofuran, admixed with 311 mg of potassium silanolate and then stirred at room temperature for 22 h. For workup, the reaction mixture was concentrated under reduced pressure; the residue was taken up with 10 ml of water and acidified with 1N hydrochloric acid, and the aqueous phase was extracted by shaking twice with 3/1 dichloromethane/isopropanol. The organic phase was dried over magnesium sulfate, filtered and concentrated under reduced pressure. The residue was admixed with acetonitrile and water and then freeze-dried. 5-{5-Fluoro-2-[3-(4-fluoro-3-trifluoromethylphenyl)-5,5-dimethyl-2,4-dioxoimidazolidin-1-ylmethyl]phenylamino}-2-methoxybenzoic acid (248) was obtained. Molecular weight 563.14 ($C_{27}H_{22}F_5N_3O_5$); retention time $R_t$=2.01 min. [B];

MS (ESI): 564.15 (MH$^+$).

Example 249

Methyl 4-{5-fluoro-2-[3-(4-fluoro-3-trifluoromethylphenyl)-5,5-dimethyl-2,4-dioxoimidazolidin-1-ylmethyl]phenylamino}-2-methoxybenzoate

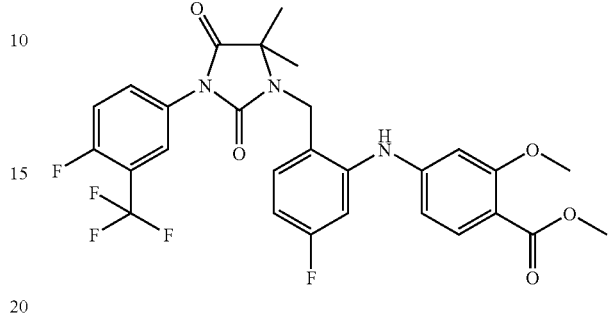

The reaction of 204.2 with methyl 4-bromo-2-methoxybenzoate under conditions as described for the preparation of the compound of Example 61 afforded methyl 4-{5-fluoro-2-[3-(4-fluoro-3-trifluoromethylphenyl)-5,5-dimethyl-2,4-dioxoimidazolidin-1-ylmethyl]phenylamino}-2-methoxybenzoate (249). Molecular weight 577.16 ($C_{28}H_{24}F_5N_3O_5$); retention time $R_t$=4.06 min. [D]; MS (ESI): 578.25 (MH$^+$).

As a further reaction product, the compound

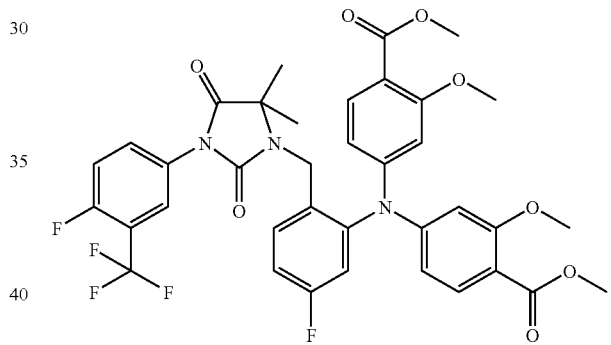

(250) was obtained. Molecular weight 741.21 ($C_{37}H_{32}F_5N_3O_8$); retention time $R_t$=4.25 min. [D]; MS (ESI): 578.25 (MH$^+$).

Example 252

4-{5-Fluoro-2-[3-(4-fluoro-3-trifluoromethylphenyl)-5,5-dimethyl-2,4-dioxoimidazolidin-1-ylmethyl]phenylamino}-2-methoxybenzoic acid

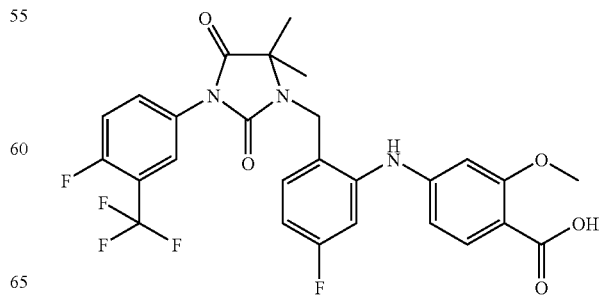

The reaction of the ester 249 with potassium silanolate in tetrahydrofuran, as described for the preparation of 248, afforded the carboxylic acid 252. Molecular weight 563.14 ($C_{27}H_{22}F_5N_3O_5$); retention time $R_t$=1.95 min. [B]; MS (ESI): 564.15 (MH+).

In an analogous manner, 251

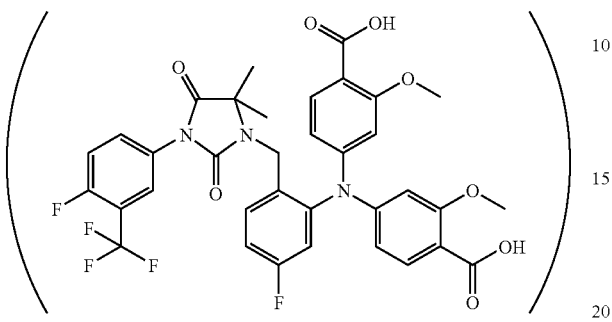

was obtained from 250. Molecular weight 714.19 ($C_{35}H_{28}F_5N_3O_8$); retention time $R_t$=1.88 min. [B]; MS (ESI): 714.19 (MH+).

Example 253

5-{3-[2-(2,4-Difluorophenylamino)-4-fluorobenzyl]-4,4-dimethyl-2,5-dioxoimidazolidin-1-yl}-4'-fluorobiphenyl-2-carbonitrile

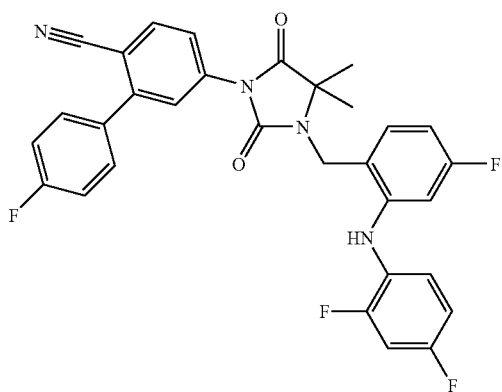

The compound of Example 253 (5-{3-[2-(2,4-difluorophenylamino)-4-fluorobenzyl]-4,4-dimethyl-2,5-dioxoimidazolidin-1-yl}-4'-fluorobiphenyl-2-carbonitrile, molecular weight 558.16 ($C_{31}H_{22}F_4N_4O_2$); retention time $R_t$=2.38 min. [B]; MS (ESI): 559.15 (MH+)) was obtained similarly to the manner described for the preparation of the compound of Example 223 via the sequence of 4-amino-2-chlorobenzonitrile→5-amino-4'-fluorobiphenyl-2-carbonitrile (253.3, ¹H NMR: 7.54-7.49, m, 3H, 7.31, t, 2H, 6.61, m, 2H, 6.25, s, 2H)→5-(4,4-dimethyl-2,5-dioxoimidazolidin-1-yl)-4'-fluorobiphenyl-2-carbonitrile (253.1, ¹H NMR: 8.73, s, 1H; 8.09, d, 1H, 7.74, s, 1H, 7.65, m, 3H, 7.41, m, 2H, 1.42, s, 6H)→5-[3-(2-bromo-4-fluorobenzyl)-4,4-dimethyl-2,5-dioxoimidazolidin-1-yl]-4'-fluorobiphenyl-2-carbonitrile (253.2, ¹H NMR: 8.1, d, 1H, 7.8, s, 1H, 7.75, d, 1H, 7.69-7.59, m, 4H; 7.41, t, 1H, 4.61, s, 2H, 1.4, s, 6H) δ 253 (from 253.2 by reaction with 2,4-difluorophenylamine).

The compound of Example 256 (tert-butyl 4-{2-[3-(6-cyano-4'-fluorobiphenyl-3-yl)-5,5-dimethyl-2,4-dioxoimidazolidin-1-ylmethyl]-5-fluorophenylamino}benzoate, molecular weight 622.23 ($C_{36}H_{32}F_2N_4O_4$); retention time $R_t$=2.56 min. [B]; MS (ESI): 623.23 (MH+)) was obtained in an analogous manner from 253.2 with tert-butyl 4-aminobenzoate.

Example 254

1-[4-Fluoro-2-(6-fluoropyridin-3-ylamino)benzyl]-3-(4-fluoro-3-trifluoromethylphenyl)-5,5-dimethylimidazolidine-2,4-dione

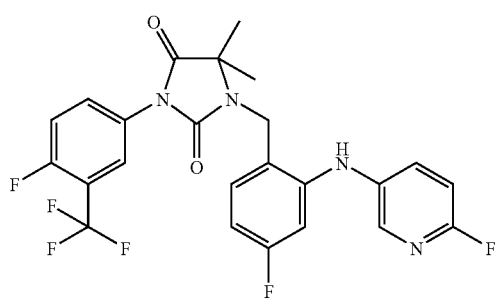

The reaction of 204.2 with 5-bromo-2-fluoropyridine under conditions as described for the preparation of the compound of Example 61 afforded 1-[4-fluoro-2-(6-fluoropyridin-3-ylamino)benzyl]-3-(4-fluoro-3-trifluoromethylphenyl)-5,5-dimethylimidazolidine-2,4-dione (254). Molecular weight 508.13 ($C_{24}H_{18}F_6N_4O_2$); retention time $R_t$=2.95 min. [E]; MS (ESI): 509.12 (MH+).

Example 255

Methyl 5-{5-fluoro-2-[3-(4-fluoro-3-trifluoromethylphenyl)-5,5-dimethyl-2,4-dioxoimidazolidin-1-ylmethyl]phenylamino}pyridine-2-carboxylate

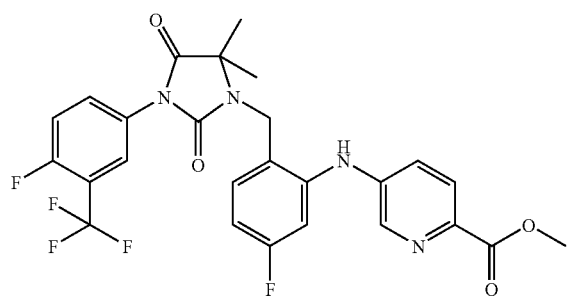

The reaction of 204.2 with methyl 5-bromopyridine-2-carboxylate under conditions as described for the preparation of the compound of Example 61 afforded methyl 5-{5-fluoro-2-[3-(4-fluoro-3-trifluoromethylphenyl)-5,5-dimethyl-2,4-dioxoimidazolidin-1-ylmethyl]phenylamino}pyridine-2-carboxylate (255). Molecular weight 548.14 ($C_{26}H_{21}F_5N_4O_4$); retention time $R_t$=2.64 min. [C]; MS (ESI): 549.11 (MH+).

Example 257

5-{5-Fluoro-2-[3-(4-fluoro-3-trifluoromethylphenyl)-5,5-dimethyl-2,4-dioxoimidazolidin-1-ylmethyl]phenylamino}pyridine-2-carboxylic acid

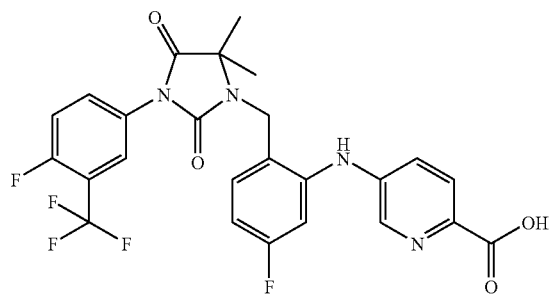

The reaction of the ester 255 with potassium silanolate in tetrahydrofuran, as described for the preparation of 248, afforded the carboxylic acid 257. Molecular weight 534.13 ($C_{25}H_{19}F_5N_4O_4$); retention time $R_t$=2.32 min. [D]; MS (ESI): 535.16 (MH$^+$).

Example 258

4-{2-[3-(6-Cyano-4'-fluorobiphenyl-3-yl)-5,5-dimethyl-2,4-dioxoimidazolidin-1-ylmethyl]-5-fluorophenylamino}benzoic acid

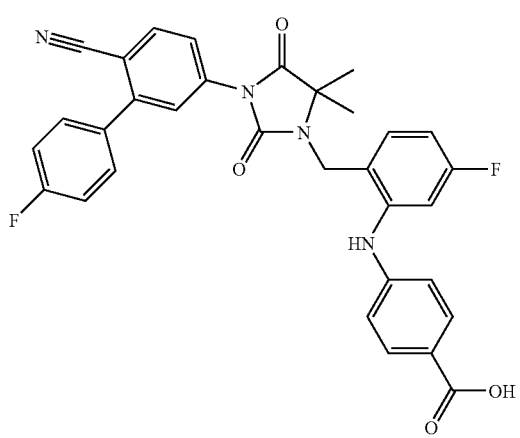

160 mg of the compound of Example 256 were dissolved in 3.2 ml of dioxane, admixed with 1.6 ml of 4N hydrochloric acid in dioxane and stirred at room temperature for 8 hours. For workup, the reaction mixture was concentrated under reduced pressure, and the residue was taken up with acetonitrile and water and then freeze-dried. 258 with the molecular weight of 566.17 ($C_{32}H_{24}F_2N_4O_4$) was obtained; retention time $R_t$=2.77 min. [C]; MS (ESI): 567.13 (MH$^+$).

Example 259

2-(4-{2-[3-(6-Cyano-4'-fluorobiphenyl-3-yl)-5,5-dimethyl-2,4-dioxoimidazolidin-1-ylmethyl]-5-fluorophenylamino}phenyl)-2-methylmalonic acid

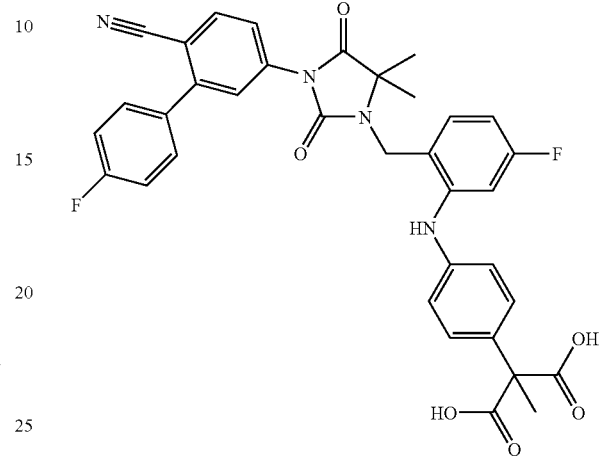

The compound of Example 259 was, as described for the preparation of Example 233, obtained via the corresponding tert-butyl ester. The di-tert-butyl ester 259.3 was obtained via the sequence of 236.1 (di-tert-butyl 2-methyl-2-(4-nitrophenyl)-malonate; $^1$H NMR: 8.22, d, 2H, 7.64, d, 2H, 1.71, s, 3H, 1.41, s, 18H)→236.2 (di-tert-butyl 2-(4-aminophenyl)-2-methylmalonate hydrochloride; molecular weight (free base) 321.19 ($C_{18}H_{27}NO_4$); retention time $R_t$=1.61 min. [C]; MS (ESI): 322.21 (MH$^+$))→259.3 (di-tert-butyl 2-(4-{2-[3-(6-cyano-4'-fluorobiphenyl-3-yl)-5,5-dimethyl-2,4-dioxoimidazolidin-1-ylmethyl]-5-fluorophenylamino}phenyl)-2-methylmalonate (by reaction with 253.3)). The reaction of the crude product with 4N hydrochloric acid in dioxane afforded compound 259; molecular weight 638.19 ($C_{35}H_{28}F_2N_4O_6$); retention time $R_t$=2.59 min. [D]; MS (ESI): 639.30 (MH$^+$).

Preparation of 260.1

4-[3-(2-Amino-4-fluorobenzyl)-4,4-dimethyl-2,5-dioxoimidazolidin-1-yl]-2-trifluoromethylbenzonitrile

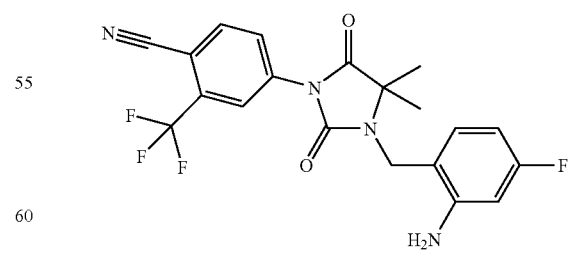

Analogously to the method as described for the preparation of 61.2, 111.2 was reacted with benzophenone imine to give 260.1. Molecular weight 420.12 ($C_{20}H_{16}F_4N_4O_2$); retention time $R_t$=2.71 min. [E]; MS (ESI): 421.08 (MH$^+$).

Example 264

4-{2-[3-(6-Cyano-4'-fluorobiphenyl-3-yl)-5,5-dimethyl-2,4-dioxoimidazolidin-1-ylmethyl]-5-fluorophenylamino}benzenesulfonamide

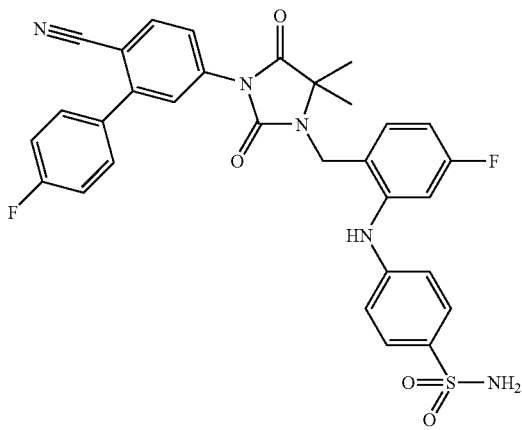

1) Preparation of 5-[3-(2-amino-4-fluorobenzyl)-4,4-dimethyl-2,5-dioxoimidazolidin-1-yl]-4'-fluorobiphenyl-2-carbonitrile (264.1)

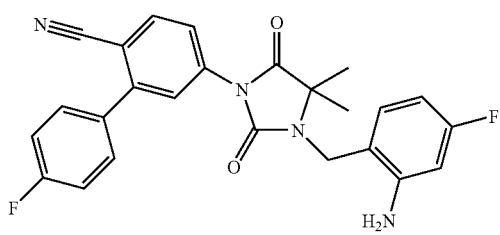

Compound 253.2 (5-[3-(2-bromo-4-fluorobenzyl)-4,4-dimethyl-2,5-dioxoimidazolidin-1-yl]-4'-fluorobiphenyl-2-carbonitrile) was, as described for the preparation of 61.2, reacted with benzophenone imine to obtain 264.1. Molecular weight 446.15 ($C_{25}H_{20}F_2N_4O_2$); retention time $R_t$=2.78 min. [E]; MS (ESI): 447.12 (MH$^+$).

2) Preparation of 4-{2-[3-(6-cyano-4'-fluorobiphenyl-3-yl)-5,5-dimethyl-2,4-dioxoimidazolidin-1-ylmethyl]-5-fluorophenylamino}-N-[1-dimethylaminomethylidene]benzenesulfonamide (264.2)

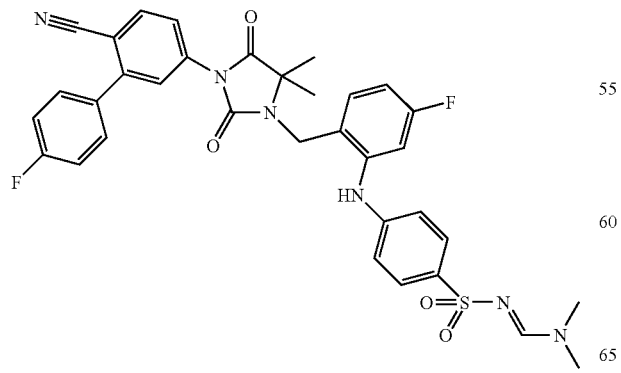

Compound 264.2 was obtained by the process as described for the preparation of 68.4, by reaction of 264.1 with 68.3. Molecular weight 656.20 ($C_{34}H_{30}F_2N_6O_4S$); retention time $R_t$=1.73 min. [F]; MS (ESI): 657.15 (MH$^+$).

3) Preparation of 4-{2-[3-(6-cyano-4'-fluorobiphenyl-3-yl)-5,5-dimethyl-2,4-dioxoimidazolidin-1-ylmethyl]-5-fluorophenylamino}benzenesulfonamide (264)

Compound 264 was obtained from 264.2 by treatment (80° C.) with concentrated hydrochloric acid in dioxane. Molecular weight 601.15 ($C_{31}H_{25}F_2N_5O_4S$); retention time $R_t$=2.60 min. [E]; MS (ESI): 602.24 (MH$^+$).

Example 266

6-{2-[3-(4-Cyano-3-trifluoromethylphenyl)-5,5-dimethyl-2,4-dioxoimidazolidin-1-ylmethyl]-5-fluorophenylamino}nicotinic acid

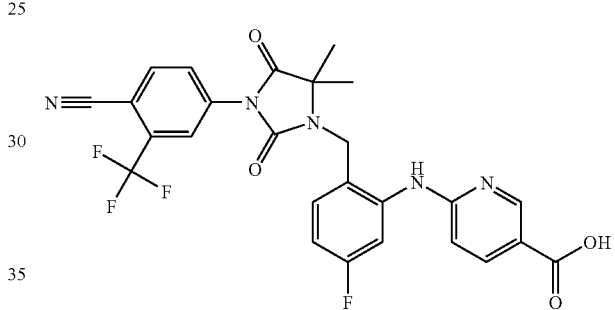

The reaction of the ester 256 with potassium silanolate in tetrahydrofuran, as described for the preparation of 248, afforded the carboxylic acid 266. Molecular weight 541.13 ($C_{26}H_{19}F_4N_5O_4$); retention time $R_t$=2.42 min. [E]; MS (ESI): 542.13 (MH$^+$).

Example 267

Methyl 4-{5-fluoro-2-[3-(4-fluoro-3-thiophen-2-ylphenyl)-5,5-dimethyl-2,4-dioxoimidazolidin-1-ylmethyl]phenylamino}benzoate, salt with trifluoroacetic acid

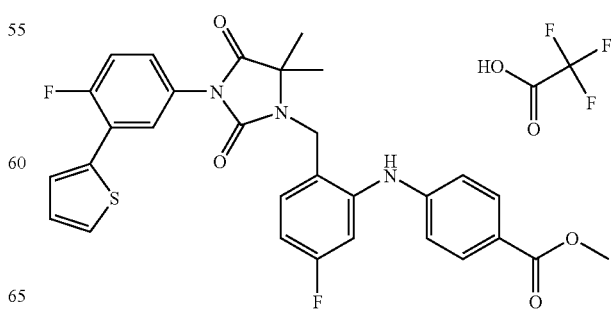

1) Preparation of 4-fluoro-3-thiophen-2-ylphenylamine (267.4)

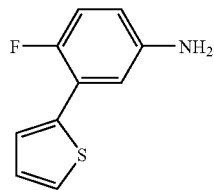

768 mg of thiophene-2-boronic acid, 90 mg of palladium (II) acetate, 328 mg of 2-dicyclohexylphosphino-2',6'-dimethoxy-1,1'-biphenyl, 1.7 g of potassium phosphate and 562 mg of 3-chloro-4-fluoroaniline were added to 8 ml of dry toluene. The mixture was stirred at 80° C. overnight under an argon atmosphere. The cooled reaction mixture was admixed with water and ethyl acetate, and filtered, and the filtrate was extracted by shaking three times with a mixture of ethyl acetate and toluene. The combined organic phases were dried over magnesium sulfate and filtered, and the filtrate was concentrated under reduced pressure. The chromatographic purification of the residue was effected by method [RP1]. 4-Fluoro-3-thiophen-2-yl-phenylamine (267.4) was obtained. Molecular weight 193.03 ($C_{10}H_8FNS$); retention time $R_t$=1.18 min. [B]; MS (ESI): 235.08 (MH$^+$+CH$_3$CN).

2) Preparation of methyl 2-[3-(4-fluoro-3-thiophen-2-ylphenyl)ureido]-2-methylpropionate (267.3)

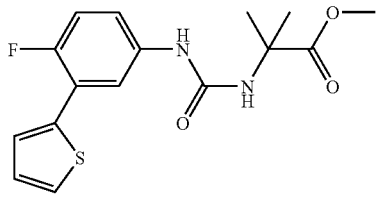

According to process "A'", 0.12 g of the trifluoroacetic acid salt of compound 267.4 was dissolved at room temperature in 5 ml of dry tetrahydrofuran, admixed with 0.17 ml of triethylamine and then admixed dropwise with a solution of 0.10 g of methyl isocyanatomethylpropionate in 2 ml of dry tetrahydrofuran. The mixture was stirred at room temperature for 2 hours. For workup, the mixture was concentrated under reduced pressure, and the residue was stirred with water, filtered, washed with water and dried. Methyl 2-[3-(4-fluoro-3-thiophen-2-ylphenyl)ureido]-2-methylpropionate (267.3) was obtained. Molecular weight 336.39 ($C_{16}H_{17}FN_2O_3S$); retention time $R_t$=1.46 min. [F]; MS (ESI): 337.05 (MH$^+$).

3) Preparation of 3-(4-fluoro-3-thiophen-2-ylphenyl)-5,5-dimethylimidazolidine-2,4-dione (267.2)

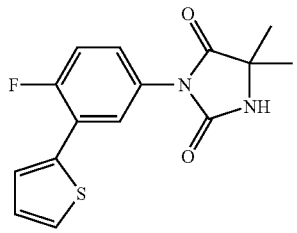

0.62 g of compound 267.3 was dissolved at room temperature in 5 ml of dry tetrahydrofuran, admixed with 0.62 ml of concentrated hydrochloric acid and stirred at 80° C. for 2 h. The cooled reaction mixture was taken up in ethyl acetate and washed with saturated sodium hydrogencarbonate solution, and the organic phase was dried over magnesium sulfate, filtered and concentrated under reduced pressure. The residue was stirred with diisopropyl ether, filtered and dried. 3-(4-Fluoro-3-thiophen-2-yl-phenyl)-5,5-dimethylimidazolidine-2,4-dione (267.2) was obtained. Molecular weight 304.06 ($C_{15}H_{13}FN_2O_2S$); retention time $R_t$=2.25 min. [E]; MS (ESI): 346.09 (MH$^+$+CH$_3$CN).

4) Preparation of 1-(2-bromo-4-fluorobenzyl)-3-(4-fluoro-3-thiophen-2-ylphenyl)-5,5-dimethylimidazolidine-2,4-dione (267.1)

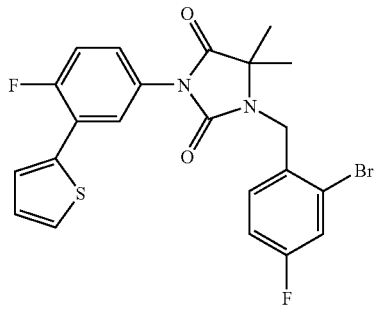

Under conditions as described for the preparation of 1.2, compound 267.2 was reacted with 2-bromo-1-bromomethyl-4-fluorobenzene and afforded 267.1. Molecular weight 490.01 ($C_{22}H_{17}BrF_2N_2O_2S$); retention time $R_t$=3.05 min. [E]; MS (ESI): 493.08 (MH$^+$)

5) Preparation of methyl 4-{5-fluoro-2-[3-(4-fluoro-3-thiophen-2-ylphenyl)-5,5-dimethyl-2,4-dioxoimidazolidin-1-ylmethyl]phenylamino}benzoate, salt with trifluoroacetic acid (267)

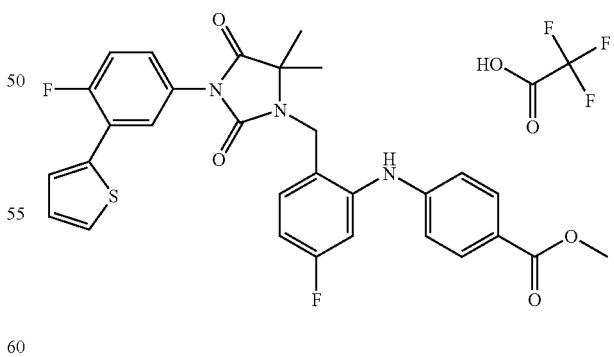

The further reaction of 267.1 with methyl 4-aminobenzoate was effected under conditions as described above for the preparation of Example 1, stage 3. 267 with the molecular weight of 561.15 ($C_{30}H_{25}F_2N_3O_4S$) was obtained; retention time $R_t$=3.08 min. [E]; MS (ESI): 562.28 (MH$^+$).

Example 268

Methyl 4-(2-{3-[3-(5-acetylthiophen-2-yl)-4-fluorophenyl]-5,5-dimethyl-2,4-dioxoimidazolidin-1-ylmethyl}-5-fluorophenylamino)benzoate

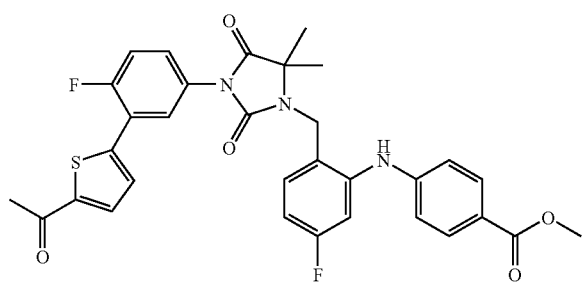

The compound of Example 268, ($^1$H NMR: 8.49, s, 1H, 8.01, d, 1H, 7.98, d, 1H, 7.82, d, 2H, 7.69, d, 1H, 7.6-7.47, m, 3H, 7.13, d, 1H, 6.98-6.2, m, 3H, 4.56, s, 2H, 3.8, s, 3H, 2.6, s, 3H, 1.38, s, 6H) was obtained in a similar manner to that described for the preparation of the compound of Example 267, via the sequence of 3-chloro-4-fluoroaniline→1-[5-(5-amino-2-fluorophenyl)thiophen-2-yl]ethanone (268.4, molecular weight 235.04 ($C_{12}H_{10}FNOS$); retention time $R_t$=1.54 min. [B]; MS (ESI): 236.17 (MH$^+$))→methyl 2-{3-[3-(5-acetylthiophen-2-yl)-4-fluorophenyl]ureido}-2-methylpropionate (268.3, molecular weight 378.43 ($C_{18}H_{19}FN_2O_4S$); retention time $R_t$=1.36 min. [F]; MS (ESI): 379.05 (MH$^+$))→3-[3-(5-acetylthiophen-2-yl)-4-fluorophenyl]-5,5-dimethylimidazolidine-2,4-dione (268.2, molecular weight 346.07 ($C_{17}H_{15}FN_2O_3S$); retention time $R_t$=2.08 min. [E]; MS (ESI): 347.18 (MH$^+$))→3-[3-(5-acetylthiophen-2-yl)-4-fluorophenyl]-1-(2-bromo-4-fluorobenzyl)-5,5-dimethylimidazolidine-2,4-dione (268.1, molecular weight 532.02 ($C_{24}H_{19}BrF_2N_2O_3S$); retention time $R_t$=2.87 min. [E]; MS (ESI): 533.05/535.03 (MH$^+$))→methyl-4-(2-{3-[3-(5-acetylthiophen-2-yl)-4-fluorophenyl]-5,5-dimethyl-2,4-dioxoimidazolidin-1-ylmethyl}-5-fluorophenylamino)benzoate (268).

Example 269

Methyl 4-(2-{3-[3-(5-cyanothiophen-2-yl)-4-fluorophenyl]-5,5-dimethyl-2,4-dioxoimidazolidin-1-ylmethyl}-5-fluorophenylamino)benzoate

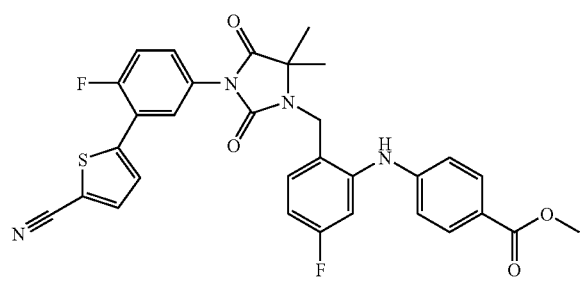

The compound of Example 269, (molecular weight 586.14 ($C_{31}H_{24}F_2N_4O_4S$); retention time $R_t$=3.02 min. [E]; MS (ESI): 587.17 (MH$^+$)) was obtained in a similar manner to that described for the preparation of the compound of Example 267, via the sequence of 3-chloro-4-fluoroaniline→5-(5-amino-2-fluorophenyl)thiophene-2-carbonitrile (269.4, molecular weight 218.03 ($C_{11}H_7FN_2S$); retention time $R_t$=1.74 min. [B]; MS (ESI): 260.19 (MH$^+$+CH$_3$CN))→methyl 2-{3-[3-(5-cyanothiophen-2-yl)-4-fluorophenyl]ureido}-2-methylpropionate (269.3, molecular weight 361.40 ($C_{17}H_{16}FN_3O_3S$); retention time $R_t$=1.38 min. [F]; MS (ESI): 362.05 (MH$^+$))→5-[5-(4,4-dimethyl-2,5-dioxoimidazolidin-1-yl)-2-fluorophenyl]thiophene-2-carbonitrile (269.2, molecular weight 329.06 ($C_{16}H_{12}FN_3O_2S$); retention time $R_t$=2.17 min. [E]; MS (ESI): 659.31 (2M+H$^+$))→5-{5-[3-(2-bromo-4-fluorobenzyl)-4,4-dimethyl-2,5-dioxoimidazolidin-1-yl]-2-fluorophenyl}thiophene-2-carbonitrile (269.1, $^1$H NMR: 8.1-8.01, m, 2H, 7.77, d, 1H, 7.66-758, m, 4H, 7.29, m, 1H, 4.61, s, 2H; 1.41, s, 6H)→methyl 4-(2-{3-[3-(5-cyanothiophen-2-yl)-4-fluorophenyl]-5,5-dimethyl-2,4-dioxoimidazolidin-1-ylmethyl}-5-fluorophenylamino)benzoate (269).

Example 270

4-{5-Fluoro-2-[3-(4-fluoro-3-thiophen-2-ylphenyl)-5,5-dimethyl-2,4-dioxoimidazolidin-1-ylmethyl]phenylamino}benzoic acid

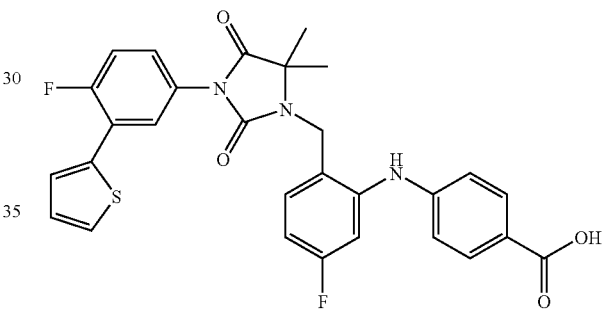

The reaction of the ester 267 with potassium silanolate in tetrahydrofuran, as described for the preparation of 248, afforded the carboxylic acid 270. Molecular weight 547.13 ($C_{29}H_{23}F_2N_3O_4S$); retention time $R_t$=2.69 min. [E]; MS (ESI): 548.22 (MH$^+$).

Pharmacological Testing:
In Vitro Tests:
In Vitro Functional Assays with Recombinant Cells:
Function-testing assays were performed by means of the FLIPR technique ("Fluorometric Imaging Plate Reader", Molecular Devices Corp.).

To this end, ligand-induced changes in the intracellular concentration of Ca$^{2+}$ in recombinant HEK293 cells, which expressed both a cannabinoid receptor (CB1 or CB2) and G-protein Galpha16, were determined. For the studies, cells were sown into 96-well microtiter plates (60 000 cells/well) and left to grow overnight. The medium was removed and the cells were incubated in buffer which contained the fluorescent dye Fluo-4. After this loading with dye, the cells were washed, test substance was added dissolved in buffer, the mixture was incubated for 20 minutes, a known cannabinoid receptor agonist as a reference agonist was added in buffer and, finally, the changes in the intracellular Ca$^{2+}$ concentration were measured in the FLIPR unit.

Results were presented as the percentage change relative to the control (0%: analogous experiment without test substance and without reference agonist, i.e. only with buffer; 100%:

analogous experiment without test substance, but with reference agonist in excess), and used to calculate dose/action curves, and $IC_{50}$ values were determined.

Results:

The values of the functional assay compared to the cannabinoid 1 receptor including illustrative selectivities compared to the cannabinoid 2 receptor can be taken from table 1 which follows.

TABLE 1

| Example No. | hCB1R: FLIPR; $IC_{50}$ [nM] | hCB2R: FLIPR; $IC_{50}$ [nM] |
|---|---|---|
| 1 | 10 | >10000 |
| 2 | 11 | >10000 |
| 3 | 22 | |
| 4 | 4 | |
| 5 | 44 | >10000 |
| 11 | 0.7 | >10000 |
| 14 | 108 | |
| 20 | 21 | |
| 21 | 10 | |
| 22 | 46 | |
| 30 | 208 | >10000 |
| 33 | 4 | |
| 35 | 15 | |
| 36 | 11 | >10000 |
| 37 | 21 | |
| 38 | 70 | |
| 39 | 69 | |
| 40 | 30 | |
| 41 | 28 | |
| 42 | 12 | >10000 |
| 43 | 77 | |
| 44 | 7 | |
| 55 | 10 | |
| 56 | 8 | >10000 |
| 57 | 36 | >10000 |
| 60 | 2 | >10000 |
| 64 | 16 | >10000 |
| 65 | 145 | |
| 66 | 25 | >10000 |
| 67 | 1 | >10000 |
| 68 | 44 | |
| 72 | 24 | |
| 73 | 7 | >10000 |
| 74 | 4 | >10000 |
| 75 | 49 | >10000 |
| 78 | 4 | >10000 |
| 80 | 33 | |
| 81 | 144 | >10000 |
| 82 | 52 | >10000 |
| 83 | 9 | >10000 |
| 85 | 7 | >10000 |
| 90 | 39 | >10000 |
| 91 | 30 | >10000 |
| 92 | 137 | >10000 |
| 95 | 31 | |
| 97 | 7 | >10000 |
| 104 | 15 | |
| 105 | 49 | |
| 106 | 12 | |
| 107 | 112 | |
| 113 | 4 | |
| 125 | 110 | |
| 127 | 7 | |
| 130 | 32 | |
| 131 | 15 | |
| 133 | 10 | |
| 135 | 1 | |
| 136 | 5 | >10000 |
| 137 | 5 | >10000 |
| 138 | 4 | |
| 140 | | >10000 |
| 142 | | >10000 |
| 143 | 13 | >10000 |
| 144 | | >10000 |
| 145 | 14 | |
| 148 | 11 | |
| 154 | 8 | |
| 56 | 10 | |
| 158 | 9 | |
| 159 | 2 | |
| 164 | 137 | |
| 166 | 76 | |
| 169 | 9 | |
| 175 | 9 | |
| 177 | 1 | |
| 178 | 4 | |
| 180 | 1 | |
| 181 | 8 | |
| 190 | 76 | |
| 197 | 19 | |
| 198 | 23 | |
| 200 | 8 | |
| 201 | 5 | |
| 204 | 46 | |
| 205 | 17 | |
| 206 | 24 | |
| 208 | 13 | |
| 209 | 62 | |
| 213 | 117 | |
| 221 | 10 | |
| 227 | 16 | |
| 228 | 61 | |
| 232 | 112 | |
| 233 | 22 | |
| 238 | 10 | |
| 239 | 103 | |
| 240 | 11 | |
| 243 | 99 | |
| 246 | 7 | |
| 253 | 29 | |
| 254 | 2 | |
| 255 | 28 | |
| 258 | 31 | |

Binding to the CB1 Receptor:

Test compounds: The compounds (3 μl, 10 mM, 100% DMSO), pipetted into 96-well PP microtiter plates, were diluted with 27 μl of 100% DMSO (dimethyl sulfoxide). Proceeding from this solution, further 3-fold dilution steps were undertaken by transferring 10 μl in each case to a new PP microtiter plate and adding a further 20 μl of 100% DMSO. In each case 6 μl of these solutions were transferred into new 96-well PP microtiter plates and made up with 144 μl of assay buffer. The end concentrations ranged from 10 μM to 0.005 μM. Negative control: AM 251, dissolved in assay buffer with 1% DMSO, was added to the dilution series in the microtiter plates as a control. The end concentration was 1 μM. Blank control: assay buffer with 1% DMSO was added to the dilution series of the microtiter plates as a blank control.

Summary of the Assay Parameters:

| | | |
|---|---|---|
| Assay volume | | 200 μl |
| Receptor | CHO-K1/cannabinoid CB1 Protein | 2 μg/well |
| Ligand | [$^3$H]-SR141716A | 0.5 nM |
| | | 0.0195 μCi/well |
| Ions | Tris-HCl | 50 mM, pH 7.4 |
| | $MgCl_2$ | 5 mM |
| | EDTA | 2.5 mM |
| | BSA (fatty acid-free) | 0.2% |
| Nonspecific binding | AM 251 | 1 μM |
| Compound | in 1% DMSO | 10 μM to 0.0050 μM |

Analysis of the Data:

High control: $^3$H binding without addition of the compound

Low control: $^3$H binding in the presence of 1 µM AM 251

The values were calculated using the corrected raw data.

$$\text{Inhibition of ligand binding (\%)} = 100 * \left(1 - \frac{(\text{sample} - \text{lowcontrol})}{(\text{highcontrol} - \text{lowcontrol})}\right)$$

The values reported were obtained as average values of a double determination. The IC$_{50}$ values were calculated from the measurements with the program Xlfit, formula 205. Ki values were obtained from the IC$_{50}$ and Kd values utilizing the Cheng-Prusoff equation:

$$Ki = \frac{IC50}{1 + \frac{C}{Kd}} \quad (C = \text{concentration of the radioligand})$$

Literature: Cheng, Y.-C., and Prusoff, W. H. (1973) Biochem. Pharmacol 22, 3099-3108

Results: K$_i$ values of example compounds; Table 2:

| Example No. | hCB1R; binding K$_i$ [nM] |
|---|---|
| 1 | 13 |
| 5 | 7 |
| 6 | 21 |
| 7 | 15 |
| 8 | 15 |
| 9 | 13 |
| 10 | 24 |
| 11 | 1 |
| 12 | 0.9 |
| 13 | 0.9 |
| 15 | 2 |
| 16 | 2 |
| 17 | 3 |
| 18 | 5 |
| 19 | 5 |
| 23 | 10 |
| 24 | 11 |
| 25 | 6 |
| 26 | 39 |
| 27 | 17 |
| 28 | 87 |
| 29 | 107 |
| 32 | 3 |
| 34 | 14 |
| 42 | 1 |
| 50 | 11 |
| 51 | 2 |
| 52 | 3 |
| 53 | 2 |
| 55 | 8 |
| 56 | 3 |
| 60 | 1 |
| 61 | 19 |
| 62 | 16 |
| 63 | 9 |
| 64 | 5 |
| 66 | 7 |
| 67 | 1 |
| 68 | 16 |
| 69 | 113 |
| 70 | 27 |
| 110 | 5 |
| 111 | 1 |
| 112 | 1 |
| 120 | 5 |
| 126 | 23 |

-continued

| Example No. | hCB1R; binding K$_i$ [nM] |
|---|---|
| 128 | 2 |
| 129 | 10 |
| 132 | 6 |
| 134 | 4 |
| 137 | 51 |
| 140 | 26 |
| 142 | 3 |
| 144 | 19 |
| 149 | 6 |
| 151 | 155 |
| 153 | 20 |
| 157 | 5 |
| 160 | 3 |
| 161 | 8 |
| 165 | 16 |
| 167 | 7 |
| 170 | 113 |
| 171 | 120 |
| 172 | 8 |
| 173 | 34 |
| 174 | 144 |
| 176 | 130 |
| 179 | 16 |
| 223 | 4 |
| 224 | 6 |
| 227 | 36 |

It can be seen from the test data that the inventive compounds of the formula I act as CB1R antagonists and are therefore very suitable for treating metabolic syndrome, type II diabetes and obesity.

In Vivo Tests:

"Milk Consumption in Mice"

The test is used to study the anorexigenic potency of the test substances. Female NMRI mice, 25-35 g in weight, are used. The mice are accustomed to the housing conditions for at least one week and to the condensed milk supplied for 2 days.

The feed is removed from the mice for 24 hours, but they have constant access to water. On the day of the experiment, the animals are put in individual cages; the cage lids can accommodate the pipettes filled with milk. The test substances are administered orally, intraperitoneally or subcutaneously. After the administration, the mice are put in their cages and receive access to the milk 30 min later. The milk consumption is read off every 30 min over 7 hours; at the same time, obvious changes in behavior of the animals are noted.

"Antagonization of CB1-Mediated Hypothermia"

The test is used to measure the potency of cannabinoid CB1 receptor (CB1) antagonists. What is measured is the extent to which the CB1 antagonists to be tested are capable of preventing or of antagonizing hypothermia induced by a CB1 agonist.

Female NMRI mice, 25-35 g in weight, are used. The mice are accustomed to the housing conditions for at least one week.

At time 0 min, the animals are treated orally, intravenously or intraperitoneally with the CB1 antagonist to be tested. 30 min later, the CB1 agonist CP55.940, 1.25 mg/kg, is administered to the mice intraperitoneally. This brings about a fall in the body temperature by 5-6° C. within 30 min. The body temperature is measured rectally for the first time 30 min before the test substance administration and then every 30 min after this administration, if appropriate immediately before a substance administration, over 4 hours.

The potency of the test substances is reported as the percentage decrease in the area under the temperature-time curve which is formed firstly by the average basal temperature, and secondly by the temperature-time curve, of the animals treated exclusively with the CB1 antagonist.

"Intestinal Motility in Mice"

The method serves firstly to study the influence of test substances themselves on the small intestinal motility, and secondly to study to what extent specifically induced effects on the small intestinal motility can be prevented or antagonized, for example the delay in the intestinal passage by the cannabinoid CB1 agonist CP55.940.

Female NMRI mice with a weight of 25-35 g are used. The mice are accustomed to the housing conditions for at least one week.

The feed is removed from the mice for 24 hours, but they have constant access to water. The test substances are administered orally, intravenously, subcutaneously, but not intraperitoneally. If a specific effect is to be antagonized, the test substance is administered 30-120 min before the specific effector. 30 min after this administration, a defined amount of a dyed, non-caloric filler is introduced into the stomach by gavage. After a further 30 min (the dyed filler has about 80% filled the small intestine at this point), the animals are sacrificed and the small intestine is dissected. The intestinal motility is reported as the passage of the dyed filler compared to the total length of the small intestine in percent. A treatment effect is reported as the difference of this passage to the vehicle control, likewise in percent.

Although the invention has been illustrated by certain of the preceding examples, it is not to be construed as being limited thereby; but rather, the invention encompasses the generic area as hereinbefore disclosed. Various modifications and embodiments can be made without departing from the spirit and scope thereof.

What is claimed is:
1. A compound of the formula I

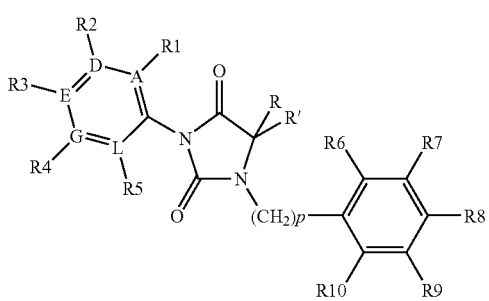

in which
R, R' are each independently H, $(C_1-C_6)$-alkyl, wherein $(C_1-C_6)$-alkyl is optionally substituted by halogen, O—R14, $S(O)_m$—R12 or NR13R15;
or R and R' together with the carbon atom to which they are attached form a ring having from three to eight carbon atoms, wherein optionally one carbon atom is replaced by O, $S(O)_m$, NR13 or NR15;
m is 0, 1 or 2;
n is 0, 1, 2, 3 or 4;
p is 1, 2, 3, 4 or 5;
q is 1, 2, 3 or 4;
r is 2, 3, 4, 5 or 6;
v is 0, 1, 2, 3 or 4;
A, D, E, G, L are each independently C or N, where there is no corresponding R1, R2, R3, R4, R5 substituent when they are defined as N;

R1, R2, R3, R4, R5 are each independently H, F, Cl, Br, I, CN, $N_3$, NC, $NO_2$, $CF_3$, $(C_1-C_8)$-alkyl, $(C_3-C_8)$-cycloalkyl, $(CH_2)_n$—[$(C_3-C_8)$-cycloalkenyl], $(CH_2)_q$—[$(C_3-C_8)$-cycloalkyl], $(CH_2)_n$—[$(C_7-C_{12})$-bicycloalkyl], $(CH_2)_n$—[$(C_7-C_{12})$-bicycloalkenyl], $(CH_2)_n$—[$(C_7-C_{12})$-tricycloalkyl], adamantan-1-yl, adamantan-2-yl, $(CH_2)_n$-aryl, $(CH_2)_n$-heteroaryl, $OCF_3$, O—R11, NR13R15, NH—CN, $S(O)_m$—R12, $SO_2$—$NH_2$, $SO_2$—N═CH—$N(CH_3)_2$, $SO_2$—NH—CO—R12, $SO_2$—NH—CO—NHR12, $SO_2$—NH—CO—R16, $SO_2$—NH—[$(C_1-C_8)$-alkyl], $SO_2$—NH—[$(C_3$-$C_8)$-cycloalkyl], $SO_2$—NH—$(CH_2)_r$—OH, $SO_2$—NH—$(CH_2)_n$-aryl, $SO_2$—NH—$(CH_2)_n$-heteroaryl, $SO_2$—N[$(C_1-C_8)$-alkyl]$_2$, $SO_2$—R16, $SF_5$, CO—O[$(C_1-C_8)$-alkyl], CO—O[$(C_3-C_8)$-cycloalkyl], CO—O—$(CH_2)_r$—$NH_2$, CO—O—$(CH_2)_n$-aryl, CO—O—$(CH_2)_n$-heteroaryl, CO—$NH_2$, CO—NH—CN, CO—NH—[$(C_1-C_8)$-alkyl], CO—NH—$(CH_2)_r$—OH, CO—N[$(C_1-C_8$-alkyl]$_2$, CO—NH—[$(C_3-C_8)$-cycloalkyl], CO—N[$(C_3-C_8$-cycloalkyl]$_2$, C(═NH)—O—[$(C_1-C_6$-alkyl)], C(═NH)—$NH_2$, C(═NH)—NHOH, C(═NH)—[NHO—$(C_1-C_6)$-alkyl], C(═NH)—NR12R13, C(═NH—R16, C(═NR13)—NR12R13, CO—NH—$SO_2$—R16, CO—NH—$SO_2$—NHR12, CO—R16, COOH, CO—$(C_1-C_8)$-alkyl, CO—$(C_3-C_8)$-cycloalkyl, CO—$(CH_2)_n$—[$(C_7-C_{12})$-bicycloalkyl], CO—$(CH_2)_n$—[$(C_7-C_{12})$-tricycloalkyl], CO-aryl, CO-heteroaryl, CH(OH)-aryl, CH(OH)-heteroaryl, CH[O—$(C_1-C_6)$-alkyl]-aryl, CH[O—$(C_1-C_6)$-alkyl]-heteroaryl, CHF-aryl, CHF-heteroaryl, $CF_2$-aryl, $CF_2$-heteroaryl, CHO, $CH_2$—OH, $CH_2$—CN, $CH_2$—O—R12, $CH_2$—O—$(CH_2)_n$—CO—O [$(C_1-C_8)$-alkyl], $CH_2$—O—$(CH_2)_n$—CO—$NH_2$ and $CH_2$—O—$(CH_2)_q$—COOH, wherein the alkyl, cycloalkyl, cycloalkenyl, bicycloalkyl, bicycloalkenyl and tricycloalkyl radicals are optionally substituted by fluorine atoms and wherein the aryl or heteroaryl radicals are optionally substituted by halogen, CN, $(C_1-C_6)$-alkyl, $(C_3-C_6)$-cycloalkyl, O—$(C_1$-$C_6)$-alkyl, $S(O)_m$—$(C_1-C_6)$-alkyl, $SO_2$—$NH_2$, COOH, $CONH_2$, CO—$O(C_1-C_6)$-alkyl, CO—$(C_1-C_6)$-alkyl and wherein the alkyl radicals are optionally substituted by fluorine atoms;

R6, R7, R8, R9, R10 are each independently R11, NR17-bicyclic heterocycle, NR17-aryl, NR17-heteroaryl, wherein the aryl or heteroaryl radical is optionally fused to a 5- or 6-membered aromatic or nonaromatic carbon ring in which one or more CH or $CH_2$ groups are optionally replaced by oxygen atoms and wherein the 5- or 6-membered aromatic or nonaromatic carbon ring is optionally substituted by F, ═O or —$(C_1-C_6)$-alkyl and wherein the bicyclic heterocycle contains from 9 to 12 ring members and up to five CH or $CH_2$ groups are each optionally and independently replaced by N, NR20, O, $S(O)_m$ or C═O and wherein the aryl or heteroaryl radical or bicyclic heterocycle are unsubstituted or optionally mono- or polysubstituted by R11, F, Cl, Br, I, CN, $N_3$, NC, $NO_2$, $CF_3$, $(CH_2)_n$—O—R11, $(CH_2)_n$—O—$(CH_2)_r$—OH, $(CH_2)_n$—O—CH$(CH_2OH)_2$, $(CH_2)_n$—O—$(CH_2)_n$—CO—O—$(CH_2)_r$—$NH_2$, $(CH_2)_n$—O—$(CH_2)_n$—CO—NH—$(CH_2)_r$—OH, $(CH_2)_n$—O-sugar, $(CH_2)_n$—O-sugar acid, $(CH_2)_n$—O-glucoside, $(CH_2)_n$—O-galactoside, $(CH_2)_n$—O-glucuronide, O—R13, $OCF_3$, $(CH_2)_n$—O—$(CH_2)_r$—$NH_2$, $(CH_2)_n$—NH—R11, $(CH_2)_n$—N[$(CH_2)_q$—CO—$O(C_1-C_6)$-alkyl]$_2$, $(CH_2)_n$—N[$(CH_2)_q$—COOH]$_2$, $(CH_2)_n$—N[$(CH_2)_q$—

CONH$_2$]$_2$, (CH$_2$)$_n$—NH—R13, (CH$_2$)$_n$—N(R13)$_2$, (CH$_2$)$_n$—NH—CN, (CH$_2$)$_n$—NH—SO$_2$—R16, (CH$_2$)$_n$—NH—(CH$_2$)$_n$—SO$_2$—R12, (CH$_2$)$_n$—NR12—CO—R16, (CH$_2$)$_n$—NR12—CO—NR12R13, (CH$_2$)$_n$—NR12—CO—N(R12)$_2$, (CH$_2$)$_n$—NR12—CO—NHR11, (CH$_2$)$_n$—NH—C(=NH)—NH$_2$, (CH$_2$)$_n$—NH—C(=NH)—R16, (CH$_2$)$_n$—NH—C(=NH—NHR12, (CH$_2$)$_n$—NR12—C(=NR13)—NHR12, (CH$_2$)$_n$—NR12—C(=NR12)—NR12R13, (CH$_2$)$_n$—NH—(CH$_2$)$_n$—CO—O—(CH$_2$)$_r$—NH$_2$, (CH$_2$)$_n$—NH—(CH$_2$)$_n$—CO—NH—[(C$_1$-C$_8$)-alkyl], (CH$_2$)$_n$—NH—(CH$_2$)$_n$—CO—NH—(CH$_2$)$_r$—OH, (CH$_2$)$_n$—NH—(CH$_2$)$_n$—CO—N[(C1-C8)-alkyl]$_2$, (CH$_2$)$_n$—NH—(CH$_2$)$_n$—CO—NH—[(C$_3$-C$_8$)-cycloalkyl], (CH$_2$)$_n$—NH—(CH$_2$)$_n$—CO—N[(C$_3$-C$_8$)-cycloalkyl]$_2$, (CH$_2$)$_n$—NH—C(CH$_3$)$_2$—CO—O(C$_1$-C$_8$)-alkyl, (CH$_2$)$_n$—NH—C(CH$_3$)$_2$—CO—O(C$_3$-C$_8$)-cycloalkyl, (CH$_2$)$_n$—NH—C(CH$_3$)$_2$—CO—O—(CH$_2$)$_r$—NH$_2$, (CH$_2$)$_n$—NH—C(CH$_3$)$_2$—CO—O—(CH$_2$)$_n$-aryl, (CH$_2$)$_n$—NH—C(CH$_3$)$_2$—CO—O—(CH$_2$)$_n$-heteroaryl, (CH$_2$)$_n$—NH—C(CH$_3$)$_2$—CO—NH$_2$, (CH$_2$)$_n$—NH—C(CH$_3$)$_2$—CO—NH—[(C$_1$-C$_8$)-alkyl], (CH$_2$)$_n$—NH—C(CH$_3$)$_2$—CO—NH—(CH$_2$)$_r$—OH, (CH$_2$)$_n$—NH—C(CH$_3$)$_2$—CO—N[(C$_1$-C$_8$)-alkyl]$_2$, (CH$_2$)$_n$—NH—(CH$_3$)$_2$—CO—NH—[(C$_3$-C$_8$)-cycloalkyl], (CH$_2$)$_n$—NH—C(CH$_3$)$_2$—CO—N[(C$_3$-C$_8$)-cycloalkyl]$_2$, (CH$_2$)$_n$—NH—C(CH$_3$)$_2$—COOH, S(O)$_m$—R12, SO$_2$—R16, SO$_2$—N=CH—N(CH$_3$)$_2$,

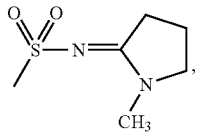

SO$_2$—NH—CO—R12, SO$_2$—NHR12, SO$_2$—NH—(CH$_2$)$_r$—OH, SO$_2$—N[(C$_1$-C$_8$)-alkyl]$_2$, SO$_2$—NH—(CH$_2$)$_r$—NH$_2$, SF$_5$, COOH, CO—NH$_2$, (CH$_2$)$_q$—CN, (CH$_2$)$_n$—CO—NH—CN, (CH$_2$)$_n$—CO—NH-piperidin-1-yl, (CH$_2$)$_n$—CO—NH—SO$_2$—NHR12, (CH$_2$)$_n$—CO—NH—SO$_2$—R18, (CH$_2$)$_n$—CHO, (CH$_2$)$_n$—C(=NH)—NH$_2$, (CH$_2$)$_n$—C(=NH)—NHOH, (CH$_2$)$_n$—C(=NH)—[NH—O—(C$_1$-C$_6$)-alkyl], (CH$_2$)$_n$—C(=NH)(R16), (CH$_2$)$_n$—C(=NR13)NHR12, (CH$_2$)$_n$—C(=NR12)NR12R13, (CH$_2$)$_n$—C(=NH)O[(C$_1$-C$_6$)-alkyl], wherein the alkyl and cycloalkyl radicals are optionally substituted by fluorine atoms and wherein the aryl or heteroaryl radicals are optionally substituted by halogen, CN, (C$_1$-C$_6$)-alkyl, (C$_3$-C$_6$)-cycloalkyl, O—(C$_1$-C$_6$)-alkyl, S(O)$_m$—(C$_1$-C$_6$)-alkyl, SO$_2$—NH$_2$, COOH, CONH$_2$, CO—O(C$_1$-C$_6$)-alkyl, CO—(C$_1$-C$_6$)-alkyl and where the alkyl radicals are optionally substituted by F, Cl, Br, I, CN, N$_3$, NC, NO$_2$, CF$_3$, (CH$_2$)$_n$—O—R11, (CH$_2$)$_n$—O—(CH$_2$)$_r$—OH, (CH$_2$)$_n$—O—CH(CH$_2$OH)$_2$, (CH$_2$)$_n$—O—(CH$_2$)$_n$—CO—O—(CH$_2$)$_r$—NH$_2$, (CH$_2$)$_n$—O—(CH$_2$)$_n$—CO—NH—(CH$_2$)$_r$—OH, (CH$_2$)$_n$—O-sugar, (CH$_2$)$_n$—O-sugar acid, (CH$_2$)$_n$—O-glucoside, (CH$_2$)$_n$—O-galactoside, (CH$_2$)$_n$—O-glucuronide, O—R13, OCF$_3$, (CH$_2$)$_n$—NH—R11, (CH$_2$)$_n$—NH—R13, (CH$_2$)$_n$—NH—CN, (CH$_2$)$_n$—NH—SO$_2$—R16, (CH$_2$)$_n$—NH—(CH$_2$)$_n$—SO$_2$—R12, (CH$_2$)$_n$—NR12-CO—R16, (CH$_2$)$_n$—NR12-CO—NR12R13, (CH$_2$)$_n$—NR12-CO—N(R12)$_2$, (CH$_2$)$_n$—NR12-CO—NHR11, (CH$_2$)$_n$—NH—C(=NH)—NH$_2$, (CH$_2$)$_n$—NH—C(=NH)—R16, (CH$_2$)$_n$—NH—C(=NH)—NHR12, (CH$_2$)$_n$—NR12—C(=NR13)—NHR12, (CH$_2$)$_n$—NR12—C(=NR12)—NR12R13, (CH$_2$)$_n$—NH—(CH$_2$)$_n$—CO—O—(CH$_2$)$_r$—NH$_2$, (CH$_2$)$_n$—NH—(CH$_2$)$_n$—CO—NH—[(C$_1$-C$_8$)-alkyl], (CH$_2$)$_n$—NH—(CH$_2$)$_n$—CO—NH—(CH$_2$)$_r$—OH, (CH$_2$)$_n$—NH—(CH$_2$)$_n$—CO—N[(C$_1$-C$_8$)-alkyl]$_2$, (CH$_2$)$_n$—NH—(CH$_2$)$_n$—CO—NH—[(C$_3$-C$_8$)-cycloalkyl], (CH$_2$)$_n$—NH—(CH$_2$)$_n$—CO—N[(C$_3$-C$_8$)-cycloalkyl]$_2$, (CH$_2$)$_n$—NH—C(CH$_3$)$_2$—CO—O(C$_1$-C$_8$)-alkyl, (CH$_2$)$_n$—NH—C(CH$_3$)$_2$—CO—O(C$_3$-C$_8$)-cycloalkyl, (CH$_2$)$_n$—NH—C(CH$_3$)$_2$—CO—O—(CH$_2$)$_r$—NH$_2$, (CH$_2$)$_n$—NH—C(CH$_3$)$_2$—CO—O—(CH$_2$)$_n$-aryl, (CH$_2$)$_n$—NH—C(CH$_3$)$_2$—CO—O—(CH$_2$)$_n$-heteroaryl, (CH$_2$)$_n$—NH—C(CH$_3$)$_2$—CO—NH$_2$, (CH$_2$)$_n$—NH—C(CH$_3$)$_2$—CO—NH—[(C$_1$-C$_8$)-alkyl], (CH$_2$)$_n$—NH—C(CH$_3$)$_2$—CO—NH—(CH$_2$)$_r$—OH, (CH$_2$)$_n$—NH—C(CH$_3$)$_2$—CO—N[(C$_1$-C$_8$)-alkyl]$_2$, (CH$_2$)$_n$—NH—(CH$_3$)$_2$—CO—NH—[(C$_3$-C$_8$)-cycloalkyl], (CH$_2$)$_n$—NH—C(CH$_3$)$_2$—CO—N[(C$_3$-C$_8$)-cycloalkyl]$_2$, (CH$_2$)$_n$—NH—C(CH$_3$)$_2$—COOH, S(O)$_m$—R12, SO$_2$—R16, SO$_2$N=CH—N(CH$_3$)$_2$,

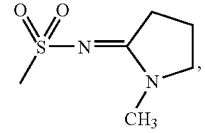

SO$_2$—NH—CO—R12, SO$_2$—NHR12, SO$_2$—NH—(CH$_2$)$_r$—OH, SO$_2$—N[(C$_1$-C$_8$)-alkyl]$_2$, SO$_2$—NH—(CH$_2$)$_r$—NH$_2$, SF$_5$, COOH, CONH$_2$, (CH$_2$)$_q$—CN, (CH$_2$)$_n$—CO—NH—CN, (CH$_2$)$_n$—CO—NH-piperidin-1-yl, (CH$_2$)$_n$—CO—NH—SO$_2$—NHR12, (CH$_2$)$_n$—CO—NH—SO$_2$—R18, (CH$_2$)$_n$—CHO, (CH$_2$)$_n$—C(=NH)NH$_2$, (CH$_2$)$_n$—C(=NH)NHOH, (CH$_2$)$_n$—C(=NH)(R16), (CH$_2$)$_n$—C(=NR13)NHR12, (CH$_2$)$_n$—C(=NR12)NR12R13, (CH$_2$)$_n$—C(=NH)O[(C$_1$-C$_6$)-alkyl], where the alkyl and cycloalkyl radicals may be substituted by fluorine atoms and where the aryl or heteroaryl radicals may be substituted by halogen, CN, (C$_1$-C$_6$)-alkyl, (C$_3$-C$_6$)-cycloalkyl, O—(C$_1$-C$_6$)-alkyl, S(O)$_m$—(C$_1$-C$_6$)-alkyl, SO$_2$—NH$_2$, COOH, CONH$_2$, CO—[O(C$_1$-C$_6$)-alkyl], CO—(C$_1$-C$_6$)-alkyl and where the alkyl radicals may be substituted by fluorine atoms;

wherein at least one of the R6, R7, R8, R9 and R10 radicals is always defined as NR17-aryl or NR17-bicyclic heterocycle or NR17-heteroaryl;

wherein one of the four radical pairs of R6 and R7, or R7 and R8, or R8 and R9, or R9 and R10 optionally in each case together form the —CH$_2$—CH$_2$—CH$_2$— or —CH$_2$—CH$_2$—CH$_2$—CH$_2$— groups in which up to two —CH$_2$— groups are optionally replaced by —O— and where the —CH$_2$—CH$_2$—CH$_2$— or —CH$_2$—CH$_2$—CH$_2$—CH$_2$— groups are optionally substituted by F, (C$_1$-C$_8$)-alkyl or =O;

R11 is H, (C$_1$-C$_8$)-alkyl, (C$_2$-C$_{10}$)-alkenyl, (C$_2$-C$_{10}$)-alkynyl, (C$_3$-C$_8$)-cycloalkyl, (CH$_2$)$_q$—[(C$_3$-C$_8$)-cycloalkyl], (CH$_2$)$_n$-[(C$_7$-C$_{12}$)-bicycloalkyl], (CH$_2$)$_n$-[(C$_3$-C$_{10}$)-cycloalkenyl], (CH$_2$)$_n$-[(C$_3$-C$_{10}$)-bicycloalkenyl], (CH$_2$)$_n$-[(C$_7$-C$_{12}$)-tricycloalkyl], (CH$_2$)$_n$-aryl, (CH$_2$)$_n$—CO—[O—(C$_1$-C$_8$)-alkyl], (CH$_2$)$_n$—CO—[O—(C$_3$-C$_8$)-cycloalkyl], (CH$_2$)$_n$—CO—[(C$_1$-C$_8$)-alkyl], (CH$_2$)$_n$—CO—[(C$_3$-C$_8$)-cycloalkyl], (CH$_2$)$_n$—CO-aryl, (CH$_2$)$_n$—CO-heteroaryl, (CH$_2$)$_n$—CO—[O—(CH$_2$)$_v$-aryl], (CH$_2$)$_n$—CO—[O—(CH$_2$)$_v$-heteroaryl], (CH$_2$)$_q$—CO—NH$_2$, (CH$_2$)$_q$—COOH, (CH$_2$)$_q$—CO—

NH—CN, (CH$_2$)$_n$—P(O)(OH)[O—(C$_1$-C$_6$)-alkyl], (CH$_2$)$_n$—P(O)[O—(C$_1$-C$_6$)-alkyl]$_2$, (CH$_2$)$_n$—P(O)(OH)(O—CH$_2$-aryl), (CH$_2$)$_n$—P(O)(O—CH$_2$-aryl)$_2$, (CH$_2$)$_n$—P(O)(OH)$_2$, (CH$_2$)$_n$—SO$_3$H, (CH$_2$)$_n$—SO$_2$—NH$_2$, (CH$_2$)$_n$—CO—NH—[(C$_1$-C$_8$)-alkyl], (CH$_2$)$_n$—CO—N[(C$_1$-C$_8$)-alkyl]$_2$, (CH$_2$)$_n$—CO—NH—[(C$_3$-C$_8$)-cycloalkyl], (CH$_2$)$_n$—CO—N[(C$_3$-C$_8$)-cycloalkyl]$_2$, (C$_2$-C$_{10}$)-alkenyl-CO—O[(C$_1$-C$_6$)-alkyl], (C$_2$-C$_{10}$)-alkenyl-CONH$_2$, (C$_2$-C$_{10}$)-alkenyl-COOH, (C$_2$-C$_{10}$)-alkynyl-CO—O[(C$_1$-C$_6$)-alkyl], (C$_2$-C$_{10}$)-alkynyl-CONH$_2$, (C$_2$-C$_{10}$)-alkynyl-COOH, (CH$_2$)$_n$—CR21-[(CO—O(C$_1$-C$_6$)-alkyl)]$_2$, (CH$_2$)$_n$—CR21(CONH$_2$)$_2$, (CH$_2$)$_n$—CR21(COOH)$_2$, (CH$_2$)$_n$—CR21R22CO—O[(C$_1$-C$_6$)-alkyl], (CH$_2$)$_n$—CR21R22CONH$_2$, (CH$_2$)$_n$—CR21R22COOH, (CH$_2$)$_n$—CO—R16, (CH$_2$)$_n$—C(CH$_3$)$_2$—CO—O[(C$_1$-C$_8$)-alkyl], (CH$_2$)$_n$—C(CH$_3$)$_2$—CO—O[(C$_3$-C$_8$)-cycloalkyl], (CH$_2$)$_n$—C(CH$_3$)$_2$—CO—O—(CH$_2$)$_r$—NH$_2$, (CH$_2$)$_n$—C(CH$_3$)$_2$—CO—O—(CH$_2$)$_n$-aryl, (CH$_2$)$_n$—C(CH$_3$)$_2$—CO—O—(CH$_2$)$_n$-heteroaryl, (CH$_2$)$_n$—C(CH$_3$)$_2$—CO—NH$_2$, (CH$_2$)$_n$—C(CH$_3$)$_2$—CO—NH—[(C$_1$-C$_8$)-alkyl], (CH$_2$)$_n$—C(CH$_3$)$_2$—CO—NH—(CH$_2$)$_r$—OH, (CH$_2$)$_n$—C(CH$_3$)$_2$—CO—N[(C$_1$-C$_8$)-alkyl]$_2$, (CH$_2$)$_n$—C(CH$_3$)$_2$—CO—NH—[(C$_3$-C$_8$)-cycloalkyl], (CH$_2$)$_n$—C(CH$_3$)$_2$—CO—N[(C$_3$-C$_8$)-cycloalkyl]$_2$, (CH$_2$)$_n$—C(CH$_3$)$_2$—COOH, (CH$_2$)$_n$—CO—NH—C(CH$_3$)$_2$—CO—O[(C$_1$-C$_8$)-alkyl], (CH$_2$)$_n$—CO—NH—C(CH$_3$)$_2$—CONH$_2$ or (CH$_2$)$_n$—CO—NH—C(CH$_3$)$_2$—COOH, wherein the alkyl, alkenyl, alkynyl and cycloalkyl, bicycloalkyl, cycloalkenyl and bicycloalkenyl radicals are optionally substituted by fluorine atoms and wherein the aryl or heteroaryl radical is optionally substituted by halogen, CN, (C$_1$-C$_6$)-alkyl, (C$_3$-C$_6$)-cycloalkyl, O—(C$_1$-C$_6$)-alkyl, S(O)$_m$—(C$_1$-C$_6$)-alkyl, SO$_2$—NH$_2$, COOH, CONH$_2$, CO—O(C$_1$-C$_6$)-alkyl, CO—(C$_1$-C$_6$)-alkyl and wherein the alkyl radicals are optionally substituted by fluorine atoms;

R12 is H, (C$_1$-C$_8$)-alkyl, (C$_3$-C$_8$)-cycloalkyl, (CH$_2$)$_q$—[(C$_3$-C$_8$)-cycloalkyl], (CH$_2$)$_n$-[(C$_7$-C$_{12}$)-bicycloalkyl], (CH$_2$)$_n$-[(C$_7$-C$_{12}$)-tricycloalkyl], (CH$_2$)$_n$-aryl or (CH$_2$)$_n$-heteroaryl, wherein the alkyl or cycloalkyl radicals are optionally substituted by fluorine atoms, and wherein the aryl or heteroaryl radical is optionally substituted by halogen, CN, (C$_1$-C$_6$)-alkyl, O—(C$_1$-C$_6$)-alkyl, SO$_2$—NH$_2$, COOH, CONH$_2$, CO—O(C$_1$-C$_6$)-alkyl, CO—(C$_1$-C$_6$)-alkyl and wherein the alkyl radicals are optionally substituted by fluorine atoms;

R13 is H, SO$_2$—[(C$_1$-C$_8$)-alkyl], SO$_2$—[(C$_3$-C$_8$)-cycloalkyl], SO$_2$—(CH$_2$)$_n$-aryl, SO$_2$—(CH$_2$)$_n$-heteroaryl, SO$_2$—(CH$_2$)$_n$—NH—R12 or SO$_2$—(CH$_2$)$_n$—N(R12)$_2$, wherein the alkyl and cycloalkyl radicals are optionally substituted by fluorine atoms and wherein the aryl or heteroaryl radical is optionally substituted by halogen, CN, CF$_3$, (C$_1$-C$_6$)-alkyl, (C$_3$-C$_6$)-cycloalkyl, O—[(C$_1$-C$_6$)-alkyl], S(O)$_m$—[(C$_1$-C$_6$)-alkyl], SO$_2$—NH$_2$, COOH, CONH$_2$, CO—[O(C$_1$-C$_6$)-alkyl], CO—(C$_1$-C$_6$)-alkyl and wherein the alkyl radicals are optionally substituted by fluorine atoms;

R14 is H, (C$_1$-C$_8$)-alkyl, (C$_3$-C$_8$)-cycloalkyl, (CH$_2$)$_q$—[(C$_3$-C$_8$)-cycloalkyl], (CH$_2$)$_n$-aryl, (CH$_2$)$_n$-heteroaryl, (CH$_2$)$_n$—CO—[O—(C$_1$-C$_8$)-alkyl], (CH$_2$)$_n$—CO—[O—(C$_3$-C$_8$)-cycloalkyl], (CH$_2$)$_n$—CO—[O—(CH$_2$)$_n$-aryl], (CH$_2$)$_n$—CO—[O—(CH$_2$)$_n$-heteroaryl], (CH$_2$)$_n$—CO—[(C$_1$-C$_8$)-alkyl], (CH$_2$)$_n$—CO—[(C$_3$-C$_8$)-cycloalkyl], (CH$_2$)$_n$—CO-aryl, (CH$_2$)$_n$—CO-heteroaryl, (CH$_2$)$_q$—CO—NH$_2$, (CH$_2$)$_q$—COOH, (CH$_2$)$_n$—SO$_2$—NH$_2$, (CH$_2$)$_n$—CO—NH—[(C$_1$-C$_8$)-alkyl], (CH$_2$)$_n$—CO—N[(C$_1$-C$_8$)-alkyl]$_2$, (CH$_2$)$_n$—CO—NH—[(C$_3$-C$_8$)-cycloalkyl], (CH$_2$)$_n$—CO—N[(C$_3$-C$_8$)-cycloalkyl]$_2$, (CH$_2$)$_n$—C(CH$_3$)$_2$—CO—O[(C$_1$-C$_8$)]-alkyl, (CH$_2$)$_n$—C(CH$_3$)$_2$—CO—O[(C$_3$-C$_8$)]-cycloalkyl, (CH$_2$)$_n$—C(CH$_3$)$_2$—CO—O—(CH$_2$)$_r$—NH$_2$, (CH$_2$)$_n$—C(CH$_3$)$_2$—CO—NH$_2$, (CH$_2$)$_n$—C(CH$_3$)$_2$—CO—NH—(CH$_2$)$_r$—OH, (CH$_2$)$_n$—C(CH$_3$)$_2$—COOH, wherein the alkyl and cycloalkyl radicals are optionally substituted by fluorine atoms and wherein the aryl or heteroaryl radical is optionally substituted by halogen, CN, (C$_1$-C$_6$)-alkyl, (C$_3$-C$_6$)-cycloalkyl, O—(C$_1$-C$_6$)-alkyl, S(O)$_m$—(C$_1$-C$_6$)-alkyl, SO$_2$—NH$_2$, COOH, CONH$_2$, CO—O(C$_1$-C$_6$)-alkyl, CO—(C$_1$-C$_6$)-alkyl and wherein the alkyl radicals are optionally substituted by fluorine atoms;

R15 is H, (C$_1$-C$_8$)-alkyl, (C$_3$-C$_8$)-cycloalkyl, (CH$_2$)$_n$-aryl, (CH$_2$)$_n$-heteroaryl, (CH$_2$)$_n$—CO—[O—(C$_1$-C$_8$)-alkyl], (CH$_2$)$_n$—CO—[O—(C$_3$-C$_8$)-cycloalkyl], (CH$_2$)$_n$—CO—[O—(CH$_2$)$_n$-aryl], (CH$_2$)$_n$—CO—[O—(CH$_2$)$_n$-heteroaryl], CO—[(C$_1$-C$_8$)-alkyl], CO—[(C3-C8)-cycloalkyl], CO-aryl, CO-heteroaryl, (CH$_2$)$_n$—CO—NH$_2$, (CH$_2$)$_q$—COOH, (CH$_2$)$_n$—SO$_2$—NH$_2$, (CH$_2$)$_n$—CO—NH—[(C$_1$-C$_8$)-alkyl], (CH$_2$)$_n$—CO—N[(C$_1$-C$_8$)-alkyl]$_2$, (CH$_2$)$_n$—CO—NH—[(C$_3$-C$_8$)-cycloalkyl], (CH$_2$)$_n$—C(CH$_3$)$_2$—CO—NH$_2$, (CH$_2$)$_n$—C(CH$_3$)$_2$—COOH, wherein the alkyl and cycloalkyl radicals are optionally substituted by fluorine atoms and wherein the aryl or heteroaryl radical is optionally substituted by halogen, CN, (C$_1$-C$_6$)-alkyl, O—(C$_1$-C$_6$)-alkyl, SO$_2$—NH$_2$, COOH, CONH$_2$, CO—O(C$_1$-C$_6$)-alkyl, CO—(C$_1$-C$_6$)-alkyl and wherein the alkyl radicals are optionally substituted by fluorine atoms;

R16 is aziridine-1-yl, azetidin-1-yl, 3-hydroxyazetidin-1-yl, piperidin-1-yl, 3-hydroxypiperidin-1-yl, 4-hydroxypiperidin-1-yl, 3-oxopiperidin-1-yl, 4-oxopiperidin-1-yl, pyrrolidin-1-yl, 3-pyrrolidinol-1-yl, 2-cyanopyrrolidin-1-yl, morpholin-N-yl, piperazin-1-yl, 4-[(C$_1$-C$_6$)-alkyl]piperazin-1-yl, piperazin-2-on-1-yl, piperazin-2-on-4-yl, piperazine-2,3-dion-1-yl, piperazine-2,6-dion-1-yl, piperazine-2,6-dion-4-yl, thiomorpholin-4-yl, thiomorpholine-1,1-dioxide-4-yl, NH—(CH$_2$)$_r$—OH, NH—CH(CH$_2$OH)$_2$, NH—C(CH$_2$OH)$_3$, N[(C$_1$-C$_6$)-alkyl-OH]$_2$, N[(C$_1$-C$_6$)-alkyl][(C$_1$-C$_6$)-alkyl-OH], D-glucamin-N-yl, N-methyl-D-glucamin-N-yl, NH—[(C$_1$-C$_8$)-alkyl]-CO—O(C$_1$-C$_6$)-alkyl, NH—[(C$_1$-C$_8$)-alkyl]-COOH, NH—[(C$_1$-C$_8$)-alkyl]-CONH$_2$, N[(C$_1$-C$_6$)-alkyl][(C$_1$-C$_8$)-alkyl]-CO—O(C$_1$-C$_6$)-alkyl, N[(C$_1$-C$_6$)-alkyl][(C$_1$-C$_8$)-alkyl]-COOH, N[(C$_1$-C$_6$)-alkyl][(C$_1$-C$_8$)-alkyl]-CONH$_2$, NH—[C(H)(aryl)]-CO—O(C$_1$-C$_6$)-alkyl, NH—[C(H)(aryl)]-COOH, NH—[C(H)(aryl)]-CONH$_2$, N[(C$_1$-C$_6$)-alkyl][C(H)(aryl)]-CO—O(C$_1$-C$_6$)-alkyl, N[(C$_1$-C$_6$)-alkyl][C(H)(aryl)]-COOH, N[(C$_1$-C$_6$)-alkyl][C(H)(aryl)]-CONH$_2$, NH—[C(H)(heteroaryl)]-CO—O(C$_1$-C$_6$)-alkyl, NH—[C(H)(heteroaryl)]-COOH, NH—[C(H)(heteroaryl)]-CONH$_2$, N[(C$_1$-C$_6$)-alkyl][C(H)(heteroaryl)]-CO—O(C$_1$-C$_6$)-alkyl, N[(C$_1$-C$_6$)-alkyl][C(H)(heteroaryl)]-COOH, N[(C$_1$-C$_6$)-alkyl][C(H)(heteroaryl)]-CONH$_2$, N[(C$_1$-C$_6$)-alkyl][(C$_3$-C$_8$)-cycloalkyl]-CO—O(C$_1$-C$_6$)-alkyl, N[(C$_1$-C$_6$)-alkyl][(C$_3$-C$_8$)-cycloalkyl]-COOH, N[(C$_1$-C$_6$)-alkyl][(C$_3$-C$_8$)-cycloalkyl]-CONH$_2$, NH—[(C$_3$-C$_8$)-cycloalkyl]-CO—O(C$_1$-C$_6$)-alkyl, NH—[(C$_3$-C$_8$)-cycloalkyl]-COOH, NH—[(C$_3$-C$_8$)-cycloalkyl]-CONH$_2$, NH—(CH$_2$)$_r$—SO2—(C$_1$-C$_6$)-alkyl, NH—[(C$_1$-C$_6$)-alkyl]-SO$_3$H, NH—[(C$_1$-C$_6$)-alkyl]-SO$_2$—NH$_2$, N[(C$_1$-C$_6$)- alkyl]{[($C_1$-$C_6$)-alkyl]-$SO_3$H}, wherein the alcohol (OH) or ketone (C=O) functions are optionally replaced by F or $CF_2$;

R17 is R18, R13, $(CH_2)_n$—CO—[O—($C_1$-$C_8$)-alkyl], $(CH_2)_n$—CO—[O—($C_3$-$C_8$)-cycloalkyl], $(CH_2)_n$—CO—[($C_1$-$C_8$)-alkyl], $(CH_2)_n$—CO—[($C_3$-$C_8$)-cycloalkyl], $(CH_2)_n$—CO-aryl, $(CH_2)_n$—CO-heteroaryl, $(CH_2)_n$—CO—[O—$(CH_2)_n$-aryl], $(CH_2)_n$—CO—$NH_2$, $(CH_2)_q$—COOH, wherein the alkyl and cycloalkyl radicals are optionally substituted by fluorine atoms and wherein the aryl or heteroaryl radical is optionally substituted by halogen, CN, ($C_1$-$C_6$)-alkyl, ($C_3$-$C_6$)-cycloalkyl, O—($C_1$-$C_6$)-alkyl, $S(O)_m$—($C_1$-$C_6$)-alkyl, $SO_2$—$NH_2$, COOH, $CONH_2$, CO—[O($C_1$-$C_6$)-alkyl], CO—($C_1$-$C_6$)-alkyl and wherein the alkyl radicals are optionally substituted by fluorine atoms;

R18 is ($C_1$-$C_8$)-alkyl, ($C_3$-$C_8$)-cycloalkyl, $(CH_2)_q$—[($C_3$-$C_8$)-cycloalkyl], $(CH_2)_n$-aryl, $(CH_2)_n$-heteroaryl, where the alkyl and cycloalkyl radicals are optionally substituted by fluorine atoms and wherein the aryl or heteroaryl radical is optionally substituted by halogen, CN, ($C_1$-$C_6$)-alkyl, O—($C_1$-$C_6$)-alkyl, $SO_2$—$NH_2$, COOH, $CONH_2$, CO—[O($C_1$-$C_6$)-alkyl], CO—($C_1$-$C_6$)-alkyl and where the alkyl radicals are optionally substituted by fluorine atoms;

R20 is H, ($C_1$-$C_6$)-alkyl, ($C_3$-$C_8$)-cycloalkyl, aryl or [($C_1$-$C_6$)-alkyl]-aryl;

R21 is H, F, $CF_3$, ($C_1$-$C_6$)-alkyl, ($C_3$-$C_8$)-cycloalkyl, OH, O—($C_1$-$C_6$)-alkyl, O—($C_3$-$C_8$)-cycloalkyl, O—$(CH_2)_n$-aryl, O—(CO)—($C_1$-$C_6$)-alkyl, O—(CO)—($C_3$-$C_8$)-cycloalkyl, O—(CO)—O—($C_1$-$C_6$)-alkyl, O—(CO)—O—($C_3$-$C_8$)-cycloalkyl, NH—[($C_1$-$C_6$)-alkyl]-aryl, $NH_2$, NH—($C_1$-$C_6$)-alkyl or NH—(CO)—($C_1$-$C_6$)-alkyl; and R22 is H, $CF_3$, ($C_1$-$C_6$)-alkyl, aryl or [($C_1$-$C_6$)-alkyl]-aryl; or a physiologically compatible salt thereof.

2. The compound of the formula I as claimed in claim 1, wherein:

R, R' are each ($C_1$-$C_6$)-alkyl, wherein ($C_1$-$C_6$)-alkyl is optionally substituted by halogen; or R and R' taken together with the carbon atom to which they are attached form a ring having from three to eight carbon atoms;

m is 0, 1 or 2;

n is 0, 1, 2, 3 or 4;

p is 1, 2 or 3;

q is 1, 2 or 3;

r is 2, 3 or 4;

v is 0, 1, 2 or 3;

A, D, E, G, L are each independently C or N, where there is no corresponding R1, R2, R3, R4, R5 substituent when they are defined as N;

R1, R2, R3, R4, R5 are each independently H, F, Cl, Br, CN, $NO_2$, $CF_3$, ($C_1$-$C_8$)-alkyl, ($C_3$-$C_8$)-cycloalkyl, $(CH_2)_q$—[($C_3$-$C_8$)-cycloalkyl], $(CH_2)_n$—[($C_7$-$C_{12}$)-bicycloalkyl], $(CH_2)_n$-[($C_7$-$C_{12}$)-tricycloalkyl], adamantan-1-yl, adamantan-2-yl, $(CH_2)_n$-aryl, $(CH_2)_n$-heteroaryl, $OCF_3$, O—R11, NR13R15, $S(O)_m$—R12, $SO_2$—$NH_2$, $SO_2$—NH—[($C_1$-$C_8$)-alkyl], $SO_2$—NH—[($C_3$-$C_8$)-cycloalkyl], $SO_2$—NH—$(CH_2)_n$-aryl, $SO_2$—N[($C_1$-$C_8$)-alkyl]$_2$, $SO_2$—R16, $SF_5$, CO—O[($C_1$-$C_8$)-alkyl], CO—O—$(CH_2)_r$—$NH_2$, CO—$NH_2$, CO—NH—[($C_1$-$C_8$)-alkyl], CO—N[($C_1$-$C_8$)-alkyl]$_2$, C(=NH)—$NH_2$, C(=NH)—NHOH, C(=NH)—[NH—O—($C_1$-$C_6$)-alkyl], C(=NH)—NR12R13, C(=NH)—R16, C(=NH)—NR13, CO—NH—$SO_2$—R16, CO—NH—$SO_2$—NHR12, CO—R16, COOH, CO—($C_1$-$C_8$)-alkyl, CO—($C_3$-$C_8$)-cycloalkyl, CO-aryl, CO-heteroaryl, CH(OH)-aryl, CH(OH)-heteroaryl, CH[O—($C_1$-$C_6$)-alkyl]-aryl, CH[O—($C_1$-$C_6$)-alkyl]-heteroaryl, CHF-aryl, CHF-heteroaryl, $CF_2$-aryl, $CH_2$—O—R12, wherein the alkyl, cycloalkyl, bicycloalkyl and tricycloalkyl radicals are optionally substituted by fluorine atoms and wherein the aryl or heteroaryl radicals are optionally substituted by halogen, CN, ($C_1$-$C_6$)-alkyl, ($C_3$-$C_6$)-cycloalkyl, O—($C_1$-$C_6$)-alkyl, $S(O)_m$—($C_1$-$C_6$)-alkyl, $SO_2$—$NH_2$, COOH, $CONH_2$, CO—O($C_1$-$C_6$)-alkyl, CO—($C_1$-$C_6$)-alkyl and where the alkyl radicals are optionally substituted by fluorine atoms;

R6, R7, R8, R9, R10 are each independently R11, NR17-bicyclic heterocycle, NR17-aryl, NR17-heteroaryl, wherein the aryl or heteroaryl radical are optionally fused to a 5- or 6-membered aromatic or nonaromatic carbon ring in which one or more CH or $CH_2$ groups are optionally replaced by oxygen atoms and where the 5- or 6-membered aromatic or nonaromatic carbon ring is optionally substituted by F, =O or —($C_1$-$C_6$)-alkyl and wherein the bicyclic heterocycle contains from 9 to 10 ring members and up to five CH or $CH_2$ groups each optionally independently is replaced by N, NR20, O, $S(O)_m$ or C=O and wherein the aryl or heteroaryl radical or bicyclic heterocycle is unsubstituted or optionally mono- or polysubstituted by R11, F, Cl, Br, CN, $NO_2$, $CF_3$, $(CH_2)_n$—O—R11, $(CH_2)_n$—O—$(CH_2)_r$—OH, $(CH_2)_n$—O—CH($CH_2OH$)$_2$, $(CH_2)_n$—O—$(CH_2)_n$—CO—O—$(CH_2)_r$—$NH_2$, $(CH_2)_n$—O-sugar, $(CH_2)_n$—O-sugar acid, $(CH_2)_n$—O-glucoside, $(CH_2)_n$—O-galactoside, $(CH_2)_n$—O-glucuronide, O—R13, $OCF_3$, $(CH_2)_n$—O—$(CH_2)_r$—$NH_2$, $(CH_2)_n$—NH—R11, $(CH_2)_n$—N[$(CH_2)_q$—CO—O($C_1$-$C_6$)-alkyl]$_2$, $(CH_2)_n$—N[$(CH_2)_q$—COOH]$_2$, $(CH_2)_n$—N[$(CH_2)_q$—$CONH_2$]$_2$, $(CH_2)_n$—NH—R13, $(CH_2)_n$—N(R13)$_2$, $(CH_2)_n$—NH—CN, $(CH_2)_n$—NH—$SO_2$—R16, $(CH_2)_n$—NH—$(CH_2)_n$—$SO_2$—R12, $(CH_2)_n$—NR12—CO—R16, $(CH_2)_n$—NR12—CO—NR12R13, $(CH_2)_n$—NR12—CO—N(R12)$_2$, $(CH_2)_n$—NR12—CO—NHR11, $(CH_2)_n$—NH—C(=NH)—$NH_2$, $(CH_2)_n$—NH—C(=NH)—R16, $(CH_2)_n$—NH—C(=NH)—NHR12, $(CH_2)_n$—NR12—C(=NR13)—NHR12, $(CH_2)_n$—NR12—C(=NR12)—NR12R13, $(CH_2)_n$—NH—$(CH_2)_n$—CO—O—$(CH_2)_r$—$NH_2$, $(CH_2)_n$—NH—$(CH_2)_n$—CO—NH—[($C_1$-$C_8$)-alkyl], $(CH_2)_n$—NH—$(CH_2)_n$—CO—NH—$(CH_2)_r$—OH, $(CH_2)_n$—NH—$(CH_2)_n$—CO—N[($C_1$-$C_8$)-alkyl]$_2$, $(CH_2)_n$—NH—$(CH_2)_n$—CO—NH—[($C_3$-$C_8$)-cycloalkyl], $(CH_2)_n$—NH—C($CH_3$)$_2$—CO—O($C_1$-$C_8$)-alkyl, $(CH_2)_n$—NH—C($CH_3$)$_2$—CO—O—$(CH_2)_r$—$NH_2$, $(CH_2)_n$—NH—C($CH_3$)$_2$—CO—$NH_2$, $(CH_2)_n$—NH—C($CH_3$)$_2$—CO—NH—$(CH_2)_r$—OH, $(CH_2)_n$—NH—C($CH_3$)$_2$—COOH, $S(O)_m$—R12, $SO_2$—R16, $SO_2$—N=CH—N($CH_3$)$_2$, $SO_2$—NH—CO—R12, $SO_2$—NHR12, $SO_2$—NH—$(CH_2)_r$—OH, $SO_2$—N[($C_1$-$C_8$)-alkyl]$_2$, $SO_2$—NH—$(CH_2)_r$—$NH_2$, $SF_5$, COOH, CO—$NH_2$, $(CH_2)_q$—CN, $(CH_2)_n$—CO—NH-piperidin-1-yl, $(CH_2)_n$—CO—NH—$SO_2$—NHR12, $(CH_2)_n$—CO—NH—$SO_2$—R18, $(CH_2)_n$—C(=NH)$NH_2$, $(CH_2)_n$—C(=NH)—NHOH, C(=NH)—[NH—O—($C_1$-$C_6$)-alkyl], $(CH_2)_n$—C(=NH)(R16), $(CH_2)_n$—C(=NR13)NHR12, $(CH_2)_n$—C(=NR12)NR12R13, $(CH_2)_n$—C(=NH)O[($C_1$-$C_6$)-alkyl], wherein the alkyl and cycloalkyl radicals are optionally substituted by fluorine atoms and wherein the aryl or heteroaryl radicals are optionally substituted by halogen, CN, $(C_1-C_6)$-alkyl, $(C_3-C_6)$-cycloalkyl, O—$(C_1-C_6)$-alkyl, $S(O)_m$—$(C_1-C_6)$-alkyl, $SO_2$—$NH_2$, COOH, $CONH_2$, CO—O$(C_1-C_6)$-alkyl, CO—$(C_1-C_6)$-alkyl and wherein the alkyl radicals are optionally substituted by F, Cl, Br, CN, $CF_3$, $(CH_2)_n$—O—R11, $(CH_2)_n$—O—$(CH_2)_r$—OH, $(CH_2)_n$—O-sugar, $(CH_2)_n$—O-sugar acid, $(CH_2)_n$—O-glucoside, $(CH_2)_n$—O-galactoside, $(CH_2)_n$—O-glucuronide, O—R13, $OCF_3$, $(CH_2)_n$—NH—R11, $(CH_2)_n$—NH—R13, $(CH_2)_n$—NH—CN, $(CH_2)_n$—NH—$SO_2$—R16, $(CH_2)_n$—NH—$(CH_2)_n$—$SO_2$—R12, $(CH_2)_n$—NR12—CO—NR12R13, $(CH_2)_n$—NR12—CO—N(R12)$_2$, $(CH_2)_n$—NR12—CO—NHR11, $(CH_2)_n$—NH—C(=NH)—NH$_2$, $(CH_2)_n$—NH—C(=NH)—R16, $(CH_2)_n$—NH—C(=NH)—NHR12, $(CH_2)_n$—NR12—C(=NR13)—NHR12, $(CH_2)_n$—NR12—C(=NR12)—NR12R13, $(CH_2)_n$—NH—$(CH_2)_n$—CO—NH—$[(C_1-C_8)$-alkyl], $(CH_2)_n$—NH—$(CH_2)_n$—CO—N$[(C_1-C_8)$-alkyl]$_2$, $(CH_2)_n$—NH—C(CH$_3$)$_2$—CO—O$(C_1-C_8)$-alkyl, $(CH_2)_n$—NH—C(CH$_3$)$_2$—CO—O$(C_3-C_8)$-cycloalkyl, $(CH_2)_n$—NH—C(CH$_3$)$_2$—CO—NH$_2$, $(CH_2)_n$—NH—C(CH$_3$)$_2$—CO—NH—$(CH_2)_r$—OH, $(CH_2)_n$—NH—C(CH$_3$)$_2$—CO—N$[(C_1-C_8)$-alkyl]$_2$, $(CH_2)_n$—NH—C(CH$_3$)$_2$—COOH, $S(O)_m$—R12, $SO_2$—R16, $SO_2$—NH—CO—R12, $SO_2$—NHR12, $SO_2$—NH—$(CH_2)_r$—OH, $SO_2$—N$[(C_1-C_8)$-alkyl]$_2$, $SF_5$, $(CH_2)_n$—COOH, $(CH_2)_n$—CONH$_2$, $(CH_2)_q$—CN, $(CH_2)_n$—CO—NH—CN, $(CH_2)_n$—CO—NH—$SO_2$—NHR12, $(CH_2)_n$—CO—NH—$SO_2$—R18, $(CH_2)_n$—C(=NH)NH$_2$, $(CH_2)_n$—C(=NH)NHOH, $(CH_2)_n$—C(=NH)(R16), $(CH_2)_n$—C(=NR13)NHR12, $(CH_2)_n$—C(=NR12)NR12R13, $(CH_2)_n$—C(=NH)O$[(C_1-C_6)$-alkyl], wherein the alkyl and cycloalkyl radicals are optionally substituted by fluorine atoms and wherein the aryl or heteroaryl radicals are optionally substituted by halogen, CN, $(C_1-C_6)$-alkyl, $(C_3-C_6)$-cycloalkyl, O—$(C_1-C_6)$-alkyl, $S(O)_m$—$(C_1-C_6)$-alkyl, $SO_2$—NH$_2$, COOH, CONH$_2$, CO—$[O(C_1-C_6)$-alkyl], and wherein the alkyl radicals are optionally substituted by fluorine atoms;

wherein at least one of the R6, R7, R8, R9 and R10 radicals is always defined as NR17-aryl or NR17-bicyclic heterocycle or NR17-heteroaryl;

wherein one of the four radical pairs of R6 and R7, or R7 and R8, or R8 and R9, or R9 and R10 optionally in each case together form the —CH$_2$—CH$_2$—CH$_2$— or —CH$_2$—CH$_2$—CH$_2$—CH$_2$— groups in which up to two —CH$_2$— groups are optionally replaced by —O— and wherein the —CH$_2$—CH$_2$—CH$_2$— or —CH$_2$—CH$_2$—CH$_2$—CH$_2$-groups are optionally substituted by F, methyl or =O;

R11 is H, $(C_1-C_6)$-alkyl, $(C_2-C_6)$-alkenyl, $(C_2-C_6)$-alkynyl, $(C_3-C_7)$-cycloalkyl, $(CH_2)_q$—$[(C_3-C_6)$-cycloalkyl], $(CH_2)_n$-$[(C_7-C_{10})$-bicycloalkyl], $(CH_2)_n$-$[(C_3-C_6)$-cycloalkenyl], $(CH_2)_n$-$[(C_7-C_{10})$-bicycloalkenyl], $(CH_2)_n$-$[(C_7-C_{12})$-tricycloalkyl], $(CH_2)_n$-aryl, $(CH_2)_n$—CO—$[O—(C_1-C_6)$-alkyl], $(CH_2)_n$—CO—$[O—(C_3-C_6)$-cycloalkyl], $(CH_2)_n$—CO—$[(C_1-C_6)$-alkyl], $(CH_2)_n$—CO—$[(C_3-C_6)$-cycloalkyl], $(CH_2)_n$—CO-aryl, $(CH_2)_n$—CO-heteroaryl, $(CH_2)_n$—CO—$[O—(CH_2)_v$-aryl], $(CH_2)_n$—CO—$[O—(CH_2)_v$-heteroaryl], $(CH_2)_q$—CO—NH$_2$, $(CH_2)_q$—COOH, $(CH_2)_n$—P(O)(OH) $[O—(C_1-C_3)$-alkyl], $(CH_2)_n$—P(O)$[O—(C_1-C_3)$-alkyl]$_2$, $(CH_2)_n$—P(O)(OH)(O—CH$_2$-aryl), $(CH_2)_n$—P(O)(O—CH$_2$-aryl)$_2$, $(CH_2)_n$—P(O)(OH)$_2$, $(CH_2)_n$—SO$_3$H, $(CH_2)_n$—SO$_2$—NH$_2$, $(CH_2)_n$—CO—NH—$[(C_1-C_6)$-alkyl], $(CH_2)_n$—CO—N$[(C_1-C_6)$-alkyl]$_2$, $(CH_2)_n$—CO—NH—$[(C_3-C_6)$-cycloalkyl], $(CH_2)_n$—CO—N$[(C_3-C_6)$-cycloalkyl]$_2$, $(C_2-C_6)$-alkenyl-CO—O$[(C_1-C_6)$-alkyl], $(C_2-C_6)$-alkenyl-CONH$_2$, $(C_2-C_6)$-alkenyl-COOH, $(C_2-C_6)$-alkynyl-CO—O$[(C_1-C_6)$-alkyl], $(C_2-C_6)$-alkynyl-CONH$_2$, $(C_2-C_6)$-alkynyl-COOH, $(CH_2)_n$—CR21$[(CO—O(C_1-C_4)$-alkyl)]$_2$, $(CH_2)_n$—CR21(CONH$_2$)$_2$, $(CH_2)$—CR21(COOH)$_2$, $(CH_2)_n$—CR21R22CO—O$[(C_1-C_4)$-alkyl], $(CH_2)_n$—CR21R22CONH$_2$, $(CH_2)_n$—CR21R22COOH, $(CH_2)_n$—CO—R16, $(CH_2)_n$—C(CH$_3$)$_2$—CO—O$[(C_1-C_6)$-alkyl], $(CH_2)_n$—C(CH$_3$)$_2$—CO—O$[(C_3-C_6)$-cycloalkyl], $(CH_2)_n$—C(CH$_3$)$_2$—CO—O—$(CH_2)_n$-aryl, $(CH_2)_n$—C(CH$_3$)$_2$—CO—O—$(CH_2)_n$-heteroaryl, $(CH_2)_n$—C(CH$_3$)$_2$—CO—NH$_2$, $(CH_2)_n$—C(CH$_3$)$_2$—CO—NH—$[(C_1-C_6)$-alkyl], $(CH_2)_n$—C(CH$_3$)$_2$—CO—NH—$(CH_2)_r$—OH, $(CH_2)_n$—C(CH$_3$)$_2$—CO—N$[(C_1-C_6)$-alkyl]$_2$, $(CH_2)_n$—C(CH$_3$)$_2$—CO—NH—$[(C_3-C_6)$-cycloalkyl], $(CH_2)_n$—C(CH$_3$)$_2$—CO—N$[(C_3-C_6)$-cycloalkyl]$_2$, $(CH_2)_n$—C(CH$_3$)$_2$—COOH, $(CH_2)_n$—CO—NH—C(CH$_3$)$_2$—CO—O $[(C_1-C_6)$-alkyl], $(CH_2)_n$—CO—NH—C(CH$_3$)$_2$—CONH$_2$, $(CH_2)_n$—CO—NH—C(CH$_3$)$_2$—COOH, wherein the alkyl, alkenyl, alkynyl and cycloalkyl, bicycloalkyl, tricycloalkyl, cycloalkenyl and bicycloalkenyl radicals are optionally substituted by fluorine atoms and wherein the aryl or heteroaryl radical are optionally substituted by halogen, CN, $(C_1-C_6)$-alkyl, $(C_3-C_6)$-cycloalkyl, O—$(C_1-C_6)$-alkyl, $S(O)_m$—$(C_1-C_6)$-alkyl, $SO_2$—NH$_2$, COOH, CONH$_2$, CO—O$(C_1-C_6)$-alkyl, CO—$(C_1-C_6)$-alkyl, and wherein the alkyl radicals are optionally substituted by fluorine atoms;

R12 is H, $(C_1-C_6)$-alkyl, $(C_3-C_6)$-cycloalkyl, $(CH_2)_q$—$[(C_3-C_6)$-cycloalkyl], $(CH_2)_n$-$[(C_7-C_{10})$-bicycloalkyl], $(CH_2)_n$-$[(C_7-C_{10})$-tricycloalkyl], $(CH_2)_n$-aryl, $(CH_2)_n$-heteroaryl, wherein the alkyl, cycloalkyl, bicycloalkyl or tricycloalkyl radicals are optionally substituted by fluorine atoms, and wherein the aryl or heteroaryl radical are optionally substituted by halogen, CN, $(C_1-C_3)$-alkyl, O—$(C_1-C_3)$-alkyl, $SO_2$—NH$_2$, COOH, CONH$_2$, CO—O$(C_1-C_3)$-alkyl, CO—$(C_1-C_3)$-alkyl and wherein the alkyl radicals are optionally substituted by fluorine atoms;

R13 is H, $SO_2$—$[(C_1-C_6)$-alkyl], $SO_2$—$[(C_3-C_6)$-cycloalkyl], $SO_2$—$(CH_2)_n$-aryl, $SO_2$—$(CH_2)_n$-heteroaryl, $SO_2$—$(CH_2)_n$—NH—R12, $SO_2$—$(CH_2)_n$—N(R12)$_2$, wherein the alkyl and cycloalkyl radicals are optionally substituted by fluorine atoms and wherein the aryl or heteroaryl radical are optionally substituted by halogen, CN, $(C_1-C_3)$-alkyl, $(C_3-C_6)$-cycloalkyl, O—$[(C_1-C_3)$-alkyl], $S(O)_m$—$[(C_1-C_3)$-alkyl], $SO_2$—NH$_2$, COOH, CONH$_2$, CO—$[O(C_1-C_3)$-alkyl], CO—$(C_1-C_3)$-alkyl, and wherein the alkyl radicals are optionally substituted by fluorine atoms;

R16 is aziridine-1-yl, azetidin-1-yl, piperidin-1-yl, 3-hydroxypiperidin-1-yl, 4-hydroxypiperidin-1-yl, 3-oxopiperidin-1-yl, 4-oxopiperidin-1-yl, pyrrolidin-1-yl, 3-pyrrolidinol-1-yl, 2-cyanopyrrolidin-1-yl, morpholin-N-yl, piperazin-1-yl, 4-$[(C_1-C_3)$-alkyl]piperazin-1-yl, piperazin-2-on-1-yl, piperazin-2-on-4-yl, piperazine-2,6-dion-1-yl, piperazine-2,6-dion-4-yl, thiomorpholine-1,1-dioxide-4-yl, NH—$(CH_2)_r$—OH, NH—CH(CH$_2$OH)$_2$, NH—C(CH$_2$OH)$_3$, N$[(C_1-C_6)$-alkyl-OH]$_2$, D-glucamin-N-yl, N-methyl-D-glucamin-N-yl, NH—[($C_1$-$C_6$)-alkyl]-CO—O($C_1$-$C_3$)-alkyl, NH—[($C_1$-$C_3$)-alkyl]-COOH, NH—[($C_1$-$C_3$)-alkyl]-CONH$_2$, N[($C_1$-$C_3$)-alkyl][($C_1$-$C_3$)-alkyl]-CO—O($C_1$-$C_3$)-alkyl, N[($C_1$-$C_3$)-alkyl][($C_1$-$C_3$)-alkyl]-COOH, N[($C_1$-$C_3$)-alkyl][($C_1$-$C_3$)-alkyl]-CONH$_2$, NH—[C(H)(aryl)]-CO—O($C_1$-$C_3$)-alkyl, NH—[C(H)(aryl)]-COOH, NH—[C(H)(aryl)]-CONH$_2$, N[($C_1$-$C_3$)-alkyl][C(H)(aryl)]-CO—O($C_1$-$C_3$)-alkyl, N[($C_1$-$C_3$)-alkyl][C(H)(aryl)]-COOH, N[($C_1$-$C_3$)-alkyl][C(H)(aryl)]-CONH$_2$, NH—[C(H)(heteroaryl)]-CO—O($C_1$-$C_3$)-alkyl, NH—[C(H)(heteroaryl)]-COOH, NH—[C(H)(heteroaryl)]-CONH$_2$, N[($C_1$-$C_3$)-alkyl][C(H)(heteroaryl)]-CO—O($C_1$-$C_3$)-alkyl, N[($C_1$-$C_3$)-alkyl][C(H)(heteroaryl)]-COOH, N[($C_1$-$C_3$)-alkyl][C(H)(heteroaryl)]-CONH$_2$, N[($C_1$-$C_3$)-alkyl][($C_3$-$C_6$)-cycloalkyl]-CO—O($C_1$-$C_3$)-alkyl, N[($C_1$-$C_3$)-alkyl][($C_3$-$C_6$)-cycloalkyl]-COOH, N[($C_1$-$C_3$)-alkyl][($C_3$-$C_6$)-cycloalkyl]-CONH$_2$, NH—[($C_3$-$C_6$)-cycloalkyl]-CO—O($C_1$-$C_3$)-alkyl, NH—[($C_3$-$C_6$)-cycloalkyl]-COOH, NH—[($C_3$-$C_6$)-cycloalkyl]-CONH$_2$, NH—($CH_2$)$_r$—SO2—($C_1$-$C_3$)-alkyl, NH—[($C_1$-$C_4$)-alkyl]-SO$_3$H, NH—[($C_1$-$C_4$)-alkyl]-SO$_2$—NH$_2$, N[($C_1$-$C_4$)-alkyl]{[($C_1$-$C_4$)-alkyl]-SO$_3$H}, wherein the alcohol (OH) or ketone (C=O) functions are optionally replaced by F or $CF_2$;

R17 is R18, R13, ($CH_2$)$_n$—CO—[O—($C_1$-$C_3$)-alkyl], ($CH_2$)$_n$—CO—[O—($C_3$-$C_6$)-cycloalkyl], ($CH_2$)$_n$—CO—[($C_1$-$C_3$)-alkyl], ($CH_2$)$_n$—CO—[($C_3$-$C_6$)-cycloalkyl], ($CH_2$)$_n$—CO-aryl, ($CH_2$)$_n$—CO-heteroaryl, ($CH_2$)$_n$—CO—[O—($CH_2$)$_n$-aryl], ($CH_2$)$_n$—CO—NH$_2$, ($CH_2$)$_q$—COOH, wherein the alkyl and cycloalkyl radicals are optionally substituted by fluorine atoms and wherein the aryl or heteroaryl radical are optionally substituted by halogen, CN, ($C_1$-$C_3$)-alkyl, ($C_3$-$C_6$)-cycloalkyl, O—($C_1$-$C_3$)-alkyl, S(O)$_m$—($C_1$-$C_3$)-alkyl, SO$_2$—NH$_2$, COOH, CONH$_2$, CO—[O($C_1$-$C_3$)-alkyl], CO—($C_1$-$C_3$)-alkyl, and wherein the alkyl radicals are optionally substituted by fluorine atoms;

R18 is ($C_1$-$C_4$)-alkyl, ($C_3$-$C_6$)-cycloalkyl, ($CH_2$)$_q$—[($C_3$-$C_6$)-cycloalkyl], ($CH_2$)$_n$-aryl, ($CH_2$)$_n$-heteroaryl, wherein the alkyl and cycloalkyl radicals are optionally substituted by fluorine atoms and wherein the aryl or heteroaryl radical are optionally substituted by halogen, CN, ($C_1$-$C_3$)-alkyl, O—($C_1$-$C_3$)-alkyl, SO$_2$—NH$_2$, COOH, CONH$_2$, CO—[O($C_1$-$C_3$)-alkyl], CO—($C_1$-$C_6$)-alkyl, and
wherein the alkyl radicals are optionally substituted by fluorine atoms;

R20 is H, ($C_1$-$C_3$)-alkyl, ($C_3$-$C_6$)-cycloalkyl, aryl or [($C_1$-$C_6$)-alkyl]-aryl;

R21 is H, F, $CF_3$, ($C_1$-$C_3$)-alkyl, ($C_3$-$C_6$)-cycloalkyl, OH, O—($C_1$-$C_3$)-alkyl, O—($C_3$-$C_6$)-cycloalkyl, O—($CH_2$)$_n$-aryl, O—(CO)—($C_1$-$C_3$)-alkyl, O—(CO)—($C_3$-$C_6$)-cycloalkyl, O—(CO)—O—($C_1$-$C_3$)-alkyl, O—(CO)—O—($C_3$-$C_6$)-cycloalkyl, NH$_2$, NH—[($C_1$-$C_3$)-alkyl]-aryl, NH—($C_1$-$C_3$)-alkyl or NH—(CO)—($C_1$-$C_3$)-alkyl; and R22 is H, $CF_3$, ($C_1$-$C_3$)-alkyl, aryl or [($C_1$-$C_6$)-alkyl]-aryl; or a physiologically compatible salt thereof.

3. The compound of the formula I as claimed in claim 1, wherein:

R, R' are each independently ($C_1$-$C_3$)-alkyl wherein ($C_1$-$C_3$)-alkyl is optionally substituted by halogen or R and R' taken together with the carbon atom to which they are attached form a ring having three to six carbon atoms;

m is 0, 1 or 2;

n is 0, 1, 2 or 3;

p is 1, 2 or 3;

q is 1 or 2;

r is 2, 3 or 4;

v is 0, 1 or 2;

A, D, E, G, L are each independently C or N, where there is no corresponding R1, R2, R3, R4, R5 substituents when they are defined as N;

R1, R2, R3, R4, R5 are each independently H, F, Cl, Br, CN, $CF_3$, ($C_1$-$C_4$)-alkyl, ($C_3$-$C_6$)-cycloalkyl, ($CH_2$)$_q$—[($C_3$-$C_6$)-cycloalkyl], ($CH_2$)$_n$-[($C_7$-$C_{10}$)-bicycloalkyl], ($CH_2$)$_n$-[($C_7$-$C_{10}$)-tricycloalkyl], adamantan-1-yl, adamantan-2-yl, ($CH_2$)$_n$-aryl, ($CH_2$)$_n$-heteroaryl, $OCF_3$, O—($C_1$-$C_6$)-alkyl, O—($C_3$-$C_7$)-cycloalkyl, O—($CH_2$)$_n$-aryl, O—($CH_2$)$_n$-heteroaryl, NH—($C_1$-$C_4$)-alkyl, N[($C_1$-$C_4$)-alkyl]$_2$, NH-aryl, NH-heteroaryl, NH—SO$_2$—($C_1$-$C_4$)-alkyl, NH—SO$_2$-aryl, S(O)$_m$—($C_1$-$C_4$)-alkyl, S(O)$_m$—($C_3$-$C_6$)-cycloalkyl, S(O)$_m$-aryl, SO$_2$—NH$_2$, SO$_2$—NH—[($C_1$-$C_4$)-alkyl], SO$_2$—NH—[($C_3$-$C_6$)-cycloalkyl], SO$_2$—NH—($CH_2$)$_n$-aryl, SO$_2$—N[($C_1$-$C_4$)-alkyl]$_2$, SF$_5$, CO—O[($C_1$-$C_4$)-alkyl], CO—NH$_2$, CO—NH—[($C_1$-$C_4$)-alkyl], CO—N[($C_1$-$C_4$)-alkyl]$_2$, C(=NH)—NH$_2$, C(=N—OH)NH$_2$, COOH, CO—($C_1$-$C_6$)-alkyl, CO—($C_3$-$C_6$)-cycloalkyl, CO-aryl, CO-heteroaryl, CH(OH)-aryl, CH(OH)-heteroaryl, CH[O—($C_1$-$C_4$)-alkyl]-aryl, CH[O—($C_1$-$C_4$)-alkyl]-heteroaryl, CHF-aryl, CHF-heteroaryl, $CF_2$-aryl, wherein the alkyl, cycloalkyl, bicycloalkyl and tricycloalkyl radicals are optionally substituted by fluorine atoms and wherein the aryl or heteroaryl radicals are optionally substituted by halogen, CN, ($C_1$-$C_4$)-alkyl, ($C_3$-$C_6$)-cycloalkyl, O—($C_1$-$C_4$)-alkyl, S(O)$_m$—($C_1$-$C_3$)-alkyl, SO$_2$—NH$_2$, COOH, CONH$_2$, CO—O($C_1$-$C_3$)-alkyl, CO—($C_1$-$C_3$)-alkyl, and wherein the alkyl radicals are optionally substituted by fluorine atoms;

R6, R7, R8, R9, R10 are each independently NR17-bicyclic heterocycle, NR17-aryl, NR17-heteroaryl, wherein the aryl or heteroaryl radical is optionally fused to a 5- or 6-membered aromatic or nonaromatic carbon ring in which one or more CH or $CH_2$ groups are optionally replaced by oxygen atoms and wherein the 5- or 6-membered aromatic or nonaromatic carbon ring is optionally substituted by F, =O or —($C_1$-$C_6$)-alkyl and wherein the bicyclic heterocycle contains from 9 to 10 ring members and up to five CH or $CH_2$ groups each independently optionally be replaced by N, NR20, O, S(O)$_m$ or C=O and wherein the aryl or heteroaryl radical or bicyclic heterocycle is unsubstituted or optionally mono- or polysubstituted by R11, F, Cl, Br, CN, NO$_2$, $CF_3$, ($CH_2$)$_n$—O—R11, ($CH_2$)$_n$—O—($CH_2$)$_r$—OH, ($CH_2$)$_n$—O—CH($CH_2$OH)$_2$, ($CH_2$)$_n$—O—($CH_2$)$_n$—CO—O—($CH_2$)$_r$—NH$_2$, ($CH_2$)$_n$—O-sugar acid, ($CH_2$)$_n$—O-glucoside, ($CH_2$)$_n$—O-galactoside, ($CH_2$)$_n$—O-glucuronide, $OCF_3$, O—R13, ($CH_2$)$_n$—O—($CH_2$)$_r$—NH$_2$, ($CH_2$)$_n$—NH—R1, ($CH_2$)$_n$—N[($CH_2$)$_q$—CO—O($C_1$-$C_4$)-alkyl]$_2$, ($CH_2$)$_n$—N[($CH_2$)$_q$—COOH]$_2$, ($CH_2$)$_n$—N[($CH_2$)$_q$—CONH$_2$]$_2$, ($CH_2$)$_n$—NH—R13, ($CH_2$)$_n$—N(R13)$_2$, ($CH_2$)$_n$—NH—SO$_2$—R16, ($CH_2$)$_n$—NH—($CH_2$)$_n$—SO$_2$—R12, ($CH_2$)$_n$—NR12—CO—R16, ($CH_2$)$_n$—NR12—CO—NR12R13, ($CH_2$)$_n$—NR12—CO—N(R12)$_2$, ($CH_2$)$_n$—NR12—CO—NHR11, ($CH_2$)$_n$—NH—C(=NH)—NH$_2$, ($CH_2$)$_n$—NH—C(=NH)—R16, ($CH_2$)$_n$—NH—C(=NH)—NHR12, ($CH_2$)$_n$—NR12—C(=NR13)—NHR12, ($CH_2$)$_n$—NR12—C(=NR12)—NR12R13, ($CH_2$)$_n$—NH—($CH_2$)$_n$—

CO—O—(CH$_2$)$_r$—NH$_2$, (CH$_2$)$_n$—NH—(CH$_2$)$_n$—CO—NH—[(C$_1$-C$_8$)-alkyl], (CH$_2$)$_n$—NH—(CH$_2$)$_n$—CO—NH—(CH$_2$)$_r$—OH, (CH$_2$)$_n$—NH—(CH$_2$)$_n$—CO—N[(C$_1$-C$_8$)-alkyl]$_2$, (CH$_2$)$_n$—NH—(CH$_2$)$_n$—CO—NH—[(C$_3$-C$_8$)-cycloalkyl], (CH$_2$)$_n$—NH—C(CH$_3$)$_2$—CO—O(C$_1$-C$_8$)-alkyl, (CH$_2$)$_n$—NH—C(CH$_3$)$_2$—CO—O—(CH$_2$)$_r$—NH$_2$, (CH$_2$)$_n$—NH—C(CH$_3$)$_2$—CO—NH$_2$, (CH$_2$)$_2$—NH—C(CH$_3$)$_2$—CO—NH—(CH$_2$)$_r$—OH, (CH$_2$)$_n$—NH—C(CH$_3$)$_2$—COOH, S(O)$_m$—R12, SO$_2$—R16, SO$_2$—N=CH—N(CH$_3$)$_2$, SO$_2$—NH—CO—R12, SO$_2$—NHR12, SO$_2$—NH—(CH$_2$)$_r$—OH, SO$_2$—N[(C$_1$-C$_8$)-alkyl]$_2$, SO$_2$—NH—(CH$_2$)$_r$—NH$_2$, SF$_5$, COOH, CO—NH$_2$, (CH$_2$)$_q$—CN, (CH$_2$)$_n$—CO—NH-piperidin-1-yl, (CH$_2$)$_n$—CO—NH—SO$_2$—NHR12, (CH$_2$)$_n$—CO—NH—SO$_2$—R18, (CH$_2$)$_n$—C(=NH)NH$_2$, (CH$_2$)$_n$—C(=NH)—NHOH, C(=NH)—[NH—O—(C$_1$-C$_6$)-alkyl], (CH$_2$)$_n$—C(=NH)(R16), (CH$_2$)$_n$—C(=NR13)NHR12, (CH$_2$)$_n$—C(=NR12)NR12R13, (CH$_2$)$_n$—C(=NH)O[(C$_1$-C$_6$)-alkyl], wherein the alkyl and cycloalkyl radicals are optionally substituted by fluorine atoms and wherein the aryl or heteroaryl radicals are optionally substituted by halogen, CN, (C$_1$-C$_6$)-alkyl, (C$_3$-C$_6$)-cycloalkyl, O—(C$_1$-C$_6$)-alkyl, S(O)$_m$—(C$_1$-C$_6$)-alkyl, SO$_2$—NH$_2$, COOH, CONH$_2$, CO—O(C$_1$-C$_6$)-alkyl, CO—(C$_1$-C$_6$)-alkyl, and wherein the alkyl radicals are optionally substituted by F, Cl, Br, CN, CF$_3$, (C$_1$-C$_6$)-alkyl, (C$_2$-C$_6$)-alkenyl, (C$_2$-C$_6$)-alkynyl, (C$_3$-C$_7$)-cycloalkyl, (CH$_2$)$_n$—OH, (CH$_2$)$_n$—O—(C$_1$-C$_4$)-alkyl, (CH$_2$)$_n$—O—(C$_3$-C$_6$)-cycloalkyl, (CH$_2$)$_n$—O-aryl, (CH$_2$)$_n$—O-glucoside, (CH$_2$)$_n$—O-glucuronide, OCF$_3$, O—R13, (CH$_2$)$_n$—NH-aryl, (CH$_2$)$_n$—NH—SO$_2$—(C$_1$-C$_4$)-alkyl, (CH$_2$)$_n$—NH—SO$_2$-aryl, (CH$_2$)$_n$—NH—CO—NH$_2$, (CH$_2$)$_n$—NH—CO—NH—(C$_1$-C$_4$)-alkyl, (CH$_2$)$_n$—NH—CO—NH—(C$_3$-C$_6$)-cycloalkyl, (CH$_2$)$_n$—NH—C(=NH)—NH$_2$, S(O)$_m$—(C$_1$-C$_4$)-alkyl, S(O)$_m$-aryl, SO$_2$—NH$_2$, SO$_2$—NH—(C$_1$-C$_4$)-alkyl, SO$_2$—N[C$_1$-C$_4$]-alkyl]$_2$, SF$_5$, (CH$_2$)$_n$—CO—[O—(C$_1$-C$_4$)-alkyl], COOH, (CH$_2$)$_q$—COOH, CONH$_2$, (CH$_2$)$_q$—CONH$_2$, (CH$_2$)$_n$—C(=NH)NH$_2$, (CH$_2$)$_n$—C(=NH)NHOH, wherein the alkyl and cycloalkyl radicals are optionally substituted by fluorine atoms and wherein the aryl or heteroaryl radicals are optionally substituted by halogen, CN, (C$_1$-C$_3$)-alkyl, (C$_3$-C$_6$)-cycloalkyl, O—(C$_1$-C$_4$)-alkyl, S(O)$_m$—(C$_1$-C$_3$)-alkyl, SO$_2$—NH$_2$, COOH, CONH$_2$, CO—[O(C$_1$-C$_3$)-alkyl] and wherein the alkyl radicals are optionally substituted by fluorine atoms;

wherein one of the R6, R7, R8, R9 and R10 radicals is always defined as NR17-aryl or NR17-bicyclic heterocycle or NR17-heteroaryl;

R11 is H, (C$_1$-C$_4$)-alkyl, (C$_2$-C$_3$)-alkenyl, (C$_2$-C$_4$)-alkynyl, (C$_3$-C$_5$)-cycloalkyl, (CH$_2$)$_q$—[(C$_3$-C$_4$)-cycloalkyl], (CH$_2$)$_n$-[(C$_7$-C$_{10}$)-bicycloalkyl], (CH$_2$)$_n$-[(C$_3$-C$_6$)-cycloalkenyl], (CH$_2$)$_n$-[(C$_7$-C$_8$)-bicycloalkenyl], (CH$_2$)$_n$-[(C$_7$-C$_8$)-tricycloalkyl], (CH$_2$)$_n$-aryl, (CH$_2$)$_n$—CO—[O—(C$_1$-C$_4$)-alkyl], (CH$_2$)$_n$—CO—[O—(C$_3$-C$_5$)-cycloalkyl], (CH$_2$)$_n$—CO—[(C$_1$-C$_3$)-alkyl], (CH$_2$)$_n$—CO—[(C$_3$-C$_5$)-cycloalkyl], (CH$_2$)$_n$—CO-aryl, (CH$_2$)$_n$—CO-heteroaryl, (CH$_2$)$_n$—CO—[O—(CH$_2$)$_v$-aryl], (CH$_2$)$_n$—CO—[O—(CH$_2$)$_v$-heteroaryl], (CH$_2$)$_q$—CO—NH$_2$, (CH$_2$)$_q$—COOH, (CH$_2$)$_n$—P(O)(OH)[O—(C$_1$-C$_3$)-alkyl], (CH$_2$)$_n$—P(O)[O—(C$_1$-C$_3$)-alkyl]$_2$, (CH$_2$)$_n$—P(O)(OH)(O—CH$_2$-aryl), (CH$_2$)$_n$—P(O)(O—CH$_2$-aryl)$_2$, (CH$_2$)$_n$—P(O)(OH)$_2$, (CH$_2$)$_n$—SO$_3$H, (CH$_2$)$_n$—SO$_2$—NH$_2$, (CH$_2$)$_n$—CO—NH—[(C$_1$-C$_6$)-alkyl], (CH$_2$)$_n$—CO—N [(C$_1$-C$_4$)-alkyl]$_2$, (CH$_2$)$_n$—CO—NH—[(C$_3$-C$_5$)-cycloalkyl], (CH$_2$)$_n$—CO—N[(C$_3$-C$_4$)-cycloalkyl]$_2$, (C$_2$-C$_4$)-alkenyl-CO—O [(C$_1$-C$_4$)-alkyl], (C$_2$-C$_4$)-alkenyl-CONH$_2$, (C$_2$-C$_4$)-alkenyl-COOH, (C$_2$-C$_4$)-alkynyl-CO—O[(C$_1$-C$_6$)-alkyl], (C$_2$-C$_4$)-alkynyl-CONH$_2$, (C$_2$-C$_4$)-alkynyl-COOH, (CH$_2$)$_n$—CR21-[(CO—O(C$_1$-C$_4$)-alkyl)]$_2$, (CH$_2$)$_n$—CR21(CONH$_2$)$_2$, (CH$_2$)$_n$—CR21(COOH)$_2$, (CH$_2$)$_n$—CR21R22CO—O[(C$_1$-C$_4$)-alkyl], (CH$_2$)$_n$—CR21R22CONH$_2$, (CH$_2$)$_n$—CR21R22COOH, (CH$_2$)$_n$—CO—R16, (CH$_2$)$_n$—C(CH$_3$)$_2$—CO—O[(C$_1$-C$_3$)-alkyl], (CH$_2$)$_n$—C(CH$_3$)$_2$—CO—O[(C$_3$-C$_5$)-cycloalkyl], (CH$_2$)$_n$—C(CH$_3$)$_2$—CO—NH$_2$, (CH$_2$)$_n$—C(CH$_3$)$_2$—CO—NH—[(C$_1$-C$_3$)-alkyl], (CH$_2$)$_n$—C(CH$_3$)$_2$—CO—NH—(CH$_2$)$_r$—OH, (CH$_2$)$_n$—C(CH$_3$)$_2$—CO—NH—[(C$_3$-C$_5$)-cycloalkyl], (CH$_2$)$_n$—CO—NH—C(CH$_3$)$_2$—CO—O[(C$_1$-C$_4$)-alkyl], (CH$_2$)$_n$—C(CH$_3$)$_2$—COOH, (CH$_2$)$_n$—CO—NH—C(CH$_3$)$_2$—CONH$_2$, (CH$_2$)$_n$—CO—NH—C(CH$_3$)$_2$—COOH, wherein the alkyl, alkenyl, alkynyl and cycloalkyl, bicycloalkyl, cycloalkenyl, bicycloalkenyl and tricycloalkyl radicals are optionally substituted by fluorine atoms and wherein the aryl or heteroaryl radical is optionally substituted by halogen, CN, (C$_1$-C$_4$)-alkyl, (C$_3$-C$_6$)-cycloalkyl, O—(C$_1$-C$_4$)-alkyl, S(O)$_m$—(C$_1$-C$_4$)-alkyl, SO$_2$—NH$_2$, COOH, CONH$_2$, CO—O(C$_1$-C$_4$)-alkyl, CO—(C$_1$-C$_3$)-alkyl, and wherein the alkyl radicals are optionally substituted by fluorine atoms;

R12 is H, (C$_1$-C$_3$)-alkyl, (C$_3$-C$_5$)-cycloalkyl, (CH$_2$)$_q$—[(C$_3$-C$_5$)-cycloalkyl], (CH$_2$)$_n$-[(C$_7$-C$_8$)-bicycloalkyl], (CH$_2$)$_n$-[(C$_7$-C$_8$)-tricycloalkyl], (CH$_2$)$_n$-aryl, (CH$_2$)$_n$-heteroaryl, wherein the alkyl, cycloalkyl, bicycloalkyl or tricycloalkyl radicals may be substituted by fluorine atoms, and wherein the aryl or heteroaryl radical are optionally substituted by halogen, CN, (C$_1$-C$_3$)-alkyl, O—(C$_1$-C$_3$)-alkyl, SO$_2$—NH$_2$, COOH, CONH$_2$, CO—O(C$_1$-C$_3$)-alkyl, CO—(C$_1$-C$_3$)-alkyl and wherein the alkyl radicals are optionally substituted by fluorine atoms;

R13 is H, SO$_2$—[(C$_1$-C$_3$)-alkyl], SO$_2$—[(C$_3$-C$_5$)-cycloalkyl], SO$_2$—(CH$_2$)$_n$-aryl, SO$_2$—(CH$_2$)$_n$-heteroaryl, SO$_2$—(CH$_2$)$_n$—NH—R12, SO$_2$—(CH$_2$)$_n$—N(R12)$_2$, wherein the alkyl and cycloalkyl radicals are optionally substituted by fluorine atoms and wherein the aryl or heteroaryl radical is optionally substituted by halogen, CN, (C$_1$-C$_3$)-alkyl, (C$_3$-C$_6$)-cycloalkyl, O—[(C$_1$-C$_3$)-alkyl], S(O)$_m$—[(C$_1$-C$_3$)-alkyl], SO$_2$—NH$_2$, COOH, CONH$_2$, CO—[O(C$_1$-C$_3$)-alkyl], CO—(C$_1$-C$_3$)-alkyl, and wherein the alkyl radicals are optionally substituted by fluorine atoms;

R16 is aziridine-1-yl, azetidin-1-yl, piperidin-1-yl, 4-hydroxypiperidin-1-yl, 3-oxopiperidin-1-yl, 4-oxopiperidin-1-yl, pyrrolidin-1-yl, 3-pyrrolidinol-1-yl, 2-cyanopyrrolidin-1-yl, morpholin-N-yl, piperazin-1-yl, 4-[(C$_1$-C$_3$)-alkyl]piperazin-1-yl, piperazin-2-on-1-yl, piperazin-2-on-4-yl, thiomorpholine-1,1-dioxide-4-yl, NH—(CH$_2$)$_r$—OH, NH—CH(CH$_2$OH)$_2$, NH—C(CH$_2$OH)$_3$, N[(C$_1$-C$_3$)-alkyl-OH]$_2$, D-glucamin-N-yl, N-methyl-D-glucamin-N-yl, NH—[(C$_1$-C$_3$)-alkyl]-CO—O(C$_1$-C$_3$)-alkyl, NH—[(C$_1$-C$_3$)-alkyl]-COOH, NH—[(C$_1$-C$_3$)-alkyl]-CONH$_2$, NH—[C(H)(aryl)]-CO—O(C$_1$-C$_3$)-alkyl, NH—[C(H)(aryl)]-COOH, NH—[C(H)(aryl)]-CONH$_2$, NH—[C(H)(heteroaryl)]-

CO—O($C_1$-$C_3$)-alkyl, NH—[C(H)(heteroaryl)]-COOH, NH—[C(H)(heteroaryl)]-CONH$_2$, NH—[($C_3$-$C_6$)-cycloalkyl]-CO—O($C_1$-$C_3$)-alkyl, NH—[($C_3$-$C_6$)-cycloalkyl]-COOH, NH—[($C_3$-$C_6$)-cycloalkyl]-CONH$_2$, NH—(CH$_2$)—SO2—($C_1$-$C_3$)-alkyl, NH—[($C_1$-$C_4$)-alkyl]-SO$_3$H, NH—[($C_1$-$C_4$)-alkyl]-SO$_2$—NH$_2$, N[($C_1$-$C_3$)-alkyl]{[($C_1$-$C_4$)-alkyl]-SO$_3$H}, wherein the alcohol (OH) or ketone (C=O) functions are optionally replaced by F or CF$_2$;

R17 is R18, H, SO$_2$—CH$_3$, SO$_2$-aryl, (CH$_2$)$_n$—CO—[O—($C_1$-$C_3$)-alkyl], (CH$_2$)$_n$—CO—[($C_1$-$C_3$)-alkyl], (CH$_2$)$_n$—CO-aryl, (CH$_2$)$_n$—CO—NH$_2$, (CH$_2$)$_q$—COOH, wherein the alkyl radicals are optionally substituted by fluorine atoms and wherein the aryl or heteroaryl radical is optionally substituted by halogen, CN, ($C_1$-$C_3$)-alkyl, O—($C_1$-$C_3$)-alkyl, S(O)$_m$—($C_1$-$C_3$)-alkyl, SO$_2$—NH$_2$, COOH, CONH$_2$, CO—[O($C_1$-$C_3$)-alkyl], CO—($C_1$-$C_3$)-alkyl, and wherein the alkyl radicals are optionally substituted by fluorine atoms;

R18 is ($C_1$-$C_4$)-alkyl, ($C_3$-$C_4$)-cycloalkyl, (CH$_2$)$_n$-aryl, (CH$_2$)$_n$-heteroaryl, wherein the alkyl and cycloalkyl radicals are optionally substituted by fluorine atoms and wherein the aryl or heteroaryl radical is optionally substituted by halogen, CN, ($C_1$-$C_3$)-alkyl, O—($C_1$-$C_3$)-alkyl, SO$_2$—NH$_2$, COOH, CONH$_2$, CO—[O($C_1$-$C_{63}$)-alkyl], CO—($C_1$-$C_3$)-alkyl, and wherein the alkyl radicals are optionally substituted by fluorine atoms;

R20 is H, ($C_1$-$C_3$)-alkyl, ($C_3$-$C_6$)-cycloalkyl, aryl or [($C_1$-$C_3$)-alkyl]-aryl;

R21 is H, F, CF$_3$, ($C_1$-$C_3$)-alkyl, ($C_3$-$C_4$)-cycloalkyl, OH, O—($C_1$-$C_3$)-alkyl, O—($C_3$-$C_4$)-cycloalkyl, O—(CH$_2$)$_n$-aryl, O—(CO)—($C_1$-$C_3$)-alkyl, O—(CO)—($C_3$-$C_4$)-cycloalkyl, O—(CO)—O—($C_1$-$C_3$)-alkyl, O—(CO)—O—($C_3$-$C_4$)-cycloalkyl, NH$_2$, NH—[($C_1$-$C_2$)-alkyl]-aryl, NH—($C_1$-$C_3$)-alkyl or NH—(CO)—($C_1$-$C_3$)-alkyl; and R22 is H, CF$_3$, ($C_1$-$C_3$)-alkyl, aryl or [($C_1$-$C_3$)-alkyl]-aryl; or a physiologically compatible salt thereof.

4. The compound of the formula I as claimed in claim 1, wherein:

R, R' are each independently ($C_1$-$C_3$)-alkyl; or R and R' taken together with the carbon atom to which they are attached form a ring having from three to six carbon atoms;

m is 0, 1 or 2;
n is 0, 1 or 2;
p is 1 or 2;
q is 1 or 2;
r is 2 or 3;
v is 0 or 1;

A, D, E, G, L are each independently C or N, where there is no corresponding R1, R2, R3, R4, R5 substituent when they are defined as N;

R1, R2, R3, R4, R5 are each independently H, F, Cl, Br, CN, CF$_3$, ($C_1$-$C_4$)-alkyl, ($C_3$-$C_6$)-cycloalkyl, (CH$_2$)$_q$—[($C_3$-$C_6$)-cycloalkyl], adamantan-1-yl, adamantan-2-yl, (CH$_2$)$_n$-aryl, (CH$_2$)$_n$-heteroaryl, OCF$_3$, O—($C_1$-$C_4$)-alkyl, O—($C_3$-$C_6$)-cycloalkyl, O—(CH$_2$)$_n$-aryl, O—(CH$_2$)$_n$-heteroaryl, NH—($C_1$-$C_4$)-alkyl, N[($C_1$-$C_4$)-alkyl]$_2$, NH-aryl, NH-heteroaryl, NH—SO$_2$—($C_1$-$C_4$)-alkyl, NH—SO$_2$-aryl, S(O)$_m$—($C_1$-$C_3$)-alkyl, S(O)$_m$—($C_3$-$C_6$)-cycloalkyl, S(O)$_m$-aryl, SO$_2$—NH$_2$, SO$_2$—NH—[($C_1$-$C_4$)-alkyl], SO$_2$—NH—[($C_3$-$C_6$)-cycloalkyl], SO$_2$—NH—(CH$_2$)$_n$-aryl, SO$_2$—N[($C_1$-$C_4$)-alkyl]$_2$, SF$_5$, CO—O[($C_{1-4}$)-alkyl], CO—NH$_2$, CO—NH—[($C_1$-$C_3$)-alkyl], CO—N[($C_1$-$C_3$)-alkyl]$_2$, COOH, CO—($C_1$-$C_3$)-alkyl, CO—($C_3$-$C_6$)-cycloalkyl, CO-aryl, CO-heteroaryl, CH(OH)-aryl, CH(OH)-heteroaryl, CH[O—($C_1$-$C_4$)-alkyl]-aryl, CH[O—($C_1$-$C_4$)-alkyl]-heteroaryl, CHF-aryl, CHF-heteroaryl, CF$_2$-aryl, wherein the alkyl or cycloalkyl radicals are optionally substituted by fluorine atoms and wherein the aryl or heteroaryl radicals are optionally substituted by halogen, CN, ($C_1$-$C_3$)-alkyl, O—($C_1$-$C_4$)-alkyl, S(O)$_m$—($C_1$-$C_3$)-alkyl, SO$_2$—NH$_2$, COOH, CONH$_2$, CO—O($C_1$-$C_3$)-alkyl, CO—($C_1$-$C_3$)-alkyl, and wherein the alkyl radicals are optionally substituted by fluorine atoms;

R6, R7, R8, R9, R10 are each independently NR17-bicyclic heterocycle, NR17-aryl, NR17-heteroaryl, wherein the aryl or heteroaryl radical are optionally fused to a 5- or 6-membered aromatic or nonaromatic carbon ring in which one or more CH or CH$_2$ groups are optionally replaced by oxygen atoms and wherein the 5- or 6-membered aromatic or nonaromatic carbon ring is optionally substituted by F, =O or —($C_1$-$C_3$)-alkyl and wherein the bicyclic heterocycle contains from 9 to 10 ring members and up to five CH or CH$_2$ groups each independently optionally be replaced by N, NR20, O, S(O)$_m$ or C=O and wherein the aryl or heteroaryl radical or bicyclic heterocycle is unsubstituted or optionally mono- or polysubstituted by R11, F, Cl, Br, CN, NO$_2$, CF$_3$, (CH$_2$), O—R11, (CH$_2$)$_n$—O—(CH$_2$)$_r$—OH, (CH$_2$)$_n$—O—CH(CH$_2$OH)$_2$, (CH$_2$)$_n$—O—(CH$_2$)$_n$—CO—O—(CH$_2$)$_r$—NH$_2$, (CH$_2$)$_n$—O-glucoside, (CH$_2$)$_n$—O-galactoside, (CH$_2$)$_n$—O-glucuronide, OCF$_3$, O—R13, (CH$_2$)$_n$—O—(CH$_2$)$_r$—NH$_2$, (CH$_2$)$_n$—NH—R11, (CH$_2$)$_n$—N[(CH$_2$)$_q$—CO—O($C_1$-$C_4$)-alkyl]$_2$, (CH$_2$)$_n$—N[(CH$_2$)$_q$—COOH]$_2$, (CH$_2$)$_n$—N[(CH$_2$)$_q$—CONH$_2$]$_2$, (CH$_2$)$_n$—NH—R13, (CH$_2$)$_n$—N(R13)$_2$, (CH$_2$)$_n$—NH—SO$_2$—R16, (CH$_2$)$_n$—NH—(CH$_2$)$_n$—SO$_2$—R12, (CH$_2$)$_n$—NR12—CO—R16, (CH$_2$)$_n$—NR12—CO—NR12R13, (CH$_2$)$_n$—NR12—CO—N(R12)$_2$, (CH$_2$)$_n$—NR12—CO—NHR11, (CH$_2$)$_n$—NH—C(=NH)—R16, (CH$_2$)$_n$—NR12—C(=NR13)—NHR12, (CH$_2$)$_n$—NR12—C(=NR12)—NR12R13, (CH$_2$)$_n$—NH—(CH$_2$)$_n$—CO—O—(CH$_2$)$_r$—NH$_2$, (CH$_2$)$_n$—NH—(CH$_2$)$_n$—CO—NH—[($C_1$-$C_3$)-alkyl], (CH$_2$)$_n$—NH—(CH$_2$)$_n$—CO—NH—(CH$_2$)$_r$—OH, (CH$_2$)$_n$—NH—(CH$_2$)$_n$—CO—N[($C_1$-$C_3$)-alkyl]$_2$, (CH$_2$)$_n$—NH—(CH$_2$)$_n$—CO—NH—[($C_3$-$C_5$)-cycloalkyl], (CH$_2$)$_n$—NH—C(CH$_3$)$_2$—CO—O($C_1$-$C_4$)-alkyl, (CH$_2$)$_n$—NH—C(CH$_3$)$_2$—CO—O—(CH$_2$)$_r$—NH$_2$, (CH$_2$)$_n$—NH—C(CH$_3$)$_2$—CO—NH$_2$, (CH$_2$)$_n$—NH—C(CH$_3$)$_2$—CO—NH—(CH$_2$)$_r$—OH, (CH$_2$)$_n$—NH—C(CH$_3$)$_2$—COOH, S(O)$_m$—R12, SO$_2$—R16, SO$_2$—N=CH—N(CH$_3$)$_2$, SO$_2$—NH—CO—R12, SO$_2$—NHR12, SO$_2$—NH—(CH$_2$)$_r$—OH, SO$_2$—N[($C_1$-$C_3$)-alkyl]$_2$, SO$_2$—NH—(CH$_2$)$_r$—NH$_2$, SF$_5$, COOH, CO—NH$_2$, (CH$_2$)$_q$—CN, (CH$_2$)$_n$—CO—NH-piperidin-1-yl, (CH$_2$)$_n$—CO—NH—SO$_2$—NHR12, (CH$_2$)$_n$—CO—NH—SO$_2$—R18, (CH$_2$)$_n$—C(=NH)—NHOH, C(=NH)—[NH—O—($C_1$-$C_3$)-alkyl], (CH$_2$)$_n$—C(=NH)(R16), (CH$_2$)$_n$—C(=NR12)NR12R13, (CH$_2$)$_n$—C(=NH)O[($C_1$-$C_3$)-alkyl], wherein the alkyl and cycloalkyl radicals are optionally substituted by fluorine atoms and wherein the aryl or heteroaryl radicals are optionally substituted by halogen, CN, ($C_1$-$C_3$)-alkyl, ($C_3$-$C_6$)-cycloalkyl, O—($C_1$-$C_3$)-alkyl, S(O)$_m$—($C_1$-$C_3$)-alkyl, SO$_2$—NH$_2$, COOH, CONH$_2$, CO—O($C_1$-$C_3$)- alkyl, CO—($C_1$-$C_3$)-alkyl, and wherein the alkyl radicals are optionally substituted by H, F, Cl, Br, CN, $CF_3$, ($C_1$-$C_6$)-alkyl, ($C_3$-$C_7$)-cycloalkyl, $(CH_2)_n$—OH, $(CH_2)_n$—O—($C_1$-$C_4$)-alkyl, $(CH_2)_n$—O—($C_3$-$C_6$)-cycloalkyl, $(CH_2)_n$—O-aryl, $(CH_2)_n$—O-glucoside, $(CH_2)_n$—O-glucuronide, $OCF_3$, O—R13, $(CH_2)_n$—NH-aryl, $(CH_2)_n$—NH—$SO_2$—($C_1$-$C_4$)-alkyl, $(CH_2)_n$—NH—$SO_2$-aryl, $(CH_2)_n$—NH—CO—$NH_2$, $(CH_2)_n$—NH—CO—NH—($C_1$-$C_3$)-alkyl, $(CH_2)_n$—NH—CO—NH—($C_3$-$C_6$)-cycloalkyl, $(CH_2)_n$—NH—C(=NH)—$NH_2$, $S(O)_m$—($C_1$-$C_4$)-alkyl, $S(O)_m$-aryl, $SO_2$—$NH_2$, $SO_2$—NH—($C_1$-$C_3$)-alkyl, $SO_2$—N[$C_1$-$C_3$]-alkyl]$_2$, $SF_5$, $(CH_2)_n$—CO—[O—($C_1$-$C_4$)-alkyl], $(CH_2)_n$—COOH, $(CH_2)_n$—$CONH_2$, $(CH_2)_n$—C(=NH)$NH_2$, wherein the alkyl and cycloalkyl radicals are optionally substituted by fluorine atoms and wherein the aryl or heteroaryl radicals are optionally substituted by halogen, CN, ($C_1$-$C_3$)-alkyl, ($C_3$-$C_6$)-cycloalkyl, O—($C_1$-$C_4$)-alkyl, $S(O)_m$—($C_1$-$C_3$)-alkyl, $SO_2$—$NH_2$, COOH, $CONH_2$, CO—[O($C_1$-$C_3$)-alkyl], and where the alkyl radicals are optionally substituted by fluorine atoms;

where at least one of the R6, R7, R8, R9 and R10 radicals is always defined as NR17-aryl or NR17-bicyclic heterocycle or NR17-heteroaryl;

R11 is H, ($C_1$-$C_4$)-alkyl, ($C_3$-$C_5$)-cycloalkyl, $(CH_2)_q$—[($C_3$-$C_4$)-cycloalkyl], $(CH_2)_n$—[($C_7$-$C_8$)-bicycloalkyl], $(CH_2)_n$—[($C_7$-$C_8$)-tricycloalkyl], $(CH_2)_n$-aryl, $(CH_2)_n$—CO—[O—($C_1$-$C_4$)-alkyl], $(CH_2)_n$—CO—[O—($C_3$-$C_5$)-cycloalkyl], $(CH_2)_n$—CO—[($C_1$-$C_3$)-alkyl], $(CH_2)_n$—CO—[($C_3$-$C_5$)-cycloalkyl], $(CH_2)_n$—CO-aryl, $(CH_2)_n$—CO-heteroaryl, $(CH_2)_n$—CO—[O—$(CH_2)_v$-aryl], $(CH_2)_n$—CO—[O—$(CH_2)_v$-heteroaryl], $(CH_2)_q$—CO—$NH_2$, $(CH_2)_q$—COOH, $(CH_2)_n$—P(O)(OH)[O—($C_1$-$C_3$)-alkyl], $(CH_2)_n$—P(O)[O—($C_1$-$C_3$)-alkyl]$_2$, $(CH_2)_n$—P(O)(OH)(O—$CH_2$-aryl), $(CH_2)_n$—P(O)(O—$CH_2$-aryl)$_2$, $(CH_2)_n$—P(O)(OH)$_2$, $(CH_2)_n$—$SO_3H$, $(CH_2)_n$—$SO_2$—$NH_2$, $(CH_2)_n$—CO—NH—[($C_1$-$C_3$)-alkyl], $(CH_2)_n$—CO—N[($C_1$-$C_3$)-alkyl]$_2$, $(CH_2)_n$—CO—NH—[($C_3$-$C_5$)-cycloalkyl], ($C_2$-$C_3$)-alkenyl-CO—O[($C_1$-$C_4$)-alkyl], ($C_2$-$C_3$)-alkenyl-$CONH_2$, ($C_2$-$C_3$)-alkenyl-COOH, ($C_2$-$C_4$)-alkynyl-CO—O[($C_1$-$C_4$)-alkyl], ($C_2$-$C_4$)-alkynyl-$CONH_2$, ($C_2$-$C_4$)-alkynyl-COOH, $(CH_2)_n$—CR21-[(CO—O($C_1$-$C_4$)-alkyl)]$_2$, $(CH_2)_n$—CR21($CONH_2$)$_2$, $(CH_2)_n$—CR21(COOH)$_2$, $(CH_2)_n$—CR21R22CO—O[($C_1$-$C_4$)-alkyl], $(CH_2)_n$—CR21R22$CONH_2$, $(CH_2)_n$—CR21R22COOH, $(CH_2)_n$—CO—R16, $(CH_2)_n$—C($CH_3$)$_2$—CO—O [($C_1$-$C_3$)]-alkyl, $(CH_2)_n$—C($CH_3$)$_2$—CO—O[($C_3$-$C_5$)]-cycloalkyl, $(CH_2)_n$—C($CH_3$)$_2$—CO—$NH_2$, $(CH_2)_n$—C($CH_3$)$_2$—CO—NH—[($C_1$-$C_3$)-alkyl], $(CH_2)_n$—C($CH_3$)$_2$—CO—NH—$(CH_2)_r$—OH, $(CH_2)_n$—C($CH_3$)$_2$—CO—NH—[($C_3$-$C_5$)-cycloalkyl], $(CH_2)_n$—C($CH_3$)$_2$—COOH, $(CH_2)_n$—CO—NH—C($CH_3$)$_2$—$CONH_2$, $(CH_2)_n$—CO—NH—C($CH_3$)$_2$—CO—O[($C_1$-$C_4$)-alkyl], $(CH_2)_n$—CO—NH—C($CH_3$)$_2$—COOH, wherein the alkyl, cycloalkyl, bicycloalkyl and tricycloalkyl radicals are optionally substituted by fluorine atoms and wherein the aryl or heteroaryl radical are optionally substituted by halogen, CN, ($C_1$-$C_4$)-alkyl, ($C_3$-$C_6$)-cycloalkyl, O—($C_1$-$C_4$)-alkyl, $S(O)_m$—($C_1$-$C_4$)-alkyl, $SO_2$—$NH_2$, COOH, $CONH_2$, CO—O($C_1$-$C_4$)-alkyl, CO—($C_1$-$C_3$)-alkyl, and wherein the alkyl radicals are optionally substituted by fluorine atoms;

R12 is H, ($C_1$-$C_3$)-alkyl, ($C_3$-$C_5$)-cycloalkyl, $(CH_2)_n$-aryl, $(CH_2)_n$-heteroaryl, wherein the alkyl or cycloalkyl radicals are optionally substituted by fluorine atoms, and wherein the aryl or heteroaryl radical are optionally substituted by halogen, CN, ($C_1$-$C_3$)-alkyl, O—($C_1$-$C_3$)-alkyl, $SO_2$—$NH_2$, COOH, $CONH_2$, CO—O($C_1$-$C_3$)-alkyl, CO—($C_1$-$C_3$)-alkyl, and wherein the alkyl radicals are optionally substituted by fluorine atoms;

R13 is H, $SO_2$—[($C_1$-$C_3$)-alkyl], $SO_2$—[($C_3$-$C_5$)-cycloalkyl], $SO_2$—$(CH_2)_n$-aryl, $SO_2$—$(CH_2)_n$-heteroaryl, $SO_2$—$(CH_2)_n$—NH—R12, $SO_2$—$(CH_2)_n$—N(R12)$_2$, wherein the alkyl and cycloalkyl radicals are optionally substituted by fluorine atoms and wherein the aryl or heteroaryl radical is optionally substituted by halogen, CN, ($C_1$-$C_3$)-alkyl, ($C_3$-$C_6$)-cycloalkyl, O—[($C_1$-$C_3$)-alkyl], $S(O)_m$—[($C_1$-$C_3$)-alkyl], $SO_2$—$NH_2$, COOH, $CONH_2$, CO—[O($C_1$-$C_3$)-alkyl], CO—($C_1$-$C_3$)-alkyl and wherein the alkyl radicals are optionally substituted by fluorine atoms;

R16 is aziridine-1-yl, azetidin-1-yl, piperidin-1-yl, 4-hydroxypiperidin-1-yl, 3-oxopiperidin-1-yl, 4-oxopiperidin-1-yl, pyrrolidin-1-yl, 3-pyrrolidinol-1-yl, 2-cyanopyrrolidin-1-yl, morpholin-N-yl, piperazin-1-yl, 4-[($C_1$-$C_3$)-alkyl]piperazin-1-yl, piperazin-2-on-1-yl, piperazin-2-on-4-yl, thiomorpholine-1,1-dioxide-4-yl, NH—$(CH_2)_r$—OH, NH—CH($CH_2$OH)$_2$, NH—C($CH_2$OH)$_3$, N[($C_1$-$C_3$)-alkyl-OH]$_2$, D-glucamin-N-yl, N-methyl-D-glucamin-N-yl, NH—[($C_1$-$C_3$)-alkyl]-CO—O($C_1$-$C_3$)-alkyl, NH—[($C_1$-$C_3$)-alkyl]-COOH, NH—[($C_1$-$C_3$)-alkyl]-$CONH_2$, NH—[C(H)(aryl)]-CO—O($C_1$-$C_3$)-alkyl, NH—[C(H)(aryl)]-COOH, NH—[C(H)(aryl)]-$CONH_2$, NH—[C(H)(heteroaryl)]-CO—O($C_1$-$C_3$)-alkyl, NH—[C(H)(heteroaryl)]-COOH, NH—[C(H)(heteroaryl)]-$CONH_2$, NH—[($C_3$-$C_6$)-cycloalkyl]-CO—O($C_1$-$C_3$)-alkyl, NH—[($C_3$-$C_6$)-cycloalkyl]-COOH, NH—[($C_3$-$C_6$)-cycloalkyl]-$CONH_2$, NH—$(CH_2)_r$—SO2—($C_1$-$C_3$)-alkyl, NH—[($C_1$-$C_4$)-alkyl]-$SO_3H$, NH—[($C_1$-$C_4$)-alkyl]-$SO_2$—$NH_2$, N[($C_1$-$C_3$)-alkyl]{[($C_1$-$C_4$)-alkyl]-$SO_3H$}, wherein the alcohol (OH) or ketone (C=O) functionalities are optionally replaced by F or $CF_2$;

R17 is H, R18, $SO_2$—$CH_3$, $SO_2$-aryl, $(CH_2)_n$—CO—[O—($C_1$-$C_3$)-alkyl], $(CH_2)_n$—CO—[($C_1$-$C_3$)-alkyl], $(CH_2)_n$—CO-aryl, $(CH_2)_n$—CO—$NH_2$, $(CH_2)_q$—COOH, wherein the alkyl and cycloalkyl radicals are optionally substituted by fluorine atoms and wherein the aryl or heteroaryl radical is optionally substituted by halogen, CN, ($C_{1-C3}$)-alkyl, O—($C_1$-$C_3$)-alkyl, $S(O)_m$—($C_1$-$C_3$)-alkyl, $SO_2$—$NH_2$, COOH, $CONH_2$, CO—[O($C_1$-$C_3$)-alkyl], CO—($C_1$-$C_3$)-alkyl, and wherein the alkyl radicals are optionally substituted by fluorine atoms;

R18 is ($C_1$-$C_4$)-alkyl, ($C_3$-$C_4$)-cycloalkyl, $(CH_2)_n$-aryl, $(CH_2)_n$-heteroaryl, wherein the alkyl and cycloalkyl radicals are optionally substituted by fluorine atoms and wherein the aryl or heteroaryl radical is optionally substituted by halogen, CN, ($C_1$-$C_3$)-alkyl, O—($C_1$-$C_3$)-alkyl, $SO_2$—$NH_2$, COOH, $CONH_2$, CO—[O($C_1$-$C_3$)-alkyl], CO—($C_1$-$C_3$)-alkyl, and wherein the alkyl radicals are optionally substituted by fluorine atoms;

R20 is H, ($C_1$-$C_3$)-alkyl, ($C_3$-$C_5$)-cycloalkyl, aryl or [($C_1$-$C_2$)-alkyl]-aryl;

R21 is H, F, $CF_3$, ($C_1$-$C_3$)-alkyl, ($C_3$-$C_4$)-cycloalkyl, OH, O—($C_1$-$C_3$)-alkyl, O—($C_3$-$C_4$)-cycloalkyl, O—$(CH_2)_n$-aryl, O—(CO)—($C_1$-$C_3$)-alkyl, O—(CO)—O—($C_1$-$C_3$)-alkyl, $NH_2$, NH—[($C_1$-$C_2$)-alkyl]-aryl, NH—($C_1$-$C_3$)-alkyl or NH—(CO)—($C_1$-$C_3$)-alkyl; and R22 is H, $CF_3$, ($C_1$-$C_3$)-alkyl, aryl, [($C_1$-$C_2$)-alkyl]-aryl;

or a physiologically compatible salt thereof.

5. The compound of the formula I as claimed in claim 1, wherein:

R, R' are each methyl;

or R and R' taken together with the carbon atom to which they are attached form a cyclohexyl ring;

n is 0, 1 or 2;

p is 1;

A, D, E, G, L are each independently C or N, where there is no corresponding R1, R2, R3, R4, R5 substituent when they are defined as N;

R1, R2, R5 are each independently H, F, Cl, Br, I, CN, $CF_3$, ($C_1$-$C_4$)-alkyl, O—($C_1$-$C_4$)-alkyl, phenyl, —O-phenyl, $SF_5$, wherein the alkyl radicals are optionally substituted by fluorine atoms and wherein the phenyl radicals are optionally substituted by F, Cl, Br, I;

R3 is F or CN;

R4 is $CF_3$, ($C_1$-$C_4$)-alkyl or O—($C_1$-$C_4$)-alkyl;

R6, R7, R8, R9, R10 are each independently H, F, Cl, Br, I, ($C_1$-$C_4$)-alkyl, O—($C_1$-$C_4$)-alkyl, wherein the alkyl radicals are optionally substituted by fluorine atoms, NR17-aryl, wherein the aryl radical is optionally substituted by F, Cl, Br, I, $(CH_2)_n$—CO—$NH_2$, $NH_2$, —$SO_2$—$NH_2$, COOH, $(CH_2)_n$—P(O)(OH)[O—($C_1$-$C_4$)-alkyl] or $(CH_2)_n$—P(O)(OH)$_2$;

wherein one of the R6, R7, R8, R9 and R10 radicals is always defined as NR17-aryl; and wherein R17 is H, ($C_1$-$C_4$)-alkyl;

or a physiologically compatible salt thereof.

6. A pharmaceutical composition comprising one or more compounds as claimed in claim 1 or a physiologically compatible salt thereof in combination with at least one pharmaceutically acceptable excipient.

7. A pharmaceutical composition comprising one or more compounds as claimed in claim 5 or a physiologically compatible salt thereof in combination with at least one pharmaceutically acceptable excipient.

8. A pharmaceutical composition comprising one or more compounds as claimed in claim 1 and at least one further active ingredient.

9. The pharmaceutical composition as claimed in claim 8, wherein said active ingredient is selected from the group consisting of antidiabetics, active hypoglycemic ingredients, HMG-CoA reductase inhibitors, cholesterol absorption inhibitors, PPAR gamma agonists, PPAR alpha agonists, PPAR alpha/gamma agonists, PPAR delta agonists, fibrates, MTP inhibitors, bile acid absorption inhibitors, MTP inhibitors, CETP inhibitors, polymeric bile acid adsorbers, LDL receptor inducers, ACAT inhibitors, antioxidants, lipoprotein lipase inhibitors, ATP citrate lyase inhibitors, squalene synthetase inhibitors, lipoprotein(a) antagonists, HM74A receptor agonists, lipase inhibitors, insulins, sulfonylureas, biguanides, meglitinides, thiazolidinediones, α-glucosidase inhibitors, active ingredients which act on the ATP-dependent potassium channel of the beta cells, glycogen phosphorylase inhibitors, glucagon receptor antagonists, activators of glucokinase, inhibitors of gluconeogenesis, inhibitors of fructose 1,6-biphosphatase, modulators of glucose transporter 4, inhibitors of glutamine: fructose-6-phosphate amidotransferase, inhibitors of dipeptidylpeptidase IV, inhibitors of 11-beta-hydroxysteroid dehydrogenase 1, inhibitors of protein tyrosine phosphatase 1B, modulators of the sodium-dependent glucose transporter 1 or 2, modulators of GPR40, inhibitors of hormone-sensitive lipase, inhibitors of acetyl-CoA carboxylase, inhibitors of phosphoenolpyruvate carboxykinase, inhibitors of glycogen synthase kinase-3 beta, inhibitors of protein kinase C beta, endothelin-A receptor antagonists, inhibitors of I kappaB kinase, modulators of the glucocorticoid receptor, CART agonists, NPY agonists, MC4 agonists, orexin agonists, H3 agonists, TNF agonists, CRF agonists, CRF BP antagonists, urocortin agonists, β3 agonists, CB1 receptor antagonists, MSH (melanocyte-stimulating hormone) agonists, CCK agonists, serotonin reuptake inhibitors, mixed serotoninergic and noradrenergic compounds, 5HT agonists, bombesin agonists, galanin antagonists, growth hormones, growth hormone-releasing compounds, TRH agonists, decoupling protein 2 or 3 modulators, leptin agonists, DA agonists (bromocriptin, doprexin), lipase/amylase inhibitors, PPAR modulators, RXR modulators or TR-β-agonists or amphetamines.

10. A method of treatment of metabolic syndrome in a patient comprising administering to said patient a therapeutically effective amount of a compound of formula (I) as claimed in claim 1 or a physiologically acceptable salt thereof.

11. A method of treatment of diabetes in a patient comprising administering to said patient a therapeutically effective amount of a compound of formula (I) as claimed in claim 1 or a physiologically acceptable salt thereof.

12. A method of treatment of obesity in a patient comprising administering to said patient a therapeutically effective amount of a compound of formula (I) as claimed in claim 1 or a physiologically acceptable salt thereof.

13. A method of treatment for weight reduction in a patient comprising administering to said patient a therapeutically effective amount of a compound of formula (I) as claimed in claim 1 or a physiologically acceptable salt thereof.

14. A method of treatment of nicotine dependence in a patient comprising administering to said patient a therapeutically effective amount of a compound of formula (I) as claimed in claim 1 or a physiologically acceptable salt thereof.

15. A method of treatment of alcohol dependence in a patient comprising administering to said patient a therapeutically effective amount of a compound of formula (I) as claimed in claim 1 or a physiologically acceptable salt thereof.

16. A method of treatment of schizophrenia in a patient comprising administering to said patient a therapeutically effective amount of a compound of formula (I) as claimed in claim 1 or a physiologically acceptable salt thereof.

17. A method of treatment of Alzheimer's disease in a patient comprising administering to said patient a therapeutically effective amount of a compound of formula (I) as claimed in claim 1 or a physiologically acceptable salt thereof.

18. A method of treatment of polycystic ovary syndrome (PCOS) in a patient comprising administering to said patient a therapeutically effective amount of a compound of formula (I) as claimed in claim 1 or a physiologically acceptable salt thereof.

19. A process for producing a pharmaceutical composition comprising one or more of the compounds as claimed in claim 1, which comprises mixing the active ingredient with a pharmaceutically suitable carrier and bringing this mixture into a form suitable for administration.

\* \* \* \* \*

UNITED STATES PATENT AND TRADEMARK OFFICE
CERTIFICATE OF CORRECTION

PATENT NO. : 7,759,366 B2
APPLICATION NO. : 12/365940
DATED : July 20, 2010
INVENTOR(S) : Gerhard Jaehne et al.

It is certified that error appears in the above-identified patent and that said Letters Patent is hereby corrected as shown below:

In column 20, line 13, delete "C=O," and insert -- C=O. --, therefor.

In column 20, line 16, delete "dihydrobenzimidazole" and insert -- dihydrobenzimidazol --, therefor.

In column 20, line 47, delete "treitol" and insert -- threitol --, therefor.

In column 24, line 65, delete "HMR1964" and insert -- HMR 1964 --, therefor.

In column 25, line 21, delete "oxadiazolidinediones," and insert -- oxazolidinones, --, therefor.

In column 30, line 29, delete "SAR7226" and insert -- SAR 7226 --, therefor.

In column 32, line 42-43, delete "WO2007009894, WO2007015162, WO2007041061, WO2007041052;" and insert the same on Col. 32 Line 41 as a continuation of the paragraph.

In column 33, line 60, delete "(bromocriptine," and insert -- (bromocriptin, --, therefor.

In column 34, line 41-42, delete "mazindol or phentermine." and insert -- mazindole or phentermin. --, therefor.

In column 43-44, in Structure GW-803430, line 5, delete

" 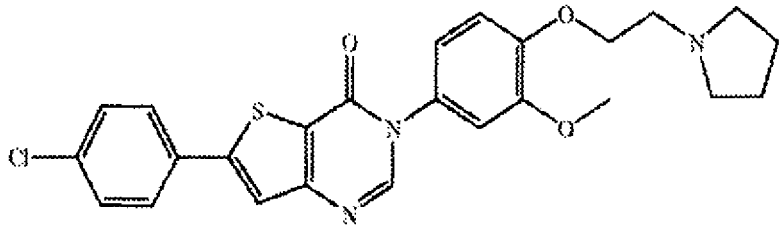 " and insert

Signed and Sealed this
Seventeenth Day of April, 2012

David J. Kappos
*Director of the United States Patent and Trademark Office*

CERTIFICATE OF CORRECTION (continued)
U.S. Pat. No. 7,759,366 B2

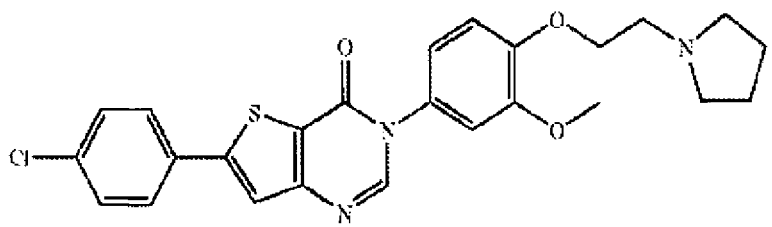

--             --, therefor.

In column 62, line 15, delete "mudandis," and insert -- mutandis, --, therefor.

In column 63, line 26, delete "mudandis," and insert -- mutandis, --, therefor.

In column 67, line 36-39, delete "Soc. 120 (1998) 9722; T. E. Barder and St. L. Buchwald, Org. Lett. 6 (2004) 2649-2652. The further conversion of the compounds K1' and L1' thus substituted by R2 can be effected as described for process "A" and "B"." and insert the same on Line 35, Col. 67 as a continuation of the paragraph.

In column 68, line 35, delete "acid)" and insert -- acid): --, therefor.

In column 92, line 20, delete "phthalamide" and insert -- phthalimide --, therefor.

In column 92, line 34, delete "phthalamide" and insert -- phthalimide --, therefor.

In column 107, line 48, delete "benzene sulfonamide" and insert -- benzenesulfonamide --, therefor.

In column 109, line 56, delete "984-" and insert -- 98 4- --, therefor.

In column 117, line 40, delete "I" and insert -- 1 --, therefor.

In column 120, line 33, delete "[B]; MS (ESI): 596.22 (MH$^+$))," and insert the same on Line 32, Col. 120 as a continuation of the paragraph.

In column 122, line 4-5, delete "Molecular weight 513.17 ($C_{26}H_{23}F_4N_5O_2$); retention time $R_t$=1.52 min. [B]; MS (ESI): 514.24 (MH$^+$)." and insert the same on Line 3, Col. 122 as a continuation of the paragraph.

In column 122, line 66, delete "5577.13" and insert -- 557.13 --, therefor.

In column 123, line 42, delete "2H," and insert -- 2H; --, therefor.

In column 124, line 33, delete "3.8, s, 3H, 1.35, s, 6H." and insert the same on Line 32, Col. 124 as a continuation of the paragraph.

CERTIFICATE OF CORRECTION (continued)
U.S. Pat. No. 7,759,366 B2

In column 125, line 12, delete "[PR1])" and insert -- [RP1]) --, therefor.

In column 127, line 5, delete "benzoate ·HCl·trifluoroacetic" and insert
-- benzoate·HCl·trifluoroacetic --, therefor.

In column 128, line 10, delete "[C]; MS (ESI): 697.33 (MH$^+$)" and insert the same on Line 9, Col. 128 as a continuation of paragraph.

In column 138, line 4-5, delete "trifluoromethylbenzonitrile trifluoroacetic" and insert
-- trifluoromethylbenzonitrile·trifluoroacetic --, therefor.

In column 147, line 9, delete "I." and insert -- 1. --, therefor.

In column 148, line 67, delete "[C]; MS (ESI): 583.14 (MH$^+$)." and insert the same on Line 66, Col. 148 as a continuation of the paragraph.

In column 151, line 67, delete "MS (ESI): 564.15 (MH$^+$)." and insert the same on Line 66, Col. 151 as a continuation of the paragraph.

In column 153, line 66, delete "δ" and insert -- → --, therefor.

In column 164, line 5, delete "56" and insert -- 156 --, therefor.

In column 168, line 5, in claim 1, delete "[($C_7$-$C_{12}$-" and insert -- [($C_7$-$C_{12}$)- --, therefor.

In column 168, line 19, in claim 1, delete "[($C_1$-$C_8$-" and insert -- [($C_1$-$C_8$)- --, therefor.

In column 168, line 20, in claim 1, delete "[($C_3$-$C_8$-" and insert -- [($C_3$-$C_8$)- --, therefor.

In column 168, line 23, in claim 1, delete "C(=NH—R16," and insert -- C(=NH)—R16, --, therefor.

In column 168, line 29, in claim 1, delete "($C_1$-$C_6$-" and insert -- ($C_1$-$C_6$)- --, therefor.

In column 169, line 8, in claim 1, delete "C(=NH—NHR12," and insert -- C(=NH)—NHR12, --, therefor.

In column 169, line 15, in claim 1, delete "[(C1-C8)-" and insert -- [($C_1$-$C_8$)- --, therefor.

In column 170, line 20, in claim 1, delete "$SO_2$N=CH" and insert -- $SO_2$—N=CH --, therefor.